(12) United States Patent
Di Fabio

(10) Patent No.: US 7,691,893 B2
(45) Date of Patent: Apr. 6, 2010

(54) CHEMICAL COMPOUNDS

(75) Inventor: Romano Di Fabio, Verona (IT)

(73) Assignee: Glaxo Group Limited, Greenford, Middlesex (GB)

( * ) Notice: Subject to any disclaimer, the term of this patent is extended or adjusted under 35 U.S.C. 154(b) by 283 days.

(21) Appl. No.: 11/851,459

(22) Filed: Sep. 7, 2007

(65) Prior Publication Data

US 2008/0114049 A1    May 15, 2008

(30) Foreign Application Priority Data

| Sep. 11, 2006 | (GB) | ................................. | 0617863.6 |
| Sep. 11, 2006 | (GB) | ................................. | 0617868.5 |
| Aug. 22, 2007 | (GB) | ................................. | 0716371.0 |

(51) Int. Cl.
*A61K 31/403* (2006.01)
*C07D 209/52* (2006.01)

(52) U.S. Cl. .................................... 514/412; 548/452

(58) Field of Classification Search ................ 548/452; 514/412
See application file for complete search history.

(56) References Cited

U.S. PATENT DOCUMENTS

| 4,131,611 | A | 12/1978 | Fanshawe et al. | ........ 260/326.8 |
| 4,435,419 | A | 3/1984 | Epstein et al. | ............ 424/274 |
| 6,288,079 | B1 | 9/2001 | Scheel-Krüger et al. | .... 514/304 |
| 6,372,919 | B1 | 4/2002 | Lippa et al. | .................. 548/452 |
| 6,569,887 | B2 | 5/2003 | Lippa et al. | .................. 514/412 |
| 6,716,868 | B2 | 4/2004 | Lippa et al. | .................. 514/412 |
| 2004/0220191 | A1 | 11/2004 | Schwink et al. | ........ 514/252.03 |

FOREIGN PATENT DOCUMENTS

| CA | 2516118 A1 | 8/2004 |
| EP | 0604352 A2 | 6/1994 |
| EP | 0965587 A1 | 12/1999 |
| WO | WO98/45263 | 10/1998 |
| WO | WO 04/072025 | 8/2004 |
| WO | WO2005/092885 A1 | 10/2005 |
| WO | WO2007/047837 A2 | 4/2007 |
| WO | WO 08/031772 | 3/2008 |

OTHER PUBLICATIONS

Rimoldi et al., "A novel and selective monoamine oxidase B substrate", *Biorganic & Medicinal Chemistry*, 13, pp. 5808-5813 (2005).
U.S. Appl. No. 12/440,852, filed Sep. 7, 2007, Bertani et al.
U.S. Appl. No. 12/440,852 — 1st Preliminary Amendment filed Mar. 11, 2009.

*Primary Examiner*—Golam M Shameem
(74) *Attorney, Agent, or Firm*—Loretta J. Sauermelch; Alan X. Scrivner; Charles M. Kinzig

(57) ABSTRACT

The present invention relates to (1S,6R)-6-(3,4-dichlorophenyl)-1-[(methyloxy)methyl]-3-azabicyclo[4.1.0]heptane, pharmaceutically acceptable salts, prodrugs or solvates thereof; processes for their preparation, intermediates used in these processes, pharmaceutical compositions containing them and their use in therapy, as serotonin (5-HT), dopamine (DA) and norepinephrine (NE), re-uptake inhibitors.

41 Claims, 8 Drawing Sheets

CHEMICAL COMPOUNDS

FIELD OF THE INVENTION

The present invention relates to novel compounds, processes for their preparation, intermediates used in these processes, pharmaceutical compositions containing them and their use in therapy, as serotonin (5-HT), dopamine (DA) and norepinephrine (NE), re-uptake inhibitors.

BACKGROUND OF THE INVENTION

Brain tissue is constituted of neuronal cells which are able to communicate with each other via specific cellular structures named synapses. The exchange of signals between neurons in the synapses happens through neurochemical messengers named neurotransmitters, acting on specific target protein molecules, both post and pre-synaptic, referred to as receptors. Monoamines represent a family of small neurotransmitter molecules sharing common chemical features, and include serotonin (5-HT), dopamine (DA) and norepinephrine (NE).

Monoamine neurotransmitters are released into the synaptic cleft between neurons and interact with receptors present on the membrane of the target cells. The switch of the neurochemical signal occurs mainly by removal of the neurotransmitter molecules through other protein molecules referred to as monoamine transporters (SERT for 5-HT, DAT for DA and NET for NE). Transporters are able to bind neurotransmitter molecules and move them into the presynaptic terminals, this cellular mechanism referred to as re-uptake. Pharmacological inhibition of the re-uptake process can cause an increase of monoamine at synaptic level and as a consequence an enhancement of the physiological activity of neurotransmitters.

Serotonergic neurotransmission in the brain is mediated by a large family of receptors comprising both the G-protein coupled receptors and ligand-gated ion channels including 14 subtypes, and is involved in a vast variety of physiologic functions.

Compounds endowed of inhibitory properties at the SERT are predicted to have the ability to treat in mammals, including humans, a variety of disorders associated with this neural system, for example eating disorders, major depression and mood disorders, obsessive compulsive disorders, panic disorders, alcoholism, pain, memory deficits and anxiety.

Included among these disorders are disorders related to depression, such as pseudodementia or Ganser's syndrome, migraine pain, bulimia, obesity, pre-menstrual syndrome or late luteal phase syndrome, tobacco abuse, panic disorder, post-traumatic syndrome, memory loss, dementia of ageing, acquired immunodeficiency syndrome dementia complex, memory dysfunction in ageing, social phobia, attention deficit hyperactivity disorder, chronic fatigue syndrome, premature ejaculation, erectile difficulty, anorexia nervosa, disorders of sleep, autism, mutism or trichotillomania.

Major depression is an affective disorder, or disorder of mood, characterized by several symptoms including feeling of profound sadness, worthlessness, despair and loss of interest in all pleasures (anhedonia), recurrent thoughts of death, mental slowing, loss of energy, an inability to take decision, often associated with anxiety and agitation. These symptoms are persistent and can range from mild to severe.

The pathophysiology of major depression is poorly understood being a multifactorial syndrome and, due to this, several neurotransmitter systems have been implicated. However, it is generally believed that the disorder stems from a decrease in the synaptic concentration of monoamine neurotransmitters, mainly NE and 5-HT, in critical brain areas, leading to the "monoamine theory" of depression.

Several lines of preclinical and clinical evidence indicate that an enhancement of serotonin-mediated neurotransmission might be effective in the treatment of major depression and actually the selective serotonin re-uptake inhibitors (SSRIs) have come to dominate the therapy of depression over the last two decades. Fluoxetine, the first SSRI to be introduced, is the prototype of this group. Other members include Paroxetine, Sertraline, Fluvoxamine, Citalopram.

However, it is not clear exactly how these agents act to relieve depression. As with other classes of antidepressant, there is a lag of several weeks before the onset of the mood-elevating effect, despite the rapid blockade of the serotonin re-uptake. It is presumed that secondary adaptive changes must occur at serotonergic synapses after chronic administration of SSRIs i.e. down-regulation of release-regulating autoreceptors and increased neurotransmitter release. The delayed onset of anti-depressant effect is considered to be a serious drawback to currently used SSRIs. Moreover, although there is generally good tolerability of SSRIs, the elevation of 5-HT levels at central and peripheral synapses leads to stimulation of receptor subtypes like 5-HT$_{2C}$ and 5-HT$_3$, which contributes to agitation and restless, along with gastrointestinal and sexual side-effects.

The success of the SSRIs rekindled interest in the development of selective norepinephrine re-uptake inhibitors (SNRIs) as potential antidepressants. A number of such compounds have been synthesized, e.g. Nisoxetine, Maprotiline, Tomoxetine and Reboxetine. Furthermore, many compounds, including old tricyclic antidepressants, have a mixed NET and SERT inhibition profile, like Imipramine and Amitriptyline (with SERT potency>NET) and Desipramine, Nortriptyline, and Protriptyline (NET potency>SERT).

The pharmacological manipulation of the DAT can in principle have the ability to elevate DA levels in the mesolimbic system, reversing the anhedonia that is a core symptom of major depression. A DAT inhibition component, in combination with a blockade of SERT and NET, can also have the ability to improve the lack of motivation and attention and enhance cognitive deficits seen in depressed patients. On the other hand, blockade of DAT has to be carefully managed in order to avoid potential reinforcing effects and abuse liability. However compounds with DAT inhibition in their pharmacology, such as Dexmethylphenidate, Methylphenidate and Bupropion, have been successfully marketed. Clinical studies indicate that patients with poor response to SSRIs benefit from combination therapy with agents that enhance dopaminergic tone. As a result, compounds with a strong SERT inhibiting activity combined with a well balanced NET blockade and moderate DAT inhibiting activity may therefore provide a replacement for current combination therapies for treating unresponsive patients, providing greater efficacy and therapeutic flexibility with a more rapid onset of anti-depressant effect.

Due to their valuable DAT inhibition, the compounds of the present invention are considered useful for the treatment of Parkinsonism, depression, obesity, narcolepsy, drug addiction or misuse, including cocaine abuse, attention-deficit hyperactivity disorders, Gilles de la Tourettes disease and senile dementia. Dopamine re-uptake inhibitors enhance indirectly via the dopamine neurones the release of acetylcholine and are therefore also useful for the treatment of memory deficits, e.g. in Alzheimers disease, presenile dementia, memory dysfunction in ageing, and chronic fatigue syndrome. Noradrenaline re-uptake inhibitors are considered useful for enhancing attention, alertness, arousal, vigilance and for treating depression.

SUMMARY OF THE INVENTION

One object of the present invention is to provide novel pharmaceutical compositions comprising compounds which are serotonin (5-HT), dopamine (DA) and norepinephrine (NE) re-uptake inhibitors.

Furthermore, the object of the present invention is to provide novel compounds which are serotonin (5-HT), dopamine (DA) and norepinephrine (NE) re-uptake inhibitors.

DETAILED DESCRIPTION OF THE INVENTION

Figure 1:
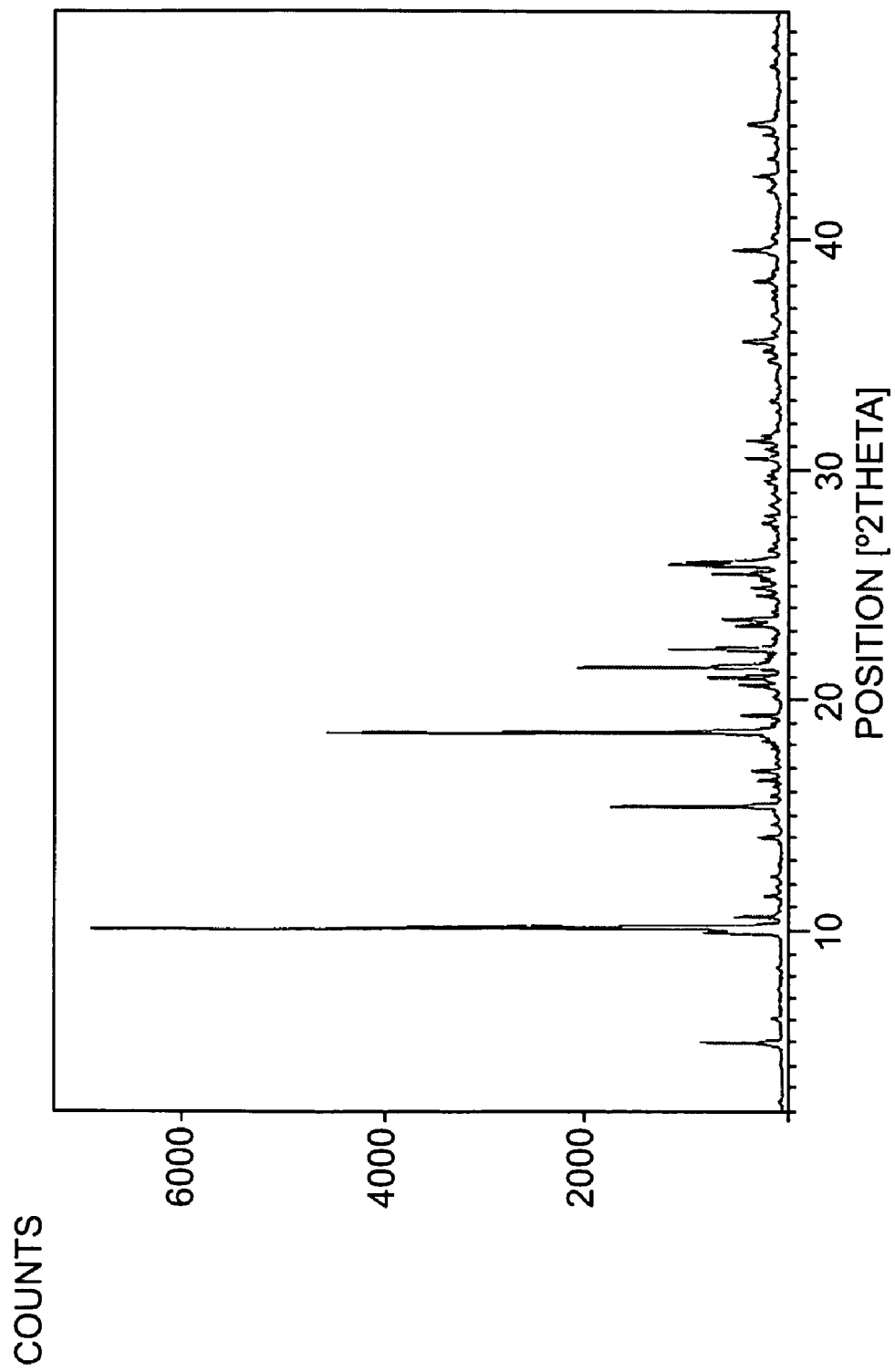
FIG. 1 is a Diffractogram of Form 1 of the title compound E38 of Example 38.

In a first aspect, the present invention provides a pharmaceutical composition comprising a compound of formula (A) or a pharmaceutically acceptable salt, solvate or prodrug thereof:

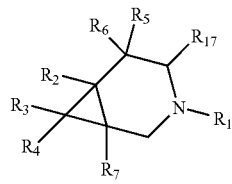

(A)

wherein
$R_1$ is hydrogen or $C_{1-4}$ alkyl;
$R_2$ is a group A, K or W
wherein
A is

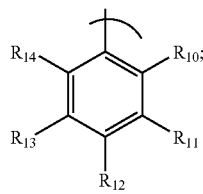

K is an α or β naphthyl group, optionally substituted by 1 or 2 groups $R_{18}$, each of them being the same or different; and
W is

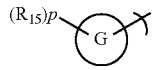

and wherein
G is a 5,6-membered monocyclic heteroaryl, or a 8- to 11-membered heteroaryl bicyclic group; such G may be substituted by $(R_{15})_p$, which can be the same or different;
p is an integer from 0 to 5;
$R_3$ is selected in the group consisting of: hydrogen, fluorine, and $C_{1-4}$ alkyl; or corresponds to a group X or $X_1$;
$R_4$ is selected in the group consisting of: hydrogen, fluorine, and $C_{1-4}$ alkyl; or corresponds to a group X or $X_1$;
$R_5$ is hydrogen or $C_{1-4}$ alkyl;
$R_7$ is hydrogen or $C_{1-4}$ alkyl; or is a group X, $X_1$, $X_2$ or $X_3$;
wherein

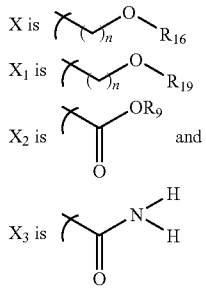

$R_6$ is hydrogen or $C_{1-4}$ alkyl; or is a group X or $X_1$;
$R_9$ is $C_{1-4}$alkyl;
$R_{10}$ is selected from a group consisting of: hydrogen, halogen, hydroxy, cyano, $C_{1-4}$alkyl, haloC$_{1-4}$alkyl, $C_{1-4}$alkoxy, haloC$_{1-4}$alkoxy, $C_{1-4}$alkanoyl and SF$_5$; or corresponds to a group $R_8$;
$R_8$ is a 5-6 membered heterocycle group, which may be optionally substituted by one or two substituents selected from a group consisting of: halogen, cyano, $C_{1-4}$alkyl, haloC$_{1-4}$alkyl, $C_{1-4}$alkoxy and $C_{1-4}$alkanoyl;
$R_{11}$ is selected from a group consisting of: hydrogen, halogen, hydroxy, cyano, $C_{1-4}$alkyl, haloC$_{1-4}$alkyl, $C_{1-4}$alkoxy, haloC$_{1-4}$alkoxy, $C_{1-4}$alkanoyl and SF$_5$; or corresponds to a group $R_8$;
$R_{12}$ is selected from a group consisting of: hydrogen, halogen, hydroxy, cyano, $C_{1-4}$alkyl, haloC$_{1-4}$alkyl, $C_{1-4}$alkoxy, haloC$_{1-4}$alkoxy, $C_{1-4}$alkanoyl and SF$_5$; or corresponds to a group $R_8$;
$R_{13}$ is selected from a group consisting of: hydrogen, halogen, hydroxy, cyano, $C_{1-4}$alkyl, haloC$_{1-4}$alkyl, $C_{1-4}$alkoxy, haloC$_{1-4}$alkoxy, $C_{1-4}$alkanoyl and SF$_5$; or corresponds to a group $R_8$;
$R_{14}$ is selected from a group consisting of: hydrogen, halogen, hydroxy, cyano, $C_{1-4}$alkyl, haloC$_{1-4}$alkyl, $C_{1-4}$alkoxy, haloC$_{1-4}$alkoxy, $C_{1-4}$alkanoyl and SF$_5$; or corresponds to a group $R_8$;
$R_{15}$ is selected from a group consisting of: halogen, hydroxy, cyano, $C_{1-4}$alkyl, haloC$_{1-4}$alkyl, $C_{1-4}$alkoxy, haloC$_{1-4}$alkoxy, $C_{1-4}$alkanoyl and SF$_5$; or corresponds to a group $R_8$;

$R_{16}$ is hydrogen, $C_{1-4}$alkyl, $C_{3-6}$cycloalkyl or $C_{3-6}$cycloalkyl$C_{1-3}$alkyl;
$R_{17}$ is hydrogen or $C_{1-4}$alkyl;
$R_{18}$ is selected from a group consisting of: halogen, cyano, $C_{1-4}$alkyl;
$R_{19}$ is halo$C_{1-2}$alkyl;
n is 1 or 2;

and a pharmaceutically acceptable carrier.

Compound 6-(4-fluorophenyl)-3-azabicyclo[4.1.0]heptane shown below

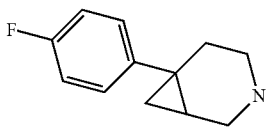

has been disclosed in the patent application No WO2004072025 ("Preparation of N-arylheterocycles as melanin concentrating hormone (MCH) antagonists") wherein it has been used as an intermediate for synthesis of final compounds. No therapeutic use has been indicated for this compound in the patent application.

Compound 3-methyl-6-phenyl-3-azabicyclo[4.1.0]heptane shown below

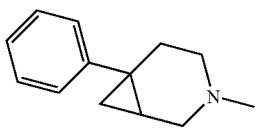

has been disclosed in the publication titled "*A Novel and Selective Monoamine Oxidase B substrate*" Rimoldi, J. et al., Bioorganic and Medicinal Chemistry (2005), 13 (20), 5808-5813. Nonetheless, no therapeutic use has been indicated for this compound.

In another aspect, the invention provides a method for the treatment of a mammal, including man, in particular for the treatment of disorders or diseases responsive to the serotonin (5-HT), dopamine (DA) and norepinephrine (NE), re-uptake inhibiting activity of the compounds, comprising administration of an effective amount of a compound of formula (A) as above defined or a pharmaceutically acceptable salt, solvate or prodrug thereof.

In one embodiment, the invention provides a method of treating a condition for which inhibition of serotonin (5-HT), dopamine (DA) and norepinephrine (NE), is beneficial, which comprises administering to a mammal (e.g. human) in need thereof an effective amount of a compound of formula (A) as above defined or a pharmaceutically acceptable salt, solvate or prodrug thereof.

In a further aspect, the invention provides a compound of formula (A) as above defined or a pharmaceutically acceptable salt, solvate or prodrug thereof for use in therapy.

In one embodiment, the invention provides a compound of formula (A) as above defined or a pharmaceutically acceptable salt, solvate or prodrug thereof, for use in the treatment of a condition in a mammal for which inhibition of serotonin (5-HT), dopamine (DA) and norepinephrine (NE) is beneficial.

In a still further aspect, the invention provides the use of a compound of formula (A) as above defined or a pharmaceutically acceptable salt, solvate or prodrug thereof, for the manufacture of a medicament for the treatment of disorders or diseases responsive to the serotonin (5-HT), dopamine (DA) and norepinephrine (NE), re-uptake inhibiting activity.

In one embodiment, the invention provides the use of a compound of formula (A) as above defined or a pharmaceutically acceptable salt, solvate or prodrug thereof in the manufacture of a medicament for the treatment of a condition in a mammal for which inhibition of serotonin (5-HT), dopamine (DA) and norepinephrine (NE) is beneficial.

In one aspect, the present invention provides a compound of formula (I) or a pharmaceutically acceptable salt, solvate or prodrug thereof:

(I)

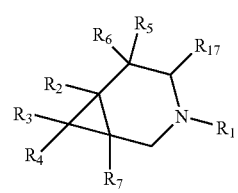

wherein $R_1$ is hydrogen or $C_{1-4}$ alkyl;
$R_2$ is a group A, K or W wherein A is

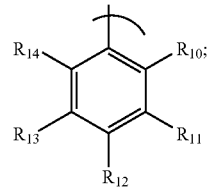

K is an α or β naphthyl group, optionally substituted by 1 or 2 groups $R_{18}$, each of them being the same or different; and
W is

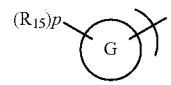

and wherein

G is a 5,6-membered monocyclic heteroaryl, or a 8- to 11-membered heteroaryl bicyclic group; such G may be substituted by $(R_{15})_p$, which can be the same or different;
p is an integer from 0 to 5;
$R_3$ is selected in the group consisting of: hydrogen, fluorine, and $C_{1-4}$ alkyl; or corresponds to a group X or $X_1$;
$R_4$ is selected in the group consisting of: hydrogen, fluorine, and $C_{1-4}$ alkyl; or corresponds to a group X or $X_1$;
$R_5$ is hydrogen or $C_{1-4}$ alkyl;
$R_7$ is hydrogen or $C_{1-4}$ alkyl; or is a group X, $X_1$, $X_2$ or $X_3$;

wherein

X is
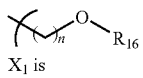

$X_1$ is
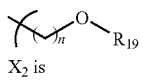

$X_2$ is
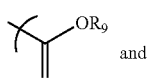 and $X_3$ is

$R_6$ is hydrogen or $C_{1-4}$ alkyl; or is a group X or $X_1$;
$R_9$ is $C_{1-4}$ alkyl;
$R_{10}$ is selected from a group consisting of: hydrogen, halogen, hydroxy, cyano, $C_{1-4}$alkyl, halo$C_{1-4}$alkyl, $C_{1-4}$alkoxy, halo$C_{1-4}$alkoxy, $C_{1-4}$alkanoyl and $SF_5$; or corresponds to a group $R_8$;
$R_8$ is a 5-6 membered heterocycle group, which may be optionally substituted by one or two substituents selected from a group consisting of: halogen, cyano, $C_{1-4}$alkyl, halo$C_{1-4}$alkyl, $C_{1-4}$alkoxy and $C_{1-4}$alkanoyl;
$R_{11}$ is selected from a group consisting of: hydrogen, halogen, hydroxy, cyano, $C_{1-4}$alkyl, halo$C_{1-4}$alkyl, $C_{1-4}$alkoxy, halo$C_{1-4}$alkoxy, $C_{1-4}$alkanoyl and $SF_5$; or corresponds to a group $R_8$;
$R_{12}$ is selected from a group consisting of: hydrogen, halogen, hydroxy, cyano, $C_{1-4}$alkyl, halo$C_{1-4}$alkyl, $C_{1-4}$alkoxy, halo$C_{1-4}$alkoxy, $C_{1-4}$alkanoyl and $SF_5$; or corresponds to a group $R_8$;
$R_{13}$ is selected from a group consisting of: hydrogen, halogen, hydroxy, cyano, $C_{1-4}$alkyl, halo$C_{1-4}$alkyl, $C_{1-4}$alkoxy, halo$C_{1-4}$alkoxy, $C_{1-4}$alkanoyl and $SF_5$; or corresponds to a group $R_8$;
$R_{14}$ is selected from a group consisting of: hydrogen, halogen, hydroxy, cyano, $C_{1-4}$alkyl, halo$C_{1-4}$alkyl, $C_{1-4}$alkoxy, halo$C_{1-4}$alkoxy, $C_{1-4}$alkanoyl and $SF_5$; or corresponds to a group $R_8$;
$R_{15}$ is selected from a group consisting of: halogen, hydroxy, cyano, $C_{1-4}$alkyl, halo$C_{1-4}$alkyl, $C_{1-4}$alkoxy, halo$C_{1-4}$alkoxy, $C_{1-4}$alkanoyl and $SF_5$; or corresponds to a group $R_8$;
$R_{16}$ is hydrogen, $C_{1-4}$alkyl, $C_{3-6}$cycloalkyl or $C_{3-6}$cycloalkyl$C_{1-3}$alkyl;
$R_{17}$ is hydrogen or $C_{1-4}$alkyl;
$R_{18}$ is selected from a group consisting of: halogen, cyano, $C_{1-4}$alkyl;
$R_{19}$ is halo$C_{1-2}$alkyl;
n is 1 or 2;

with the proviso that:
if $R_2$ is A, $R_3$, $R_4$, $R_5$, $R_6$, $R_7$, $R_{10}$, $R_{11}$, $R_{13}$, $R_{14}$ are hydrogen, and $R_{12}$ is fluorine, $R_1$ is $C_{1-4}$ alkyl;
if $R_2$ is A, $R_3$, $R_4$, $R_5$, $R_6$, $R_7$, $R_{10}$, $R_{11}$, $R_{13}$, $R_{14}$ are hydrogen, and $R_1$ is methyl, $R_{12}$ is halogen, hydroxy, cyano, $C_{1-4}$alkyl, halo$C_{1-4}$alkyl, $C_{1-4}$alkoxy, halo$C_{1-4}$alkoxy, $C_{1-4}$alkanoyl and $SF_5$; or corresponds to a group $R_8$.

In another aspect, the present invention provides a compound of formula (IF) or a pharmaceutically acceptable salt, solvate or prodrug thereof:

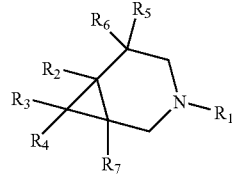
(IF)

wherein
$R_1$ is hydrogen or $C_{1-4}$ alkyl;
$R_2$ is a group A or W wherein
A is

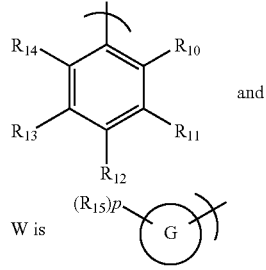

and wherein
G is a 5,6-membered monocyclic heteroaryl, or a 8- to 11-membered heteroaryl bicyclic group; such G may be substituted by $(R_{15})_p$, which can be the same or different;
p is an integer from 0 to 5;
$R_3$ is selected in the group consisting of: hydrogen, fluorine, and $C_{1-4}$ alkyl; or corresponds to a group X or $X_1$;
$R_4$ is selected in the group consisting of: hydrogen, fluorine, and $C_{1-4}$ alkyl; or corresponds to a group X or $X_1$;
$R_5$ is hydrogen or $C_{1-4}$ alkyl;
$R_6$ is hydrogen or $C_{1-4}$ alkyl; or is a group X or $X_1$ wherein X is    $X_1$ is 

$X_2$ is  and $X_3$ is 

and wherein
$R_7$ is hydrogen or $C_{1-4}$ alkyl; or is a group X, $X_1$, $X_2$ or $X_3$;
$R_8$ is a 5-6 membered heterocycle group, which may be substituted by one or two substituents selected from a group consisting of: halogen, cyano, $C_{1-4}$alkyl, halo$C_{1-4}$alkyl, $C_{1-4}$alkoxy and $C_{1-4}$alkanoyl;
$R_9$ is $C_{1-4}$alkyl $R_{10}$ is selected from a group consisting of: hydrogen, halogen, hydroxy, cyano, $C_{1-4}$alkyl, haloC$_{1-4}$alkyl, $C_{1-4}$alkoxy, haloC$_{1-4}$alkoxy, $C_{1-4}$alkanoyl and SF$_5$; or corresponds to a group $R_8$;

$R_{11}$ is selected from a group consisting of: hydrogen, halogen, hydroxy, cyano, $C_{1-4}$alkyl, haloC$_{1-4}$alkyl, $C_{1-4}$alkoxy, haloC$_{1-4}$alkoxy, $C_{1-4}$alkanoyl and SF$_5$; or corresponds to a group $R_8$;

$R_{12}$ is selected from a group consisting of: hydrogen, halogen, hydroxy, cyano, $C_{1-4}$alkyl, haloC$_{1-4}$alkyl, $C_{1-4}$alkoxy, haloC$_{1-4}$alkoxy, $C_{1-4}$alkanoyl and SF$_5$; or corresponds to a group $R_8$;

$R_{13}$ is selected from a group consisting of: hydrogen, halogen, hydroxy, cyano, $C_{1-4}$alkyl, haloC$_{1-4}$alkyl, $C_{1-4}$alkoxy, haloC$_{1-4}$alkoxy, $C_{1-4}$alkanoyl and SF$_5$; or corresponds to a group $R_8$;

$R_{14}$ is selected from a group consisting of: hydrogen, halogen, hydroxy, cyano, $C_{1-4}$alkyl, haloC$_{1-4}$alkyl, $C_{1-4}$alkoxy, haloC$_{1-4}$alkoxy, $C_{1-4}$alkanoyl and SF$_5$; or corresponds to a group $R_8$;

$R_{15}$ is selected from a group consisting of: halogen, hydroxy, cyano, $C_{1-4}$alkyl, haloC$_{1-4}$alkyl, $C_{1-4}$alkoxy, haloC$_{1-4}$alkoxy, $C_{1-4}$alkanoyl and SF$_5$; or corresponds to a group $R_8$;

$R_{16}$ is hydrogen, $C_{1-4}$alkyl, $C_{3-6}$cycloalkyl or $C_{3-6}$cycloalkylC$_{1-3}$alkyl;

n is 1 or 2;

with the proviso that:
if one group of $R_{11}$ or $R_{13}$ is not hydrogen, at least one group of $R_{10}$, $R_{12}$ or $R_{14}$ is not hydrogen;
if $R_2$ is A, $R_3$, $R_4$, $R_5$, $R_6$, $R_7$, $R_{10}$, $R_{11}$, $R_{13}$, $R_{14}$ are hydrogen, and $R_{12}$ is fluorine, $R_1$ is not hydrogen;
if $R_2$ is A, $R_3$, $R_4$, $R_5$, $R_6$, $R_7$, $R_{10}$, $R_{11}$, $R_{13}$, $R_{14}$ are hydrogen, and $R_1$ is methyl, $R_{12}$ is not hydrogen.

In a further aspect, the present invention provides a compound of formula (IG) or a pharmaceutically acceptable salt, solvate or prodrug thereof:

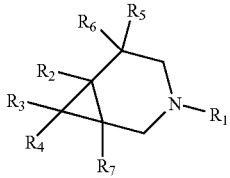

(IG)

wherein
$R_1$ is hydrogen or $C_{1-4}$ alkyl;
$R_2$ is

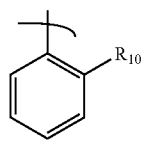

p is an integer from 0 to 5;
$R_3$ is selected in the group consisting of: hydrogen, fluorine, and $C_{1-4}$ alkyl; or corresponds to a group X or $X_1$;
$R_4$ is selected in the group consisting of: hydrogen, fluorine, and $C_{1-4}$ alkyl; or corresponds to a group X or $X_1$;
$R_5$ is hydrogen or $C_{1-4}$ alkyl;

$R_6$ is hydrogen or $C_{1-4}$ alkyl; or is a group X or $X_1$ wherein

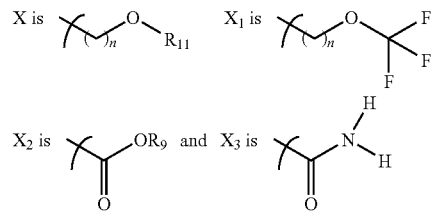

and wherein
$R_7$ is hydrogen or $C_{1-4}$ alkyl; or is a group X, $X_1$, $X_2$ or $X_3$;
$R_8$ is a 5-6 membered heterocycle group, which may be substituted by one or two substituents selected from a group consisting of: halogen, cyano, $C_{1-4}$alkyl, haloC$_{1-4}$alkyl, $C_{1-4}$alkoxy and $C_{1-4}$alkanoyl;
$R_9$ is $C_{1-4}$alkyl
$R_{10}$ is selected from a group consisting of: halogen, hydroxy, cyano, $C_{1-4}$alkyl, haloC$_{1-4}$alkyl, $C_{1-4}$alkoxy, haloC$_{1-4}$alkoxy, $C_{1-4}$alkanoyl and SF$_5$; or corresponds to a group $R_8$;
$R_{11}$ is hydrogen, $C_{1-4}$alkyl, $C_{3-6}$cycloalkyl or $C_{3-6}$cycloalkylC$_{1-3}$alkyl;
n is 1 or 2.

Because of the presence of the fused cyclopropane ring, compounds of formula (I) are believed to have a "cis" disposition of the substituents (both groups $R_2$ and $R_7$ linked to the bicyclic ring system are on the same face of this bicyclic ring system).

It will be appreciated that compounds of formula (I) possess at least two stereogenic centers, namely at position 1 and 6 in the 3-azabicyclo[4.1.0]heptane portion of the molecule. Thus, the compounds may exist in two stereoisomers which are enantiomers with respect to the stereogenic centers in the cyclopropane ring. It will also be appreciated, in common with most biologically active molecules that the level of biological activity may vary between the individual stereoisomers of a given molecule. It is intended that the scope of the invention includes all individual stereoisomers (diastereoisomers and enantiomers) and all mixtures thereof, including but not limited to racemic mixtures, which demonstrate appropriate biological activity with reference to the procedures described herein.

In one embodiment of the present invention compounds of formula (I)' are provided which correspond to the compounds of formula (I), or pharmaceutically acceptable salts, solvates or prodrugs thereof, having "cis" disposition, represented by the bold highlight of the two bonds near the cyclopropyl moiety:

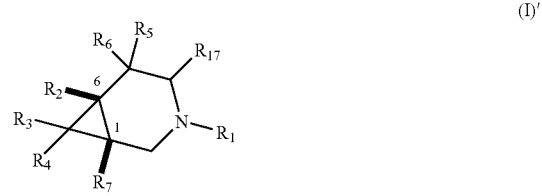

(I)' wherein $R_1$, $R_2$, $R_3$, $R_4$, $R_5$, $R_6$, $R_7$, $R_{17}$ are defined as above for compounds of formula (I).

From now on throughout the document, the symbol ' (prime) is used to identify compounds having "cis" disposition for the bonds bearing groups $R_2$ and $R_7$, represented by the bold highlight of the two bonds near the cyclopropyl moiety.

In one embodiment of the present invention, the bold highlight of the two bonds near the cyclopropyl moiety bearing groups $R_2$ and $R_7$, indicate, mixtures (including but not limited to racemic mixtures) of those cis isomers.

In compounds of formula (I)' there are at least two stereogenic centers, which are located in the cyclopropane portion, as depicted below; through optical resolution of a mixture containing the two stereoisomers which are enantiomers with respect to the stereogenic centers at positions named 1 and 6, steroisomers of compounds of formula (I)' having a single absolute configuration at stereogenic centers named 1 and 6, may be obtained as shown in the scheme below:

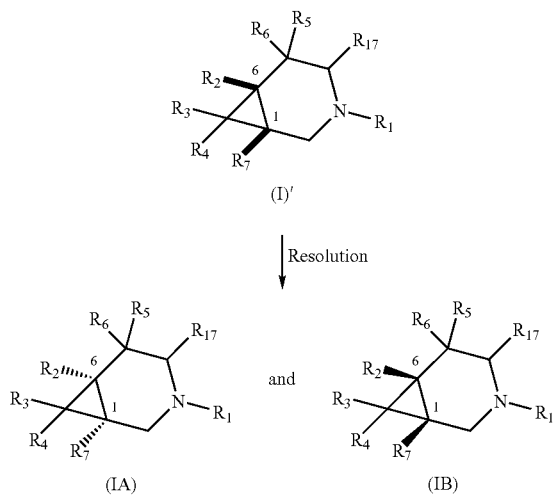

Absolute configuration of stereogenic centers at position named 1 and 6 may be assigned using Cahn-Ingold-Prelog nomenclature based on groups' priorities.

In another embodiment of the present invention compounds of formula (I)" are provided which correspond to the compounds of formula (I), or pharmaceutically acceptable salts, solvates or prodrugs thereof, as stereochemical isomers having a "cis" disposition for bonds bearing groups $R_2$ and $R_7$, and a single but unknown configuration at stereogenic centers named 1 and 6:

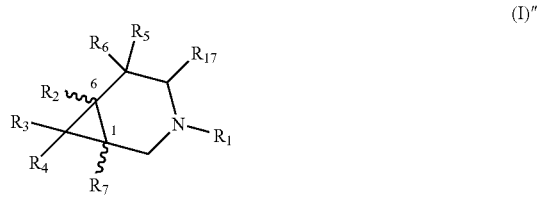

wherein $R_1$, $R_2$, $R_3$, $R_4$, $R_5$, $R_6$, $R_7$, $R_{17}$ are defined as above for compounds of formula (I).

In the context of the present invention, the representation shown above in compounds of formula (I)" for the two bonds near the cyclopropyl moiety bearing groups $R_2$ and $R_7$ indicate a cis stereoisomer, which has a single but unknown absolute configuration at stereogenic centers named 1 and 6.

It is intended in the context of the present invention that stereochemical isomers of formula (I)" are enriched in one configuration at centers named 1 and 6. In one embodiment, the isomers correspond to at least 90% e.e. (enantiomeric excess). In another embodiment the isomers correspond to at least 95% e.e. In another embodiment the isomers correspond to at least 99% e.e.

From now on throughout the document, the symbol " (double prime) is used to identify stereochemical isomers of the compounds of the invention having "cis" disposition for the two bonds near the cyclopropyl moiety bearing groups $R_2$ and $R_7$ and indicated with the representation shown above for compounds of formula (I)", those stereoisomers having a single but unknown absolute configuration at stereogenic centers named 1 and 6.

The absolute configuration of the optical isomers of some compounds of the present invention was assigned using ab initio VCD (vibrational circular dichroism).

Chiral molecules exhibit vibrational circular dichroism (VCD). Vibrational circular dichroism (VCD) is the differential interaction of a chiral molecule with left and right circularly polarized infrared radiation during vibrational excitation.

The VCD spectrum of a chiral molecule is dependent on its three-dimensional structure. Most importantly, the VCD spectrum of a chiral molecule is a sensitive function of its absolute configuration and, in the case of flexible molecules, of its conformation. In principle, therefore, VCD permits the determination of the structure of a chiral molecule. VCD spectra were first measured in the 1970s. Subsequently, VCD instrumentation has developed enormously in spectral range and in sensitivity. Currently, VCD spectra of liquids and solutions can be measured over the majority of the fundamental infrared (IR) spectral range ($v \geq 650$ cm−1) with high sensitivity at acceptable resolution (1-5 cm−1) using both dispersive and Fourier Transform (FT) VCD instrumentation. Very recently, commercial FT VCD instrumentation has become available, greatly enhancing the accessibility of VCD spectra.

The use of VCD as a reliable method for the determination of absolute configuration of chiral molecules is now well established (see for example Shah R D, et al., Curr Opin Drug Disc Dev 2001; 4:764-774; Freedman T B, et al., Helv Chim Acta 2002; 85:1160-1165; Dyatkin A B, et al. Chirality 2002; 14:215-219; Solladié-Cavallo A, Balaz M et al., Tetrahedron Assym 2001; 12:2605-2611; Nafie L A, et al. Circular dichroism, principles and applications, 2nd ed. New York: John Wiley & Sons; 2000. p 97-131; Nafie L A, et al. in: Yan B, Gremlish H-U, editors. Infrared and Raman spectroscopy of biological materials. New York: Marcel Dekker; 2001. p 15-54; Polavarapu P L, et al., J Anal Chem 2000; 366:727-734; Stephens P J, et al., Chirality 2000; 12:172-179; Solladié-Cavallo A, et al., Eur J Org Chem 2002: 1788-1796).

The method entails comparison of observed IR and VCD spectra with calculations of the spectra for a specific configuration and provides information both on the absolute configuration and on the solution conformation.

Given an experimental spectrum of a chiral molecule whose absolute configuration and/or conformation are unknown and to be determined, the general procedure is as follows: 1) all possible structures are defined; 2) the spectra of these structures are predicted; and 3) predicted spectra are compared to the experimental spectrum. The correct structure will give a spectrum in agreement with experiment; incorrect structures will give spectra in disagreement with experiment.

VCD spectra are always measured simultaneously with vibrational unpolarized absorption spectra ("infrared (IR) spectra") and the two vibrational spectra together provide more information than does the VCD spectrum alone. In addition, vibrational unpolarized absorption spectra are automatically predicted simultaneously with VCD spectra.

For ab initio assignments, VCD and unpolarized IR spectra were calculated using the Gaussian 98 software package.

In one embodiment of the present invention compounds of formula (IA) are provided that correspond to stereochemical isomers of compounds of formula (I)', having the configuration shown in the picture below at stereogenic centers at position named 1 and 6:

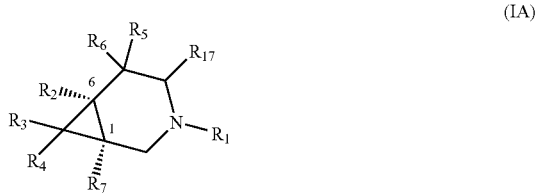

(IA)

wherein $R_1$, $R_2$, $R_3$, $R_4$, $R_5$, $R_6$, $R_7$, $R_{17}$ are defined as above for compounds of formula (I), or pharmaceutically acceptable salts, solvates or prodrugs thereof.

It is intended in the context of the present invention that stereochemical isomers of formula (IA) are enriched in one configuration at stereogenic centers named 1 and 6. In one embodiment, the isomers correspond in one embodiment to at least 90% e.e. (enantiomeric excess). In another embodiment the isomers correspond to at least 95% e.e. In another embodiment the isomers correspond to at least 99% e.e.

From now on throughout the document, the suffix "A" in brackets is used to identify stereochemical isomers of compounds of the invention having the configuration shown above for compounds of formula (IA) at stereogenic centers at positions named 1 and 6.

In another embodiment of the present invention compounds of formula (IB) are provided that correspond to stereochemical isomers of compounds of formula (I)', having the configuration shown in the picture below at stereogenic centers at position named 1 and 6:

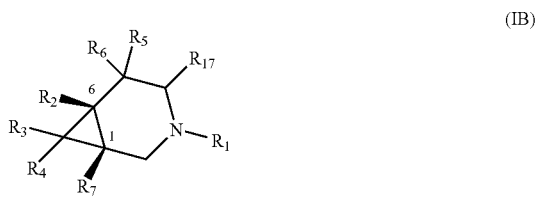

(IB)

wherein $R_1$, $R_2$, $R_3$, $R_4$, $R_5$, $R_6$, $R_7$, $R_{17}$ are defined as above for compounds of formula (I), or or pharmaceutically acceptable salts, solvates or prodrugs thereof.

It is intended in the context of the present invention that stereochemical isomers of formula (IB) are enriched in one configuration at centers named 1 and 6. In one embodiment, the isomers correspond in one embodiment to at least 90% e.e. (enantiomeric excess). In another embodiment the isomers correspond to at least 95% e.e. In another embodiment the isomers correspond to at least 99% e.e.

From now on throughout the document, the suffix "B" in brackets is used to identify stereochemical isomers of compounds of the invention having the configuration shown above for compounds of formula (IB) at stereogenic centers at positions named 1 and 6.

The term "$C_{1-4}$alkyl" refers to an alkyl group having from one to four carbon atoms, in all isomeric forms, such as methyl, ethyl, propyl, isopropyl, butyl, isobutyl, sec-butyl and tert-butyl.

The term '$C_3$-$C_6$ cycloalkyl group' as used herein means a non aromatic monocyclic hydrocarbon ring of 3 to 6 carbon atom such as, for example, cyclopropyl, cyclobutyl, cyclopentyl, or cyclohexyl; while unsaturated cycloalkyls include cyclopentenyl and cyclohexenyl, and the like.

The term '$C_{3-6}$cycloalkyl$C_{1-3}$alkyl' as used herein means an alkyl having from one to three carbon atoms wherein one hydrogen atom is replaced with a $C_3$-$C_6$ cycloalkyl group as above defined, for example methylcyclopropane.

The term "$C_{1-4}$alkoxy" refers to a linear chain or branched chain alkoxy (or "alkyloxy") group having from one to four carbon atoms, such as methoxy, ethoxy, propoxy, isopropoxy, butoxy, isobutoxy, sec-butoxy and tert-butoxy.

The term '$C_{1-4}$ alkanoyl group' as used herein may be a linear or a branched chain alkanoyl group, for example acetyl, ethylcarbonyl, n-propylcarbonyl, i-propyl carbonyl, n-butylcarbonyl or t-butylcarbonyl and the like.

The term 'halo $C_{1-4}$ alkyl' as used herein means an alkyl group having one or more carbon atoms and wherein at least one hydrogen atom is replaced with halogen, preferably fluorine, such as for example a trifluoromethyl group and the like.

The term 'halo $C_{1-4}$ alkoxy group' as used herein may be a $C_{1-4}$ alkoxy group as defined before substituted with at least one halogen, such as $OCH_2CF_3$, $OCHF_2$, or $OCF_3$.

The term 'halo $C_{1-2}$ alkyl group' as used herein may be a $C_{1-2}$ alkyl group as defined before substituted with at least one halogen, preferably fluorine, such as —$CH_2CF_3$, —$CHF_2$, or —$CF_3$.

The term "$SF_5$" refers to pentafluorosulfanyl.

The term "halogen" and its abbreviation "halo" refer to fluorine (F), chlorine (Cl), bromine (Br) or iodine (I). Where the term "halo" is used before another group, it indicates that the group is substituted by one or more halogen atoms.

The term '5,6-membered monocyclic heteroaryl' as used herein means an aromatic monocyclic heterocycle ring of 5 or 6 members and having at least one heteroatom selected from nitrogen, oxygen and sulfur, and containing at least 1 carbon atom. Representative 5, 6 membered monocyclic heteroaryl groups include (but are not limited to): furyl, thiophenyl, pyrrolyl, pyridyl, oxazolyl, isooxazolyl, pyrazolyl, imidazolyl, thiazolyl, isothiazolyl, pyridazinyl, pyrimidinyl, pyrazinyl, triazinyl, triazolyl and tetrazolyl.

The term '8,11-membered bicyclic heteroaryl' as used herein means an aromatic bicyclic heterocycle ring of 8 to 11 members and having at least one heteroatom selected from nitrogen, oxygen and sulfur, and containing at least 1 carbon atom.

Representative 8, to 11 membered bicyclic heteroaryl groups include (but are not limited to): benzofuranyl, benzothiophenyl, indolyl, isoindolyl, azaindolyl, quinolinyl, isoquinolinyl, benzoxazolyl, benzimidazolyl, benzothiazolyl, quinazolinyl and phthalazinyl.

The term 5-6 membered heterocycle means a 5-6 monocyclic heterocyclic ring which is either saturated, unsaturated or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized. Heterocycles include heteroaryl groups as defined above. The heterocycle may be attached via any heteroatom or carbon atom. Thus, the term include (but is not limited to) morpholinyl, pyridinyl, pyrazinyl, pyrazolyl, thiazolyl, triazolyl, imidazolyl, oxadiazolyl, oxazolyl, isoxazolyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydropyrimidinyl, tetrahydrothiophenyl, tetrahydrothiopyranyl, and the like.

Any of these groups may be attached to the rest of the molecule at any suitable position.

In one embodiment, $R_1$ is hydrogen or $C_{1-4}$ alkyl (for example methyl). In another embodiment, $R_1$ is hydrogen.

In one embodiment, $R_2$ is a group A or K. In another embodiment, $R_2$ is a group A. In a further embodiment, $R_2$ is a group K.

In one embodiment, the group K is a β naphthyl group.

In one embodiment, $R_3$ is hydrogen or a group X. In another embodiment, $R_3$ is hydrogen. In a further embodiment, $R_3$ is a group X.

In one embodiment, $R_4$ is hydrogen.

In one embodiment, $R_5$ is hydrogen.

In one embodiment, $R_6$ is hydrogen.

In one embodiment, $R_7$ is hydrogen or a group X, $X_1$ or $X_2$. In another embodiment, $R_7$ is hydrogen. In a further embodiment, $R_7$ is a group X, $X_1$ or $X_2$.

In one embodiment, $R_7$ is a group X.

In one embodiment, $R_7$ is a group $X_1$.

In one embodiment, $R_7$ is a group $X_2$.

In one embodiment, n is 1 or 2. In another embodiment, n is 1.

In one embodiment, $R_{16}$ is hydrogen, $C_{1-4}$alkyl, $C_{3-6}$cycloalkyl or $C_{3-6}$cycloalkyl$C_{1-3}$alkyl. In another embodiment, $R_{16}$ is hydrogen or $C_{1-4}$alkyl. In a further embodiment, $R_{16}$ is hydrogen. In a still further embodiment, $R_{16}$ is $C_{1-4}$alkyl (for example methyl or ethyl).

In one embodiment, $R_{17}$ is hydrogen or $C_{1-4}$alkyl. In another embodiment, $R_{17}$ is hydrogen. In a further embodiment, $R_{17}$ is $C_{1-4}$alkyl (for example methyl).

In one embodiment, $R_{18}$ is halogen. In another embodiment, $R_{18}$ is chlorine.

In one embodiment, $R_{10}$ is hydrogen.

In one embodiment, $R_{14}$ is hydrogen.

In one embodiment, $R_{10}$ is hydrogen.

In one embodiment, $R_{11}$ is hydrogen, halogen, halo$C_{1-4}$alkyl, halo$C_{1-4}$alkoxy. In another embodiment, $R_{11}$ is hydrogen, halogen (for example chlorine) or halo$C_{1-4}$alkyl (for example trifluoromethyl). In a further embodiment, $R_{11}$ is halogen (for example chlorine) or halo$C_{1-4}$alkyl (for example trifluoromethyl). In a still further embodiment, $R_{11}$ is chlorine.

In one embodiment, $R_{12}$ is halogen, halo$C_{1-4}$alkyl, halo$C_{1-4}$ alkoxy. In another embodiment, $R_{12}$ is halogen (for example chlorine or fluorine), halo$C_{1-4}$alkyl (for example trifluoromethyl) or halo$C_{1-4}$alkoxy (for example trifluoromethoxy). In still another embodiment, $R_{12}$ is chlorine.

In one embodiment, $R_{13}$ is hydrogen, halogen, halo$C_{1-4}$alkyl, halo$C_{1-4}$alkoxy. In another embodiment, $R_{13}$ is hydrogen.

In one embodiment, a compound of formula (IC) or a pharmaceutically acceptable salt, solvate or prodrug thereof is provided, wherein $R_1$, $R_2$, $R_7$ and $R_{17}$ are as defined for formula (I):

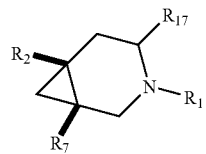

(IC)

In Formula (IC), in one embodiment, $R_1$ is hydrogen or $C_{1-4}$ alkyl (for example methyl), $R_2$ is a group A or K, $R_7$ is hydrogen or a group X, $X_1$ or $X_2$ and $R_{17}$ is hydrogen or $C_{1-4}$alkyl.

In Formula (IC), in a further embodiment, $R_1$ is hydrogen, $R_2$ is a group A or K, $R_7$ is hydrogen or a group X, $X_1$ or $X_2$ and $R_{17}$ is hydrogen.

In one embodiment, a compound of formula (ID) or a pharmaceutically acceptable salt, solvate or prodrug thereof is provided, wherein $R_7$ is a group X and $R_2$, $R_{16}$ and n are as defined for formula (I):

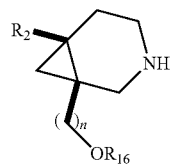

(ID)

In Formula (ID), in one embodiment, $R_2$ is a group A.

In Formula (ID), in another embodiment, $R_2$ is a group A, $R_{16}$ is hydrogen, $C_{1-4}$alkyl, $C_{3-6}$cycloalkyl or $C_{3-6}$cycloalkyl$C_{1-3}$alkyl, $R_{10}$ is hydrogen, $R_{14}$ is hydrogen, $R_{11}$ is hydrogen, halogen, halo$C_{1-4}$alkyl or halo$C_{1-4}$alkoxy, $R_{12}$ is halogen, halo$C_{1-4}$alkyl or halo$C_{1-4}$alkoxy, $R_{13}$ is hydrogen, halogen, halo$C_{1-4}$alkyl or halo$C_{1-4}$alkoxy and n is 1.

In Formula (ID), in one embodiment, $R_2$ is a group K.

In Formula (ID), in another embodiment, $R_2$ is a group K, which is an unsubstituted β-naphthyl ring, $R_{16}$ is hydrogen, $C_{1-4}$alkyl, $C_{3-6}$cycloalkyl or $C_{3-6}$cycloalkyl$C_{1-3}$alkyl and n is 1.

In one embodiment, a compound of formula (IE) or a pharmaceutically acceptable salt, solvate or prodrug thereof is provided, wherein $R_1$, $R_2$, $R_3$ and $R_{17}$ are as defined for formula (I):

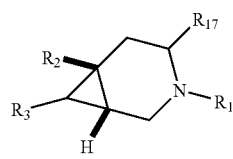

(IE)

In Formula (IE), in one embodiment, $R_1$ is hydrogen, $R_2$ is a group A or K, $R_3$ is a group X or $X_1$ and $R_{17}$ is hydrogen or $C_{1-4}$alkyl.

In Formula (IE), in another embodiment, $R_1$ is hydrogen, $R_2$ is a group A, $R_3$ is a group X, $R_{17}$ is hydrogen, $R_{16}$ is hydrogen, $C_{1-4}$alkyl, $C_{3-6}$cycloalkyl or $C_{3-6}$cycloalkyl$C_{1-3}$ alkyl, $R_{10}$ is hydrogen, $R_{14}$ is hydrogen, $R_{11}$ is hydrogen, halogen, halo$C_{1-4}$alkyl or halo$C_{1-4}$alkoxy, $R_{12}$ is halogen, halo$C_{1-4}$alkyl or halo$C_{1-4}$alkoxy, $R_{13}$ is hydrogen, halogen, halo$C_{1-4}$alkyl or halo$C_{1-4}$alkoxy and n is 1.

In one embodiment, compounds of formula (IC), (ID) and (IE) as above defined, having a single but unknown configuration at stereogenic centers at position named 1 and 6, are provided. Those compounds are named (IC)", (ID)" and (IE)".

In another embodiment, compounds of formula (IC), (ID) and (IE) as above defined, having the configuration shown above for compounds of formula (IA) at stereogenic centers at position named 1 and 6, are provided. Those compounds are named (ICA), (IDA) and (IEA).

In a further embodiment, compounds of formula (IC), (ID) and (IE) as above defined, having the configuration shown above for compounds of formula (IB) at stereogenic centers at position named 1 and 6, are provided. Those compounds are named (ICB), (IDB) and (IEB).

In the context of the present invention all the aspects and embodiments of the invention described for compounds of formula (I) are intended to apply also to compounds of formula (A).

For example, corresponding embodiments to those described for compounds of formula (I) are also provided for compounds of formula (A) [i.e. compounds of formula (A)', (A)", (AA), (AB), (AC), (AD), (AE) etc.], pharmaceutically acceptable salts, solvates and prodrug thereof being included in the present invention.

Certain groups/substituents included in the present invention may be present as isomers. The present invention includes within its scope all such isomers, including racemates, enantiomers, tautomers and mixtures thereof.

Certain groups in compounds of formula (I) or in intermediates used to prepare them, may exist in one or more tautomeric forms. The present invention includes within its scope all such tautomeric forms, including mixtures.

As used herein, the term "salt" refers to any salt of a compound according to the present invention prepared from an inorganic or organic acid or base, quaternary ammonium salts and internally formed salts and also includes pharmaceutically acceptable salts. Pharmaceutically acceptable salts are particularly suitable for medical applications because of their greater aqueous solubility relative to the parent compounds. Such salts must clearly have a physiologically acceptable anion or cation.

Salts of compounds of formula (I) may be prepared through conventional methods and are included within the scope of the present invention.

Certain of the compounds of the invention may form acid or base addition salts with one or more equivalents of the acid or of the base. The present invention includes within its scope all possible stoichiometric and non-stoichiometric forms.

Pharmaceutically acceptable salts may also be prepared from other salts, including other pharmaceutically acceptable salts, of the compound of formula (I) using conventional methods.

Suitably pharmaceutically acceptable salts of the compounds of the present invention include acid addition salts formed with inorganic acids such as hydrochloric, hydrobromic, hydroiodic, phosphoric, metaphosphoric, nitric and sulfuric acids, and with organic acids, such as tartaric, acetic, trifluoroacetic, citric, malic, lactic, fumaric, benzoic, naphtoic, formic, propionic, glycolic, gluconic, maleic, succinic, camphorsulfuric, isothionic, mucic, gentisic, isonicotinic, saccharic, glucuronic, furoic, glutamic, ascorbic, anthranilic, salicylic, phenylacetic, mandelic, embonic (pamoic), methanesulfonic, ethanesulfonic, pantothenic, stearic, sulfinilic, alginic, galacturonic and arylsulfonic, for example benzenesulfonic and p-toluenesulfonic, acids; base addition salts formed with alkali metals and alkaline earth metals and organic bases such as N,N-dibenzylethylenediamine, chloroprocaine, choline, diethanolamine, ethylenediamine, meglumaine (N-methylglucamine), lysine and procaine; and internally formed salts. Salts having a non-pharmaceutically acceptable anion or cation are within the scope of the invention as useful intermediates for the preparation of pharmaceutically acceptable salts and/or for use in non-therapeutic, for example, in vitro, situations.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compounds of the invention are within the scope of the invention. The compounds of formula (I) may readily be isolated in association with solvent molecules by crystallisation or evaporation of an appropriate solvent to give the corresponding solvates.

In addition, prodrugs are also included within the context of this invention. As used herein, the term "prodrug" means a compound which is converted within the body, e.g. by hydrolysis in the blood, into its active form that has medical effects. Pharmaceutically acceptable prodrugs are described in T. Higuchi and V. Stella, Prodrugs as Novel Delivery Systems, Vol. 14 of the A.C.S. Symposium Series, Edward B. Roche, ed., Bioreversible Carriers in Drug Design, American Pharmaceutical Association and Pergamon Press, 1987, and in D. Fleisher, S. Ramon and H. Barbra "Improved oral drug delivery: solubility limitations overcome by the use of prodrugs", Advanced Drug Delivery Reviews (1996) 19(2) 115-130.

Prodrugs are generally prepared by modifying functional groups in a way such that the modification is cleaved, either by routine manipulation or in vivo, yielding the parent compound. Prodrugs include, for example, compounds of this invention wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol, sulfhydryl and amine functional groups of the compounds of structure (I). Further, in the case of a carboxylic acid (—COOH), esters may be employed, such as methyl esters, ethyl esters, and the like. Esters may be active in their own right and/or be hydrolysable under in vivo conditions in the human body. Suitable pharmaceutically acceptable in vivo hydrolysable ester groups include those which break down readily in the human body to leave the parent acid or its salt.

Hereinafter, compounds of formula (I) and their pharmaceutically acceptable salts, solvates and prodrugs defined in any aspect of the invention (except intermediate compounds in chemical processes) are referred to as "compounds of the invention".

Furthermore, some of the crystalline forms of the compounds of the present invention, may exist as polymorphs, which are included in the present invention.

Those skilled in the art will appreciate that in the preparation of the compounds of the invention, it may be necessary and/or desirable to protect one or more sensitive groups in the molecule to prevent undesirable side reactions. Suitable protecting groups for use according to the present invention are well known to those skilled in the art and may be used in a conventional manner. See, for example, "Protective groups in organic synthesis" by T. W. Greene and P. G. M. Wuts (John Wiley & sons 1991) or "Protecting Groups" by P. J. Kocienski (Georg Thieme Verlag 1994). Examples of suitable amino protecting groups include acyl type protecting groups (e.g. formyl, trifluoroacetyl, acetyl), aromatic urethane type protecting groups (e.g. benzyloxycarbonyl (Cbz) and substituted Cbz), aliphatic urethane protecting groups (e.g. 9-fluorenylmethoxycarbonyl (Fmoc), t-butyloxycarbonyl (Boc), isopropyloxycarbonyl, cyclohexyloxycarbonyl) and alkyl type protecting groups (e.g. benzyl, trityl, chlorotrityl). Examples of suitable oxygen protecting groups may include for example alky silyl groups, such as trimethylsilyl or tert-butyldimethylsilyl; alkyl ethers such as tetrahydropyranyl or tert-butyl; or esters such as acetate.

The present invention also includes isotopically-labelled compounds, which are identical to those recited in formula (I) and following, but for the fact that one or more atoms are replaced by an atom having an atomic mass or mass number different from the atomic mass or mass number usually found in nature. Examples of isotopes that can be incorporated into compounds of the invention and pharmaceutically acceptable salts thereof include isotopes of hydrogen, carbon, nitrogen, oxygen, phosphorous, sulphur, fluorine, iodine, and chlorine, such as $^2H$, $^3H$, $^{11}C$, $^{13}C$, $^{14}C$, $^{15}N$, $^{17}O$, $^{18}O$, $^{31}P$, $^{32}P$, $^{35}S$, $^{18}F$, $^{36}Cl$, $^{123}I$ and $^{125}I$.

Compounds of the present invention and non-pharmaceutically acceptable salts thereof that contain the aforementioned isotopes and/or other isotopes of other atoms are within the scope of the present invention. Isotopically-labelled compounds of the present invention, for example those into which radioactive isotopes such as $^3H$, $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. $^{11}C$ and $^{18}F$ isotopes are particularly useful in PET (positron emission tomography), and $^{125}I$ isotopes are particularly useful in SPECT (single photon emission computerized tomography), all useful in brain imaging. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of the present invention and non-pharmaceutically acceptable salts thereof can generally be prepared by carrying out the procedures disclosed in the Schemes and/or in the Examples below, by substituting a readily available isotopically labelled reagent for a non-isotopically labelled reagent.

In one embodiment, the compounds of the invention are selected from the list consisting of:
(1S,6R/1R,6S)-6-(3,4-dichlorophenyl)-1-[(methyloxy)methyl]-3-azabicyclo[4.1.0]heptane;
(1S,6R/1R,6S)-6-(3,4-dichlorophenyl)-3-azabicyclo[4.1.0]hept-1-yl]methanol;
(1R,6S/1S,6R)-6-(3,4-dichlorophenyl)-3-azabicyclo[4.1.0]heptane;

and pharmaceutically acceptable salts, solvates, or prodrugs thereof.

In another embodiment, the compounds of the invention are selected from the list consisting of:
(1S,6R/1R,6S)-6-(3,4-dichlorophenyl)-1-[(methyloxy)methyl]-3-azabicyclo[4.1.0]heptane;
(1S,6R)-6-(3,4-dichlorophenyl)-1-[(methyloxy)methyl]-3-azabicyclo[4.1.0]heptane;
(1R,6S)-6-(3,4-dichlorophenyl)-1-[(methyloxy)methyl]-3-azabicyclo[4.1.0]heptane;
[(1S,6R/1R,6S)-6-(3,4-dichlorophenyl)-3-azabicyclo[4.1.0]hept-1-yl]methanol;
[(1S,6R or 1R,6S)-6-(3,4-dichlorophenyl)-3-azabicyclo[4.1.0]hept-1-yl]methanol;
[(1R,6S or 1S,6R)-6-(3,4-dichlorophenyl)-3-azabicyclo[4.1.0]hept-1-yl]methanol;
(1R,6S/1S,6R)-6-(3,4-dichlorophenyl)-3-azabicyclo[4.1.0]heptane;
(1R,6S)-6-(3,4-dichlorophenyl)-3-azabicyclo[4.1.0]heptane;
(1S,6R)-6-(3,4-dichlorophenyl)-3-azabicyclo[4.1.0]heptane;
(1S,4R,6R/1R,4S,6S)-6-(3,4-dichlorophenyl)-4-methyl-1-[(methyloxy)methyl]-3-azabicyclo[4.1.0]heptane;
(1S,6R)-6-(3,4-dichlorophenyl)-3-methyl-1-[(methyloxy)methyl]-3-azabicyclo[4.1.0]heptane;
(1R,6S/1S,6R)-6-[4-chloro-3-(trifluoromethyl)phenyl]-1-[(methyloxy)methyl]-3-azabicyclo[4.1.0]heptane;
(1R,6S/1S,6R)-6-(4-chlorophenyl)-1-[(methyloxy)methyl]-3-azabicyclo[4.1.0]heptane;
(1R,6S/1S,6R)-6-(3,4-dichlorophenyl)-1-[(ethyloxy)methyl]-3-azabicyclo[4.1.0]heptane;
(1R,6S or 1S,6R)-6-(3,4-dichlorophenyl)-1-[(ethyloxy)methyl]-3-azabicyclo[4.1.0]heptane;
(1S,6R or 1R,6S)-6-(3,4-dichlorophenyl)-1-[(ethyloxy)methyl]-3-azabicyclo[4.1.0]heptane;
(1S,6R/1R,6S)-1-[(methyloxy)methyl]-6-{4-[(trifluoromethyl)oxy]phenyl}-3-azabicyclo[4.1.0]heptane;
(1S,6R/1R,6S)-6-[3-chloro-4-(trifluoromethyl)phenyl]-1-[(methyloxy)methyl]-3-azabicyclo[4.1.0]heptane;
(1R,6S/1S,6R)-1-[(methyloxy)methyl]-6-(2-naphthalenyl)-3-azabicyclo[4.1.0]heptane;
(1R,6S or 1S,6R)-1-[(methyloxy)methyl]-6-(2-naphthalenyl)-3-azabicyclo[4.1.0]heptane;
(1S,6R or 1R,6S)-1-[(methyloxy)methyl]-6-(2-naphthalenyl)-3-azabicyclo[4.1.0]heptane;
(1S,6R/1R,6S)-6-(3-chloro-4-fluorophenyl)-1-[(methyloxy)methyl]-3-azabicyclo[4.1.0]heptane;
(1R,6S/1S,6R)-6-(3,4-dichlorophenyl)-1-{[(2,2,2-trifluoroethyl)oxy]methyl}-3-azabicyclo[4.1.0]heptane;
(1S,6R,7R/1R,6S,7S)-6-(3,4-dichlorophenyl)-7-[(methyloxy)methyl]-3-azabicyclo[4.1.0]heptane;

and pharmaceutically acceptable salts, solvates, or prodrugs thereof.

In a further embodiment, the compounds of the invention are selected from the list consisting of:
(1R,6S/1S,6R)-6-[4-chloro-3-(trifluoromethyl)phenyl]-1-[(methyloxy)methyl]-3-azabicyclo[4.1.0]heptane;
(1R,6S or 1S,6R)-6-[4-chloro-3-(trifluoromethyl)phenyl]-1-[(methyloxy)methyl]-3-azabicyclo[4.1.0]heptane;
(1S,6R or 1R,6S)-6-[4-chloro-3-(trifluoromethyl)phenyl]-1-[(methyloxy)methyl]-3-azabicyclo[4.1.0]heptane;
(1S,6R/1R,6S)-6-[3-chloro-4-(trifluoromethyl)phenyl]-1-[(methyloxy)methyl]-3-azabicyclo[4.1.0]heptane; (1S,6R or 1R,6S)-6-[3-chloro-4-(trifluoromethyl)phenyl]-1-[(methyloxy)methyl]-3-azabicyclo[4.1.0]heptane;

and pharmaceutically acceptable salts, solvates, or prodrugs thereof.

In another embodiment, the compounds of the invention are selected from the list consisting of:
(1R,6S/1S,6R)-6-phenyl-3-azabicyclo[4.1.0]heptane;
(1R,6S)-6-phenyl-3-azabicyclo[4.1.0]heptane;
(1S,6R)-6-phenyl-3-azabicyclo[4.1.0]heptane;
(1R,6S/1S,6R)-6-[4-(trifluoromethyl)phenyl]-3-azabicyclo[4.1.0]heptane;
(1R,6S/1S,6R)-6-[3-(trifluoromethyl)phenyl]-3-azabicyclo[4.1.0]heptane;
(1S,6R)-6-(3,4-dichlorophenyl)-3-(1-methylethyl)-1-[(methyloxy)methyl]-3-azabicyclo[4.1.0]heptane;

(1R,6S or 1S,6R)-6-[3-chloro-4-(trifluoromethyl)phenyl]-1-
[(methyloxy)methyl]-3-azabicyclo[4.1.0]heptane;
(1S,6R)-6-(3,4-dichlorophenyl)-1-[(methyloxy)methyl]-3-
azabicyclo[4.1.0]heptane;
(1S,6R or 1R,6S)-1-[(methyloxy)methyl]-6-(2-naphthalenyl)-3-azabicyclo[4.1.0]heptane;

and pharmaceutically acceptable salts, solvates, or prodrugs thereof.

In a still further embodiment, the compounds of the invention are selected from the list consisting of:
(1S,6R)-6-(3,4-dichlorophenyl)-1-[(methyloxy)methyl]-3-
azabicyclo[4.1.0]heptane;
(1S,6R or 1R,6S)-1-[(methyloxy)methyl]-6-(2-naphthalenyl)-3-azabicyclo[4.1.0]heptane;

and pharmaceutically acceptable salts, solvates, or prodrugs thereof.

In another embodiment, the compound of the invention is (1S,6R)-6-(3,4-dichlorophenyl)-1-[(methyloxy)methyl]-3-azabicyclo[4.1.0]heptane or a pharmaceutically acceptable salt thereof.

In a further embodiment, the compound of the invention is (1S,6R or 1R,6S)-1-[(methyloxy)methyl]-6-(2-naphthalenyl)-3-azabicyclo[4.1.0]heptane or a pharmaceutically acceptable salt thereof.

In another embodiment, compound of the invention is:
(1S,6R)-6-(3,4-dichlorophenyl)-1-[(methyloxy)methyl]-3-
azabicyclo[4.1.0]heptane;
(1S,6R)-6-(3,4-dichlorophenyl)-1-[(methyloxy)methyl]-3-
azabicyclo[4.1.0]heptane hydrochloride;
(1S,6R)-6-(3,4-dichlorophenyl)-1-[(methyloxy)methyl]-3-
azabicyclo[4.1.0]heptane (2R,3R)-2,3-dihydroxybutanedioate (L-tartrate salt);
(1S,6R)-6-(3,4-dichlorophenyl)-1-[(methyloxy)methyl]-3-
azabicyclo[4.1.0]heptane butanedioate (Mono-Succinate salt);
(1S,6R)-6-(3,4-dichlorophenyl)-1-[(methyloxy)methyl]-3-
azabicyclo[4.1.0]heptane phosphate;

or a solvate thereof.

The present invention also provides a process for preparing a compound of formula (I) or a salt thereof as defined above.

Compounds of the invention may be prepared in a variety of ways. In the following reaction schemes and hereafter, unless otherwise stated $R_1$ to $R_{19}$, A, K, W, G, p, X, $X_1$, $X_2$, $X_3$ and n are as for compounds of formula (I).

Throughout the specification, general formulae are designated by Roman numerals (I), (II), (III), (IV) etc. Subsets of these general formulae are defined as (Ia), (Ib), (Ic) etc. . . . (IVa), (IVb), (IVc) etc.

Compounds of the invention may be prepared according to the following synthetic schemes.

Synthetic Schemes

Compounds of formula (Ib), i.e. compounds of formula (I) wherein $R_1$=$C_{1-4}$ alkyl, $R_7$=a group X (wherein n=1 and $R_{16}$=$C_{1-4}$ alkyl or $C_{1-3}$alkyl$C_{3-6}$cycloalkyl) may be obtained starting from compounds of formula (Ia) wherein $R_1$=H and $R_{16}$=$C_{1-4}$ alkyl or $C_{1-3}$alkyl$C_{3-6}$cycloalkyl, according to Scheme 1, following standard alkylation procedures, e.g. using a RY alkylating agent (R=$C_{1-4}$ alkyl, Y=halogen), such as $CH_3I$, a trialkylamine, such as TEA, in DCM, at temperature between 0° C. and room temperature.

Alternatively, compounds of formula (Ib) may be obtained through reductive amination using a suitable aldehyde RCHO (R=$C_{1-3}$ alkyl), a reducing agent such as NaCNBH$_3$, in aprotic or protic solvent (e.g. Toluene, THF or MeOH), at temperature between 80° C. and room temperature.

Scheme 1

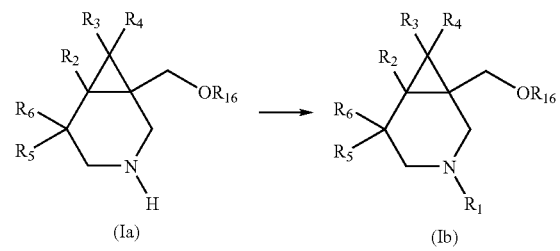

Compounds of formula (Ia), i.e. compounds of formula (I) wherein $R_7$=a group X (wherein n=1), may be obtained, according to Scheme 2, starting from compounds of formula (II), wherein Pg is a suitable N-protecting group, typically Boc or benzyl, through deprotection of N-Pg group.

For example, for Boc removal, TFA in DCM at temperature between 0° C. and room temperature may be used.

For example, for N-benzyl removal, either H$_2$ and Pd/C or alfa-chloroethyl chloroformate at reflux in DCE and then in MeOH may be used.

Scheme 2

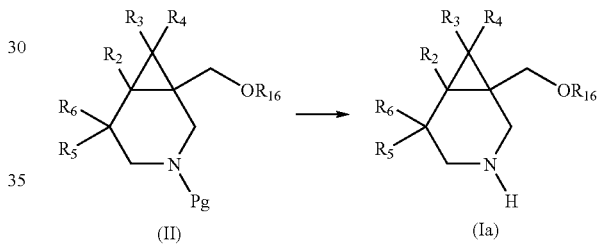

Compounds of formula (IIb), i.e. compounds of formula (II) wherein $R_{16}$=$C_{1-4}$ alkyl or $C_{1-3}$alkyl$C_{3-6}$cycloalkyl and wherein Pg is a suitable N-protecting group, typically Boc or benzyl, may be obtained starting from compounds of formula (IIa), wherein $R_{16}$=H, according to Scheme 3, following standard alkylation procedures, e.g. using a $R_{16}$Y alkylating agent ($R_{16}$=$C_{1-4}$alkyl or $C_{1-3}$alkyl$C_{3-6}$cycloalkyl, Y=halogen), such as $CH_3I$, in the presence of a strong base, such as NaH, in aprotic solvent, e.g. DMF, at temperature between 0° C. and room temperature.

Scheme 3

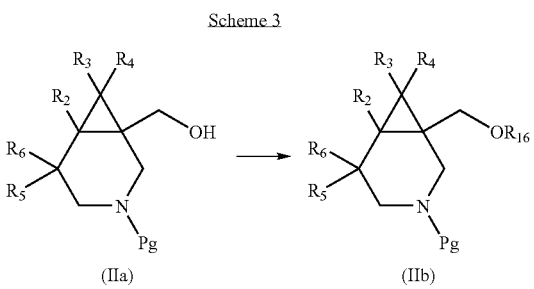

Compounds of formula (IIa$_1$), i.e. compounds of formula (IIa) wherein $R_3$=$R_4$=H, may be obtained starting from compounds of formula (III), wherein Pg is a suitable N-protecting group, typically Boc or benzyl, according to Scheme 4, through the standard Simmons-Smith cyclopropanation procedure (using ZnEt$_2$, CH$_2$I$_2$ in DCM).

Scheme 4

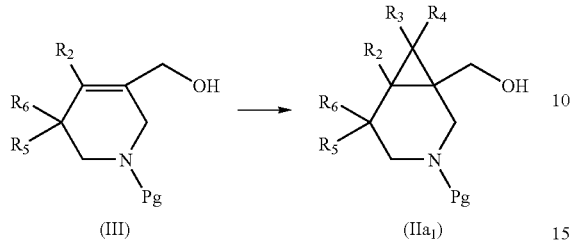

Compounds of formula (Ic), i.e. compounds of formula (I) wherein R$_1$=R$_3$=R$_4$=R$_{16}$=H, may be obtained starting from compounds of formula (III) wherein Pg is a suitable N-protecting group, typically Boc, according to Scheme 5, through Simmons-Smith cyclopropanation procedure (using ZnEt$_2$, CH$_2$I$_2$ in DCM) modified by adding an amine such as 2,6-bis(1,1-dimethylethyl)-4-methylpyridine.

Scheme 5

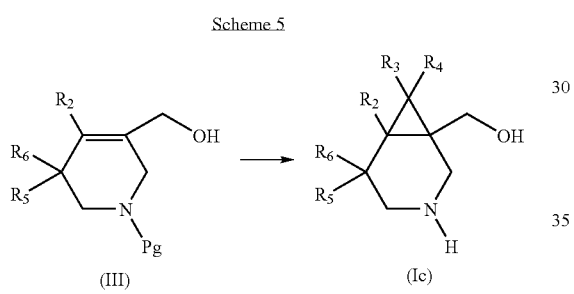

Compounds of formula (IIa$_1$), i.e. compounds of formula (IIa), wherein R$_3$=R$_4$=H and wherein Pg is a suitable N-protecting group, typically Boc, may be obtained starting from compounds of formula (Ic), according to Scheme 6 following the standard procedures, for example using Boc anhydride and TEA in DCM at temperature between 0° C. and room temperature.

Scheme 6

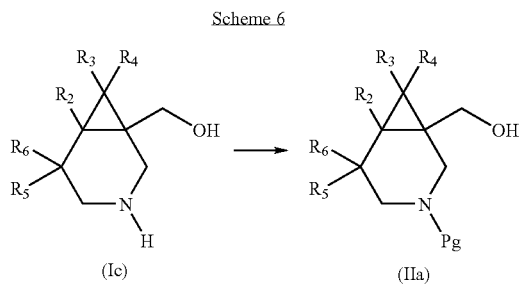

Compounds of formula (IIa$_2$), i.e. compounds of formula (IIa) wherein R$_3$=R$_4$=F, may be obtained starting from compounds of formula (III), according to Scheme 7 using dibromodifluoromethane following the method reported in the Journal of Fluorine Chemistry (2003), 119(1), 75-80.

Scheme 7

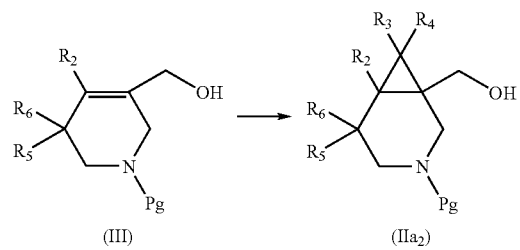

Compounds of formula (IIa$_3$), i.e. compounds of formula (IIa) wherein R$_3$=R$_4$=CH$_3$ may be obtained starting from compounds of formula (III), according to Scheme 8 in analogy with the method reported in Synlett (2002), (1), 176-178, a modified Simmons-Smith cyclopropanation procedure in which 2,2-diiodopropane is used.

Scheme 8

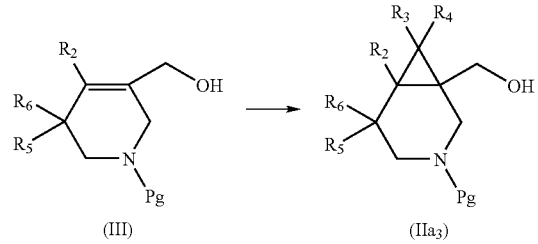

Compounds of formula (III), may be obtained starting from compounds of formula (IV), wherein Pg is a suitable N-protecting group, typically Boc, according to Scheme 9, using appropriate reducing agents, such as for example LiAlH$_4$, in aprotic solvent e.g. diethyl ether of THF, at temperature between −40 and −10° C.

Scheme 9

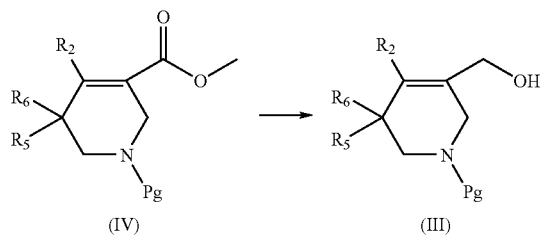

Compounds of formula (IV), may be obtained starting from compounds of formula (V), according to Scheme 10, following the standard Suzuky coupling procedure using the suitable aryl boronic acids or boronate esters, Pd(PPh$_3$)$_4$ and a base, e.g. Na$_2$CO$_3$ in a mixture of solvent e.g. toluene, ethanol and water at 80° C.

Scheme 10

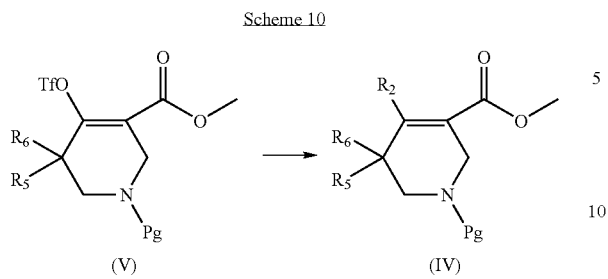

Compounds of formula (V), wherein —OTf represents a triflate group, may be obtained according to Scheme 11, starting from compounds of formula (VI), wherein Pg is a suitable N-protecting group, typically Boc, by reaction with a base (eg sodium hydride), and then with a triflating agent, such as N-phenyltrifluoromethanesulfonimide, in an aprotic solvent (eg DMF), at temperature between 0° C. and room temperature.

Scheme 11

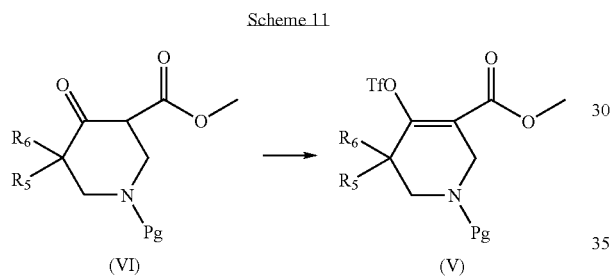

Compound of formula (VIa), wherein $R_5=R_6=H$, and Pg is a suitable protecting group, such as Boc, may be obtained, according to Scheme 12, by reacting the commercially available compound of formula (VII), wherein $R_5=R_6=H$, with Boc anhydride and TEA in DCM, at temperature between 0° C. and room temperature.

Scheme 12

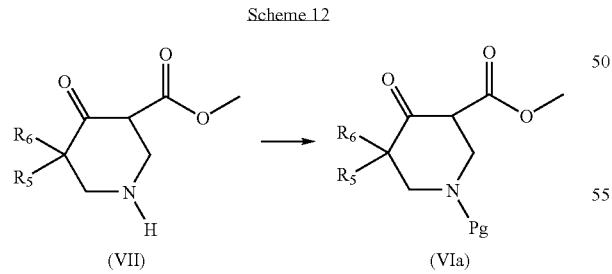

Compounds of formula (VIb), wherein $R_5=R_6=CH_3$ and Pg is a suitable protecting group, may be obtained, according to Scheme 13, through acylation of compound (VIII), wherein $R_5=R_6=CH_3$ and Pg is a suitable protecting group, in analogy with the method reported in *J. Org. Chem.*, 1995. 60, 5825.

Scheme 13

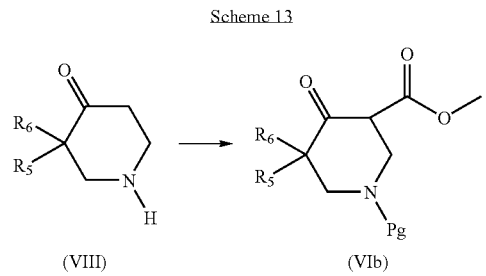

Compounds of formula (VIII), wherein $R_6=R_5=CH_3$ and Pg is a suitable protecting group, such as Boc, may be prepared starting from compound (IX), wherein $R_6=R_5=CH_3$, according to Scheme 14, as reported in WO2002085886.

Scheme 14

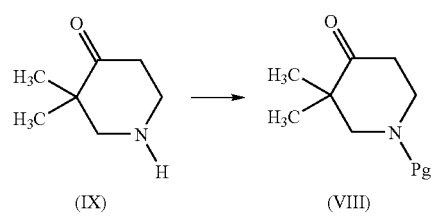

Compounds of formula (Id), i.e. compounds of formula (I) wherein $R_1=C_{1-4}$ alkyl, may be obtained starting from compounds of formula (Ie), according to Scheme 15, with analogous procedures to those described above for Scheme 1.

Scheme 15

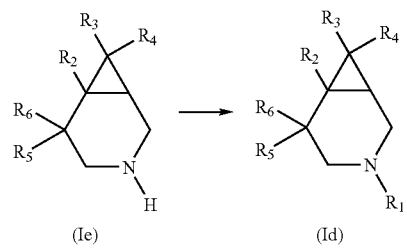

Compounds of formula (Ie$_1$), i.e. compounds of formula (I) wherein $R_6=R_5=H$ or $CH_3$, and $R_3=R_4=CH_3$ may be obtained, according to Scheme 16, starting from compounds of formula (X), in analogy with the method reported in Synlett (2002), (1), 176-178, a modified Simmons-Smith cyclopropanation procedure in which 2,2-diiodopropane is used, followed by usual N-Pg deprotection.

Scheme 16

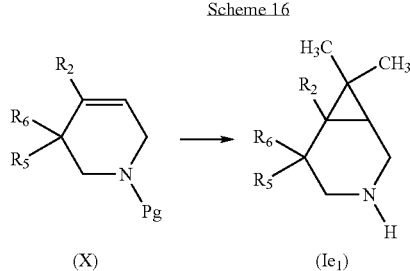

Compounds of formula (Ie$_2$), wherein R$_6$=R$_5$=H or —CH$_3$, and R$_3$=R$_4$=F, may be obtained starting from compounds of formula (X), according to Scheme 17, using dibromodifluoromethane, as described in the Journal of Fluorine Chemistry (2003), 119(1), 75-80, followed by usual N-Boc deprotection.

Scheme 17

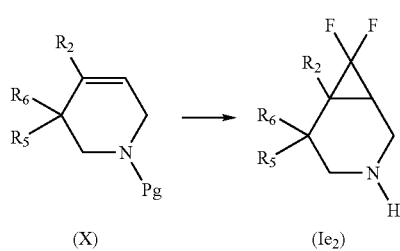

Compounds of formula (Ie$_3$), i.e. compounds of formula (I), wherein R$_6$=R$_5$=H or —CH$_3$, and R$_3$=R$_4$=H, may be obtained starting from compounds of formula (X), according to Scheme 18, through the standard Simmons-Smith cyclopropanation procedure, followed by usual N-Pg deprotection.

Scheme 18

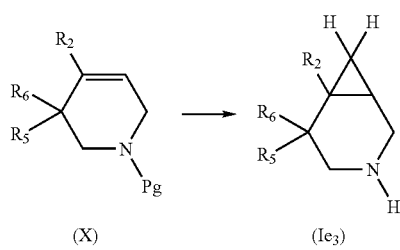

Compounds of formula (Ie$_4$), i.e. compounds of formula (I), wherein R$_6$=R$_5$=H or —CH$_3$ and R$_{16}$=H, C$_{1-4}$alkyl or C$_{1-3}$alkylC$_{3-6}$cycloalkyl, may be obtained starting from compounds of formula (XI), wherein R$_6$=R$_5$=H or —CH$_3$ and R$_{16}$=H, C$_{1-4}$alkyl or C$_{1-3}$alkylC$_{3-6}$cycloalkyl and Pg is a suitable protecting group, according to Scheme 19, after usual N-Pg deprotection.

Scheme 19

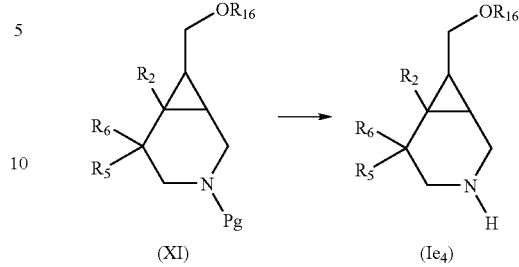

Compounds of formula (XIa), i.e. compounds of formula (XI), wherein R$_{16}$=C$_{1-4}$alkyl or C$_{1-3}$alkylC$_{3-6}$cycloalkyl, may be obtained starting from compounds of formula (XIb), as below defined, according to Scheme 20, through standard alkylation procedures, e.g. using a R$_{16}$Y alkylating agent (R$_{16}$=C$_{1-4}$ alkyl, Y=halogen), such as CH$_3$I, in the presence of a strong base, such as NaH, in aprotic solvent, e.g. DMF, at temperature between 0° C. and room temperature.

Scheme 20

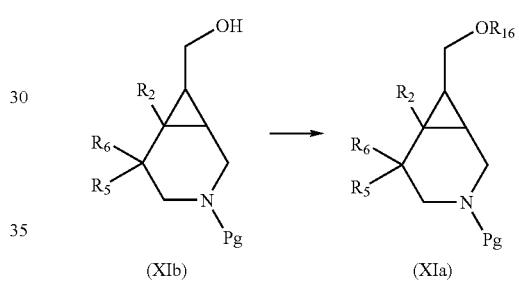

Compounds of formula (XIb), i.e. compounds of formula (XI), wherein R$_{16}$=H, may be obtained starting from compounds of formula (XII), wherein R$_6$=R$_5$=H or CH$_3$ and Pg is a suitable protecting group, according to Scheme 21, in analogy with the method reported in Synlett (2002), (1), 176-178, using ethyl diazoacetate and rhodium acetate, in aprotic solvent (e.g. DCE, DCM or MeCN), at temperature between room temperature and 80° C., followed by reduction of the ester with an appropriate reducing agent, such as LiAlH$_4$ or BH$_3$ THF, at temperature between −20° C. and 70° C.

Scheme 21

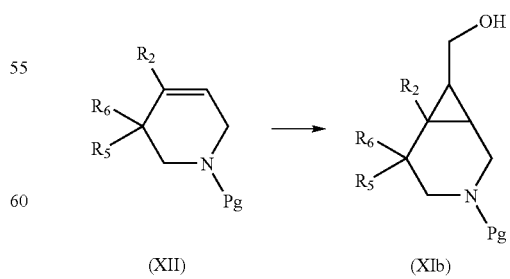

Compounds of formula (XII), wherein R$_6$=R$_5$=H or CH$_3$ and Pg is a suitable protecting group, may be obtained starting from compounds of formula (XIII), according to Scheme 22, following the above cited Suzuky coupling procedure, using the suitable aryl boronic acids or esters.

Scheme 22

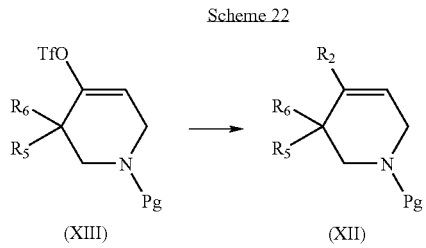

(XIII)   (XII)

Compounds of formula (XIII), wherein $R_6=R_5=H$ or $CH_3$, —OTf represents a triflate group and Pg is a suitable protecting group, may be obtained starting from compounds of formula (VIII), wherein $R_6=R_5=H$ or $CH_3$ and Pg is a suitable protecting group, according to Scheme 23, by reaction with a base (eg sodium hydride), then with a triflating agent, such as N-phenyltrifluoromethanesulfonimide, in an aprotic solvent (eg DMF), at temperature between 0° C. and room temperature.

Scheme 23

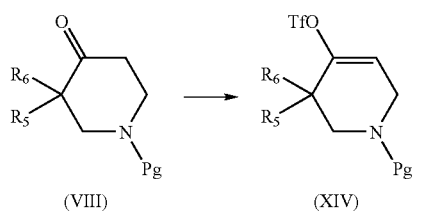

(VIII)   (XIV)

Compounds of formula (If), i.e. compounds of formula (I) wherein $R_1=C_{1-4}$ alkyl or $C_{1-3}$alkyl$C_{3-6}$cycloalkyl, $R_5=H$, $R_6=$a group X (wherein n=1, $R_{16}=C_{1-4}$ alkyl) and $R_7=H$, may be obtained starting from compounds of formula (Ig), i.e. compounds of formula (I) wherein $R_1=H$, $R_5=H$, $R_6=$a group X (wherein n=1, $R_{16}=C_{1-4}$ alkyl or $C_{1-3}$alkyl$C_{3-6}$cycloalkyl) and $R_7=H$, according to Scheme 24, through standard alkylation procedures, e.g. using a $R_1Y$ alkylating agent ($R_1=C_{1-4}$ alkyl, Y=halogen), such as $CH_3I$, a trialkylamine, such as TEA, in DCM, at temperature between 0° C. and room temperature. Alternatively, compounds of formula (If) may be obtained by reductive amination using a suitable aldehyde RCHO($R=C_{1-3}$ alkyl), a reducing agent such as NaCNBH$_3$, in aprotic or protic solvent e.g. Toluene, THF or MeOH, at temperature between 80° C. and room temperature.

Scheme 24

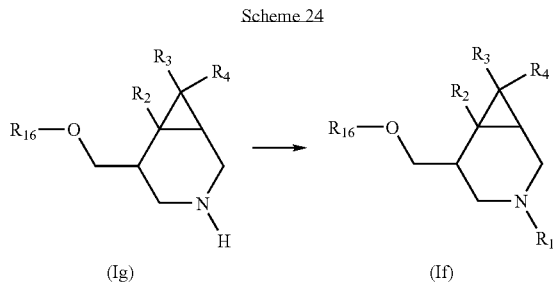

(Ig)   (If)

Compounds of formula (Ig), wherein $R_{16}=C_{1-4}$ alkyl or $C_{1-3}$alkyl$C_{3-6}$cycloalkyl, may be obtained starting from compounds of formula (XV), through usual N-Pg deprotection procedures according to Scheme 25.

Scheme 25

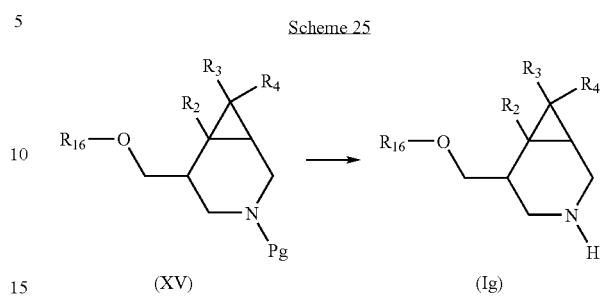

(XV)   (Ig)

Compounds of formula (XV), wherein $R_3=R_4=H$, F or —CH$_3$, $R_{16}=C_{1-4}$ alkyl or $C_{1-3}$alkyl$C_{3-6}$cycloalkyl, may be obtained, according to Scheme 26, starting from compounds of formula (XVI), wherein $R_{16}=C_{1-4}$ alkyl or $C_{1-3}$alkyl$C_{3-6}$ cycloalkyl, through the method described respectively in the Schemes 5, 6 and 7.

Scheme 26

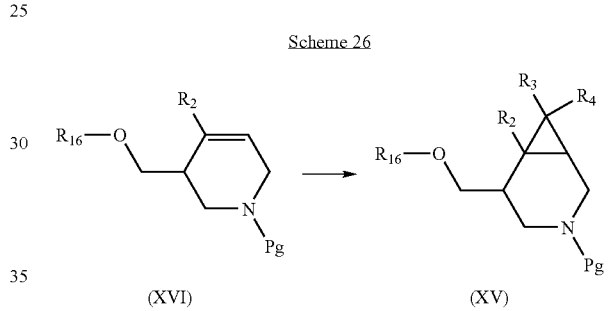

(XVI)   (XV)

Compounds of formula (XVI), wherein $R_{16}=C_{1-4}$alkyl or $C_{1-3}$alkyl$C_{3-6}$cycloalkyl, may be obtained, according to Scheme 27, starting from compounds of formula (XVII) through alkylation procedure using a suitable alkylating agent (e.g. MeI) in the presence of a strong base (e.g. NaH) in an aprotic solvent such as THF or DMF at temperature between 0° C. and room temperature.

Scheme 27

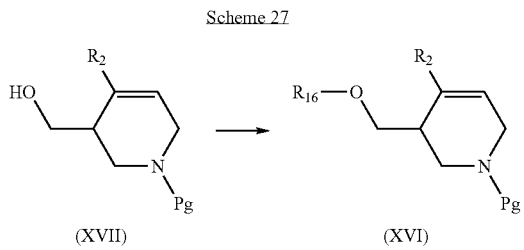

(XVII)   (XVI)

Compounds of formula (XVII), wherein Pg is a suitable protecting group such as —CH$_2$-Ph, may be obtained through the Prins reaction as reported in *European J. of Org. Chemistry*, (15), 3336, 2004.

Compounds of formula (Ih), i.e. compounds of formula (I) wherein $R_6=R_6=R_5=R_4=R_3=R_1=H$, may be isolated through chromatographic separation from the corresponding regioisomers of formula (XVIII), as depicted in Scheme 28.

Scheme 28

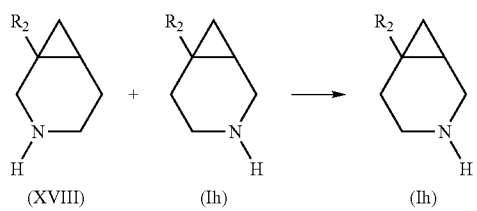

Compounds of formula (Ih), i.e. compounds of formula (I) wherein $R_6=R_5=R_4=R_3=R_1=H$, and compounds of formula (XVIII) may be obtained by the respective precursors, i.e. compounds of formula (XIX) and (XXX), by reduction for example with borane in THF at refluxing temperature, according to Scheme 29.

Scheme 29

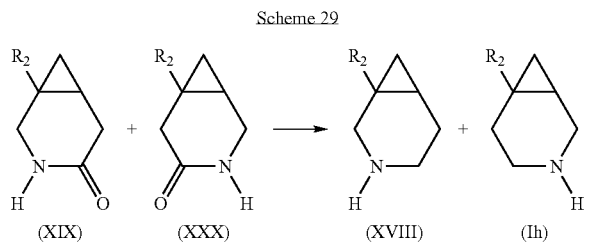

Compounds of formula (XIX) and (XXX) may be obtained starting from compounds of formula (XXXI) via Beckmann rearrangement for example using tosyl chloride in acetone from room temperature to reflux, according to Scheme 30.

Scheme 30

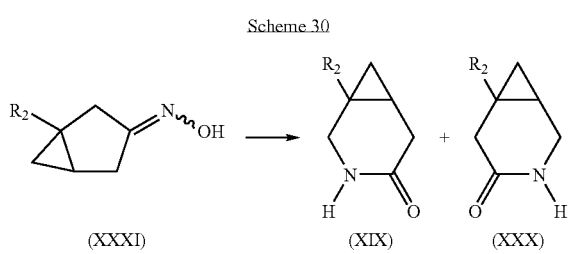

Compounds of formula (XXXI) may be prepared starting from compounds of formula (XXXII), according to Scheme 31, for example using hydroxylamine monohydrate in ethanol at room temperature.

Scheme 31

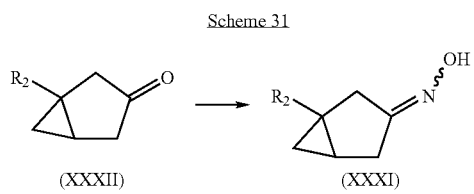

Compounds of formula (XXXII), may be prepared starting from compounds of formula (XXXIII), according to Scheme 32, by rearrangement of the appropriate propargylic aldehyde after reaction with the allylic derivative (XXXIV) where M can be $SiMe_2Cl$ or MgBr, as described in *J. Am. Chem. Soc.* 2004, 126, 8654.

Scheme 32

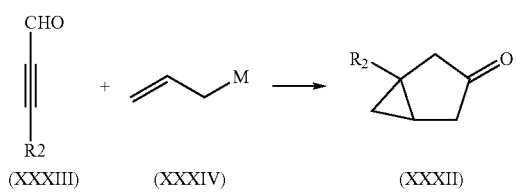

Compounds of formula (XXXIII) may be prepared by oxidation for example with Dess-Martin periodinane in DCM at room temperature from the appropriate alcohol (XXXV) according to Scheme 33.

Scheme 33

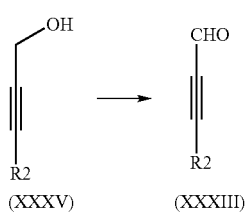

Compounds of formula (XXXV) may be prepared from propargyl alcohol and appropriate Iodo arene (XXXVI), in analogy with the method described in JOC, 2005, 70, 4043 and according to Scheme 34.

Scheme 34

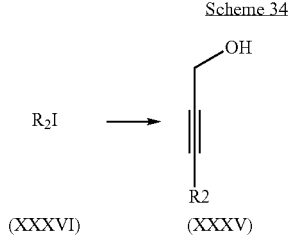

Compounds of formula (IIa$_1$), i.e. compounds of formula (IIa) wherein $R_3=R_4=H$, Pg is a suitable N-protecting group (typically Boc), may be obtained starting from compounds of formula (XXXVII) as below defined, through reduction with borane in THF at refluxing temperature, according to Scheme 35.

Scheme 35

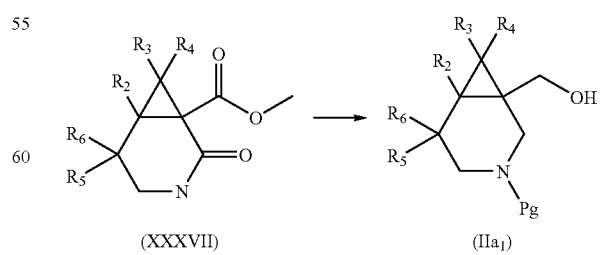

Compounds of formula (XXXVII), wherein $R_3=R_4=R_5=R_6=H$, may be obtained starting from compounds (XXXVIII), wherein $R_3=R_4=R_5=R_6=H$, through reaction with sodium hydride in DMF, at temperature from 0° C. to room temperature, for 1-3 h, according to Scheme 36.

Scheme 36

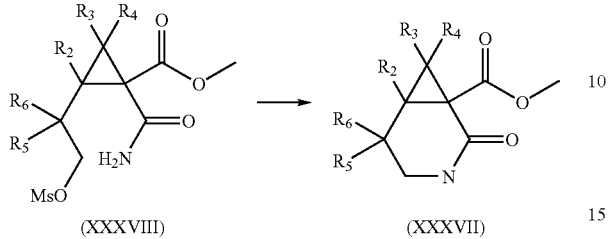

(XXXVIII)     (XXXVII)

Compounds of formula (XXXVIII), wherein $R_3=R_4=R_5=R_6=H$, may be obtained starting from compounds (XXXIX) wherein $R_2$ is an aromatic or heteroaromatic group, $R_3=R_4=R_5=R_6=H$, through reaction with mesyl chloride and TEA in DCM, at temperature from 0° C. to room temperature, according to Scheme 37.

Scheme 37

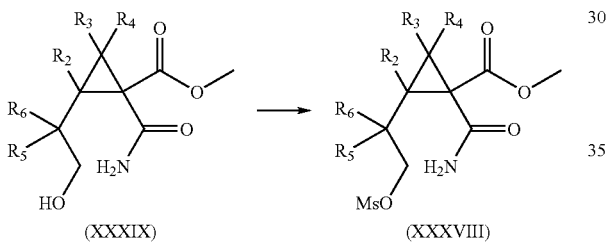

(XXXIX)     (XXXVIII)

Compounds of formula (XXXIX), wherein $R_3=R_4=R_5=R_6=H$, may be obtained starting from compounds (XL) wherein $R_3=R_4=R_5=R_6=H$ and Pg a silyl protective group (e.g: 1,1-dimethylethyl)diphenylsilane), for example by standard Pg removal with TBAF in THF followed by reaction with ammonium hydroxide in a mixture of solvents, such as THF and methanol, at room temperature for several hours, according to Scheme 38

Scheme 38

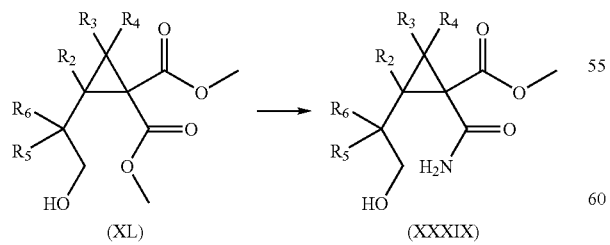

(XL)     (XXXIX)

Compounds of formula (XL), wherein $R_3=R_4=R_5=R_6=H$ and Pg a silyl protective group (e.g: 1,1-dimethylethyl)diphenylsilane), may be obtained by reacting compounds (XLI) with diazomalonate (prepared as described in *Synthetic Comunication*, 1987, 17, 1709-1716) and rhodium (II) acetate, at 100° C., in analogy with the method reported in WO/2005/058884, according to Scheme 39.

Scheme 39

(XLI)     (XL)

Compounds of formula (XLI), wherein Pg is a silyl protective group (e.g: 1,1-dimethylethyl)diphenylsilane), may be obtained starting from compounds (XLII), wherein Pg is defined as before, by the Suzuky coupling procedure using the appropriate aryl or heteroaryl boronic acids or boronate esters, $Pd(PPh_3)_4$ and a base (e.g. $Na_2CO_3$), in a mixture of solvent (e.g. toluene, ethanol and water) at 80° C., according to Scheme 40.

Scheme 40

(XLII)     (XLI)

When Pg corresponds to the meaning defined above in Scheme 39 and 40, the corresponding compound of formula (XLII), [(3-bromo-3-buten-1-yl)oxy](1,1-dimethylethyl)diphenylsilane, can be prepared by reacting the corresponding compound of formula (XLIII), 3-bromo-3-buten-1-ol, with chloro(1,1-dimethylethyl)diphenylsilane and imidazole in DCM, at room temperature, according to Scheme 41.

Scheme 41

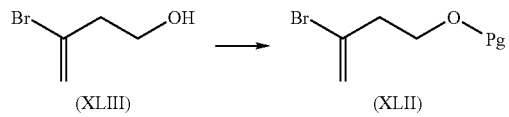

(XLIII)     (XLII)

Alternatively, compounds of formula (Im), i.e. compounds of formula (I) as above defined wherein $R_1$, $R_3$, $R_4$, $R_5$, $R_6$ are hydrogen and $R_7$ is a group X (wherein n=1), may be obtained from compounds of formula (XLIV) wherein Pg is a N-protecting group, typically Boc, through deprotection of N-Pg group according to Scheme 42. For example, when Pg is Boc, using TFA in DCM at temperature between 0° C. and room temperature.

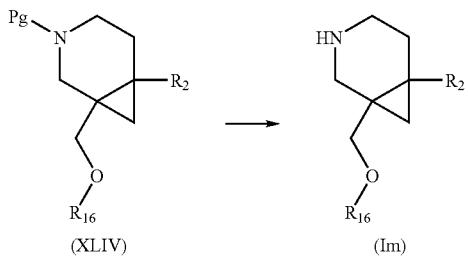

Compounds of formula (XLIV) as above defined may be obtained starting from compounds of formula (XLV), wherein $R_{16}$=H, following standard alkylation procedures according to Scheme 43, e.g. using a $R_{16}Y$ alkylating agent such as MeI in the presence of a strong base, such as NaH, in aprotic solvent, e.g. DMF, or THF, at temperature between 0° C. and room temperature.

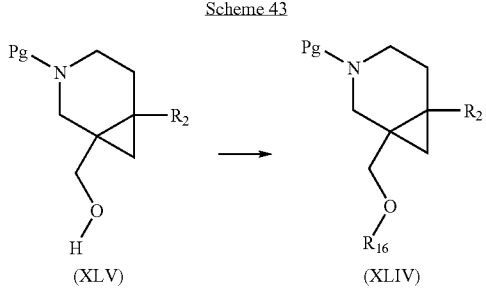

Compounds of formula (XLV) as above defined may be obtained from compounds of formula (XLVI) where $R_j$ is an alkyl group, according to Scheme 44, by simultaneous reduction of amide and ester groups with $BH_3$ or $LiAlH_4$ in aprotic solvent, mainly THF, at reflux and subsequent "in situ" nitrogen protection with a Pg group, typically Boc, for example by using Boc anhydride under basic conditions at room temperature.

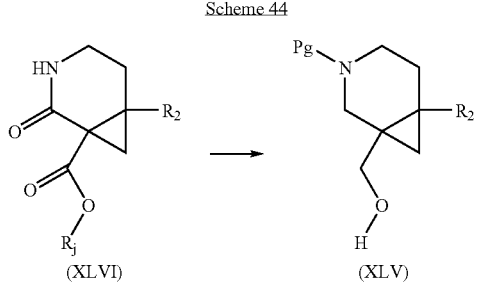

Compounds of formula (XLVI) may be obtained according to Scheme 45 from compounds of formula (XLVII) wherein $R_j$ is as above defined and L is a suitable leaving group, by nucleophilic displacement of the leaving group (L) e.g. mesylate, with $NH_3$ in MeOH under pressure in a hydrogenation apparatus (for example Parr), followed under the same conditions by intramolecular cyclisation of the intermediate amine to amide.

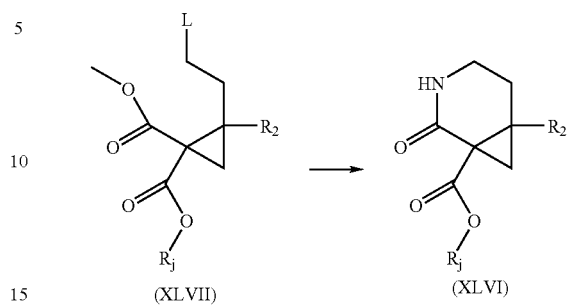

Compounds of formula (XLVII) as above defined, may be obtained according to Scheme 46 from compounds of formula (XLVIII), wherein L is as above defined, by carbene mediated cyclopropanation with dimethyl diazopropandioate and rhodium catalyst, for example $Rh_2(OAc)_2$, in chlorinated solvent, e.g. chlorobenzene or DCE, at temperature between 40° C. and 80° C. If asymmetric rhodium catalyst is used, the reaction can be stereospecific.

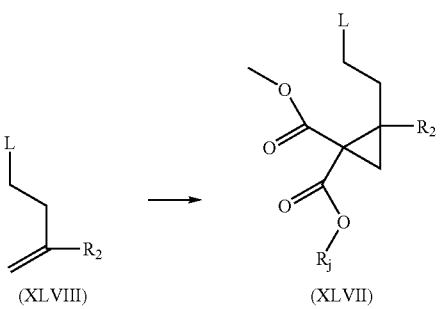

Compounds of formula (XLVIII), as above defined, may be obtained according to Scheme 47 from compounds of formula (XLIX) by suitable oxygen functionalisation aimed to obtain a leaving group as mesylate or tosylate e.g. using methansulfonyl chloride or tosyl chloride in DCM under basic condition at 0° C. or room temperature.

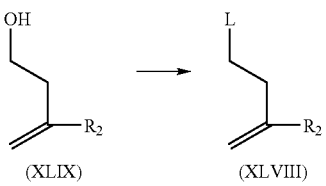

Compounds of formula (XLIX) may be obtained according to Scheme 48 from compounds of formula (L) following the standard Suzuky coupling procedure using suitable boronic acids, $Pd(PPh_3)_4$ and a base e.g. $Na_2CO_3$ in a mixture of solvents e.g. toluene, ethanol and water at 80° C.

Scheme 48

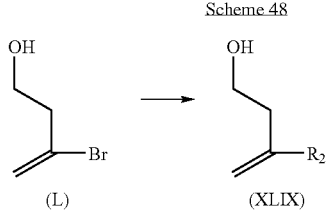

Alternatively, compounds of formula (Im), i.e. compounds of formula (I) as above defined wherein $R_1$, $R_3$, $R_4$, $R_5$, $R_6$ are hydrogen and $R_7$ is a group X (wherein n=1), may be obtained from compounds of formula (LXIV), wherein groups $R_2$ and $R_{16}$ are defined as for formula (I), through deprotection of t-butoxycarbonyl protecting group and contemporary double bond reduction according to Scheme 49. For example, reaction conditions may comprise treatment with trifluoroacetic acid and triethylsilane in toluene at room temperature. Alternative reducing agents may be used, for example Sodium triacetoxyboronhydride or Sodium boronhydride. Alternative solvents may also be used, for example dichloromethane, trifluorotoluene or chlorobenzene.

Scheme 49

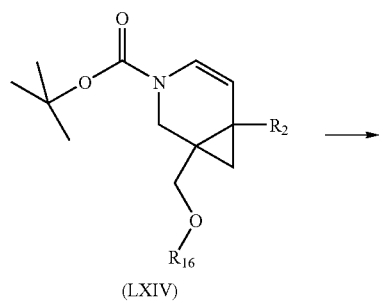

Compounds of formula (LXIV), as above defined, may be obtained from compounds of formula (LI), wherein group $R_2$ is defined as for formula (I), through alkylation of hydroxyl group with an alkylating agent $R_{16}Y$ [wherein Y is a leaving group, an halogen or a group —$OSO_2R$(R=aryl or alkyl group)] according to Scheme 50. For example, reaction conditions may comprise treatment with potassium hydroxide in DMSO at room temperature of compound of formula (LI) and consequent addition of $R_{16}Y$. Alternative bases may be used, for example sodium hydroxide, potassium t-butoxide, cesium hydroxide or lithium hydroxide. Alternative solvents may also be used, for example dichloromethane or tetrahydrofurane.

Scheme 50

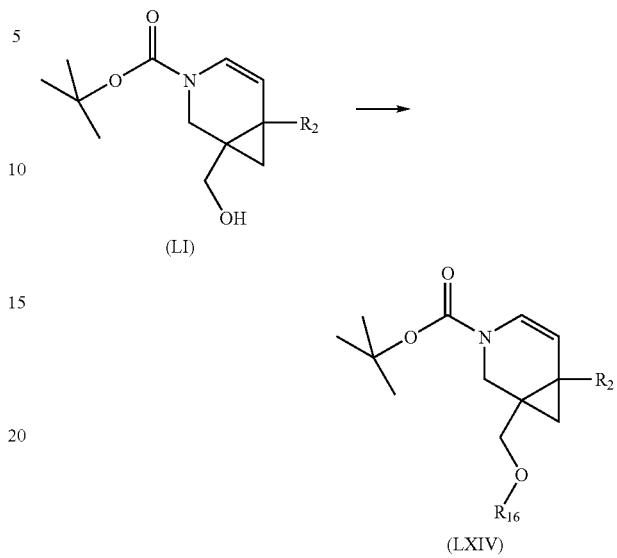

Compounds of formula (LI), as above defined, may be obtained from compounds of formula (LI), wherein group $R_2$ and $X_2$ are defined as for formula (I), through reduction of the esther moiety in group $X_2$ according to Scheme 51. For example, reaction conditions may comprise treatment with lithium boronhydride and EtOH in THF at room temperature. Alternative other reducing agents may be used, for example lithium aluminumhydride, sodiumboronhydride or diisobuylaluminium hydride.

Scheme 51

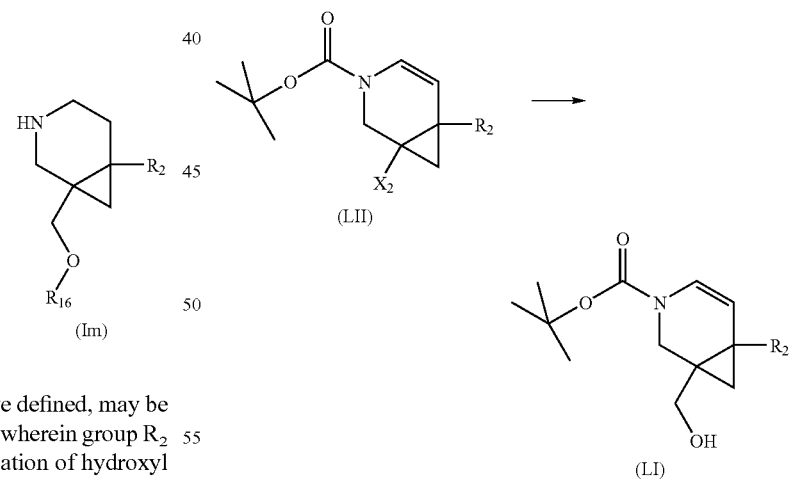

Compounds of formula (LII), as above defined, may be obtained from compounds of formula (LIII), wherein group $R_2$ and $X_2$ are defined as for formula (I), through reaction with an appropriate base in the presence of the appropriate alkylating agent according to Scheme 52. For example, reaction conditions may comprise treatment with Lithium t-butoxide and $CH_2ICl$ in N-methylpyrrolidone at low temperature (for example −20 to +10° C.). Alternative alkylating agents may be used, for example $CH_2I_2$. Alternative solvents may be

Scheme 52

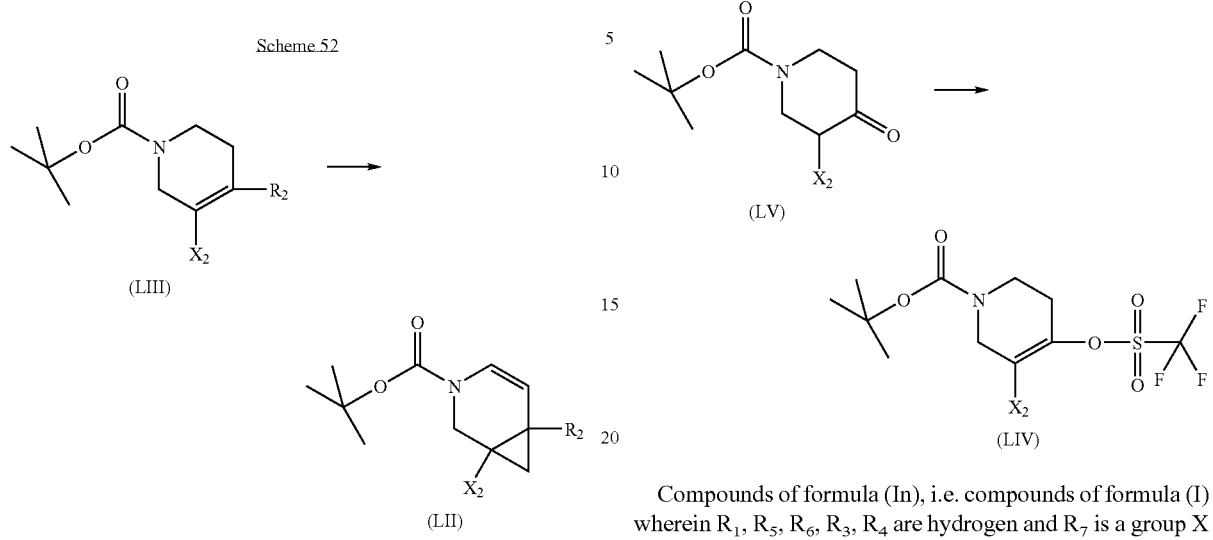

Compounds of formula (LIII), as above defined, may be obtained from compounds of formula (LIV), wherein group $X_2$ is defined as for formula (I), through coupling reaction with an appropriate boronic acid $R_2B(OH)_2$, wherein $R_2$ is as defined for compounds of formula (I), according to Scheme 53. For example, reaction conditions may comprise treatment with $R_2B(OH)_2$ as above defined, in the presence of Pd(OAc)$_2$, PPh$_3$ and diisopropylethylamine toluene and water at a temperature ranging from room temperature to 80° C. Alternative catalysts may be used, for example Pd(PPh$_3$)$_4$, PdCl$_2$(dppf).

Scheme 53

Compounds of formula (LIV), as above defined, may be obtained from compounds of formula (LV), wherein group $X_2$ is defined as for formula (I), through formation of the triflate derivative according to Scheme 54. For example, reaction conditions may comprise treatment with triflic anhydride, in the presence of diisopropylethylamine and in toluene at a temperature ranging from 0° C. to room temperature.

Scheme 54

Compounds of formula (In), i.e. compounds of formula (I) wherein $R_1$, $R_5$, $R_6$, $R_3$, $R_4$ are hydrogen and $R_7$ is a group X wherein n is 1, may be prepared according to Scheme 55 through the procedures below described, starting from compound of formula (LXII):

Scheme 55

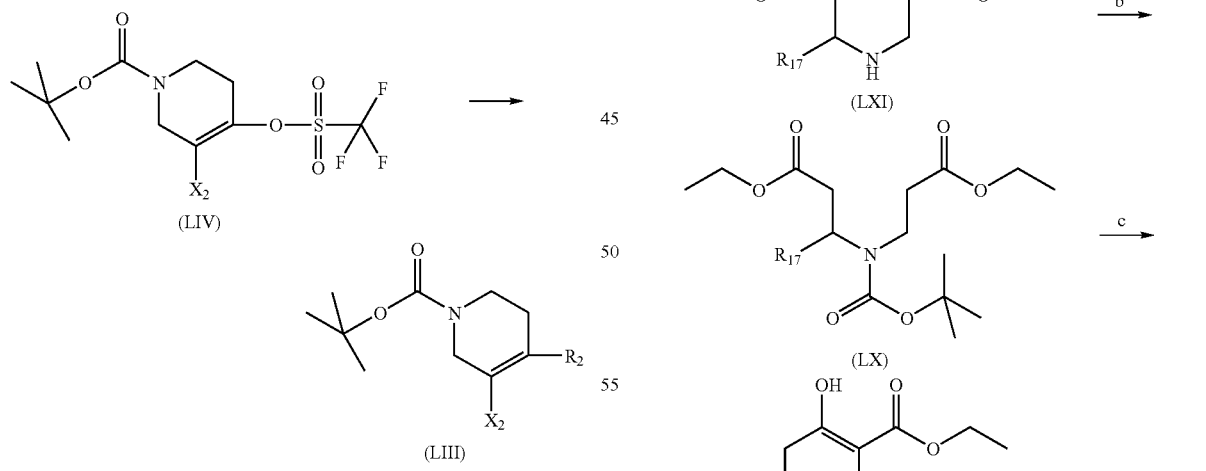

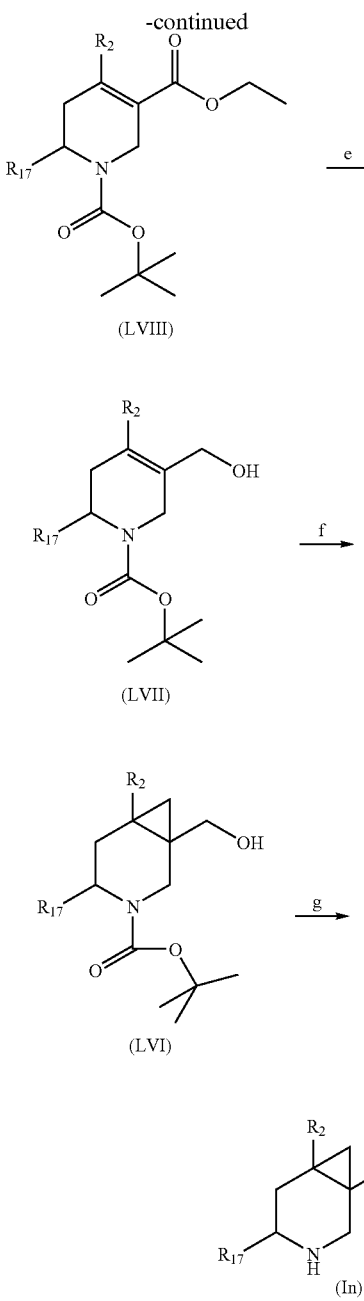

(LVIII)

(LVII)

(LVI)

(In)

Example of Reaction conditions: a=EtOH, 8 hrs, RT; b=BOC$_2$O; K$_2$CO$_3$, from 0° C. to RT for 48 hrs; c=EtONa, Toluene, from 0° C. to RT, overnight; d=1) NaH and 1,1,1-trifluoro-N-phenyl-N-[(trifluoromethyl)sulfonyl]methanesulfonamide, DMF, 1 h; 2) toluene/EtOH; R$_2$B(OH)$_2$, K$_2$CO$_3$, Pd(Ph$_3$P)$_4$, 80° C., 1 h.; e=LiAlH$_4$, THF from −20° C. to RT, 2 h.; f=Et$_2$Zn, CH$_2$I$_2$ DCM, RT, overnight; g=NaH, R$_{16}$I, DMF, 0° C. to RT.

Compounds of formula (Io), i.e. compounds of formula (I) wherein R$_1$, R$_5$, R$_6$, R$_3$, R$_4$ are hydrogen and R$_1$ is an alkyl group, may be prepared according to Scheme 56, starting from compounds of formula (XXX) through the procedures below described:

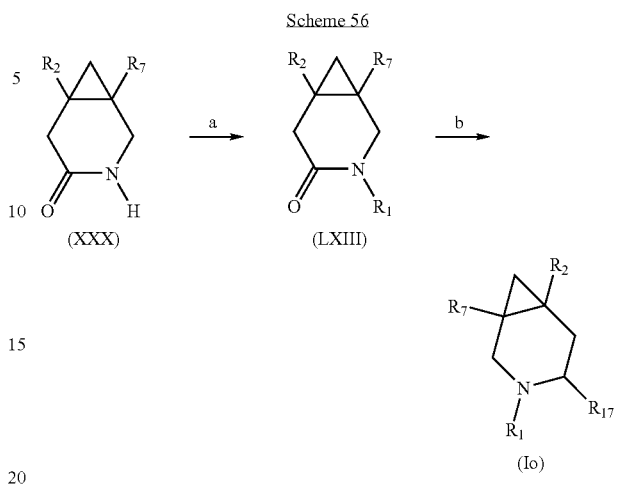

Scheme 56

Example of Reaction conditions: a=R$_1$Y, NaH, DMF; b=R$_{17}$MgBr, THF, NaCNBH$_3$.

When a specific enantiomer or diastereoisomer of a compound of formula (I)' or salts thereof, is required, this may be obtained for example by resolution of a corresponding enantiomeric or diastereoisomeric mixture using conventional methods.

Thus, for example, specific enantiomers or diastereoisomers of the compounds may be obtained from the corresponding enantiomeric or diastereoisomeric mixture using chiral chromatographic methods such as for example chiral HPLC (for reference procedure see for example separation of E2a and E3a, of E5a and E6a, of E9a and E10a, of E19a and E20a, of E26a and E27a).

Alternatively, specific enantiomers or diastereoisomers of the compounds may be obtained from the corresponding enantiomeric or diastereoisomeric mixture using chiral crystallization methods such as precipitation with chiral acids (for reference procedure see for example E34 and E35).

Furthermore a specific enantiomer or diastereoisomer of a compound of the invention may be synthesised from the appropriate optically active intermediate using any of the general processes described herein.

Alternatively, a specific enantiomer or diastereoisomer of a compound the invention may be synthesised from the appropriate stereochemically enriched intermediate using any of the general processes described herein and by combining it with any of the conventional resolution methods above described.

Optically active intermediates or stereochemically enriched intermediates, may be generated by resolution of a corresponding enantiomeric or diastereoisomeric mixtures using conventional methods (for reference procedure see for example P60), or by performance of stereoselective reactions (for reference procedure see for example P67) or by combining different resolution techniques.

Also specific enantiomers or diastereoisomers of the compounds may be obtained by combining conventional methods above described.

The compounds of the present invention are useful in the treatment of disorders or diseases responsive to the monoamine neurotransmitter re-uptake inhibiting activity of the compounds. This activity of the compounds of the invention may make them useful in the treatment of Parkinsonism, depression, eating disorders, sleep disorders, substance related disorders, attention-deficit hyperactivity disorders, anxiety disorders, cognition impairment, sexual dysfunctions, obsessive compulsive spectrum disorders, Gilles de la Tourettes disease and senile dementia, as well as other disorders sensitive to the monoamine neurotransmitter re-uptake-inhibiting activity of the compounds.

Within the context of the present invention, the terms describing some indications used herein are classified in the Diagnostic and Statistical Manual of Mental Disorders, 4th Edition, published by the American Psychiatric Association (DSM-IV) and/or the International Classification of Diseases, 10th Edition (ICD-10). The various subtypes of the disorders mentioned herein are contemplated as part of the present invention. Numbers in brackets after the listed diseases below refer to the classification code in DSM-IV.

The term "depression" includes:

Depression and mood disorders including Major Depressive Episode, Manic Episode, Mixed Episode and Hypomanic Episode; Depressive Disorders including Major Depressive Disorder, Dysthymic Disorder (300.4), Depressive Disorder Not Otherwise Specified (311); Other Mood Disorders including Mood Disorder Due to a General Medical Condition (293.83) which includes the subtypes With Depressive Features, With Major Depressive-like Episode, With Manic Features and With Mixed Features), Substance-Induced Mood Disorder (including the subtypes With Depressive Features, With Manic Features and With Mixed Features) and Mood Disorder Not Otherwise Specified (296.90): Bipolar Disorders including Bipolar I Disorder, Bipolar II Disorder (Recurrent Major Depressive Episodes with Hypomanic Episodes) (296.89), Cyclothymic Disorder (301.13) and Bipolar Disorder Not Otherwise Specified (296.80);

The term "anxiety disorders" includes:

Anxiety disorders including Panic Attack; Panic Disorder including Panic Disorder without Agoraphobia (300.01) and Panic Disorder with Agoraphobia (300.21); Agoraphobia; Agoraphobia Without History of Panic Disorder (300.22), Specific Phobia (300.29, formerly Simple Phobia) including the subtypes Animal Type, Natural Environment Type, Blood-Injection-Injury Type, Situational Type and Other Type), Social Phobia (Social Anxiety Disorder, 300.23), Obsessive-Compulsive Disorder (300.3), Posttraumatic Stress Disorder (309.81), Acute Stress Disorder (308.3), Generalized Anxiety Disorder (300.02), Anxiety Disorder Due to a General Medical Condition (293.84), Substance-Induced Anxiety Disorder, Separation Anxiety Disorder (309.21), Adjustment Disorders with Anxiety (309.24) and Anxiety Disorder Not Otherwise Specified (300.00):

The term "substance related disorder" includes:

Substance-related disorders including Substance Use Disorders such as Substance Dependence, Substance Craving and Substance Abuse; Substance-Induced Disorders such as Substance Intoxication, Substance Withdrawal, Substance-Induced Delirium, Substance-Induced Persisting Dementia, Substance-Induced Persisting Amnestic Disorder, Substance-Induced Psychotic Disorder, Substance-Induced Mood Disorder, Substance-Induced Anxiety Disorder, Substance-Induced Sexual Dysfunction, Substance-Induced Sleep Disorder and Hallucinogen Persisting Perception Disorder (Flashbacks); Alcohol-Related Disorders such as Alcohol Dependence (303.90), Alcohol Abuse (305.00), Alcohol Intoxication (303.00), Alcohol Withdrawal (291.81), Alcohol Intoxication Delirium, Alcohol Withdrawal Delirium, Alcohol-Induced Persisting Dementia, Alcohol-Induced Persisting Amnestic Disorder, Alcohol-Induced Psychotic Disorder, Alcohol-Induced Mood Disorder, Alcohol-Induced Anxiety Disorder, Alcohol-Induced Sexual Dysfunction, Alcohol-Induced Sleep Disorder and Alcohol-Related Disorder Not Otherwise Specified (291.9); Amphetamine (or Amphetamine-Like)-Related Disorders such as Amphetamine Dependence (304.40), Amphetamine Abuse (305.70), Amphetamine Intoxication (292.89), Amphetamine Withdrawal (292.0), Amphetamine Intoxication Delirium, Amphetamine Induced Psychotic Disorder, Amphetamine-Induced Mood Disorder, Amphetamine-Induced Anxiety Disorder, Amphetamine-Induced Sexual Dysfunction, Amphetamine-Induced Sleep Disorder and Amphetamine-Related Disorder Not Otherwise Specified (292.9); Caffeine Related Disorders such as Caffeine Intoxication (305.90), Caffeine-Induced Anxiety Disorder, Caffeine-Induced Sleep Disorder and Caffeine-Related Disorder Not Otherwise Specified (292.9); Cannabis-Related Disorders such as Cannabis Dependence (304.30), Cannabis Abuse (305.20), Cannabis Intoxication (292.89), Cannabis Intoxication Delirium, Cannabis-Induced Psychotic Disorder, Cannabis-Induced Anxiety Disorder and Cannabis-Related Disorder Not Otherwise Specified (292.9); Cocaine-Related Disorders such as Cocaine Dependence (304.20), Cocaine Abuse (305.60), Cocaine Intoxication (292.89), Cocaine Withdrawal (292.0), Cocaine Intoxication Delirium, Cocaine-Induced Psychotic Disorder, Cocaine-Induced Mood Disorder, Cocaine-Induced Anxiety Disorder, Cocaine-Induced Sexual Dysfunction, Cocaine-Induced Sleep Disorder and Cocaine-Related Disorder Not Otherwise Specified (292.9); Hallucinogen-Related Disorders such as Hallucinogen Dependence (304.50), Hallucinogen Abuse (305.30), Hallucinogen Intoxication (292.89), Hallucinogen Persisting Perception Disorder (Flashbacks) (292.89), Hallucinogen Intoxication Delirium, Hallucinogen-Induced Psychotic Disorder, Hallucinogen-Induced Mood Disorder, Hallucinogen-Induced Anxiety Disorder and Hallucinogen-Related Disorder Not Otherwise Specified (292.9); Inhalant-Related Disorders such as Inhalant Dependence (304.60), Inhalant Abuse (305.90), Inhalant Intoxication (292.89), Inhalant Intoxication Delirium, Inhalant-Induced Persisting Dementia, Inhalant-Induced Psychotic Disorder, Inhalant-Induced Mood Disorder, Inhalant-Induced Anxiety Disorder and Inhalant-Related Disorder Not Otherwise Specified (292.9); Nicotine-Related Disorders such as Nicotine Dependence (305.1), Nicotine Withdrawal (292.0) and Nicotine-Related Disorder Not Otherwise Specified (292.9); Opioid-Related Disorders such as Opioid Dependence (304.00), Opioid Abuse (305.50), Opioid Intoxication (292.89), Opioid Withdrawal (292.0), Opioid Intoxication Delirium, Opioid-Induced Psychotic Disorder, Opioid-Induced Mood Disorder, Opioid-Induced Sexual Dysfunction, Opioid-Induced Sleep Disorder and Opioid-Related Disorder Not Otherwise Specified (292.9); Phencyclidine (or Phencyclidine-Like)-Related Disorders such as Phencyclidine Dependence (304.60), Phencyclidine Abuse (305.90), Phencyclidine Intoxication (292.89), Phencyclidine Intoxication Delirium, Phencyclidine-Induced Psychotic Disorder, Phencyclidine-Induced Mood Disorder, Phencyclidine-Induced Anxiety Disorder and Phencyclidine-Related Disorder Not Otherwise Specified (292.9); Sedative-, Hypnotic-, or Anxiolytic-Related Disorders such as Sedative, Hypnotic, or Anxiolytic Dependence (304.10), Sedative, Hypnotic, or Anxiolytic Abuse (305.40), Sedative, Hypnotic, or Anxiolytic Intoxication (292.89), Sedative, Hypnotic, or Anxiolytic Withdrawal (292.0), Sedative, Hypnotic, or Anxiolytic Intoxication Delirium, Sedative, Hypnotic, or Anxiolytic Withdrawal Delirium, Sedative-, Hypnotic-, or Anxiolytic-Persisting Dementia, Sedative-, Hypnotic-, or Anxiolytic-Persisting Amnestic Disorder, Sedative-, Hypnotic-, or Anxiolytic-Induced Psychotic Disorder, Sedative-, Hypnotic-, or Anxiolytic-Induced Mood Disorder, Sedative-, Hypnotic-, or Anxiolytic-Induced Anxiety Disorder Sedative-, Hypnotic-, or Anxiolytic-Induced Sexual Dysfunction, Sedative-, Hypnotic-, or Anxiolytic-Induced Sleep Disorder and Sedative-, Hypnotic-, or Anxiolytic-Related Disorder Not Otherwise Specified (292.9); Polysubstance-Related Disorder such as Polysubstance Dependence (304.80); and Other (or Unknown) Substance-Related Disorders such as Anabolic Steroids, Nitrate Inhalants and Nitrous Oxide;

The term "Sleep disorder" includes:

Sleep disorders including primary sleep disorders such as Dyssomnias such as Primary Insomnia (307.42), Primary Hypersomnia (307.44), Narcolepsy (347), Breathing-Related Sleep Disorders (780.59), Circadian Rhythm Sleep Disorder (307.45) and Dyssomnia Not Otherwise Specified (307.47); primary sleep disorders such as Parasomnias such as Nightmare Disorder (307.47), Sleep Terror Disorder (307.46), Sleepwalking Disorder (307.46) and Parasomnia Not Otherwise Specified (307.47); Sleep Disorders Related to Another Mental Disorder such as Insomnia Related to Another Mental Disorder (307.42) and Hypersomnia Related to Another Mental Disorder (307.44); Sleep Disorder Due to a General Medical Condition; and Substance-Induced Sleep Disorder including the subtypes Insomnia Type, Hypersomnia Type, Parasomnia Type and Mixed Type;

The term "eating disorder" include:

Eating disorders such as Anorexia Nervosa (307.1) including the subtypes Restricting Type and Binge-Eating/Purging Type; Bulimia Nervosa (307.51) including the subtypes Purging Type and Nonpurging Type; Obesity; Compulsive Eating Disorder; Binge Eating Disorder; and Eating Disorder Not Otherwise Specified (307.50):

The term "Attention-Deficit/Hyperactivity Disorder" includes:

Attention-Deficit/Hyperactivity Disorder including the subtypes Attention-Deficit/Hyperactivity Disorder Combined Type (314.01), Attention-Deficit/Hyperactivity Disorder Predominantly Inattentive Type (314.00), Attention-Deficit/Hyperactivity Disorder Hyperactive-Impulse Type (314.01) and Attention-Deficit/Hyperactivity Disorder Not Otherwise Specified (314.9); Hyperkinetic Disorder; Disruptive Behaviour Disorders such as Conduct Disorder including the subtypes childhood-onset type (321.81), Adolescent-Onset Type (312.82) and Unspecified Onset (312.89), Oppositional Defiant Disorder (313.81) and Disruptive Behaviour Disorder Not Otherwise Specified; and Tic Disorders such as Tourette's Disorder (307.23);

The term "Cognition impairment" includes:

Cognition impairment including cognition impairment in other diseases such as schizophrenia, bipolar disorder, depression, other psychiatric disorders and psychotic conditions associated with cognitive impairment, e.g. Alzheimer's disease;

The term "Sexual dysfunctions" includes:

Sexual dysfunctions including Sexual Desire Disorders such as Hypoactive Sexual Desire Disorder (302.71), and Sexual Aversion Disorder (302.79); sexual arousal disorders such as Female Sexual Arousal Disorder (302.72) and Male Erectile Disorder (302.72); orgasmic disorders such as Female Orgasmic Disorder (302.73), Male Orgasmic Disorder (302.74) and Premature Ejaculation (302.75); sexual pain disorder such as Dyspareunia (302.76) and Vaginismus (306.51); Sexual Dysfunction Not Otherwise Specified (302.70); paraphilias such as Exhibitionism (302.4), Fetishism (302.81), Frotteurism (302.89), Pedophilia (302.2), Sexual Masochism (302.83), Sexual Sadism (302.84), Transvestic Fetishism (302.3), Voyeurism (302.82) and Paraphilia Not Otherwise Specified (302.9); gender identity disorders such as Gender Identity Disorder in Children (302.6) and Gender Identity Disorder in Adolescents or Adults (302.85); and Sexual Disorder Not Otherwise Specified (302.9);

The term "Obsessive compulsive spectrum disorder" includes:

Obsessive compulsive spectrum disorder including Obsessive compulsive disorders (300.3), somatoform disorders including body dysmorphic disorder (300.7) and hypochondriasis (300.7), bulimia nervosa (307.51), anorexia nervosa (307.1), eating disorders not elsewhere classified (307.50) such as binge eating, impulse control disorders not elsewhere classified (including intermitted explosive disorder (312.34), compulsive buying or shopping, repetitive self-mutilation, onychophagia, psychogenic excoriation, kleptomania (312.32), pathological gambling (312.31), trichotillomania (312.39) and internet addiction), paraphilia (302.70) and non-paraphilic sexual addictions, Sydeham's chorea, torticollis, autistic disorders (299.0), compulsive hoarding, and movement disorders, including Tourette's syndrome (307.23).

All of the various forms and sub-forms of the disorders mentioned herein are contemplated as part of the present invention.

In an embodiment, compounds of the invention may be useful as analgesics. For example they may be useful in the treatment of chronic inflammatory pain (e.g. pain associated with rheumatoid arthritis, osteoarthritis, rheumatoid spondylitis, gouty arthritis and juvenile arthritis); musculoskeletal pain; lower back and neck pain; sprains and strains; neuropathic pain; sympathetically maintained pain; myositis; pain associated with cancer and fibromyalgia; pain associated with migraine; pain associated with influenza or other viral infections, such as the common cold; rheumatic fever; pain associated with functional bowel disorders such as non-ulcer dyspepsia, non-cardiac chest pain and irritable bowel syndrome; pain associated with myocardial ischemia; post operative pain; headache; toothache; and dysmenorrhea.

Compounds of the invention may be useful in the treatment of neuropathic pain. Neuropathic pain syndromes can develop following neuronal injury and the resulting pain may persist for months or years, even after the original injury has healed. Neuronal injury may occur in the peripheral nerves, dorsal roots, spinal cord or certain regions in the brain. Neuropathic pain syndromes are traditionally classified according to the disease or event that precipitated them. Neuropathic pain syndromes include: diabetic neuropathy; sciatica; non-specific lower back pain; multiple sclerosis pain; fibromyalgia; HIV-related neuropathy; post-herpetic neuralgia; trigeminal neuralgia; and pain resulting from physical trauma, amputation, cancer, toxins or chronic inflammatory conditions. These conditions are difficult to treat and although several drugs are known to have limited efficacy, complete pain control is rarely achieved. The symptoms of neuropathic pain are incredibly heterogeneous and are often described as spontaneous shooting and lancinating pain, or ongoing, burning pain. In addition, there is pain associated with normally non-painful sensations such as "pins and needles" (paraesthesias and dysesthesias), increased sensitivity to touch (hyperesthesia), painful sensation following innocuous stimulation (dynamic, static or thermal allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia).

Compounds of the invention may also be useful in the amelioration of inflammatory disorders, for example in the treatment of skin conditions (e.g. sunburn, burns, eczema, dermatitis, psoriasis); ophthalmic diseases such as glaucoma, retinitis, retinopathies, uveitis and of acute injury to the eye tissue (e.g. conjunctivitis); lung disorders (e.g. asthma, bronchitis, emphysema, allergic rhinitis, respiratory distress syndrome, pigeon fancier's disease, farmer's lung, chronic obstructive pulmonary disease, (COPD); gastrointestinal tract disorders (e.g. aphthous ulcer, Crohn's disease, atopic gastritis, gastritis varialoforme, ulcerative colitis, coeliac disease, regional ileitis, irritable bowel syndrome, inflammatory bowel disease, gastroesophageal reflux disease); other conditions with an inflammatory component such as migraine, multiple sclerosis, myocardial ischemia.

In one embodiment, compounds of the invention are useful in the treatment of depression and anxiety disorders.

In another embodiment, compounds of the invention are useful in the treatment of depression.

"Treatment" includes prophylaxis, where this is appropriate for the relevant condition(s).

In an alternative or further aspect there is provided a method for the treatment of a mammal, including man, in particular in the treatment of disorders or diseases responsive to the monoamine neurotransmitter re-uptake inhibiting activity of the compounds, comprising administration of an effective amount of a compound of the invention.

In one embodiment, the invention provides a method of treating a condition for which inhibition of serotonin (5-HT), dopamine (DA) and norepinephrine (NE), is beneficial, which comprises administering to a mammal (e.g. human) in need thereof an effective amount of a compound of the invention.

In another embodiment, the invention provides a method of treating a condition for which inhibition of serotonin (5-HT), dopamine (DA) and norepinephrine (NE), is beneficial, which comprises administering to a mammal (e.g. human) in need thereof an effective amount of (1S,6R)-6-(3,4-dichlorophenyl)-1-[(methyloxy)methyl]-3-azabicyclo[4.1.0]heptane or a pharmaceutically acceptable salt thereof.

In a further embodiment, the invention provides a method of treating depression which comprises administering to a mammal (e.g. human) in need thereof an effective amount of (1S,6R)-6-(3,4-dichlorophenyl)-1-[(methyloxy)methyl]-3-azabicyclo[4.1.0]heptane or a pharmaceutically acceptable salt thereof.

In another embodiment, the invention provides a method of treating a condition for which inhibition of serotonin (5-HT), dopamine (DA) and norepinephrine (NE), is beneficial, which comprises administering to a mammal (e.g. human) in need thereof an effective amount of (1S,6R or 1R,6S)-1-[(methyloxy)methyl]-6-(2-naphthalenyl)-3-azabicyclo[4.1.0]heptane or a pharmaceutically acceptable salt thereof.

In another aspect, the invention provides a compound of the invention for use in therapy.

In a further embodiment, the invention provides a compound of the invention for use in the treatment of a condition in a mammal for which inhibition of serotonin (5-HT), dopamine (DA) and norepinephrine (NE) is beneficial.

In one aspect, the invention provides the use of compounds of the invention, for the manufacture of a medicament for the treatment of disorders or diseases responsive to monoamine neurotransmitter re-uptake inhibiting activity.

In one embodiment, the invention provides the use of a compound of a compound of the invention in the manufacture of a medicament for the treatment of a condition in a mammal for which inhibition of serotonin (5-HT), dopamine (DA) and norepinephrine (NE) is beneficial.

In a further embodiment, the invention provides the use of (1S,6R)-6-(3,4-dichlorophenyl)-1-[(methyloxy)methyl]-3-azabicyclo[4.1.0]heptane or a pharmaceutically acceptable salt thereof, for the manufacture of a medicament for the treatment of a condition in a mammal for which inhibition of serotonin (5-HT), dopamine (DA) and norepinephrine (NE) is beneficial.

In another embodiment, the invention provides the use of (1S,6R or 1R,6S)-1-[(methyloxy)methyl]-6-(2-naphthalenyl)-3-azabicyclo[4.1.0]heptane or a pharmaceutically acceptable salt thereof, for the manufacture of a medicament for the treatment of a condition in a mammal for which inhibition of serotonin (5-HT), dopamine (DA) and norepinephrine (NE) is beneficial.

The compounds of the invention may also be used in combination with other therapeutic agents. The invention thus provides, in a further aspect, a combination comprising a compound of the invention together with a further therapeutic agent.

The compounds of the invention may be used in combination with the following agents to treat or prevent psychotic disorders: i) antipsychotics; ii) drugs for extrapyramidal side effects, for example anticholinergics (such as benztropine, biperiden, procyclidine and trihexyphenidyl), antihistamines (such as diphenhydramine) and dopaminergics (such as amantadine); iii) antidepressants; iv) anxiolytics; and v) cognitive enhancers for example cholinesterase inhibitors (such as tacrine, donepezil, rivastigmine and galantamine).

The compounds of the invention may be used in combination with antidepressants to treat or prevent depression and mood disorders.

The compounds of the invention may be used in combination with the following agents to treat or prevent bipolar disease: i) mood stabilisers; ii) antipsychotics; and iii) antidepressants.

The compounds of the invention may be used in combination with the following agents to treat or prevent anxiety disorders: i) anxiolytics; and ii) antidepressants.

The compounds of the invention may be used in combination with the following agents to improve nicotine withdrawal and reduce nicotine craving: i) nicotine replacement therapy for example a sublingual formulation of nicotine beta-cyclodextrin and nicotine patches; and ii) bupropion.

The compounds of the invention may be used in combination with the following agents to improve alcohol withdrawal and reduce alcohol craving: i) NMDA receptor antagonists for example acamprosate; ii) GABA receptor agonists for example tetrabamate; and iii) Opioid receptor antagonists for example naltrexone.

The compounds of the invention may be used in combination with the following agents to improve opiate withdrawal and reduce opiate craving: i) opioid mu receptor agonist/opioid kappa receptor antagonist for example buprenorphine; ii) opioid receptor antagonists for example naltrexone; and iii) vasodilatory antihypertensives for example lofexidine.

The compounds of the invention may be used in combination with the following agents to treat or prevent sleeping disorders: i) benzodiazepines for example temazepam, lormetazepam, estazolam and triazolam; ii) non-benzodiazepine hypnotics for example zolpidem, zopiclone, zaleplon and indiplon; iii) barbiturates for example aprobarbital, butabarbital, pentobarbital, secobarbita and phenobarbital; iv) antidepressants; v) other sedative-hypnotics for example chloral hydrate and chlormethiazole.

The compounds of the invention may be used in combination with the following agents to treat anorexia: i) appetite stimulants for example cyproheptidine; ii) antidepressants; iii) antipsychotics; iv) zinc; and v) premenstral agents for example pyridoxine and progesterones.

The compounds of the invention may be used in combination with the following agents to treat or prevent bulimia: i) antidepressants; ii) opioid receptor antagonists; iii) antiemetics for example ondansetron; iv) testosterone receptor antagonists for example flutamide; v) mood stabilisers; vi) zinc; and vii) premenstral agents.

The compounds of the invention may be used in combination with the following agents to treat or prevent autism: i) antipsychotics; ii) antidepressants; iii) anxiolytics; and iv) stimulants for example methylphenidate, amphetamine formulations and pemoline.

The compounds of the invention may be used in combination with the following agents to treat or prevent ADHD: i) stimulants for example methylphenidate, amphetamine formulations and pemoline; and ii) non-stimulants for example norepinephrine reuptake inhibitors (such as atomoxetine), alpha 2 adrenoceptor agonists (such as clonidine), antidepressants, modafinil, and cholinesterase inhibitors (such as galantamine and donezepil).

The compounds of the invention may be used in combination with the following agents to treat personality disorders: i) antipsychotics; ii) antidepressants; iii) mood stabilisers; and iv) anxiolytics.

The compounds of the invention may be used in combination with the following agents to treat or prevent male sexual dysfunction: i) phosphodiesterase V inhibitors, for example vardenafil and sildenafil; ii) dopamine agonists/dopamine transport inhibitors for example apomorphine and buproprion; iii) alpha adrenoceptor antagonists for example phentolamine; iv) prostaglandin agonists for example alprostadil; v) testosterone agonists such as testosterone; vi) serotonin transport inhibitors for example serotonin reuptake inhibitors; v) noradrenaline transport inhibitors for example reboxetine and vii) 5-HT1A agonists, for example flibanserine.

The compounds of the invention may be used in combination with the same agents specified for male sexual dysfunction to treat or prevent female sexual dysfunction, and in addition an estrogen agonist such as estradiol.

Antipsychotic drugs include Typical Antipsychotics (for example chlorpromazine, thioridazine, mesoridazine, fluphenazine, perphenazine, prochlorperazine, trifluoperazine, thiothixine, haloperidol, molindone and loxapine); and Atypical Antipsychotics (for example clozapine, olanzapine, risperidone, quetiapine, aripirazole, ziprasidone and amisulpride).

Antidepressant drugs include serotonin reuptake inhibitors (such as citalopram, escitalopram, fluoxetine, paroxetine and sertraline); dual serotonin/noradrenaline reuptake inhibitors (such as venlafaxine, duloxetine and milnacipran); Noradrenaline reuptake inhibitors (such as reboxetine); tricyclic antidepressants (such as amitriptyline, clomipramine, imipramine, maprotiline, nortriptyline and trimipramine); monoamine oxidase inhibitors (such as isocarboxazide, moclobemide, phenelzine and tranylcypromine); and others (such as bupropion, mianserin, mirtazapine, nefazodone and trazodone).

Mood stabiliser drugs include lithium, sodium valproate/valproic acid/divalproex, carbamazepine, lamotrigine, gabapentin, topiramate and tiagabine.

Anxiolytics include benzodiazepines such as alprazolam and lorazepam.

For use in medicine, the compounds of the present invention are usually administered as a standard pharmaceutical composition. The present invention therefore provides in a further aspect a pharmaceutical composition comprising a compound of the invention and a pharmaceutically (i.e. physiologically) acceptable carrier. The pharmaceutical composition can be for use in the treatment of any of the conditions described herein.

In one embodiment, a pharmaceutical composition comprising (1S,6R)-6-(3,4-dichlorophenyl)-1-[(methyloxy)methyl]-3-azabicyclo[4.1.0]heptane or a pharmaceutically acceptable salt thereof, and a pharmaceutically acceptable carrier is provided.

The compounds of the invention may be administered by any convenient method, for example by oral, parenteral (e.g. intravenous), buccal, sublingual, nasal, rectal or transdermal administration and the pharmaceutical compositions adapted accordingly.

The compounds of the invention which are active when given orally can be formulated as liquids or solids, for example syrups, suspensions or emulsions, tablets, capsules and lozenges.

A liquid formulation will generally consist of a suspension or solution of the compound or salt in a suitable liquid carrier(s) for example an aqueous solvent such as water, ethanol or glycerine, or a non-aqueous solvent, such as polyethylene glycol or an oil. The formulation may also contain a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active substance in a pharmaceutically acceptable aqueous or non-aqueous solvent and are usually presented in single or multidose quantities in sterile form in a sealed container, which can take the form of a cartridge or refill for use with an atomising device. Alternatively the sealed container may be a unitary dispensing device such as a single dose nasal inhaler or an aerosol dispenser fitted with a metering valve which is intended for disposal once the contents of the container have been exhausted. Where the dosage form comprises an aerosol dispenser, it will contain a propellant which can be a compressed gas such as compressed air or an organic propellant such as a fluorochloro-hydrocarbon. The aerosol dosage forms can also take the form of a pump-atomiser.

Compositions suitable for buccal or sublingual administration include tablets, lozenges and pastilles, wherein the active ingredient is formulated with a carrier such as sugar and acacia, tragacanth, or gelatin and glycerin.

Compositions for rectal administration are conveniently in the form of suppositories containing a conventional suppository base such as cocoa butter. Compositions suitable for transdermal administration include ointments, gels and patches.

In one embodiment, the composition is in unit dose form such as a tablet, capsule or ampoule.

Each dosage unit for oral administration contains for example from 0.5 to 250 mg (and for parenteral administration contains for example from 0.05 to 25 mg) of a compound of the invention calculated as the free base.

The pharmaceutically acceptable compounds of the invention will normally be administered in a daily dosage regimen (for an adult patient) of, for example, an oral dose of between 1 mg and 500 mg, for example between 1 mg and 400 mg, e.g. between 10 and 250 mg or an intravenous, subcutaneous, or intramuscular dose of between 0.1 mg and 100 mg, for example between 0.1 mg and 50 mg, e.g. between 1 and 25 mg of the compound of the formula (I) or a salt thereof calculated as the free base, the compound being administered 1 to 4 times per day, for example 1 to 2 time a day. In one embodiment, the compound of the invention may be administered once a day. Suitably the compounds will be administered for a period of continuous therapy, for example for a week or more.

For oral administration a typical dose may be in the range of 1 to 200 mg per day, for example 60 to 200 mg per day.

When a compound of the invention or a pharmaceutically acceptable derivative thereof is used in combination with a second therapeutic agent active against the same disease state the dose of each compound may differ from that when the compound is used alone. Appropriate doses will be readily appreciated by those skilled in the art. It will be appreciated that the amount of a compound of the invention required for use in treatment will vary with the nature of the condition being treated and the age and the condition of the patient and will be ultimately at the discretion of the attendant physician or veterinarian.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations by any convenient route.

The invention is also directed to a novel kit-of-parts that is suitable for use in the treatment of disorders as above defined comprising a first dosage form comprising a compound of the invention and a second dosage form comprising another therapeutic agent, for simultaneous, separate or sequential administration.

When administration is sequential, either the compound of the invention or the second therapeutic agent may be administered first. When administration is simultaneous, the combination may be administered either in the same or different pharmaceutical composition.

When combined in the same formulation it will be appreciated that the two compounds must be stable and compatible with each other and the other components of the formulation. When formulated separately they may be provided in any convenient formulation, conveniently in such manner as are known for such compounds in the art.

Biological Assays

Cell Biology a) Generation of Stable LLCPK Cell Lines Expressing hSERT, hNET, and hDAT Stable cell line expressing human serotonin transporter (hSERT) may be created by transfecting Lewis Lung Carcinoma Porcine tubule Kidney (LLC-PK1 or LLCPK) cells with hSERT cloned into the mammalian expression vector pcDNA3.1 Hygro(+).

Stable cell line expressing human norepinephrine transporter (hNET) may be created by transfecting LLCPK cells with hNET cloned into the mammalian expression vector pRC/CMV.

Stable cell line expressing human dopamine transporter (hDAT) may be created by transfecting LLCPK cells with hDAT cloned into the mammalian expression vector pDESTCDNA3.1.

One example of reference procedure for transfecting LLCPK cells with hDAT, hSERT and hNET may be found in H. Gu, S. C. Wall and G. Rudnick, J. Biol. Chem. (1994) 269: 7124-7130.

Each cell line is cultured independently in Dulbecco's modified Eagle's medium (DMEM) containing 10% of Foetal Bovine Serum (FBS) supplemented with 400 µg/ml hygromicin (hSERT) or geneticin at 500 pg/ml (hNET) or at 1000 µg/ml (hDAT). Cells are maintained at 37° C. in a humidified environment containing 5% CO2 in air.

b) Generation of BacMam Viruses for the Expression of hSERT, hNET, and hDAT in Mammalian Cells Membranes for the SPA-binding assays are produced by HEK-293F cell infection with BacMam viruses generated for each single human SERT, NET, and DAT transporter. hSERT and hDAT are cloned into pFBMRfA vector whereas hNET is cloned into pFASTBacMam1 vector. The generation and use of BacMam viruses is described in Condreay J P et al, Proc. Natl. Acad. Sci. USA, 1999, 96:127-132 and Hassan N J et al, Protein Expression and Purification, 47(2): 591-598, 2006.

Affinity to the Human Transporters SERT .NET and DAT

The affinities of the compounds of the invention for the human serotonin transporter (SERT), human norepinephrine transporter (NET) and for the human dopamine transporter (DAT) may be determined by one of the assays described below. Such affinity is typically calculated from the $IC_{50}$ obtained in competition experiments as the concentration of a compound necessary to displace 50% of the radiolabeled ligand from the transporter, and is reported as a "$K_i$" value calculated by the following equation:

$$K_i = \frac{IC_{50}}{1 + L/K_D}$$

where L=radioligand and $K_D$=affinity of radioligand for transporter (Cheng and Prusoff, *Biochem. Pharmacol.* 22:3099, 1973). In the context of the present invention pKi values (corresponding to the antilogarithm of Ki) are used instead of Ki; pKi results are only estimated to be accurate to about 0.3-0.5.

a) Filtration Binding Assay on Membranes form hSERT, hNET, and hDAT LLCPK Cell Lines Membrane Preparation hSERT-LLCPK or hDAT-LLCPK or hNET-LLCPK cell lines are used for the membrane preparations for radioligand binding assays. Each cell line is cultured independently in Dulbecco's modified Eagle's medium (DMEM) containing 10% of Foetal Bovine Serum (FBS) supplemented with 400 µg/ml hygromicin (hSERT) or geneticin at 500 µg/ml (hNET) or at 1000 µg/ml (hDAT). When cells are at 70-80% of confluence, the culture medium is removed and the cells harvested with phosphate buffered saline (PBS) containing 5 mM EDTA. Cell suspension is centrifuged at 900 g for 5 minutes at 4° C. The resultant pellets are re-suspended in 30-50 volumes of Assay Buffer (50 mM Tris pH 7.7 containing 120 mM NaCl, 5 mM KCl, 10 µM pargyline and 0.1% ascorbic acid) and homogenized using a glass-teflon Potter homogeniser and centrifuged at 48000 g for 20 minutes at 4°

C. The resultant membrane pellets are re-suspended in the same volume of Assay Buffer, incubated for 20 minutes at 37° C. and centrifuged as before at 48000 g. The final protein concentration for each preparation is adjusted to give approximately 480 pg protein/ml for hSERT-LLCPK, hDAT-LLCPK and hNET-LLCPK, as determined by the Bio-Rad Protein Assay kit. Membranes are stored at −80° C. as 1 ml aliquots until required.

Filtration Assay Protocol for hSERT, hNET, and hDAT

General references for monoamine transporters filtration binding assay may be: Michael J. Owens, et al, *Neurotransmitter receptor and transporter binding profile of antidepressants and their metabolites, JPET,* 283:1305-1322, 1997; *Per Allard, Jan O. Marcusson, Svate B. Ross, [3H]WIN-35,428 binding in the human brain, Brain Res.,* 706:347-350, 1996. The affinity of the compounds of the invention to bind the re-uptake site of SERT may be assessed using [$^3$H]citalopram filtration binding assay performed on hSERT-LLCPK cell membranes. In details, competition binding assay is conducted in deep-well 96 well plate (1 ml, NUNC, cod.260252) in a total volume of 400 μl, with each concentration in duplicate. 4 μl of test compound (100× solution in neat DMSO as 7 point curve ranging from $10^{-6}$ to $10^{-12}$M, final concentration) or DMSO (to define total binding) or a final concentration of 10 μM fluoxetine in DMSO (to define non-specific binding, NSB) are added to wells; after this, 200 μl of [N-Methyl-3H]citalopram (Amersham Biosciences, 80 Ci/mmol) at the final concentration of 0.25 nM in Assay Buffer, is added to all wells and finally the reaction is started by adding 200 μl/well of membranes diluted 1:80 in Assay Buffer at concentration of about 2.5 μg/well of protein. The reaction is carried out at room temperature for 2 hours and then stopped by rapid filtration through GF/B Unifilter 96-filterplate (Perkin-Elmer) pre-soaked in 0.5% polyethylenimmine (PEI) using a Perkin-Elmer FilterMat-196 harvester. Filterplate is washed 3 times with 1 ml/well ice-cold 0.9% NaCl solution. The plate is dried in an oven for 60 min at 50° C. then opaque bottom-seal is placed on the underside of the plate and 50 μl of Microscint 20 (Perkin-Elmer) added to each well. Plate is sealed with a TopSeal and the radioactivity in the samples is counted for 4 min using TopCount liquid scintillation counter (Packard-Perkin-Elmer) and recorded as counts per minute (CPM). Competition binding assay for hNET may be conducted essentially as previously reported for hSERT in 96 well format and in a final assay volume of 400 μl, except for the use of hNET-LLCPK cell membranes (1:40 dilution i.e. 4.8 μg of protein/well) and [$^3$H]nisoxetine as radioligand (1.5 nM [N-methyl-3H]nisoxetine, Amersham Biosciences, 84 Ci/mmol). 10 μM desipramine is used for NSB.

Competition binding assay for hDAT may be conducted essentially as previously reported for hSERT and hNET in 96 well format and in a final assay volume of 400 μl, except for the use of hDAT-LLCPK cell membranes (1:20 i.e. 9.6 μg of protein/well) and [$^3$H]WIN-35,428 as radioligand (10 nM [N-Methyl-$^3$H]WIN-35,428, Perkin Elmer, 85.6 Ci/mmol). Furthermore, 10 μM GBR-12909 is used for NSB and the incubation time of the binding reaction is 1 hour at room temperature.

b) Scintillation Proximity Assay (SPA) for human DAT, NET and SERT Binding

Transduction of HEK-293F cells with hSERT/hDAT/hNET BacMam viruses The HEK-293F suspension cell line (Invitrogen) is routinely grown in 293_Freestyle Expression media (Invitrogen) in shake flask suspension culture. The culture is transduced with the appropriate transporter BacMam at a MOI (multiplicity of infection) of 100 virus particles per cell and incubated for 48 hrs at 37° C., 5% $CO_2$ in air, shaken at 90 rpm in a humidified shaker incubator. The culture is then harvested by centrifugation at 1000 g, 4° C., for 10 minutes and the cell pellet stored at −80° C. until required.

Preparation of BacMam hSERT/hDAT/hNET-HEL293F Cell Membranes

Transduced cell pellets are re-suspended to 10× volume with buffer-A (50 mM HEPES, 1 mM EDTA, 1 mM leupeptin, 25 ug/mL bacitracin, 1 mM phenylmethylsulfonylfluoride, PMSF, 2 μM pepstatin A, pH 7.7) and homogenised with 2× 15 second bursts in a glass Warning blender. The homogenate is then centrifuged for 20 minutes at 500 g. Following this, the supernatant is pooled and centrifuged at 13,000 g for 30 minutes. Pellets are then re-suspended to 4× original pellet volume with buffer-B (50 mM TRIS pH 7.4, 130 mM NaCl) and forced through a 0.8 mm needle to give a homogeneous suspension. Membrane aliquots are stored at −80° C. until required. The protein concentration is quantified by Bradford assay.

SPA-Binding Assay Protocol for hSERT, hNET, and hDAT

The affinity of the compounds of the invention to the hSERT, hNET or hDAT can be also assessed by using the [$^3$H]citalopram, [$^3$H]nisoxetine or [$^3$H]WIN-35,428 binding assays with the SPA technology on BacMam-recombinant human SERT, NET and DAT membranes produced as described before. With the SPA technology (GE Healthcare, Amersham) only transporter-bound radioactivity can elicit bead excitation thus no separation of the bound/unbound radioligand is required.

The protocol for hSERT binding SPA is based on Trilux beta-counter (Wallac, Perkin-Elmer). Briefly, 0.5 μL of test compound in neat DMSO (or 1 μM fluoxetine as positive control) is added by 50 μL of the SPA mixture, containing 2 mg/mL SPA beads (Amersham RPNQ0001), 4 pg/mL hSERT Bacmam membranes, 0.01% pluronic F-127, 2.5 nM [$^3$H]citalopram in the assay buffer (20 mM HEPES, 145 mM NaCl, 5 mM KCl, pH 7.3). Incubation are performed at room temperature for at least 2 hours. Counts are stable and could be read up to 3 days.

Alternatively, hDAT hNET and hSERT SPA-binding assays are performed by using a Viewlux beta-counter (Wallac, Perkin-Elmer) with imaging PS-WGA beads (Amersham RPNQ0260) in a final assay volume of 30 μL and in a 384-well plate format (Greiner 781075). Briefly, 0.3 μL of test compound in neat DMSO and 0% and 100% effect controls (DMSO for total binding and 10 or 1 μM indatraline as positive control) are added to the wells by using a Hummingbird (Genomic Solutions), followed by the addition of 30 μL of the SPA mixture, containing 1 mg/mL SPA beads (hSERT) or 2 mg/ml SPA beads (hDAT and hNET), 40 μg/ml or 20 μg/ml or 6 μg/ml of hDAT or hNET or hSERT BacMam membranes, 0.02% pluronic F-127, 10 nM [$^3$H]WIN-35,428 or 10 nM [$^3$H]nisoxetine or 3 nM [$^3$H]citalopram for hDAT or hNET or hSERT binding SPA in the assay buffer (20 mM HEPES, 145 mM NaCl, 5 mM KCl, pH 7.3-7.4). Incubation is performed at room temperature for at least 2 hours, best overnight in the dark. Bound radioactivity is recorded by using a 600s 6× binning and 613 nm emission filter with the Viewlux instrument.

Compound Affinity Range for Human Transporters SERT, NET, and DAT

The compounds of formula (I)' typically show pKi greater than 4.5 towards each of the three transporters SERT, NET and DAT. In one embodiment, the compounds of formula (I) typically show pKi greater than 5.5 for each of the three transporters. In another embodiment, the compounds of formula (I)' typically show pKi greater than 6.5 for each of the three transporters. In a further embodiment, the compounds of formula (I)' typically show pKi greater than 7.5 for each of the three transporters.

In one embodiment, the present invention provides compounds of formula (I)' having a hSERT pKi comprised between 7 and 8.5. In another embodiment, the present invention provides compounds of formula (I)' having a hSERT pKi comprised between 8.5 and 10.

In one embodiment, the present invention provides compounds of formula (I) having a hDAT pKi comprised between 6.5 and 7.5. In another embodiment, the present invention provides compounds of formula (I)' having a hDAT pKi comprised between 7.5 and 8.5.

In one embodiment, the present invention provides compounds of formula (I)' having a hNET pKi comprised between 6.5 and 7.5. In another embodiment, the present invention provides compounds of formula (I)' having a hNET pKi comprised between 7.5 and 8.5.

In one embodiment, the present invention provides compounds of formula (I)' having a hSERT pKi comprised between 8.5 and 10, a hNET pKi comprised between 7.5 and 8.5 and a hDAT pKi comprised between 7.5 and 8.5.

In one embodiment, the present invention provides compounds of formula (I)' having a hSERT pKi comprised between 9 and 10, a hNET pKi comprised between 8.0 and 8.5 and a hDAT pKi comprised between 7.5 and 8.0.

EXAMPLES

The invention is further illustrated by the following non-limiting examples.

In the procedures that follow, after each starting material, reference to a Preparation or Example by number is typically provided. This is provided merely for assistance to the skilled chemist. The starting material may not necessarily have been prepared from the batch referred to.

Where reference is made to the use of a "similar" or "analogous" procedure, as will be appreciated by those skilled in the art, such a procedure may involve minor variation, for example reaction temperature, reagent/solvent amount, reaction time, work-up conditions or chromatographic purification conditions.

Compounds are named using ACD/Name PRO 6.02 chemical naming software (Advanced Chemistry Development Inc., Toronto, Ontario, M5H2L3, Canada).

All temperatures refer to ° C.

Proton Magnetic Resonance (NMR) spectra are typically recorded either on Varian instruments at 300, 400 or 500 MHz, or on a Bruker instrument at 300 and 400 MHz. Chemical shifts are reported in ppm (d) using the residual solvent line as internal standard. Splitting patterns are designed as s, singlet; d, doublet; t, triplet; q, quartet; m, multiplet; b, broad. The NMR spectra were recorded at a temperature ranging from 25 to 90° C. When more than one conformer was detected the chemical shifts for the most abundant one is reported.

Mass spectra (MS) are typically taken on a 4 II triple quadrupole Mass Spectrometer (Micromass UK) or on a Agilent MSD 1100 Mass Spectrometer, operating in ES (+) and ES (-) ionization mode or on an Agilent LC/MSD 1100 Mass Spectrometer, operating in ES (+) and ES (-) ionization mode coupled with HPLC instrument Agilent 1100 Series. In the mass spectra only one peak in the molecular ion cluster is reported.

When HPLC walk-up retention time is reported, the analysis is done on a HPLC Agilent 1100 Series Instrument with the following method: Column: Luna C18 100A 50×2 mm, 3 micron; Mobile Phase:(MeCN+0.05% TFA)/(H2O+0.05% TFA) gradient 0/100 to 95/5 in 8 minutes; Flux 1 ml/min.

Flash silica gel chromatography was carried out on silica gel 230-400 mesh (supplied by Merck AG Darmstadt, Germany) or over Varian Mega Be—Si pre-packed cartridges or over pre-packed Biotage silica cartridges.

In a number of preparations, purification was performed using either Biotage manual flash chromatography (Flash+) or automatic flash chromatography (Horizon or SP1) systems. All these instruments work with Biotage Silica cartridges.

X-Ray Powder Diffraction (XRPD): It will be recognised that spectra and diffraction data will vary slightly according to various factors such as the temperature, concentration and instrumentation used. The skilled person will recognise that XRPD peak positions are affected by differences in sample height. The peak positions quoted herein are thus subject to a variation. The skilled person will also recognise that the relative intensities of peaks may change due to preferred orientation effects.

Differential Scanning Calorimetry (DSC): It should be recognized that the endotherm peak as measured is dependent under a number of factors including the machine employed, the rate of heating, the calibration standard, humidity and the purity of the sample used. Melting points reported in the experimentals are estimated on the basis of the onset of endotherm peaks registered during DSC analysis.

The following abbreviations are used in the text: TBAF=tetrabutylammonium fluoride, DCE=dichloroethane, Tlc refers to thin layer chromatography on silica plates, and dried refers to a solution dried over anhydrous sodium sulphate, r.t. (RT) refers to room temperature, Rt=retention time, DMSO=dimethyl sulfoxide; DCM=dichloromethane; DMF=N,N'-dimethylformamide; MeOH=methanol; TEA or Et$_3$N=triethylamine; THF=tetrahydrofurane; EA, AcOEt or EtOAc=ethyl acetate; cy=cyclohexane; EtOH=ethyl alcohol; ZnEt$_2$=diethylzinc; MTBE=methyl t-butyl ether; TFA=trifluoroacetic acid; Et$_2$O=diethyl ether; IPA=isopropyl alcohol; DMPU=1,3-Dimethyl-3,4,5,6-tetrahydro-2(1H)-pyrimidinone; SPE Cartridge=Solid Phase Extraction Cartridge; SCX Cartridge=Strong Cation Exchange Cartridge; MCX: mixed mode-cation exchange cartridge; NH column: secondary amine functionalised silica cartridge.

Preparation 1: 1-(1,1-dimethylethyl) 3-methyl 4-hydroxy-5,6-dihydro-1,3(2H)-pyridinedicarboxylate (P1)

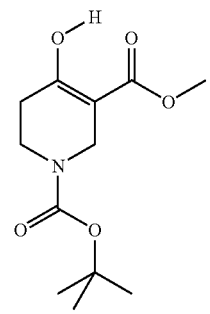

To a stirred solution of methyl 4-oxo-3-piperidinecarboxylate hydrochloride (14.94 g) in dry DCM (250 mL), at 0° C. and under a nitrogen atmosphere, TEA (43 mL) was added dropwise over 5 minutes. The mixture was stirred at 0° C. for 5 minutes, then allowed to reach room temperature, bis(1,1-dimethylethyl)dicarbonate (18.6 g) was then added in one portion and the solution was left stirring overnight at room temperature under Nitrogen. Saturated aqueous NH$_4$Cl solution (350 ml) was poured into the solution and the mixture was transferred in a separator funnel. The reaction flask was washed with DCM (100 ml) and this volume was poured into the separator funnel. The phases were separated and the watery one was washed with DCM (3×70 mL). The combined organic phases were dried on anhydrous Na$_2$SO$_4$, the solvent removed under reduced pressure, the crude product purified by flash-chromatography (eluting with ethyl acetate/cyclohexane 1:3) to give the title compound (19.8 g).

NMR ($^1$H, CDCl$_3$): δ 11.95-12.02 (m, 1H) 4.07 (br. s., 2H) 3.77-3.82 (m, 3H) 3.58 (t, 2H) 2.34-2.43 (m, 2H) 1.46-1.50 (m, 9H)

Preparation 2: 1-(1,1-dimethylethyl) 3-methyl 4-{[(trifluoromethyl)sulfonyl]oxy}-5,6-dihydro-1,3(2H)-pyridinedicarboxylate (P2)

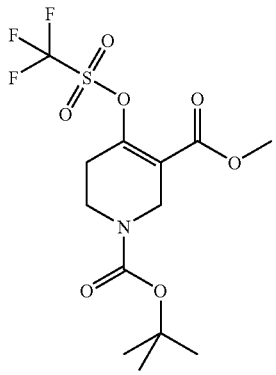

Method A: to a stirred solution of 1-(1,1-dimethylethyl) 3-methyl 4-oxo-1,3-piperidinedicarboxylate (500 mg, P1) in dry DMF (5 mL) at 0° C. and under a nitrogen atmosphere, NaH (60% on mineral oil, 117 mg) was added portionwise and the reaction mixture was stirred at 0° C. for 10 minutes, then a solution of N-phenyl-bis(trifluoromethanesulfonimide) (0.847 g) in dry DMF (2 mL) was added dropwise and stirring was continued for 0.5 h. Saturated NH$_4$Cl (30 mL) and diethyl ether (30 mL) were poured into the reaction mixture, the phases were separated and the watery one was washed with diethyl ether (3×15 mL). The combined organic phases were dried on anhydrous Na$_2$SO$_4$ and the solvent was removed under reduced pressure to give 1.5 g. of the crude title compound.

Method B: to a stirred solution of 1-(1,1-dimethylethyl) 3-methyl 4-oxo-1,3-piperidinedicarboxylate (500 mg, P1) in dry THF (12 mL) at 0° C. and under a nitrogen atmosphere, NaH (60% on mineral oil, 156 mg) was added portionwise and the reaction mixture was stirred at 0° C. for 30 minutes, then N-phenyl-bis(trifluoromethanesulfonimide) (1.028 g) was added in one portion and stirring was continued at 0° C. for 1 hour and at rt overnight. 10 g of ice were poured into the stirred mixture and THF was evaporated at rt under reduced pressure. The residue was taken up with ethyl acetate (30 mL) and the mixture was washed with aqueous Na$_2$CO$_3$ (10%, 3×20 mL). The organic layer was dried on anhydrous Na$_2$SO$_4$ and the solvent was removed under reduced pressure, obtaining 1.7 g. of the crude title compound.

The crude products from Method A and B were combined and purified by flash-chromatography (eluting with ethyl acetate/cycloexane 1:9) to give 1.340 g. of the title compound.

NMR ($^1$H, CDCl$_3$): δ 4.29 (br. s., 2H) 3.82-3.87 (m, 3H) 3.64 (t, 2H) 2.50-2.57 (m, 2H) 1.46-1.52 (m, 9H). MS (m/z): 390 [MH]+, 412 [MNa]+.

Preparation 3: 1-(1,1-dimethylethyl) 3-methyl 4-(3,4-dichlorophenyl)-5,6-dihydro-1,3(2H)-pyridinedicarboxylate (P3)

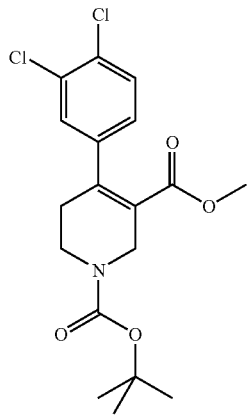

To a mixture of 1-(1,1-dimethylethyl) 3-methyl 4-{[(trifluoromethyl)sulfonyl]oxy}-5,6-dihydro-1,3(2H)-pyridinedicarboxylate (200 mg, P2), 3,4-dichlorophenylboronic acid (108 mg) and Pd(PPh$_3$)$_4$ (21 mg) under nitrogen, toluene (2.5 mL), ethanol (2 mL) and Na$_2$CO$_3$ (aqueous 2M solution, 2 mL) were added in sequence. The mixture was stirred at 80° C. for 1 hour then the reaction mixture was allowed to reach room temperature. Saturated aqueous NH$_4$Cl solution (15 mL) was poured into the solution and the mixture was transferred in a separator funnel. The mixture was extracted with ethyl acetate (3×20 mL), the combined organic phases were dried on anhydrous Na$_2$SO$_4$ and the solvent evaporated obtaining a crude product that was purified by flash-chromatography (eluting with ethyl acetate/cycloexane 1:3) to give the title compound (198 mg).

NMR ($^1$H, CDCl$_3$): δ 7.42 (d, 1H) 7.25 (d, 1H) 6.98 (dd, 1H) 4.26 (br. s., 2H) 3.61 (t, 2H) 3.55-3.58 (m, 3H) 2.47 (br. s., 2H) 1.50-1.54 (m, 9H)

Preparation 4: 1,1-dimethylethyl-4-(3,4-dichlorophenyl)-5-(hydroxymethyl)-3,6-dihydro-1(2H)-pyridinecarboxylate (P4)

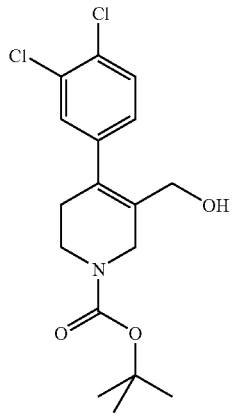

To a stirred solution of 1-(1,1-dimethylethyl) 3-methyl 4-(3,4-dichlorophenyl)-5,6-dihydro-1,3(2H)-pyridinedicarboxylate (538 mg, P3) in dry diethyl ether (10 mL) under N$_2$ atmosphere, at −20° C., LiAlH$_4$ (1M in diethyl ether, 1 mL) was added dropwise over 1 minute, the reaction mixture was left stirring at −20° for 15 minutes then aqueous saturated NH₄Cl solution (50 mL) and diethyl ether (50 mL) were poured into the solution and the mixture was vigorously stirred for 20 minutes at room temperature. The phases were separated, and the watery one was extracted with diethyl ether (3×20 mL). The combined organic phases were dried on anhydrous Na₂SO₄ and the solvent was removed under reduced pressure, obtaining a crude product that was purified by flash-chromatography (eluting with ethyl acetate/cycloexane 1:3) to give the title compound (474 mg).

NMR (¹H, DMSO-d6): δ 7.62 (d, 1H) 7.56 (d, 1H) 7.26 (dd, 1H) 4.90 (t, 1H) 4.02 (br. s., 2H) 3.79 (d, 2H) 3.49 (t, 2H) 2.35 (br. s., 2H) 1.42-1.46 (m, 9H)

Preparation 5: (1S,6R/1R,6S)-1,1-dimethylethyl-6-(3,4-dichlorophenyl)-1-(hydroxymethyl)-3-azabicyclo[4.1.0]heptane-3-carboxylate (P5)

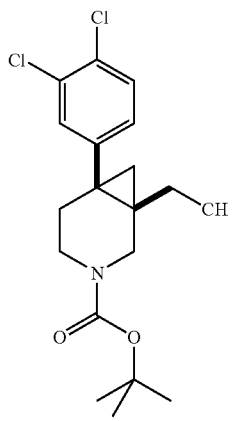

Method A:

To a stirred solution of CH₂I₂ (13.39 g) in dry DCM (83 mL) under Argon atmosphere, at 0° C., ZnEt₂ (1M in hexane, 25 mL) was added dropwise, the mixture was stirred at 0° C. for 20 minutes and then cooled at −20° C. At this point a solution of 1,1-dimethylethyl-4-(3,4-dichlorophenyl)-5-(hydroxymethyl)-3,6-dihydro-1(2H)-pyridinecarboxylate (734 mg, P4) in dry DCM (3.5 mL) was added dropwise, the reaction mixture was stirred for additional 30 mins, then 40 mins at 0° C. and overnight at room temperature. Saturated aqueous NH₄Cl solution (100 mL) was poured into the reaction flask and the mixture was vigorously stirred for 10 minutes, the phases were separated and the organic layer was evaporated under reduced pressure. The residue was taken up with diethyl ether (50 mL) and this volume was added to the previous NH₄Cl solution: the total mixture was poured into a separator funnel. The organic phase was treated with saturated NH₄Cl (3×20 mL), then with HCl (5%) (20 mL), the organic and aqueous acidic phases were separated and submitted to two different processing.

The organic phase was evaporated obtaining a crude product (280 mg) that was purified by flash-chromatography (eluting with ethyl acetate/cycloexane 1:3) to give the still impure title compound (70 mg).

The watery phase was washed with diethyl ether (50 mL) and strongly basified with NaOH 2N, then the basic solution was extracted with diethyl ether (3×50 mL), the combined organic phases were dried on anhydrous Na₂SO₄ and the solvent was removed under reduced pressure, obtaining a crude material (210 mg) containing as major component [(1S,6R/1R,6S)-6-(3,4-dichlorophenyl)-3-azabicyclo[4.1.0]hept-1-yl]methanol)].

MS (m/z): 272 [MH]⁺.

A portion of this crude material (159 mg) was dissolved in dry DCM (5 mL) under Argon atmosphere and stirred at rt, bis(1,1-dimethylethyl) dicarbonate (156 mg) was added at room temperature and the mixture was left stirring overnight. The solvent was evaporated under reduced pressure and the residue was taken up with diethyl ether (15 mL). This solution was washed with saturated NH₄Cl (15 mL), the watery phase was extracted with diethyl ether (3×10 mL), the combined organic phases were dried on anhydrous Na₂SO₄ and the solvent was removed under reduced pressure obtaining a crude product that was combined with the previously obtained 70 mg of the impure title compound. This material was again purified by flash-chromatography (eluting with diethyl ether/n-hexane 1:2 to 1:1) to give a still impure title compound as a mixture with 1,1-dimethylethyl-4-(3,4-dichlorophenyl)-5-(hydroxymethyl)-3,6-dihydro-1(2H)-pyridinecarboxylate (170 mg).

MS (m/z): 372 [MH]⁺.

Method B: bis(1,1-dimethylethyl) dicarbonate (838 mg) was added at room temperature to a solution of [(1S,6R/1R,6S)-6-(3,4-dichlorophenyl)-3-azabicyclo[4.1.0]hept-1-yl]methanol (840 mg, E4, impure compound obtained as described in E4, Method A) in dry DCM (25 mL), and the mixture was stirred overnight. The mixture was heated at 40° C. for 2 hours and then cooled at room temperature. Saturated NH₄Cl (50 mL) and DCM (20 mL) were added to the reaction mixture and, after stirring for 10 mins, the phases were separated. The organic phase was evaporated and the residue was dissolved in diethyl ether (50 mL). The organic phase was washed with saturated NH₄Cl (3×30 mL), was dried on anhydrous Na₂SO₄ and the solvent was removed under reduced pressure. The crude oil (920 mg) obtained was purified by flash-chromatography (eluting with ethyl acetate/cyclohexane 1:3) to give an impure title compound as a mixture with 1,1-dimethylethyl-4-(3,4-dichlorophenyl)-5-(hydroxymethyl)-3,6-dihydro-1(2H)-pyridinecarboxylate (260 mg) and impure 1,1-dimethylethyl (1R,6S)-6-(3,4-dichlorophenyl)-1-[({[(1,1-dimethylethyl)oxy]carbonyl}oxy)methyl]-3-azabicyclo[4.1.0]heptane-3-carboxylate (185 mg) [MS (m/z): 472 [MH]⁺]. 1,1-dimethylethyl (1R,6S)-6-(3,4-dichlorophenyl)-1-[({[(1,1-dimethylethyl)oxy]carbonyl}oxy)methyl]-3-azabicyclo[4.1.0]heptane-3-carboxylate was dissolved in MeOH (7 mL) under argon and the stirred solution was cooled at 0°. NaOH (0.5M, 3 mL) was added dropwise and the mixture was stirred for 20 mins at 0° C., 30 mins at 50° C. and 1.5 hours at 70° C. MeOH was evaporated under reduced pressure, the watery residue was diluted with water (20 mL) and extracted with diethyl ether (3×20 mL). The combined organic phases were dried on anhydrous Na₂SO₄ and the solvent was removed under reduced pressure to give another batch of the still impure title compound as a mixture with 1,1-dimethylethyl-4-(3,4-dichlorophenyl)-5-(hydroxymethyl)-3,6-dihydro-1(2H)-pyridinecarboxylate (130 mg).

MS (m/z): 372 [MH]⁺.

Method C: to a stirred solution of methyl 6-(3,4-dichlorophenyl)-2-oxo-3-azabicyclo[4.1.0]heptane-1-carboxylate (P16, 0.19 g) in THF (3 mL), at 0° C. and under a nitrogen atmosphere, BH₃THF complex (1M/THF, 2.38 mL) was added dropwise, then the reaction mixture was allowed to reach RT and stirred at reflux for 4 h. The reaction mixture was cooled to 0° C. and the pH was adjusted to 2-3 with aqueous 20% HCl solution, then the ice-bath was removed and the mixture was stirred at RT for 15 min. DCM was added and the pH was brought to 8-9 with aqueous 2N NaOH solution. The organic phase was washed with brine, dried over Na$_2$SO$_4$ and the solvent evaporated under reduced pressure. The crude product was dissolved in DCM, Boc$_2$O (0.136 g) was added and the reaction mixture stirred for 1 h at RT. The reaction was extracted with ether, the organic phase washed with aqueous saturated NaHCO3 solution, brine, dried over Na2SO4 and the solvent removed under reduced pressure to give 0.195 g of the crude Title compound as a colourless oil that was used without any further purification.

Preparation 6: (1S,6R/1R,6S)-1,1-dimethylethyl-6-(3,4-dichlorophenyl)-1-[(methyloxy)methyl]-3-azabicyclo[4.1.0]heptane-3-carboxylate (P6)

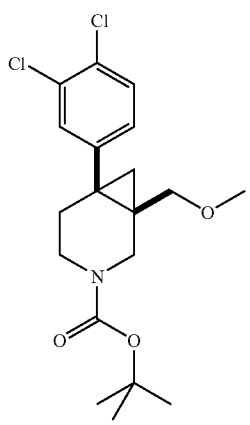

To a stirred solution of (1S,6R/1R,6S)-1,1-dimethylethyl 6-(3,4-dichlorophenyl)-1-(hydroxymethyl)-3-azabicyclo [4.1.0]heptane-3-carboxylate (110 mg, P5, impure compound obtained as described in P5, Method A) in dry THF (2 mL) under Argon atmosphere, at 0° C., NaH (60% on mineral oil, 11.7 mg) was added in one portion and the stirring continued for 30 minutes. After this period CH$_3$I (18.2 µL) was added dropwise and the reaction was allowed to reach room temperature and stirred for 1.5 h, then an additional amounts of NaH (5.3 mg) and CH$_3$I (8.3 µL) were added. The reaction mixture was left stirring for 2 hour at room temperature, then was cooled to 0° C., aqueous saturated NH$_4$Cl solution (15 mL) and diethyl ether (20 mL) were added and the mixture was vigorously stirred for 10 minutes at room temperature. The phases were separated and the watery one was extracted with diethyl ether (3×10 mL). The combined organic phases were washed with brine (3×20 mL), dried on anhydrous Na$_2$SO$_4$, the solvent evaporated obtaining a crude product (106 mg) that was purified by flash-chromatography (eluting with diethyl ether/n-hexane 40:60) to give the still impure titled compound as a mixture with 1,1-dimethylethyl 4-(3,4-dichlorophenyl)-5-[(methyloxy)methyl]-3,6-dihydro-1(2H)-pyridinecarboxylate (80 mg).

MS (m/z): 386 [MH]+

Preparation 7: 3-(3,4-dichlorophenyl)-2-propyn-1-ol (P7)

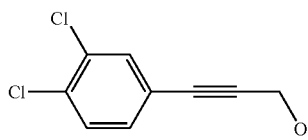

Method A: The title compound (2.94 g) was prepared in analogy with the method described in *JOC* 2005, 70, 4043-4053 starting from 3,4-dichloroiodobenzene (4 g, two preparation were carried out).

Method B: a mixture of 3,4-dichloroiodobenzene (300 mg), propargyl alcohol (128 µL), CuI (10 mg), K$_2$CO$_3$ (302 mg), Pd(PPh$_3$)$_4$ (12 mg) in DMF (2 mL) was irradiated with MicroWave at 100° C. for 20 min. Aqueous saturated solution NH$_4$Cl was then added followed by DCM. After separation of the two phases the organic layer was dried and evaporated in vacuo. The crude product was purified by flash chromatography (eluting with cyclohexane/ethyl acetate 7/3) to give the title compound (40 mg).

NMR ($^1$H, CDCl$_3$): δ 7.58 (s, 1H), 7.41 (d, 1H), 7.27 (d, 1H), 4.52 (d, 2H), 1.75 (t, 1H)

Preparation 8: 3-(3,4-dichlorophenyl)-2-propynal (P8)

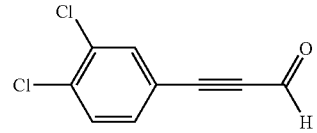

To a solution of 3-(3,4-dichlorophenyl)-2-propyn-1-ol (2.980 g, P7, from Method A and B described for P7) in dry DCM (74 mL) and Dess-Martin periodinane (9.43 g) was added. The mixture was stirred at room temperature over night. NaS$_2$O$_3$ (19 g) and NaHCO$_3$ saturated solution were then added to the mixture and it was stirred at room temperature for 1 hour. Then the organic phase was separated and washed with brine. The organic layer was dried and concentrated under reduced pressure to give the crude title product (2.9 g) that was used without further purification.

NMR ($^1$H, CDCl$_3$): δ 9.48 (s, 1H), 7.73 (s, 1H), 7.55 (d, 1H), 7.42 (m, 1H).

Preparation 9: (1S,5S/1R,5R)-1-(3,4-dichlorophenyl) bicyclo[3.1.0]hexan-3-one (P9)

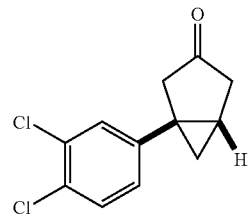

The title compound was prepared in analogy with the method described in *J. Am. Chem. Soc.* 2004, 126, 8654 from 3-(3,4-dichlorophenyl)-2-propynal (2.9 g, P8) in 880 mg yield as an orange foam.

NMR ($^1$H, CDCl$_3$): δ 7.45 (d, 1H), 7.28 (s, 1H), 7.11 (d, 1H), 2.89 (m, 2H), 2.70 (d, 1H), 2.42 (d, 1H), 2.05 (m, 1H), 1.38 (m, 1H), 0.72 (m, 1H).

Preparation 10: (1S,5S/1R,5R)-1-(3,4-dichlorophenyl)bicyclo[3.1.0]hexan-3-one oxime (P10)

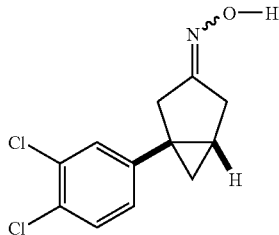

To a solution of hydroxylamine mono hydrate (1.26 g) and sodium acetate (2.3 g) in water (7 mL), a solution of (1S,5S/1R,5R)-1-(3,4-dichlorophenyl)bicyclo[3.1.0]hexan-3-one (0.860 g, P9) in ethanol (18 ml) was added at room temperature and the reaction mixture was stirred over night. After ethanol elimination under reduced pressure, the aqueous solution was extracted with DCM. The organic phase was dried and concentrated under reduced pressure to give the title compound (870 mg).

NMR ($^1$H, CDCl$_3$): δ 7.40 (d, 1H), 7.26 (m, 1H), 7.05 (m, 1H), 3.33-2.60 (m, 4H), 1.89 (m, 1H), 1.15 (m, 1H), 0.68 (m, 1H). MS (m/z): 256 [MH]+.

Preparation 11: (1R,6R/1S,6S)-1-(3,4-dichlorophenyl)-3-azabicyclo[4.1.0]heptan-4-one and (1R,6S/1S,6R)-6-(3,4-dichlorophenyl)-3-azabicyclo[4.1.0]heptan-4-one (P11)

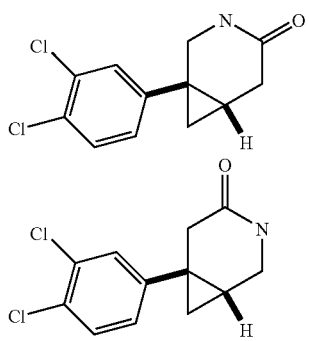

To a solution of (1S,5S/1R,5R)-1-(3,4-dichlorophenyl)bicyclo[3.1.0]hexan-3-one oxime (0.870 g, P10) in acetone (29 ml) sodium carbonate (solution 5% w/w in water, 25 ml) was added. Then, under vigorous stirring, a solution of tosyl chloride (969 mg) in acetone was added and the mixture stirred at room temperature for 30 minutes. The reaction mixture was heated at reflux for 4 h and at room temperature over night. After acetone elimination under reduced pressure, the residue was dissolved in NaHCO$_3$ saturated solution and it was extracted with DCM. The organic phase was dried and concentrated under reduced pressure. The crude was purified by flash chromatography (DCM/MeOH from 98/2 to 95/5) to give 640 mg of the mixture of title compounds.

MS (m/z): 256 [MH]+.

Preparation 12: [(3-bromo-3-buten-1-yl)oxy](1,1-dimethylethyl)diphenylsilane (P12)

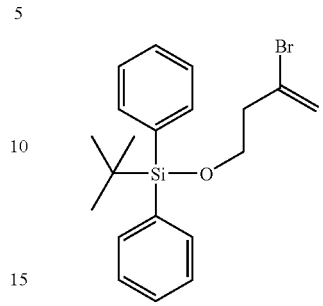

The title compound was prepared in 8.7 g yield as a colourless oil, following an analogous procedure to that reported in WO2005058884, starting from 3-bromo-3-buten-1-ol (4 g), chloro(1,1-dimethylethyl)diphenylsilane (8.27 ml), imidazole (2.34 g) and N,N-dimethyl-4-pyridineamine (0.025 g).

Preparation 13: {[3-(3,4-dichlorophenyl)-3-buten-1-yl]oxy}(1,1-dimethylethyl)diphenylsilane (P13)

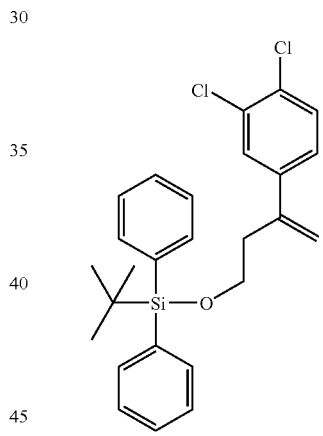

[(3-Bromo-3-buten-1-yl)oxy](1,1-dimethylethyl)diphenylsilane (P12, 3.50 g) and (3,4-dichlorophenyl)boronic acid (2.06 g) were dissolved in toluene (45 mL), the stirred solution was degassed, then tetrakis(triphenylphosphine)palladium(0) (0.363 g) and ethanol (33 mL) were added and the mixture was degassed again. A 2N aqueous solution of Na$_2$CO$_3$ (24 mL) was added and the mixture was heated to 80° C. and stirred under nitrogen atmosphere for 3 h at this temperature. After cooling to RT, the reaction mixture was extracted with ethyl ether, the organic phase was washed with brine, dried over Na$_2$SO$_4$ and the solvent removed under reduced pressure. The crude product was purified by flash chromatography (eluting with cy/EA from 100/0 to 95/5) to give the title compound (2.65 g) as a colourless oil.

NMR ($^1$H, CDCl$_3$): δ 7.55-7.69 (m, 4H), 7.40-7.47 (m, 3H), 7.34-7.40 (m, 4H), 7.32 (d, 1H), 7.11 (dd, 1H), 5.25 (dd, 2H), 3.75 (t, 2H), 2.28-3.12 (m, 2H), 0.62-1.26 (m, 9H).

Preparation 14: dimethyl 2-(3,4-dichlorophenyl)-2-(2-{[(1,1-di methylethyl)(diphenyl)silyl]oxy}ethyl)-1,1-cyclopropanedicarboxylate (P14)

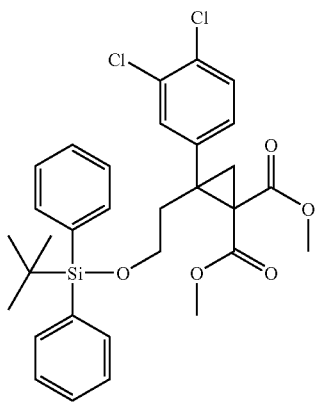

{[3-(3,4-Dichlorophenyl)-3-buten-1-yl]oxy}(1,1-dimethylethyl)diphenylsilane (P13, 2.25 g), dimethyl diazopropanedioate (1.2 g) (prepared in an analogous manner as reported in *Synthetic Communications*, 17(4), 1709-16, 1987) and rhodium (II) acetate dimer (0.060 g) were mixed together and heated at 100° C. for 40 min. After cooling, the residue was treated with DCM and the mixture was filtered. The filtrate was evaporated under reduced pressure and the crude product was purified by flash chromatography (Cy/EA from 1/0 to 95/5) to give the title compound (2.38 g) as a colourless oil.

NMR ($^1$H, CDCl$_3$): δ 7.51-7.61 (m, 4H), 7.25-7.47 (m, 8H), 7.05 (dd, 1H) 3.83 (s, 3H), 3.45 (s, 3H), 3.30-3.62 (m, 2H), 2.00-2.29 (m, 2H), 1.83 (d, 1H), 1.57 (s, 1H), 0.94-1.13 (m, 9H).

Preparation 15: methyl 1-(aminocarbonyl)-2-(3,4-dichlorophenyl)-2-(2-hydroxyethyl)cyclopropanecarboxylate (P15)

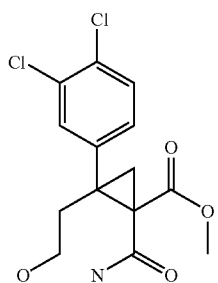

Tetrabutylammonium fluoride (TBAF) (5.6 mL, 1.1M/TFH) was added dropwise to a stirred solution of dimethyl 2-(3,4-dichlorophenyl)-2-(2-{[(1,1-dimethylethyl)(diphenyl)silyl]oxy}ethyl)-1,1-cyclopropanedicarboxylate (P14, 2.38 g) in THF (27 mL), at 0° C. After 4 h the ice-bath was removed and the reaction mixture was stirred for 3 h at RT. The solvent was removed under reduced pressure, the residue was treated with ether and water, the organic phase washed with brine, dried over Na$_2$SO$_4$ and the solvent evaporated under vacuum to give the crude lactone intermediate (2.08 g). This product was dissolved in a mixture of THF (15 mL) and methanol (10 mL), at RT, aqueous NH$_4$OH (28%, 16 mL) was added dropwise and the reaction mixture was stirred for 4 h. The mixture was concentrated under reduced pressure, the residue was taken up with DCM and water, the organic phase was washed with brine, dried over Na$_2$SO$_4$ and the solvent evaporated under vacuum. The crude product was purified by FC (eluting with DCM/methanol from 1/0 to 9/1) to give the title compound (0.89 g) as a white foam.

NMR ($^1$H, CDCl$_3$): δ 8.14 (br. s., 1H), 7.60 (dd, 1H), 7.41-7.50 (m, 2H), 5.79 (br. s., 1H), 3.47-3.59 (m, 2H), 3.13-3.15 (m, 3H), 2.29-2.33 (m, 1H), 2.23-2.26 (m, 1H), 2.04-2.22 (m, 2H).

Preparation 16: methyl (1S,6R/1R,6S)-6-(3,4-dichlorophenyl)-2-oxo-3-azabicyclo[4.1.0]heptane-1-carboxylate (P16)

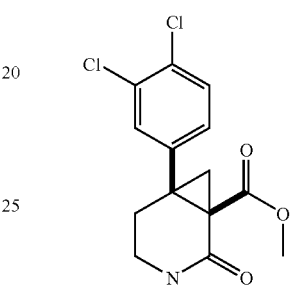

o a stirred solution of methyl 1-(aminocarbonyl)-2-(3,4-dichlorophenyl)-2-(2-hydroxyethyl)cyclopropanecarboxylate (P15, 0.46 g) in DCM (6 mL), at 0° C., triethylamine (0.25 mL) was added followed by methanesulfonyl chloride (0.16 mL). The ice-bath was removed and the reaction mixture was stirred at RT for 3 h. The mixture was extracted with further DCM, the organic phase washed with saturated NH$_4$Cl, brine, dried over Na$_2$SO$_4$ and the solvent evaporated under reduced pressure to give 0.54 g of the intermediate mesylate as a white foam. To a stirred solution of this product in DMF (6 mL), at RT, NaI (0.22 g) was added followed by NaH (60% in oil, 63 mg) portionwise, and the reaction mixture was stirred for 0.5 h. The reaction mixture was extracted with ether and NH$_4$Cl solution, the organic phase washed with water, brine, dried over Na$_2$SO$_4$ and the solvent evaporated under vacuum. The crude product was purified by FC (eluting with cy/EA from 9/1 to 1/9) to give the Title product (0.19 g).

NMR ($^1$H, CDCl$_3$): δ 7.45 (d, 1H) 7.39 (d, 1H) 7.19 (dd, 1H) 5.79 (br. s., 1H) 3.52 (s, 3H) 3.29-3.38 (m, 1H) 3.20-3.28 (m, 1H) 2.37 (td, 1H) 2.29 (d, 1H) 2.12-2.17 (m, 1H) 1.97 (d, 1H). MS (m/z): 314 [MH]$^+$.

Preparation 18: ethyl 3-{[3-(ethyloxy)-3-oxopropyl]amino}butanoate (P18)

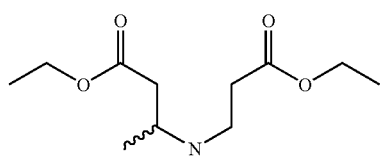

A solution of ethyl 3-aminobutanoate (4.2 g) and of ethyl 2-propenoate (3.83 mL) in EtOH (20 mL) was stirred at room temperature for 8 h. The solvent was evaporated under reduced pressure and the residue purified by chromatography on NH column eluting with a gradient from 100% cyclohexane to 90% ethyl acetate/cyclohexane. The title compound was isolated as a colourless oil, 3.9 g (MS (m/z): 232 [MH]⁺.

Preparation 19: ethyl 3-{{[(1,1-dimethylethyl)oxy]carbonyl}[3-(ethyloxy)-3-oxopropyl]amino}butanoate (P19)

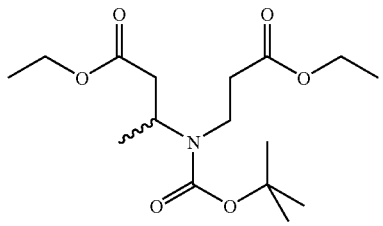

A mixture containing ethyl 3-{[3-(ethyloxy)-3-oxopropyl]amino}butanoate (P18, 3.5 g), 1,4-dioxane (8.1 mL), water (16.2 mL) and a 5% solution of potassium carbonate (8.4 mL) was cooled with an ice-bath. Di-tert-butyl dicarbonate (3.51 mL) was added slowly with stirring. The stirring was maintained for 15 min and then continued at room temperature for 3 h. The mixture was left at room temperature for 48 hours. After concentration under reduced pressure, the residue was extracted with diethyl ether (2×200 mL). The ethereal phase was washed first with 1N HCl, then with water (20 mL) and finally dried. Evaporation of the solvents afforded a crude material (4.6 g) which was then used without further purification.

NMR (¹H, CDCl₃): δ 4.08-4.20 (m, 4H), 3.64-3.72 (m, 1H), 3.32-3.53 (m, 2H), 2.39-2.74 (m, 4H), 1.43-1.52 (m, 9H), 1.19-1.33 (m, 9H)

Preparation 20: 1-(1,1-dimethylethyl) 3-ethyl 4-hydroxy-6-methyl-5,6-dihydro-1,3(2H)-pyridinedicarboxylate and 1-(1,1-dimethylethyl) 3-ethyl 4-hydroxy-2-methyl-5,6-dihydro-1,3(2H)-pyridinedicarboxylate (P20)

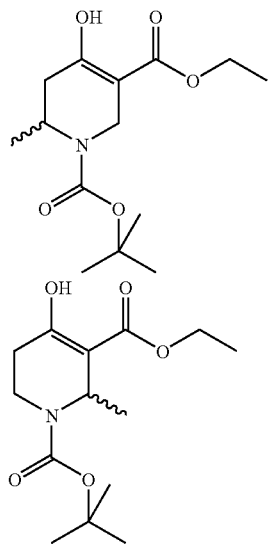

Ethyl 3-{{[(1,1-dimethylethyl)oxy]carbonyl}[3-(ethyloxy)-3-oxopropyl]amino}butanoate (P19, 2.5 g) was dissolved in toluene (15 mL) and added at 0° C. to a solution of sodium ethoxide preformed by adding slowly and portionwise sodium hydride 60% dispersed on mineral oil (0.453 g) to a solution of ethanol (0.7 mL) in toluene (5 mL). The mixture was stirred at room temperature overnight. Then the solvent was evaporated under reduced pressure and the residue dissolved in ethyl acetate (20 mL), washed with 1N HCl (20 mL), dried and concentrated under vacuum. Purification by flash chromatography on silica gel eluting with a gradient 5-50% ethyl acetate/cyclohexane afforded the title compounds as pale yellow oil (0.7 g) as mixture of regioisomers.

MS (m/z): 230 [M−56]⁺, 186 [MH−100]⁺.

Preparation 21: 1-(1,1-dimethylethyl) 3-ethyl 4-(3,4-dichlorophenyl)-6-methyl-5,6-dihydro-1,3(2H)-pyridinedicarboxylate and 1-(1,1-dimethylethyl) 3-ethyl 4-(3,4-dichlorophenyl)-2-methyl-5,6-dihydro-1,3(2H)-pyridinedicarboxylate (P21)

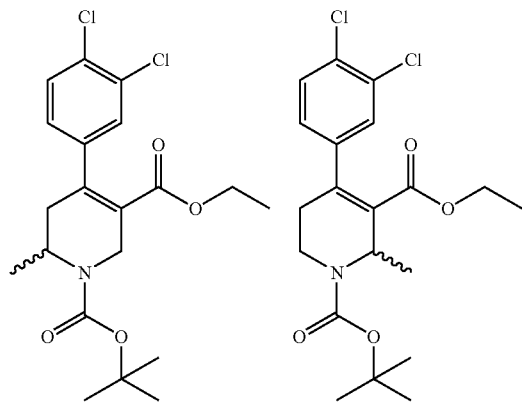

To a stirred solution of a mixture of regioisomers 1-(1,1-dimethylethyl) 3-ethyl 6-methyl-4-oxo-1,3-piperidinedicarboxylate and 1-(1,1-dimethylethyl) 3-ethyl 4-(3,4-dichlorophenyl)-2-methyl-5,6-dihydro-1,3(2H)-pyridinedicarboxylate (P20, 0.7 g) in dry DMF (6 mL) at 0° C. under nitrogen, sodium hydride 60% dispersed on mineral oil (0.118 g) was added portionwise and the reaction mixture was stirred at 0° C. for 10 min. Then a solution of 1,1,1-trifluoro-N-phenyl-N-[(trifluoromethyl)sulfonyl]methanesulfonamide (0.88 g) in dry DMF (1 mL) was added dropwise and stirring was continued for 1 h. Saturated NH₄Cl (10 mL) and diethyl ether (30 mL) were poured into the reaction mixture. The organic phase was separated, dried and concentrated under vacuum. The residue was then purified by chromatography on silica gel eluting with a gradient 5-50% ethyl acetate/cyclohexane. The isolated material (MS (m/z): 440 [M+Na]⁺, 362 [MH−56]⁺), (0.65 g) was dissolved in a mixture toluene (15 mL) and ethanol (11 mL); (3,4-dichlorophenyl)boronic acid (0.357 g) and sodium carbonate 2.0M solution (4.7 mL) were added and the suspension was degassed with a steam of nitrogen for few minutes. Then Pd(Ph₃P)₄ (0.045 g) was added and the reaction mixture was heated to 80° C. for 1 h. Then it was cooled to room temperature, the solvent was evaporated under reduced pressure and the residue partitioned between ethyl acetate (50 mL) and water (50 mL). The organic layer was washed with brine (20 mL), dried and concentrated. Purification by chromatography on silica gel eluting with a gradient 5-25% ethyl acetatecyclohexane afforded the title compounds as a mixture of regioisomers as pale yellow oil (0.45 g).

MS (m/z): 437 [M+Na]⁺.

Preparation 22: 1,1-dimethylethyl 4-(3,4-dichlorophenyl)-5-(hydroxymethyl)-2-methyl-3,6-dihydro-1(2H)-pyridinecarboxylate (P22)

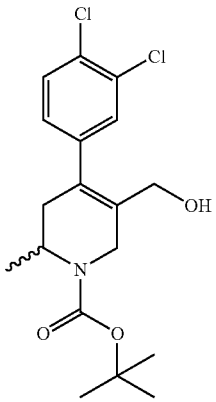

A mixture of regioisomers 1-(1,1-dimethylethyl) 3-ethyl 4-(3,4-dichlorophenyl)-6-methyl-5,6-dihydro-1,3(2H)-pyridinedicarboxylate and 1-(1,1-dimethylethyl) 3-ethyl 4-(3,4-dichlorophenyl)-2-methyl-5,6-dihydro-1,3(2H)-pyridinedicarboxylate (P21, 0.45 g) was dissolved in toluene (15 mL) and cooled to −20° C. Lithium aluminium hydride 1.0M in THF (0.869 mL) was added dropwise at −20° C. and the mixture was stirred at this temperature for 2 h. The reaction was then quenched with a saturated solution of NH$_4$Cl (10 mL) and diluted with ethyl acetate (20 mL); the organic layer was separated, washed with water (20 mL), dried and concentrated in vacuo. Purification by chromatography on silica gel eluting with a gradient 100% cyclohexane-50% cyclohexane/ethyl acetate afforded 240 mg of title compound as colourless oil. The structure of the major regioisomer was confirmed by nOe NMR experiments.

NMR ($^1$H, CDCl$_3$): δ 7.42 (d, 1H), 7.28 (d, 1H), 7.03 (dd, 1H), 4.52-4.63 (m, 1H), 4.44-4.45 (m, 1H), 3.97-4.09 (m, 2H), 3.69-3.79 (m, 1H), 2.69-2.81 (m, 1H), 2.00-2.08 (m, 1H), 1.47-1.54 (m, 9H), 1.38-1.43 (m, 1H), 1.19 (d, 3H).

Preparation 23: ({3-[4-chloro-3-(trifluoromethyl)phenyl]-3-buten-1-yl}oxy)(1,1-dimethylethyl)diphenylsilane (P23)

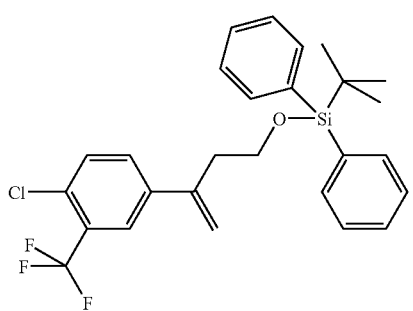

The title compound (1.85 g) was obtained starting from [(3-bromo-3-buten-1-yl)oxy](1,1-dimethylethyl)diphenylsilane (P12, 1.0 g) according to a similar procedure to that previously described for Preparation 13.

NMR ($^1$H, CDCl$_3$): δ 7.17-7.22 (m, 1H), 7.08-7.15 (m, 4H), 6.83-6.98 (m, 7H), 6.77-6.80 (m, 1H), 4.87-4.91 (m, 1H), 4.69-4.74 (m, 1H), 3.22-3.30 (m, 2H), 2.22-2.29 (m, 2H), 0.50-0.56 (m, 9H).

Preparation 24: dimethyl-2-[4-chloro-3-(trifluoromethyl)phenyl]-2-(2-{[(1,1-dimethylethyl)(diphenyl)silyl]oxy}ethyl)-1,1-cyclopropanedicarboxylate (P24)

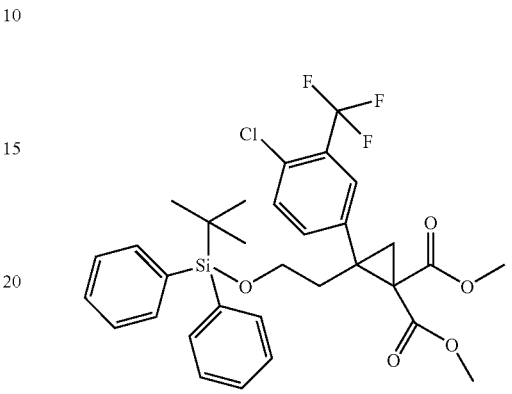

The title compound (1.92 g) was obtained as a colourless oil starting from ({3-[4-chloro-3-(trifluoromethyl)phenyl]-3-buten-1-yl}oxy)(1,1-dimethylethyl)diphenylsilane (P23, 1.85 g) according to a similar procedure to that previously described for Preparation 14.

NMR ($^1$H, CDCl$_3$): δ 7.50-7.62 (m, 5H), 7.29-7.46 (m, 8H), 3.82-3.85 (m, 3H), 3.50-3.59 (m, 1H), 3.36-3.44 (m, 4H), 2.17-2.26 (m, 2H), 1.85-1.89 (m, 1H), 1.59-1.72 (m, 1H), 1.01-1.08 (m, 9H)

Preparation 25: methyl-1-(aminocarbonyl)-2-[4-chloro-3-(trifluoromethyl)phenyl]-2-(2-hydroxyethyl)cyclopropanecarboxylate (P25)

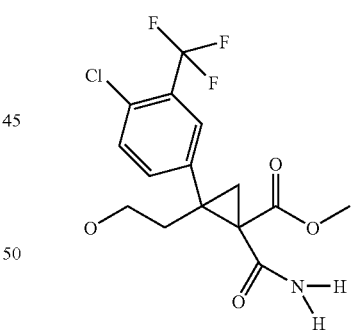

The title compound (0.64 g) was obtained as a white solid after crystallization from DCM/5% hexane) by reacting dimethyl 2-[4-chloro-3-(trifluoromethyl)phenyl]-2-(2-{[(1,1-dimethylethyl)(diphenyl)silyl]oxy}ethyl)-1,1-cyclopropanedicarboxylate (P24, 1.92 g) with TBAF 1.1M in THF (4.7 mL) in THF 20 mL and then treating the crude intermediate with NH$_4$OH 28% (14 mL) in a mixture THF (10 mL)/MeOH (7 mL), according to a similar procedure to that previously described for Preparation 15.

NMR ($^1$H, CDCl$_3$): δ 8.18 (br. s., 1H), 7.59-7.61 (m, 1H), 7.46-7.48 (m, 1H), 7.44-7.46 (m, 1H), 5.79 (br. s., 1H), 3.48-3.58 (m, 2H), 3.14-3.15 (m, 3H), 2.30-2.33 (m, 1H), 2.23-2.26 (m, 1H), 2.05-2.22 (m, 2H)

Preparation 26: methyl (1R,6S/1S,6R)-6-[4-chloro-3-(trifluoromethyl)phenyl]-2-oxo-3-azabicyclo[4.1.0]heptane-1-carboxylate (P26)

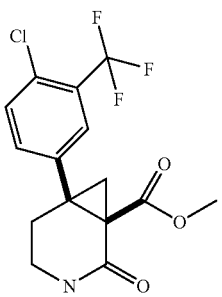

The title compound (0.35 g) was obtained reacting methyl 1-(aminocarbonyl)-2-[4-chloro-3-(trifluoromethyl)phenyl]-2-(2-hydroxyethyl)cyclopropanecarboxylate (P25, 0.64 g) with Et$_3$N (0.37 mL) and trifluoromethane sulfonyl chloride (0.19 mL) in DCM (10 mL) and then treating the intermediate with sodium hydride 60% dispersed on mineral oil (84 mg) in DMF (5 mL), according to a similar procedure to that previously described for Preparation 16, Method A.

NMR ($^1$H, CDCl$_3$): δ 7.64-7.73 (m, 1H), 7.45-7.48 (m, 2H), 6.83 (br. s., 1H), 3.47-3.50 (m, 3H), 3.32-3.41 (m, 1H), 3.19-3.28 (m, 1H), 2.26-2.42 (m, 2H), 2.11-2.19 (m, 1H), 2.00-2.04 (m, 1H).

Preparation 27: 1,1-dimethylethyl (1R,6S/1S,6R)-6-[4-chloro-3-(trifluoromethyl)phenyl]-1-(hydroxymethyl)-3-azabicyclo[4.1.0]heptane-3-carboxylate (P27)

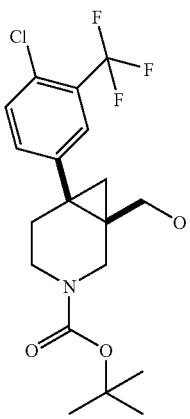

To a stirred solution of (1R,6S/1S,6R)-6-[4-chloro-3-(trifluoromethyl)phenyl]-2-oxo-3-azabicyclo[4.1.0]heptane-1-carboxylate (P26, 0.35 g) in THF (8 mL), at 0° C. and under a nitrogen atmosphere, BH$_3$THF complex (1M/THF, 4.03 mL) was added dropwise, then the reaction mixture was allowed to reach RT and stirred at reflux for 4 h. The reaction mixture was cooled to 0° C. and the pH was adjusted to 2-3 with aqueous 20% HCl, then the ice-bath was removed and the mixture was stirred at RT for 15 min. DCM was added and the pH was brought to 8-9 with 2N NaOH. The organic phase was separated, dried over Na$_2$SO$_4$ and the solvent evaporated under reduced pressure. The crude product thus obtained (310 mg) was treated with di-tert-butyl dicarbonate (220 mg) in DCM (10 mL) at at 0° C. and stirred under these conditions for 1 hour. Then NH$_4$Cl was added, the organic phase was separated and washed with NaHCO$_3$, brine, dried and evaporated under reduced pressure to give a crude. This was the purified by flash chromatography eluting with AcOEt/Cy 1:9 to 1:1 to afford the title compound (300 mg).

MS (m/z): 406 [MH]$^+$, 350 [MH–56]$^+$.

Preparation 28: 1-(1,1-dimethylethyl) 3-methyl 4-oxo-1,3-piperidinedicarboxylate (P28)

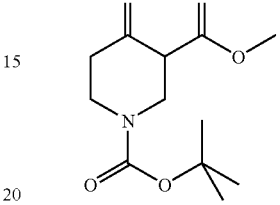

To an ice cooled suspension of methyl 4-oxo-3-piperidinecarboxylate hydrochloride (15.01 g) in dichloromethane (250 mL) was added bis(1,1-dimethylethyl)dicarbonate (17.76 g), then triethylamine (27 mL) was added dropwise. The resulting mixture was allowed to reach room temperature and stirred for 4 h. Saturated NH$_4$Cl was poured into the reaction mixture and the phases were separated, the organic layer was dried over Na$_2$SO$_4$, filtered and evaporated under reduced pressure. Diethylether was added to the residue and filtered over a celite pad. The solvent was removed under reduced pressure to obtain the title compound (16.96 g).

MS (m/z): 258 [MH]$^+$, 202 [MH–56]$^+$.

Preparation 29: 1-(1,1-dimethylethyl) 3-methyl 4-(4-chlorophenyl)-5,6-dihydro-1,3(2H)-pyridinedicarboxylate (P29)

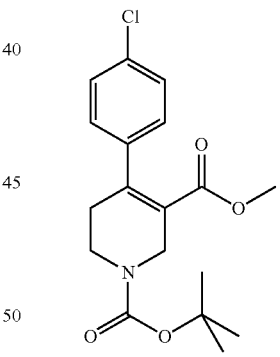

To an ice cooled solution of 1-(1,1-dimethylethyl) 3-methyl 4-oxo-1,3-piperidinedicarboxylate (P28, 8.5 g) in N,N-dimethylformamide (85 mL), sodium hydride 60% in mineral oil (1.46 g) was added and the resulting mixture was stirred for 10 min at 0° C. To the mixture was added a solution of 1,1,1-trifluoro-N-phenyl-N-[(trifluoromethyl)sulfonyl]methanesulfonamide (12.39 g) in N,N-dimethylformamide (62 mL) and the resulting mixture was allowed to room temperature and stirred for 1 h. Diethylether and saturated NH$_4$Cl were added. The aqueous layer was washed with diethylether, and then the collected organic layers were washed with water. The organic phase was dried over Na$_2$SO$_4$, filtered and evaporated under reduced pressure. The crude was purified by flash-chromatography (eluting with cyclohexane/ethylacetate from 1/0 to 9/1) to obtain 1-(1,1-dimethylethyl) 3-methyl 4-{[(trifluoromethyl)sulfonyl]oxy}-5,6-dihydro-1,3

(2H)-pyridinedicarboxylate (7.73 g). To a solution of this compound (3 g) and (4-chlorophenyl)boronic acid (1.38 g) in toluene (41 mL), a solution of Pd(PPh$_3$)$_4$ (0.32 g) in ethanol (30 mL) was added followed by Na$_2$CO$_3$ (2M, 22.5 mL) and the resulting mixture was heated at 80° C. for 2 h. The reaction mixture was allowed to reach room temperature, then diethylether was added and the phases were separated. The organic layer was dried over Na$_2$SO$_4$, filtered and evaporated under reduced pressure. The resulting crude was purified by flash-chromatography (eluting with cyclohexane/ethylacetate from 1/0 to 8/2) to afford the title compound (2.35 g).

MS (m/z): 352 [MH]$^+$, 296 [MH−56]$^+$.

Preparation 30: 1,1-dimethylethyl 4-(4-chlorophenyl)-5-(hydroxymethyl)-3,6-dihydro-1(2H)-pyridinecarboxylate (P30)

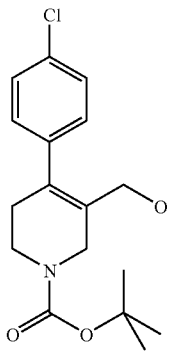

To a stirred solution of 1-(1,1-dimethylethyl) 3-methyl 4-(4-chlorophenyl)-5,6-dihydro-1,3(2H)-pyridinedicarboxylate (P29, 1.85 g) in diethylether (37.04 mL) at −20° C., LiAlH$_4$ 1M solution in diethylether (3.68 mL) was added dropwise and the resulting mixture was stirred at −20° C. for 20 min. A solution of HCl 2% in water (4.44 mL), diethylether and water were added and the organic phase was separated, dried over Na$_2$SO$_4$, filtered and evaporated under reduced pressure to obtain the title compound (1.487 g).

NMR ($^1$H, CDCl$_3$): δ ppm 7.33 (d, 2H) 7.12 (d, 2H) 4.13 (s, 2H) 4.03 (s, 2H) 3.61 (t, 2H) 2.40 (s, 2H) 1.46-1.52 (m, 9H)

Preparation 31: 1,1-dimethylethyl (1R,6S/1S,6R)-6-(4-chlorophenyl)-1-(hydroxymethyl)-3-azabicyclo[4.1.0]heptane-3-carboxylate (P31).

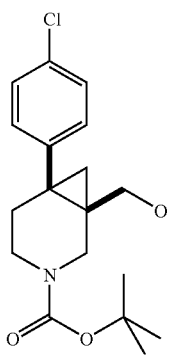

To an ice cooled suspension of diethylzinc (1M in hexane, 24.07 mL) in anhydrous dichloromethane (19.6 mL), diiodomethane (3.88 mL) was added and the resulting mixture was stirred for 15 min. To the cooled mixture was rapidly added a solution of 1,1-dimethylethyl 4-(4-chlorophenyl)-5-(hydroxymethyl)-3,6-dihydro-1(2H)-pyridinecarboxylate (P30, 1.04 g) in anhydrous dichloromethane (11.3 mL), allowed to reach room temperature and then 2,6-bis(1,1-dimethylethyl)-4-methylpyridine (9.88 g) was added and then the mixture stirred for 2 h. Aqueous HCl (1M, 30 mL) was added and left stirring for 30 min. The organic phase was separated and extracted with HCl, the acid phase was basified with NaOH 3M to reach pH~12 and then extracted with diethylether. The organic layer was separated, dried over Na$_2$SO$_4$, filtered and evaporated under reduced pressure. The resulting crude was purified via flash-chromatography (eluting with dichloromethane/methanol/ammonia, 90/7.5/2.5) to obtain a mixture of [6-(4-chlorophenyl)-3-azabicyclo[4.1.0]hept-1-yl]methanol and [4-(4-chlorophenyl)-1,2,5,6-tetrahydro-3-pyridinyl]methanol (190 mg), which was solubilized (188 mg) in anhydrous dichloromethane (8 mL). To that solution bis(1,1-dimethylethyl)dicarbonate (181.15 mg) was added and the resulting mixture was stirred for 2 h. Triethylamine (0.055 mL) was then added dropwise and the mixture stirred for 2 h. Dichloromethane (5 mL) and saturated NH$_4$Cl (10 mL) were added and the mixture was vigorously stirred for 10 min. The organic layer was separated, dried over Na$_2$SO$_4$, filtered and evaporated under reduced pressure to obtain the title compound, still impure for the presence of 1,1-dimethylethyl 4-(4-chlorophenyl)-5-(hydroxymethyl)-3,6-dihydro-1 (2H)-pyridinecarboxylate (270 mg).

MS (m/z): 338 [MH]$^+$, 282 [MH−56]$^+$; 324 [MH]$^+$, 270 [MH−56]$^+$.

Preparation 32: 1,1-dimethylethyl (1R,6S/1S,6R)-6-(4-chlorophenyl)-1-[(methyloxy)methyl]-3-azabicyclo[4.1.0]heptane-3-carboxylate (P32)

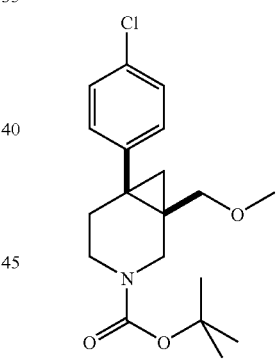

Impure 1,1-dimethylethyl (1R,6S/1S,6R)-6-(4-chlorophenyl)-1-(hydroxymethyl)-3-azabicyclo[4.1.0]heptane-3-carboxylate (P31, 270 mg) and NaH (60% in mineral oil, 28.8 mg) was degassed with a steam of nitrogen, then N,N-dimethylformamide (7.5 mL) was added at 0° C. The resulting mixture was allowed to reach room temperature and stirred for 30 min. Iodomethane (0.099 mL) was added dropwise and left stirring for 2 h. Three further additions of NaH (60% in mineral oil, 9.6 mg, 9.6 mg and 19.2 mg respectively) at 0° C. and of iodomethane (0.049 mL, 0.049 ml and 0.074 mL respectively) were made, and overall the mixture was stirred for 18 h. After this period of time, ethylacetate, water and ice were poured into the mixture and the phases were separated. The organic layer was washed with brine, dried over Na$_2$SO$_4$ and evaporated under reduced pressure to obtain the title compound impure for the presence of 1,1-dimethylethyl 4-(4-chlorophenyl)-5-[(methyloxy)methyl]-3,6-dihydro-1(2H)-pyridinecarboxylate (280 mg).

MS (m/z): 352 [MH]$^+$, 296 [MH−56]$^+$; 338 [MH]$^+$.

Preparation 33: 1-(1,1-dimethylethyl) 3-methyl 4-{4-[(trifluoromethyl)oxy]phenyl}-5,6-dihydro-1,3(2H)-pyridinedicarboxylate (P33)

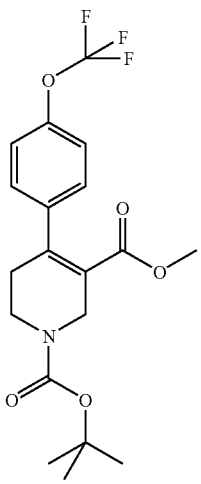

To a mixture of 1-(1,1-dimethylethyl) 3-methyl 4-{[(trifluoromethyl)sulfonyl]oxy}-5,6-dihydro-1,3(2H)-pyridinedicarboxylate (2.5 g, P2), {4-[(trifluoromethyl)oxy]phenyl}boronic acid (1.52 g) and Pd(PPh$_3$)$_4$ (265 mg) under nitrogen, toluene (34 mL), ethanol (25 mL) and Na$_2$CO$_3$ (2M, 19 mL) were added in sequence. The mixture was stirred at 80° C. for 2 hours then the reaction mixture was allowed to reach room temperature. The aqueous phase was extracted with Et$_2$O (2 times), the combined organic phases were dried on anhydrous Na$_2$SO$_4$ and the solvent was evaporated obtaining a crude product that was purified by flash-chromatography (eluting with ethyl acetate/cyclohexane from 1:9 to 3:7) to give the title compound (2.5 g)
NMR ($^1$H, CDCl$_3$): δ ppm 7.10-7.27 (m, 4H) 4.13-4.35 (m, 2H) 3.57-3.68 (m, 2H) 3.53 (s, 3H) 2.30-2.58 (m, 2H) 1.53 (s, 9H); MS (m/z): 402 [MH]$^+$.

Preparation 34: 1,1-dimethylethyl-5-(hydroxymethyl)-4-{4-[(trifluoromethyl)oxy]phenyl}-3,6-dihydro-1(2H)-pyridinecarboxylate (P34)

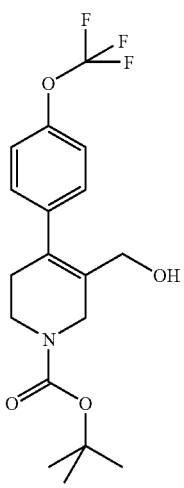

To a stirred solution of 1-(1,1-dimethylethyl) 3-methyl 4-{4-[(trifluoromethyl)oxy]phenyl}-5,6-dihydro-1,3(2H)-pyridinedicarboxylate (P33, 2 g) in dry diethyl ether (40 mL) under N$_2$ atmosphere, at −20° C., LiAlH$_4$ (1M in diethyl ether, 3.6 mL) was added dropwise. The reaction mixture was left stirring at −20° for 20 minutes then saturated NH$_4$Cl and diethyl ether were poured into the solution and the mixture was vigorously stirred for 30 minutes at room temperature. The two phases were separated, and the aqueous layer was extracted with diethyl ether. The combined organic phases were dried on anhydrous Na$_2$SO$_4$ and the solvent was removed under reduced pressure, obtaining the title compound (1.69 g).
NMR ($^1$H, CDCl$_3$): δ ppm 7.12-7.26 (m, 4H) 4.15 (s, 2H) 3.95-4.09 (m, 2H) 3.63 (t, 2H) 2.31-2.52 (m, 2H) 1.53 (s, 9H); MS (m/z): 374 [MH]$^+$.

Preparation 35:

(1S,6R/1R,6S)-6-{4-[(trifluoromethyl)oxy]phenyl}-3-azabicyclo[4.1.0]hept-1-yl)methanol (P35)

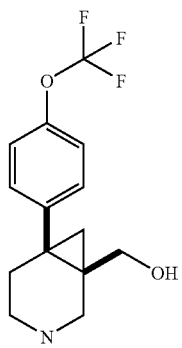

To a stirred solution of CH$_2$I$_2$ (36 g) and 2,6-bis(1,1-dimethylethyl)-4-methylpyridine (28 g) in dry DCM (150 mL) under N$_2$ atmosphere, at 0° C., ZnEt$_2$ (1M in hexane, 68 mL) was added dropwise; the mixture was stirred at 0° C. for 30 minutes and then cooled to −20° C. A solution of 1,1-dimethylethyl-5-(hydroxymethyl)-4-{4-[(trifluoromethyl)oxy]phenyl}-3,6-dihydro-1(2H)-pyridinecarboxylate (P34, 1.69 g) in dry DCM (50 mL) was added dropwise and the reaction mixture was stirred at −20° C. for 30 minutes, then overnight at room temperature. HCl 1M was added into the reaction flask and the mixture was vigorously stirred for 30 minutes; the two phases were separated and the aqueous layer was basified with NaOH 3N. The basic solution was extracted with diethyl ether (2 times). The combined organic layers were concentrated in vacuo and the residue was taken up with diethyl ether. This solution was washed with saturated NH$_4$Cl aqueous solution and the aqueous phase was basified with NaOH 3N. The basic solution was extracted with diethyl ether (2 times). The combined organic layers were dried on anhydrous Na$_2$SO$_4$ and the solvent was removed under reduced pressure obtaining the title compound (170 mg).
NMR ($^1$H, CDCl$_3$): δ ppm 7.36 (d, 2H) 7.16 (d, 2H) 3.39 (d, 1H) 3.05-3.29 (m, 3H) 2.64-2.86 (m, 2H) 1.85-2.07 (m, 2H) 1.05-1.13 (m, 1H) 0.96-1.05 (m, 1H); MS (m/z): 288 [MH]$^+$.

Preparation 36: (1S,6R/1R,6S)-1,1-dimethylethyl-1-(hydroxymethyl)-6-{4-[(trifluoromethyl)oxy]phenyl}-3-azabicyclo[4.1.0]heptane-3-carboxylate (P36)

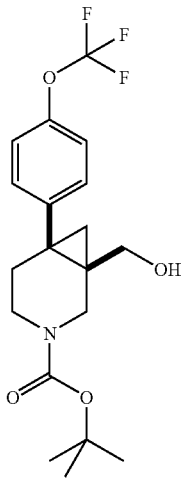

To a stirred solution of (1S,6R/1R,6S)-6-{4-[(trifluoromethyl)oxy]phenyl}-3-azabicyclo[4.1.0]hept-1-yl)methanol (170 mg) (P35) in dry DCM (6 mL) under N$_2$ atmosphere, at 0° C., di-tert-butyl dicarbonate (129 mg) was added and the reaction mixture was left stirring at 0° C. for 15 minutes. Saturated NH$_4$Cl aqueous solution and DCM were added to the solution and then the organic phase was separated, dried and the solvent was removed under reduced pressure. The crude was purified by flash-chromatography (eluting with cyclohexane/ethyl acetate from 8:2 to 7:3) to give the title compound (173 mg).

NMR ($^1$H, CDCl$_3$): δ ppm 7.35 (d, 2H) 7.17 (d, 2H) 3.73-3.90 (m, 2H) 3.09-3.51 (m, 4H) 2.06-2.20 (m, 1H) 1.89-2.06 (m, 1H) 1.51 (s, 9H) 1.03-1.10 (m, 1H) 0.93-1.02 (m, 1H).

Preparation 37: 3-methyl 1-(phenylmethyl) 4-oxo-1,3-piperidinedicarboxylate (P37)

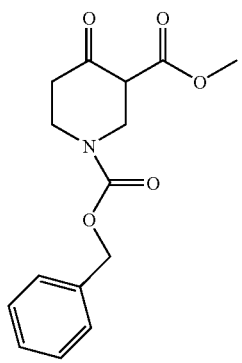

To a stirred solution of 4-oxo-3-piperidinecarboxylate (5 g) in dry DCM (50 ml), under N$_2$ atmosphere, TEA (9 mL) was added at rt and then, at 0° C., benzylchloroformate (4.2 mL) was added slowly and stirring was continued for 30 minutes at 0° C. and 1 h at RT. The mixture was quenched at 0° C. with HCl 2N. The aqueous phase was extracted with DCM (2 times) and the combined organic layers were washed with saturated NaCl aqueous solution, dried and concentrated in vacuo to give the title compound (7.5 g).

NMR ($^1$H, CDCl$_3$): δ ppm 12.00 (s, 1H) 7.31-7.50 (m, 5H) 5.19 (s, 2H) 4.16 (s, 2H) 3.80 (s, 3H) 3.67 (t, 2H) 2.42 (s, 2H)

Preparation 38: 3-methyl 1-(phenylmethyl) 4-{[(trifluoromethyl)sulfonyl]oxy}-1,3-piperidinedicarboxylate (P38)

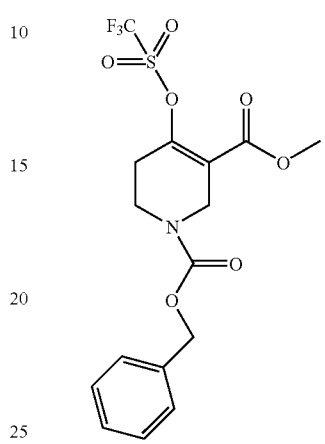

To a stirred solution of 3-methyl 1-(phenylmethyl) 4-oxo-1,3-piperidinedicarboxylate (7.5 g) (P37) in dry DMF (80 ml) under N$_2$ atmosphere at 0° C., NaH 60% on mineral oil (1.13 g) was added. After 10 min stirring at 0° C., 1,1,1-trifluoro-N-phenyl-N-[(trifluoromethyl)sulfonyl]methanesulfonamide (9.64 g) was added and the mixture was stirred for 1 h. The mixture was then quenched with saturated NH$_4$Cl aqueous solution and the phase was extracted with Et$_2$O (2 times). The combined organic layers were washed with saturated NaCl aqueous solution, dried and concentrated under vacuum obtaining the title compound (10 g).

NMR ($^1$H, CDCl$_3$): δ ppm 7.34-7.46 (m, 5H) 5.19 (s, 2H) 4.38 (s, 2H) 3.85 (s, 3H) 3.72 (t, J=5.31 Hz, 2H) 2.55 (s, 2H); MS (m/z): 424 [MH]$^+$

Preparation 39: 3-methyl 1-(phenyl methyl) 4-[3-chloro-4-(trifluoromethyl)phenyl]-5,6-dihydro-1,3(2H)-pyridinedicarboxylate (P39)

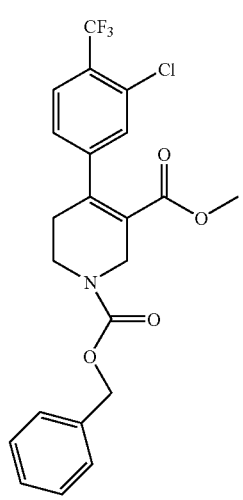

To a stirred solution of 3-methyl 1-(phenylmethyl) 4-{[(trifluoromethyl)sulfonyl]oxy}-1,3-piperidinedicarboxylate (3 g) (P38) and [3-chloro-4-(trifluoromethyl)phenyl]boronic acid (1.826 g) in dry toluene (37 mL) under $N_2$ atmosphere at 0° C., Pd(PPh$_3$)$_4$ (292 mg) dissolved in absolute EtOH (26 ml), was added followed by Na$_2$CO$_3$ 2M (21 mL). The reaction mixture was heated to 80° C. for 2 h. Et$_2$O was then added to the solution and the organic phase was separated. The aqueous layer was extracted with Et$_2$O and the combined organic phases were washed with saturated NaCl aqueous solution, dried and concentrated under vacuum. The crude was purified by flash-chromatography (eluting with cyclohexane/ethyl acetate from 9:1 to 8:2) to give the title compound (3.03 g).

NMR ($^1$H, CDCl$_3$): δ ppm 7.43-7.52 (m, 2H) 7.31-7.43 (m, 5H) 7.24 (d, 1H) 5.21 (s, 2H) 4.21-4.44 (m, 2H) 3.64-3.77 (m, 2H) 3.55 (s, 3H) 2.51 (s, 2H); MS (m/z): 454 [MH]+

Preparation 40: phenyl methyl 4-[3-chloro-4-(trifluoromethyl)phenyl]-5-(hydroxymethyl)-3,6-dihydro-1(2H)-pyridinecarboxylate (P40)

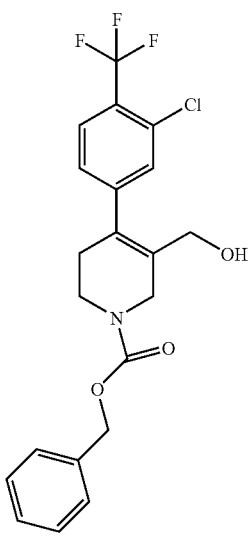

To a stirred solution of 3-methyl 1-(phenylmethyl) 4-[3-chloro-4-(trifluoromethyl)phenyl]-5,6-dihydro-1,3(2H)-pyridinedicarboxylate (P39, 3.03 g) in dry diethyl ether (60 mL) under $N_2$ atmosphere, at –20° C., LiAlH$_4$ (1M in diethyl ether, 6.25 mL) was added dropwise. The reaction mixture was left stirring at –20° for 20 minutes then saturated NH$_4$Cl aqueous solution and diethyl ether were added to the reaction mixture. The two phases were separated and the aqueous layer was extracted with diethyl ether. The combined organic phases were washed with brine, dried on anhydrous Na$_2$SO$_4$ then the solvent was removed under reduced pressure, obtaining a crude product that was purified by flash-chromatography (eluting with cyclohexane/ethyl acetate from 9:1 to 7:3) to give the title compound (700 mg).

NMR ($^1$H, CDCl$_3$): δ ppm 7.30-7.56 (m, 8H) 5.21 (s, 2H) 4.25 (s, 2H) 3.94-4.08 (m, 2H) 3.72 (t, 2H) 2.44 (s, 2H); MS (m/z): 426 [MH]$^+$ Preparation 41: (1S,6R/1R,6S)-phenylmethyl 6-[3-chloro-4-(trifluoromethyl)phenyl]-1-(hydroxymethyl)-3-azabicyclo[4.1.0]heptane-3-carboxylate (P41)

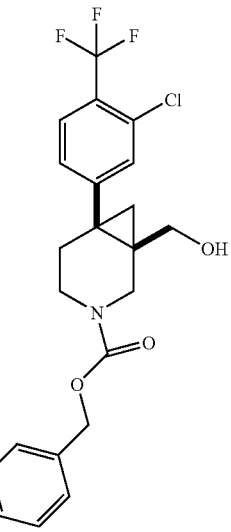

To a stirred solution of CH$_2$I$_2$ (13.25 g) in dry DCM, under $N_2$ atmosphere, at 0° C., ZnEt$_2$ 1M in hexane (24 mL) was added and after 30 min the reaction mixture was cooled to –20° C. Phenylmethyl 4-[3-chloro-4-(trifluoromethyl)phenyl]-5-(hydroxymethyl)-3,6-dihydro-1(2H)-pyridinecarboxylate (700 mg) (P40) in dry DCM, was added (total amount of DCM 60 ml); the solution was stirred for 30 min at –20° C. and at RT overnight. The reaction mixture was quenched with HCl 0.1M and stirred for 30 min. The organic layer was separated, washed with saturated NaCl aqueous solution, dried and concentrated in vacuo. The crude was purified by flash-chromatography (eluting with cyclohexane/ethyl acetate from 9:1 to 7:3) to give 430 mg of impure title compound in a mixture with phenylmethyl 4-[3-chloro-4-(trifluoromethyl)phenyl]-5-(hydroxymethyl)-3,6-dihydro-1(2H)-pyridinecarboxylate (ratio=2:1 form NMR analysis).
MS (m/z): 440 [MH]$^+$, 426 [MH]$^+$ Preparation 42: 3-methyl 1-(phenylmethyl) 4-(2-naphthalenyl)-5,6-dihydro-1,3(2H)-pyridinedicarboxylate (P42)

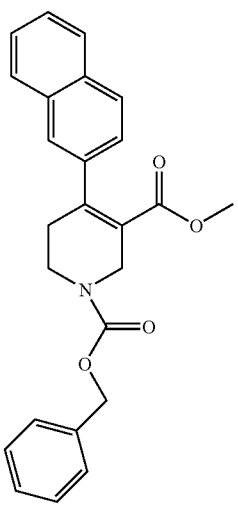

The title compound was prepared according to a similar procedure to that previously described for Preparation 33 in 2.28 g yield starting from 3-methyl 1-(phenylmethyl) 4-{[(trifluoromethyl)sulfonyl]oxy}-1,3-piperidinedicarboxylate (3 g, P38).

NMR (¹H, CDCl₃): δ ppm 7.08-7.90 (m, 12H) 5.23 (s, 2H) 4.28-4.48 (m, 2H) 3.64-3.84 (m, 2H) 3.49 (s, 3H) 2.53-2.72 (bs, 2H)

Preparation 43: phenylmethyl 5-(hydroxymethyl)-4-(2-naphthalenyl)-3,6-dihydro-1(2H)-pyridinecarboxylate (P43)

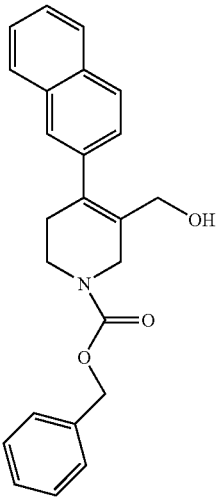

The title compound was prepared according to a similar procedure to that previously described for Preparation 34 in 1.275 g yield starting from 3-methyl 1-(phenylmethyl) 4-(2-naphthalenyl)-5,6-dihydro-1,3(2H)-pyridinedicarboxylate (2.28 g, P42).

NMR (¹H, CDCl₃): δ ppm 7.21-7.91 (m, 12H) 5.23 (s, 2H) 4.20-4.37 (m, 2H) 4.00-4.18 (m, 2H) 3.64-3.83 (m, 2H) 2.43-2.63 (m, 2H)

Preparation 44: (1S,6R/1R,6S)-phenylmethyl-1-[(methyloxy)methyl]-6-(2-naphthalenyl)-3-azabicyclo[4.1.0]heptane-3-carboxylate (P44)

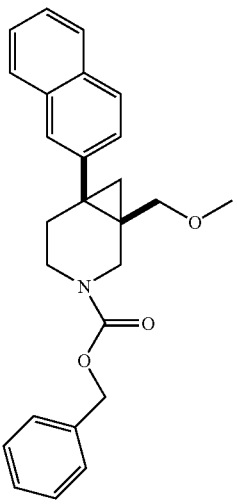

Step a)
An impure batch of Phenylmethyl (1R,6S)-1-(hydroxymethyl)-6-(2-naphthalenyl)-3-azabicyclo[4.1.0]heptane-3-carboxylate (850 mg) was prepared starting from phenylmethyl-5-(hydroxymethyl)-4-(2-naphthalenyl)-3,6-dihydro-1(2H)-pyridinecarboxylate (1.275 g) (P43) according to a similar procedure to that previously described for Preparation 41.

Step b)
The title compound was prepared starting from Phenylmethyl (1R,6S)-1-(hydroxymethyl)-6-(2-naphthalenyl)-3-azabicyclo[4.1.0]heptane-3-carboxylate (850 mg) according to a similar procedure to that described for E14, Step A, in 600 mg yield.

NMR (¹H, CDCl₃): δ ppm 7.04-7.90 (m, 12H) 5.20 (t, 2H) 4.01 (m, 1H) 3.78-3.92 (d, 1H) 3.44-3.56 (m, 2H) 3.16-3.24 (m, 1H) 3.10 (s, 3H) 2.98-3.03 (m, 1H) 2.16-2.30 (m, 1H) 1.95-2.12 (m, 1H) 1.16-1.25 (m, 1H) 1.01-1.12 (m, 1H); MS (m/z): 402 [MH]⁺

Preparation 45: {[3-(3-chloro-4-fluorophenyl)-3-buten-1-yl]oxy}(1,1-dimethylethyl)diphenylsilane (P45)

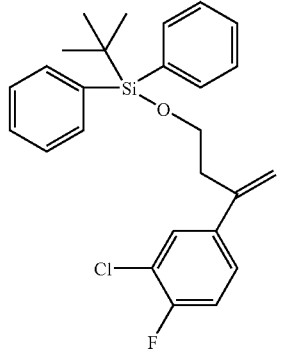

The title compound was prepared according to a similar procedure to that previously described for Preparation 13 in 3.624 g yield starting from [(3-bromo-3-buten-1-yl)oxy](1,1-dimethylethyl)diphenylsilane (3.890 g, P12).

NMR (¹H, CDCl₃): δ ppm 7.00-7.65 (m, 13H) 5.29 (m, 1H) 5.11 (m, 1H) 3.74 (t, 2H) 2.70 (t, 2H) 1.02 (s, 9H)

Preparation 46: dimethyl-2-(3-chloro-4-fluorophenyl)-2-(2-{[(1,1-dimethylethyl)(diphenyl)silyl]oxy}ethyl)-1,1-cyclopropanedicarboxylate (P46)

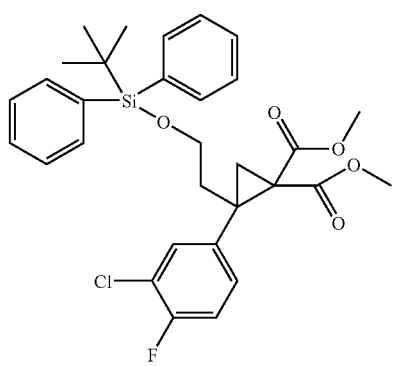

The title compound was prepared in 2.61 g yield starting from {[3-(3-chloro-4-fluorophenyl)-3-buten-1-yl]oxy}(1,1- dimethylethyl)diphenylsilane (P45, 3.624 g) and from dimethyl diazenylpropanedioate (1.98 g) according to a similar procedure described for Preparation 14.

NMR (¹H, CDCl₃): δ ppm 7.25-7.62 (m, 11H) 7.04-7.11 (m, 1H) 6.99 (t, 1H) 3.82 (s, 3H) 3.49-3.59 (m, 1H) 3.33-3.46 (m, 4H) 2.10-2.26 (m, 2H) 1.76-1.87 (m, 1H) 1.59-1.66 (m, 1H) 0.99-1.10 (m, 9H); MS (m/z): 569 [MH]⁺

Preparation 47: methyl-1-(aminocarbonyl)-2-(3-chloro-4-fluorophenyl)-2-(2-hydroxyethyl)cyclopropanecarboxylate (P47)

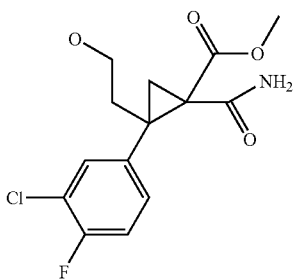

The title compound was prepared in 1.05 g yield starting from dimethyl 2-(3-chloro-4-fluorophenyl)-2-(2-{[(1,1-dimethylethyl)(diphenyl)silyl]oxy}ethyl)-1,1-cyclopropanedicarboxylate (2.61 g, P46) according to a similar procedure to that previously described for Preparation 15.

NMR (¹H, CDCl₃): δ ppm 8.19 (s, 1H) 7.34 (d, 1H) 7.14-7.22 (m, 1H) 7.10 (t, 1H) 5.76 (s, 1H) 3.42-3.66 (m, 2H) 3.06-3.26 (m, 3H) 1.89-2.35 (m, 4H); MS (m/z): 316 [MH]⁺

Preparation 48: (1S,6R/1R,6S)-methyl 6-(3-chloro-4-fluorophenyl)-2-oxo-3-azabicyclo[4.1.0]heptane-1-carboxylate (48)

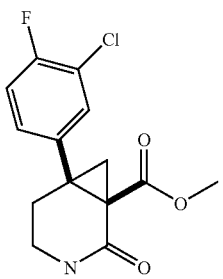

The title compound was prepared in 360 mg yield starting from methyl 1-(aminocarbonyl)-2-(3-chloro-4-fluorophenyl)-2-(2-hydroxyethyl)cyclopropanecarboxylate (1.05 g, P47) according to a similar procedure described for Preparation 16.

NMR (¹H, CDCl₃): δ ppm 7.42 (dd, 1H) 7.21-7.27 (m, 1H) 7.10 (t, 1H) 5.83 (s, 1H) 3.53 (s, 3H) 2.85-3.42 (m, 2H) 2.33-2.48 (m, 1H) 2.24-2.32 (m, 1H) 2.09-2.22 (m, 1H) 1.99 (d, 1H); MS (m/z): 298 [MH]+

Preparation 49: (1S,6R/1R,6S)-1,1-dimethylethyl 6-(3-chloro-4-fluorophenyl)-1-(hydroxymethyl)-3-azabicyclo[4.1.0]heptane-3-carboxylate (P49)

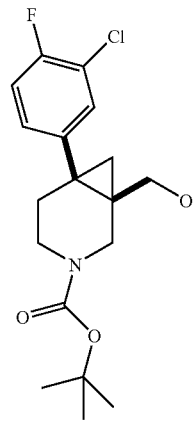

The title compound was prepared in 184 mg yield starting from (1S,6R/1R,6S)-methyl-6-(3-chloro-4-fluorophenyl)-2-oxo-3-azabicyclo[4.1.0]heptane-1-carboxylate (360 mg, P48) according to a similar procedure described for Preparation 5 (Method C).

NMR (¹H, CDCl₃): δ ppm 7.37 (dd, 1H) 7.16-7.24 (m, 1H) 7.09 (t, 1H) 3.72-3.89 (m, 2H) 3.26-3.46 (m, 3H) 3.11-3.26 (m, 1H) 1.90-2.16 (m, 2H) 1.51 (s, 9H) 1.01 (dd, 2H)

Preparation 50: (1S,6R/1R,6S)-1,1-dimethylethyl-6-(3-chloro-4-fluorophenyl)-1-[(methyloxy)methyl]-3-azabicyclo[4.1.0]heptane-3-carboxylate (P50)

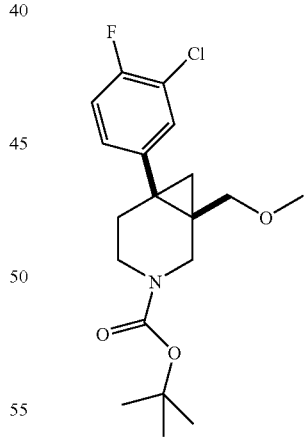

The title compound was prepared in 164 mg yield starting from (1S,6R/1R,6S)-1,1-dimethylethyl 6-(3-chloro-4-fluorophenyl)-1-(hydroxymethyl)-3-azabicyclo[4.1.0]heptane-3-carboxylate (184 mg, P49) according to a similar procedure to that described for Example 14, Step A.

NMR (¹H, CDCl₃): δ ppm 7.38 (d, 1H) 7.14-7.23 (m, 1H) 7.07 (t, 1H) 3.86 (s, 1H) 3.70 (d, 1H) 3.27-3.42 (m, 2H) 3.15 (s, 3H) 3.00-3.11 (m, 1H) 2.86 (d, 1H) 1.92-2.13 (m, 2H) 1.44-1.54 (m, 9H) 0.90-1.03 (m, 2H)

Preparation 51: 1,1-dimethylethyl (1R,6S/1S,6R)-6-(3,4-dichlorophenyl)-1-[(ethyloxy)methyl]-3-azabicyclo[4.1.0]heptane-3-carboxylate (P51)

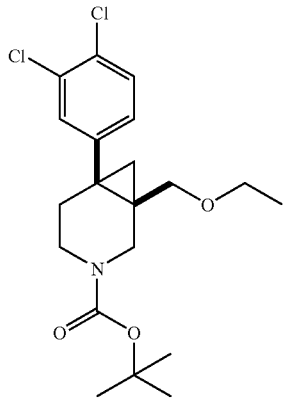

To a stirred solution of (1S,6R/1R,6S)-1,1-dimethylethyl-6-(3,4-dichlorophenyl)-1-(hydroxymethyl)-3-azabicyclo[4.1.0]heptane-3-carboxylate (P5, 0.1 g) in dry DMF (2 mL), under a nitrogen atmosphere, sodium hydride (60% in mineral oil, 13 mg) was added and the stirring continued for 5 min. After this period of time iodoethane (28 µL) was added and the reaction mixture was stirred overnight at RT. An additional amount of sodium hydride (3 mg) and iodoethane (28 µL) were added and the mixture was stirred for further 4 h. Aqueous saturated NaHCO₃ solution was added and the mixture was extracted with DCM. The organic phase was concentrated under vacuum and the crude product was purified by flash-chromatography (eluting with cy/EA from 1/0 to 8/2) to give the title compound (79 mg).

NMR ($^1$H, MeOH-d$_4$): δ 7.48 (s, 1H) 7.35 (d, 1H) 7.15 (d, 1H) 3.7-3.4 (m, 2H) 3.3 (m, 3H) 3.15 (m, 2H) 2.85 (d, 1H) 2.0 (m, 2H) 1.5 (s, 9H) 1.1 (t, 3H) 0.95 (m, 2H);

MS (m/z): 422 [M+Na]⁺

Preparation 52: 1,1-dimethylethyl 4-{[(trifluoromethyl)sulfonyl]oxy}-3,6-dihydro-1(2H)-pyridinecarboxylate (P52)

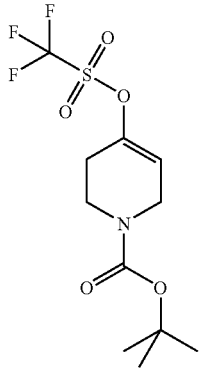

To a stirred solution of diisopropylamine (0.77 ml) in dry THF (12 mL) at −78° C. and under a nitrogen atmosphere, butyl lithium (2.5M in hexane, 2.2 ml) was added and the reaction mixture was stirred at −78° C. for 15 minutes. DMPU (1.8 ml) and a solution of 1,1-dimethylethyl 4-oxo-1-piperidinecarboxylate (1 g) in THF (5 ml) were added and the reaction mixture was stirred at −78° C. for 2 hours. Then a solution of N-phenyl-bis(trifluoromethanesulfonimide) (1.97 g) in THF (6 ml) was added and stirring was continued at 0° C. for 9 hours and at room temperature per 16 h. The solvent was removed under reduced pressure and the crude purified by flash-chromatography (eluting with ethyl acetate/cycloexane 2:8) to give 1.375 g of the title compound.

NMR ($^1$H, CDCl₃): δ 5.79 (br. s., 2H) 4.07 (m, 2H) 3.65 (m, 2H) 2.47 (m, 2H) 1.50 (s, 9H).

Preparation 53: 1,1-dimethylethyl 4-(3,4-dichlorophenyl)-3,6-dihydro-1(2H)-pyridinecarboxylate (P53)

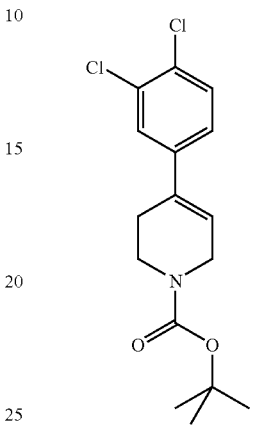

To a mixture of 1,1-dimethylethyl 4-{[(trifluoromethyl)sulfonyl]oxy}-3,6-dihydro-1(2H)-pyridinecarboxylate (P52, 500 mg), 3,4-dichlorophenylboronic acid (330 mg) and Pd(PPh₃)₄ (50 mg) under nitrogen, toluene (6.5 mL), ethanol (5 mL) and Na₂CO₃ (2M, 5 mL) were added in sequence. The mixture was stirred at 80° C. for 2 hours then the reaction mixture was allowed to reach room temperature. Saturated NH₄Cl (30 mL) was poured into the solution and the mixture was transferred in a separator funnel. The mixture was extracted with ethyl acetate (3×40 mL), the combined organic phases were dried on anhydrous Na₂SO₄ and the solvent evaporated obtaining a crude product that was purified by flash-chromatography (eluting with ethyl acetate/cycloexane 1:9) to give the title compound (400 mg).

MS (m/z): 328 [MH]⁺

Preparation 54: 3-(1,1-dimethylethyl) 7-ethyl (1S,6R/1R,6S)-6-(3,4-dichlorophenyl)-3-azabicyclo[4.1.0]heptane-3,7-dicarboxylate and 1,1-dimethylethyl 4-(3,4-dichlorophenyl)-6-[2-(ethyloxy)-2-oxoethyl]-3,6-dihydro-1(2H)-pyridinecarboxylate (P54)

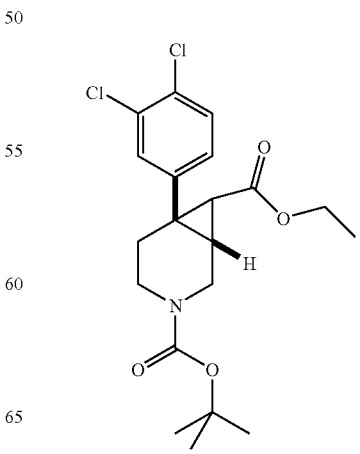

-continued

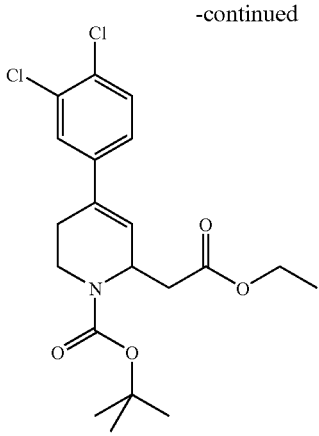

To a solution of 1,1-dimethylethyl 4-(3,4-dichlorophenyl)-3,6-dihydro-1(2H)-pyridinecarboxylate (P53, 825 mg) in DCE (10 ml) was added rhodium acetate dimer (110 mg). The mixture was heated at 40° C. and a solution of ethyl diazoacetate (0.31 ml) in DCE (2.5 ml) was added with a syringe pump in 4 h maintaining the internal temperature at 50° C. during the addition. The solvent was removed under reduced pressure and the crude purified by flash-chromatography (eluting with ethyl acetate/cycloexane 2:8) to give 170 mg of a mixture of title compounds.

MS (m/z): 414 [MH]+

Preparation 55: 1,1-dimethylethyl (1S,6R/1R,6S)-6-(3,4-dichlorophenyl)-7-(hydroxymethyl)-3-azabicyclo[4.1.0]heptane-3-carboxylate and 1,1-dimethylethyl 4-(3,4-dichlorophenyl)-6-(2-hydroxyethyl)-3,6-dihydro-1(2H)-pyridinecarboxylate (P55)

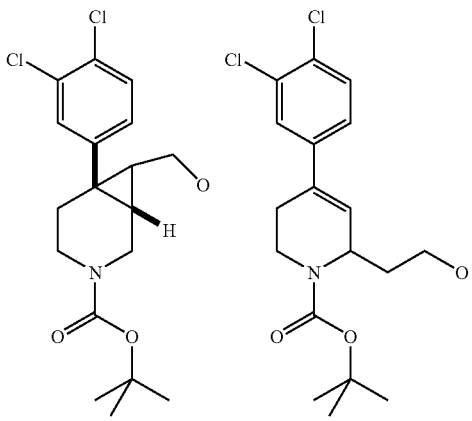

To a stirred solution of (1,1-dimethylethyl) 7-ethyl (1S,6R/1R,6S)-6-(3,4-dichlorophenyl)-3-azabicyclo[4.1.0]heptane-3,7-dicarboxylate and 1,1-dimethylethyl 4-(3,4-dichlorophenyl)-6-[2-(ethyloxy)-2-oxoethyl]-3,6-dihydro-1(2H)-pyridinecarboxylate (P54, obtained following an analogous procedure to that previously described for P54, 38 mg) in dry toluene (1 mL) under $N_2$ atmosphere, at –20° C., LiAlH$_4$ (1M in diethyl ether, 0.37 mL) was added dropwise. The reaction mixture was left stirring at –20° for 1 hour then saturated NH$_4$Cl was added and the products extracted with ethyl acetate. The phases were separated, the organic phase was dried over Na$_2$SO$_4$ and the solvent was removed under reduced pressure to give a mixture of the title compounds as crude (30 mg).

MS (m/z): 372 [MH]+

Preparation 56: 1,1-dimethylethyl (1S,6R/1R,6S)-6-(3,4-dichlorophenyl)-7-[(methyloxy)methyl]-3-azabicyclo[4.1.0]heptane-3-carboxylate and 1,1-dimethylethyl 4-(3,4-dichlorophenyl)-6-[2-(methyloxy)ethyl]-3,6-dihydro-1(2H)-pyridinecarboxylate (P56)

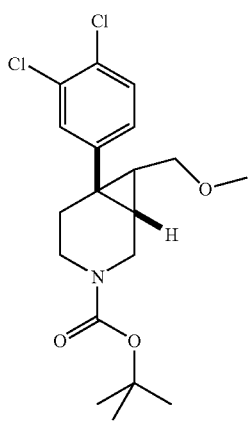

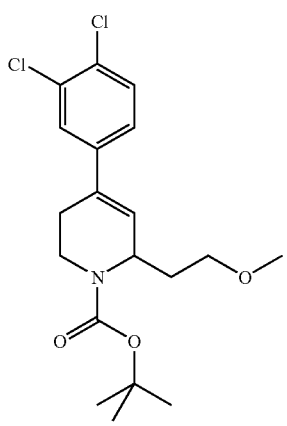

To a stirred solution of 1,1-dimethylethyl (1S,6R/1R,6S)-6-(3,4-dichlorophenyl)-7-(hydroxymethyl)-3-azabicyclo[4.1.0]heptane-3-carboxylate and 1,1-dimethylethyl 4-(3,4-dichlorophenyl)-6-(2-hydroxyethyl)-3,6-dihydro-1(2H)-pyridinecarboxylate (P55, 30 mg) in dry DMF (1 mL) under nitrogen atmosphere, at 0° C., NaH (60% on mineral oil, 5 mg) was added and the mixture stirred for 30 minutes at 0° C. Methyl iodide (10 µL) was added and the reaction was allowed to reach room temperature and stirred for 2 h. Chilly water was added and the product extracted with ethyl acetate. The organic phase was washed with brine, dried over Na$_2$SO$_4$, and the solvent evaporated under reduced pressure to give a mixture of the title compounds as crude material (35 mg).

MS (m/z): 386 [MH]+

Preparation 57: 3-(1,1-dimethylethyl) 1-ethyl (1S, 6R/1R,6S)-6-(3,4-dichlorophenyl)-3-azabicyclo[4.1.0]hept-4-ene-1,3-dicarboxylate (P57)

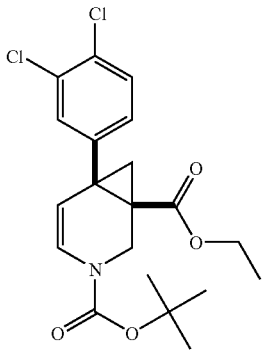

Step a)

A 50-L Jacketed laboratory reactor was charged with lithium tert-butoxide (1.85 Kg, 23.1 mol, 3 eq) and 1-methyl-2-pyrrolidinone (19.1 Kg). The mixture was stirred for ~30 min, and the resulting solution was charged into a pressure vessel for later use.

A clean, 50-L Jacketed laboratory reactor was charged with a solution of 1-(1,1-dimethylethyl) 3-ethyl 4-(3,4-dichlorophenyl)-5,6-dihydro-1,3(2H)-pyridinedicarboxylate in toluene (prepared in a similar manner to that described in P72, containing P72 in a theoretical amount of 3.09 Kg) through a 0.45 μm Meissner™ in-line filter. The lines and filter were washed with a small amount of toluene. The toluene was completely removed from the reaction mixture by distillation under reduced pressure. 1-methyl-2-pyrrolidinone (16.0 Kg) was added and the resulting solution cooled to 20° C., and held overnight due to time constraints. Chloroiodomethane (4.15 Kg, 3.05 eq) was charged into the reactor, and the resulting slurry was cooled to −4° C. A portion of the previously prepared solution of lithium tert-butoxide in 1-methyl-2-pyrrolidinone (16.9 Kg, ~2.4 eq of base) was added over 28 min, and the resulting solution was warmed to 19° C. and stirred for 80 min. Acetic acid (0.69 Kg, 1.5 eq) was added all at once, followed by a slow addition of water (8.5 Kg) over ~10 min. The mixture was stirred for ~5 min, and water (13.1 Kg) was added over 18 min. The resulting slurry was cooled to 11° C. and held for 100 min. The solids were collected by filtration. Water (3.9 Kg) and methanol (9.21 Kg) were charged into the reactor to rinse it, and the resulting aqueous methanol solution was used to wash the product cake. The resulting yellow solids were dried to a constant weight in a 55° C. vacuum oven to provide 2.57 Kg of the title compound in 81% yield.

NMR ($^1$H, CDCl$_3$): δ 7.32 (2H, m), 7.08 (1H, m), 6.62 (1H, br m), 5.13 (1H, br m), 4.24 (1H, br m), 3.76 (3H, br m), 2.29 (1H, m), 1.56 (1H, m), 1.49 (9H, s), 0.91 (3H, br m)

Step B) (Recrystallization)

A 50-L jacketed laboratory reactor was charged with (±)-3-(1,1-dimethylethyl) 1-ethyl (1S,6R)-6-(3,4-dichlorophenyl)-3-azabicyclo[4.1.0]hept-4-ene-1,3-dicarboxylate (P57, 4.40 Kg, 11.0 moles, 1 eq) and heptane (15.1 Kg, 22.1 L, 5 vol). The resulting slurry is heated to approximately 80° C. and filtered into a clean 50-L jacketed laboratory reactor. The filter and lines were rinsed with heptane (3.0 Kg, 4.4 L, 1 vol) and the rinse was combined with the filtrate. The solution was heated to 80° C. and then cooled to 22° C. over 107 min. No crystals had formed so a small aliquot was taken out. Crystals formed spontaneously in the aliquot and were returned to the reactor which caused rapid crystallization. The slurry was heated back to 80° C. and cooled to 22° C. over 105 min. During the cool, a small aliquot was pulled at 52° C. The wall of the vial holding the aliquot was scratched to initiate crystallization and the resulting slurry was combined with the bulk solution when its temperature had reached 47° C. The solids were collected by filtration, the reactor was rinsed with heptane (3.0 Kg, 4.4 L, 1 vol), and the rinse was used to wash the filter cake. The solids were dried to a constant weight in a 50-60° C. vacuum oven to provide 2.954 Kg, 67% yield, of title compound as an off-white solid.

NMR ($^1$H, CDCl$_3$): δ 7.35 (2H, m), 7.27 (CDCl$_3$), 7.11 (1H, m), 6.65 (1H, br m), 5.16 (1H, br m), 4.27 (1H, br m), 3.79 (3H, br m), 2.32 (1H, m), 1.59 (1H, m), 1.52 (9H, s), 0.94 (3H, br m)

Preparation 58: 1,1-dimethylethyl (1S,6R/1R,6S)-6-(3,4-dichlorophenyl)-1-(hydroxymethyl)-3-azabicyclo[4.1.0]hept-4-ene-3-carboxylate (P58)

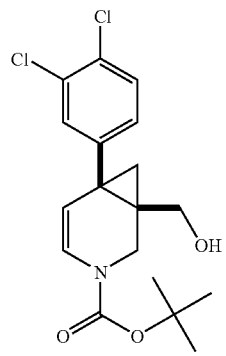

3-(1,1-dimethylethyl) 1-ethyl (1S,6R/1R,6S)-6-(3,4-dichlorophenyl)-3-azabicyclo[4.1.0]hept-4-ene-1,3-dicarboxylate (P57, 39.97 g, 0.9694 mol, 1 eq) was dissolved in THF (80 mL, 2 vol). A solution of 2M LiBH$_4$ in THF (120 mL, 0.242 mol, 2.5 eq) was added and the resulting solution was cooled with a room temperature water bath. Ethanol (28.5 mL, 0.485 mol, 5 eq) was added over 65 min. The reaction was stirred for 40 min, and heptane (200 mL, 5 vol) was added. Water was added (10 mL, 550 mole, 5.7 eq) over ~10 min, and the resulting slurry was stirred for 15-20 min. More water was added (200 mL, 5 vol), the mixture was stirred for 15 min, and the layers were allowed to settled, and separated. The organic layer was washed with water (200 mL, 5 vol), and then filtered through Whatman brand #2 filter paper and concentrated in vacuo. The resulting oil was dried in a 60° C. vacuum oven for ~72 h to provide 29.48 g, 82% yield, of title compound as a glassy solid.

NMR ($^1$H, CDCl$_3$): δ 7.38 (2H, br m), 7.15 (1H, br m), 6.60 (1H, br m), 5.12 (1H, br m), 4.24 (1H, br m), 3.38 (2H, br m), 3.29 (1H, br m), 1.51 (10H, br m), 1.30 (1H br m).

Preparation 59: 1,1-dimethylethyl (1S,6R/1R,6S)-6-(3,4-dichlorophenyl)-1-[(methyloxy)methyl]-3-azabicyclo[4.1.0]hept-4-ene-3-carboxylate (P59)

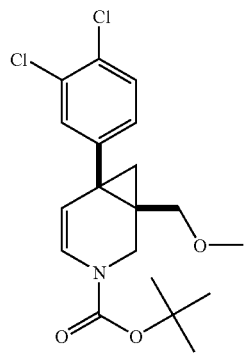

1,1-dimethylethyl (1S,6R/1R,6S)-6-(3,4-dichlorophenyl)-1-(hydroxymethyl)-3-azabicyclo[4.1.0]hept-4-ene-3-carboxylate (P58, 28.4 g, 76.7 mmol) was dissolved in DMSO (225 ml). The solution was then treated with potassium hydroxide (powder, 17.2 g, 0.3 mol) and stirred for 15 min. Iodomethane (9.5 ml, 0.15 mol) was added dropwise over 15 min and the reaction stirred for 90 min at room temperature. It was then quenched with water (115 ml) and MTBE (250 ml) and stirred for 1 h. The phases were then separated and the top (organic) phase washed with water (115 ml) and concentrated in vacuo to give the title compound as an oil (32 g crude weight).

NMR ($^1$H, CDCl$_3$): δ 7.40 (1H, d, J=4 Hz), 7.37 (1H, d, J=8 Hz), 7.15 (1H, dd, J=8, 4 Hz), 6.55 (1H, br m), 5.08 (1H, br m), 4.19 (1H, br m), 3.27 (1H, br m), 3.10 (3H, br s), 3.04 (1H, br m), 2.96 (1H, br m), 1.49 (9H, br s), 1.42 (1H, d, J=4 Hz), 1.28 (1H, br m). MS (m/z): 328 [M-t-Bu+2H]+

Preparation 60: 1,1-dimethylethyl (1S,6R)-6-(3,4-dichlorophenyl)-1-[(methyloxy)methyl]-3-azabicyclo[4.1.0]hept-4-ene-3-carboxylate (P60)

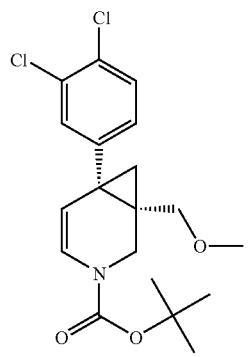

1,1-dimethylethyl (1S,6R/1R,6S)-6-(3,4-dichlorophenyl)-1-[(methyloxy)methyl]-3-azabicyclo[4.1.0]hept-4-ene-3-carboxylate (P59, 36 grams, 9.4 mmol) was dissolved in 370 mL (5% IPA in heptane) and the two enantiomers separated by chiral HPLC. Rt=5.7 min [Column used for processing: Chiralpak AD, 20 um, 20×250 mm, (ambient temp.) Processing parameters: Flow: 15 mL/min; Detection: 225 & 280 nm; Feed stock: 100 mg/mL]

After the solvent was evaporated, the product was isolated as an oil (16.2 g, optical purity, 99.2%).

Preparation 61: 3-(3,4-dichlorophenyl)-3-buten-1-ol (P61)

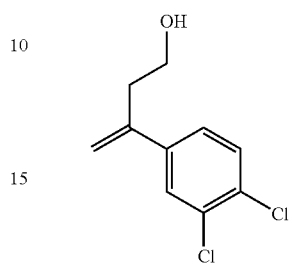

In a round-bottomed flask equipped with mechanical stirrer, under an argon atmosphere, 3,4-dichlorophenylboronic acid (128 g, 672 mmol) and 3-bromo-3-buten-1-ol (78 g, 517 mmol) were dissolved in toluene (1230 ml) and ethanol (492 ml). To this solution, tetrakis(triphenylphosphine)palladium (0) (29.8 g, 25.8 mmol) was added followed by sodium carbonate 2M aqueous solution (517 ml, 1033 mmol). The resulting mixture was heated at an internal temperature of 75° C. After 30 minutes, a thick precipitate formed. After 1 h, water (50 ml) was added to make the solid re-dissolved and the reaction mixture turned slightly yellow opalescent. At 3 h the reaction was worked-up.

Flask was cooled down to room T (a precipitate was formed) and the mixture was taken up with aqueous NaHCO$_3$ sat. solution (468 mL), water (468 mL) and AcOEt (468 mL). At addition of water solid dissolved; phases were separated and aqueous one back extracted with AcOEt (2×936 mL). Combined organics were dried (Na$_2$SO$_4$), concentrated under vacuum to give crude material (200 g) as black thick oil. This oil was purified by silica gel flash chromatography, eluting with cyclohexane/AcOEt from 8/2 to 7/3. Evaporation of solvent afforded the title compound (73 g), as dark thick oil.

NMR ($^1$H, CDCl$_3$): δ ppm 7.51 (d, 1H), 7.41 (d, 1H), 7.26 (dd, 1H), 5.34-5.53 (m, 1H), 5.02-5.29 (m, 1H), 3.60-3.95 (m, 2H), 2.57-2.94 (m, 2H), 1.50 (t, 1H)

Preparation 62: 3-(3,4-dichlorophenyl)-3-buten-1-yl methanesulfonate (P62)

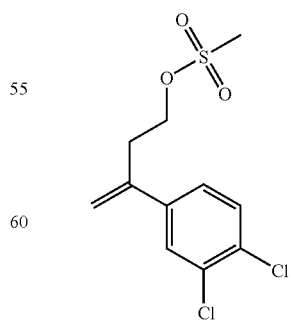

In a round-bottomed flask, 3-(3,4-dichlorophenyl)-3-buten-1-ol (P61, 73 g, 336 mmol) was dissolved in DCM (900 ml) to give a yellow solution. Then triethylamine (69.9 ml, 504 mmol) was added keeping the internal temperature below +5° C. with an ice bath.

Methanesulfonyl chloride (36.7 ml, 471 mmol) was then added dropwise in 30 min. keeping the internal temperature below +5° C. with an ice bath. The mixture was allowed to reach room temperature while stirring. After 3 h, the reaction mixture (suspension) was quenched by careful addition of aqueous ammonium chloride sat. solution (400 ml) keeping the internal temperature below +10° C. with an ice bath. At the end of the addition the pH of the aqueous phase was nearly 1. The two layers were separated. The aqueous layer was back-extracted with DCM (3×300 mL). The combined organic layers were washed with water (2×200 mL), dried ($Na_2SO_4$), and evaporated to give a crude product (101 g) that was purified over a silica gel pad (1000 g) eluting with cyclohexane/EtOAc from 9/1 to 1/1 to afford the title compound (90.8 g) as a dark yellow oil.

NMR ($^1H$, $CDCl_3$): δ ppm 7.49 (d, 1H), 7.44 (d, 1H), 7.24 (dd, 1H), 5.46 (d, 1H), 5.25 (d, 1H), 4.32 (t, 2H), 2.98 (s, 3H), 2.93 (t, 2H)

HPLC (walk-up): Rt=5.37 min

Preparation 63: dimethyl 2-(3,4-dichlorophenyl)-2-{2-[(methylsulfonyl)oxy]ethyl}-1,1-cyclopropanedicarboxylate (P63)

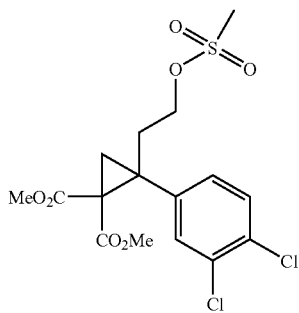

In a round-bottomed flask, 3-(3,4-dichlorophenyl)-3-buten-1-yl methanesulfonate (P62, 90.8 g, 308 mmol) was dissolved in chlorobenzene (200 ml) to give a green solution. Rhodium acetate dimer (6.80 g, 15.38 mmol) was added. The suspension was warmed to an internal temperature of +65° C. and dimethyl diazopropanedioate (78 g, 492 mmol, for a reference procedure of preparation see *Synthetic Communication* 1987, 17 (14), 1709-1716) dissolved in chlorobenzene (150 ml) was added dropwise (during 2.5 hrs), keeping the internal temperature below 65-67° C. At the end of the addition, the mixture was cooled to room temperature. It was diluted with DCM (300 ml) and filtered over a celite pad to separate the catalyst.

The solution was evaporated in vacuo to ⅓ of the volume and the crude (277 g) purified over a silica pad (silica gel 1.3 Kg) eluting with cyclohexane/ethyl acetate from 7/3 to 1/1 to afford the title compound (128.25 g).

NMR ($^1H$, $CDCl_3$): δ ppm 7.41 (d, 1H), 7.39 (d, 1H), 7.15 (dd, 1H), 4.08-4.22 (m, 1H), 3.94-4.06 (m, 1H), 3.85 (s, 3H), 3.48 (s, 3H), 2.95 (s, 3H), 2.42 (dt, 1H), 2.21 (d, 1H), 1.89-2.03 (m, 1H), 1.82 (d, 1H)

HPLC (walk-up): Rt=5.15 min

Preparation 64: methyl (1S,6R/1R,6S)-6-(3,4-dichlorophenyl)-2-oxo-3-azabicyclo[4.1.0]heptane-1-carboxylate (P64)

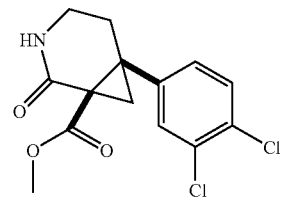

In a 5 L Parr reactor, dimethyl 2-(3,4-dichlorophenyl)-2-{2-[(methylsulfonyl)oxy]ethyl}-1,1-cyclopropanedicarboxylate (P63, 158 g, 372 mmol) was dissolved in ammonia 2M in methanol (3000 ml) to give a yellow solution.

The solution was warmed to +75° C. and the resulting mixture was stirred at this temperature overnight (internal pressure=2 atm). After 24 hrs, reaction was complete. The solution was concentrated to obtain a residue that was mixed with a residue (89.3 g) coming from an analogous preparation performed on another batch of 2-(3,4-dichlorophenyl)-2-{2-[(methylsulfonyl)oxy]ethyl}-1,1-cyclopropanedicarboxylate. The solvent was evaporated to obtain a crude oil (280 g). To this oil, AcOEt (5 L) and 1M aqueous HCl (2.5 L) were added and the mixture was vigorously stirred for 30 min in a 10 L reactor.

A diluted suspension (a mixture of organic phase, aqueous phase and solid) was obtained. The solid was filtered, washed with ethyl acetate and dried to afford a first batch of title compound (54.9 g).

The organic and aqueous layers were separated. The organic phase was then washed with aqueous HCl 1M (2 L), dried ($Na_2SO_4$) and concentrated to 1/10 of the volume. A solid precipitated out. It was filtered, washed with diethyl ether (150 ml) and dried under vacuum to afford a second batch of title compound (34.4 g).

The mother liquours of filtration were concentrated in vacuo to obtain a brown oil. This residue was triturated with ethyl ether (1×50 mL). The resulting solid was filtered, washed with cold ethyl ether and dried to give a third batch of title compound (7.27 g) as a off white solid.

The mother liquours were concentrated and chromatographed on Biotage 75M (silica gel) eluting with AcOEt to give a solid that was triturated in ethyl ether (35 ml) to give a fourth batch of title compound (6.2 g).

An overall amount of 102.7 g of product was thus obtained.

NMR ($^1H$, $CDCl_3$): δ ppm 7.47 (d, 1H), 7.41 (d, 1H), 7.20 (dd, 1H), 5.73 (br. s., 1H), 3.54 (s, 3H), 3.07-3.41 (m, 2H), 2.32-2.45 (m, 1H), 2.28 (d, 1H), 2.17 (d, 1H), 1.93 (d, 1H)

Preparation 65: 1,1-dimethylethyl (1S,6R/1R,6S)-6-(3,4-dichlorophenyl)-1-(hydroxymethyl)-3-azabicyclo[4.1.0]heptane-3-carboxylate (P65)

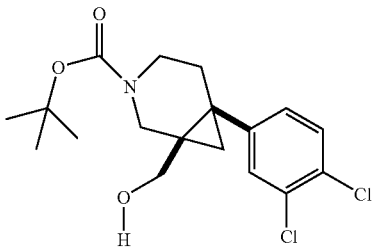

Step a)

In a round-bottomed flask, methyl (1S,6R/1R,6S)-6-(3,4-dichlorophenyl)-2-oxo-3-azabicyclo[4.1.0]heptane-1-carboxylate (P64, 90 g, 286 mmol) was dissolved in THF (1450 ml) to give a grey suspension. Borane tetrahydrofuran compex 1M (1633 ml, 1633 mmol) was added dropwise keeping the internal temperature below +5°. The resulting mixture was gently refluxed for 7 hrs. The mixture was cooled to +3° C. and quenched by careful addition of methanol (200 ml); then aqueous HCl 6M (450 ml) was added keeping the internal temperature below +6° C. The mixture was stirred at room temperature for 5 h. The acidic solution was concentrated under vacuum to remove THF, then water (900 ml) was added. The pH of the final solution was nearly 1. This solution was washed with ethyl ether (2×200 ml). The aqueous solution was basified by portionwise addition of potassium carbonate until pH 8-9, then THF (1200 ml) was added and the resulting mixture used directly in the next step.

Step b)

A round-bottomed flask was charged with the mixture coming from step a) (approximately 2700 ml, pH=8-9). Di-tert-butyl dicarbonate (80 ml, 343 mmol) was added portionwise at room temperature and the mixture was stirred overnight. The organic and aqueous layers were separated. The aqueous layer was back-extracted with ethyl acetate (3×600 mL). The combined organic layers were dried (Na$_2$SO$_4$) and concentrated to obtain a crude oil (165 g) that was purified over a silica pad (silica gel 1500 g), eluting with cyclohexane/ethyl acetate 8/2 to give the title compound (110 g) as a foamy colourless oil.

NMR ($^1$H, CDCl$_3$): δ ppm 7.39-7.42 (m, 1H), 7.37 (d, 1H), 7.17 (d, 1H), 3.73-3.90 (m, 2H), 2.99-3.49 (m, 4H), 1.91-2.13 (m, 2H), 1.48 (s, 9H), 0.92-1.07 (m, 2H).

HPLC (walk-up): Rt=6.12 min

Preparation 66: 1,1-dimethylethyl (1S,6R/1R,6S)-6-(3,4-dichlorophenyl)-1-[(methyloxy)methyl]-3-azabicyclo[4.1.0]heptane-3-carboxylate (P66)

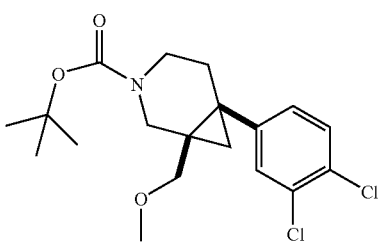

In a 1 L round-bottomed flask, 1,1-dimethylethyl (1S,6R/1R,6S)-6-(3,4-dichlorophenyl)-1-(hydroxymethyl)-3-azabicyclo[4.1.0]heptane-3-carboxylate (P65, 47.56 g, 128 mmol) was dissolved in THF (800 ml) to give a colourless solution. Sodium hydride (10.22 g, 256 mmol) was added keeping the internal temperature at 0° C. After 30 min, MeI (15.98 ml, 256 mmol) was added dropwise at the same temperature. The resulting mixture was stirred overnight at room temperature.

The mixture was quenched by dropwise addition of aqueous NaHCO$_3$ sat. (500 ml) keeping the internal temperature below +15° C. The resulting suspension was filtered, the solid was dissolved with water (200 ml). The two phases were separated and the aqueous phase was extracted with ethyl acetate (3×200 ml). The combined organic layers, dried (Na$_2$SO$_4$), were evaporated to give crude material (54 g) that was purified by silica gel chromatography, eluting with cyclohexane/ethyl acetate from 95/5 to 75/25 to give the title compound as a colourless oil (42.33 g).

NMR ($^1$H, CDCl$_3$): δ ppm 7.40-7.43 (m, 1H), 7.36 (d, 1H), 7.16 (d, 1H), 3.85 (d, 1H), 3.67 (d, 1H), 3.26-3.40 (m, 2H), 3.14 (s, 3H), 2.97-3.10 (m, 1H), 2.81-2.91 (m, 1H), 1.90-2.07 (m, 2H), 1.49 (s, 9H), 0.91-1.02 (m, 2H)

HPLC (walk-up): Rt=7.15 min

Preparation 67: dimethyl (2S)-2-(3,4-dichlorophenyl)-2-{2-[(methylsulfonyl)oxy]ethyl}-1,1-cyclopropanedicarboxylate and dimethyl (2R)-2-(3,4-dichlorophenyl)-2-{2-[(methylsulfonyl)oxy]ethyl}-1,1-cyclopropanedicarboxylate (P67)

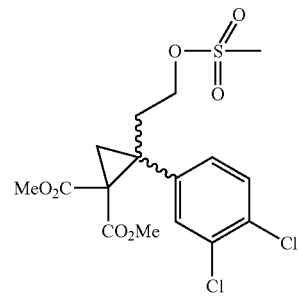

3-(3,4-dichlorophenyl)-3-buten-1-yl methanesulfonate (2.0 g, 6.78 mmol) and R2-[(S)-4-Cl-nttl]-4 (preparation of the catalyst described in Helv. Chem. Act., vol. 88 (2005), p. 216 and ss.) (0.105 g, 0.066 mmol) were dissolved in chlorobenzene (10 ml) at 25° C. A solution of dimethyl diazopropanedioate (1.7 g, 10.75 mmol) in chlorobenzene (10 ml) was added dropwise in 2 h.

The chlorobenzene was evaporated and the residue chromatographed over silica (230-400 Mesh) eluting with cyclohexane/AcOEt 8/2, 7/3 to afford the title compound (2.65 g).

NMR ($^1$H, CDCl$_3$): δ ppm 7.41 (d, 1H), 7.39 (d, 1H), 7.15 (dd, 1H), 4.08-4.22 (m, 1H), 3.94-4.06 (m, 1H), 3.85 (s, 3H), 3.48 (s, 3H), 2.95 (s, 3H), 2.42 (dt, 1H), 2.21 (d, 1H), 1.89-2.03 (m, 1H), 1.82 (d, 1H)

Chiral HPLC (Column: Chiralpak AD-H (25×0.46 cm); Mobile phase: n-Hexane/Ethanol 70/30% v/v; Flow rate: 1.0 ml/min; DAD:210-340: Enant1 (Rt=9.6 min)/Enant2 (Rt=11.7 min)=60/40 area %

Preparation 68: 1,1-dimethylethyl (1S,6R/1R,6S)-6-(3,4-dichlorophenyl)-1-(hydroxymethyl)-4-methyl-3-azabicyclo[4.1.0]heptane-3-carboxylate (P68)

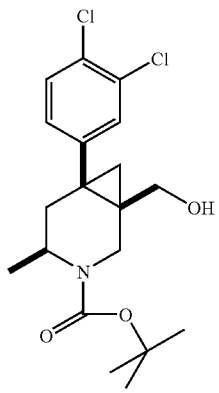

1,1-dimethylethyl 4-(3,4-dichlorophenyl)-5-(hydroxymethyl)-2-methyl-3,6-dihydro-1(2H)-pyridinecarboxylate (P22, two batches prepared in an analogous manner to that previously described for P22, 260 mg) were dissolved in DCM (5 mL). It was added at −20° C. to a suspension obtained by addition of diethylzinc 1.0M in hexane (4.19 mL) to a solution of diiodomethane (0.676 mL) in DCM (10 mL). The suspension was stirred at room temperature overnight. The reaction mixture was then quenched with 20 mL of a saturated solution of NH$_4$Cl and the two phases were stirred for 30 min. The organic layer was washed with brine (20 mL), dried and concentrated. Purification by chromatography on silica gel eluting with a gradient 5-40% ethyl acetate/cyclohexane afforded 75 mg of a colourless oil.

NMR ($^1$H, CDCl$_3$): δ 7.40-7.42 (m, 1H), 7.38 (d, 1H), 7.17 (dd, 1H), 3.39-3.48 (m, 2H), 3.20-3.27 (m, 1H), 2.44 (m, 1H), 2.06-2.16 (m, 1H), 1.81-1.91 (m, 1H), 1.61-1.69 (m, 1H), 1.47-1.50 (s, 9H), 1.24-1.28 (d, 3H), 0.84-0.94 (m, 2H).

Preparation 69: 1,1-dimethylethyl (1R,6S/1S,6R)-6-(3,4-dichlorophenyl)-1-{[(methylsulfonyl)oxy]methyl}-3-azabicyclo[4.1.0]heptane-3-carboxylate (P69)

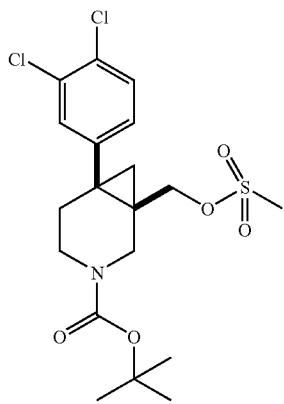

1,1-dimethylethyl (1R,6S/1S,6R)-6-(3,4-dichlorophenyl)-1-(hydroxymethyl)-3-azabicyclo[4.1.0]heptane-3-carboxylate (P5, 132 mg) and triethyl amine (74 µL) were dissolved in DCM (5 mL). Methanesulfonyl chloride (38 µL) was added at room temperature. After overnight stirring, DCM and NH$_4$Cl saturated solution were added. The organic solvent was evaporated obtaining the title compound (140 mg).

NMR ($^1$H, CDCl$_3$): δ 7.4 (m, 2H) 7.1 (d, 1H) 3.9 (d, 2H) 3.75 (m, 1H) 3.7 (s, 2H) 3.4 (m, 2H) 2.9 (m, 3H) 1.7 (m, 1H) 1.5 (s, 9H) 1.1-1.2 (dd, 2H); MS (m/z): 450 [MH]+

Preparation 70: 1-(1,1-dimethylethyl) 3-ethyl 4-oxo-1,3-piperidinedicarboxylate (P70)

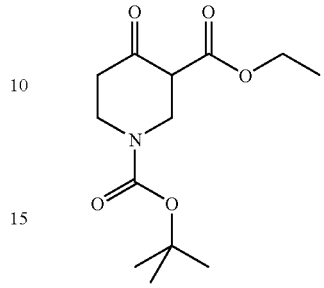

To a suspension of 3-ethylcarboxylate-4-piperidone hydrochloride (5 kg, 24.08 moles, Alfa Aesar) in heptane (12.7, kg) was charged triethylamine (7.25 kg, Alfa Aesar) at room temperature and the suspension was then stirred for 15 minutes. Di-tert-butyldicarbonate (6.3 kg, 28.89 moles, 1.2 eq., Alfa Aesar) was then added to the reaction over 20 minutes as a solution in heptane (4.1 Kg) at room temperature. The reaction was stirred at room temperature for approximately 40 min. Then water (25 L) was charged to the reaction at room temperature and stirred for 15 minutes. The layers are then allowed to separate and the aqueous layer removed. The organic layer was then washed with 1N HCl (25 L) and water (22 L). The resulting organic layer was then concentrated to an oil by vacuum distillation, with a jacket temperature of 20° C. Once concentrated to an oil, ethanol (13.7 kg)/water (17.5 kg) was then charged to the reaction and warmed to 50° C. Once reaction temperature has stabilized, the reaction is then cooled to −10° C. at a rate of 0.25° C./min. The reaction is held at −10° C. for greater than 6 hours. The resulting solids are then filtered, and the filtrate used to rinse the reactor and wash the filter cake. The recovered solids are then dried at room temperature under full vacuum with a N$_2$ bleed. Isolated 6354 grams of title compound (97% yield).

NMR ($^1$H, DMSO-d6): δ ppm 1.13-1.30 (m, 3H) 1.40 (s, 9H) 2.32 (t, J=5.98 Hz, 2H) 3.48 (t, J=5.98 Hz, 2H) 3.95 (s, 2H) 4.21 (q, J=7.08 Hz, 2H)

Preparation 71: 1-(1,1-dimethylethyl) 3-ethyl 4-{[(trifluoromethyl)sulfonyl]oxy}-5,6-dihydro-1,3(2H)-pyridinedicarboxylate (P71)

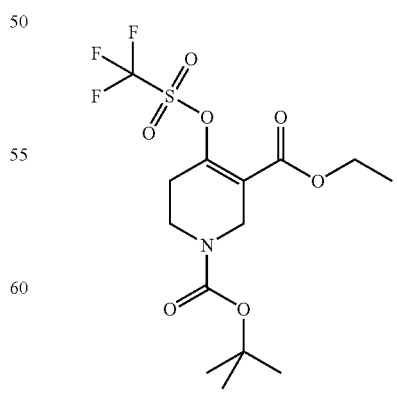

1-(1,1-Dimethylethyl) 3-ethyl 4-oxo-1,3-piperidinedicarboxylate (P70, 380.48 g, 1.40 moles) was dissolved in toluene (2.97 Kg). The solution was stirred for 10 mins and then cooled to −7° C. and then treated with N,N-diisopropylethylamine (271.56 g, 2.10 mol) while maintaining the reaction below −7° C. After stirring the reaction mixture for approximately 10 minutes, trifluoromethanesulfonic anhydride (436.29 g, 1.55 mol) was added while maintaining the temperature below 5° C. The reaction mixture was stirred at 1° C. for 31 minutes.

HPLC: Rt=2.69 min (HPLC instrument Agilent 1100 Series analysis performed on a Agilent Zorbax SB C18 (50× 3.0 mm, 1.8 um), mobile phase: water:acetonitrile:TFA (0.05%), gradient from 0 to 95% in 2.5 min, hold for 0.2 min, then re-equilibrate; T=60° C.; flow=1.5 mL/min)

Preparation 72: 1-(1,1-dimethylethyl) 3-ethyl 4-(3,4-dichlorophenyl)-5,6-dihydro-1,3(2H)-pyridinedicarboxylate (P72)

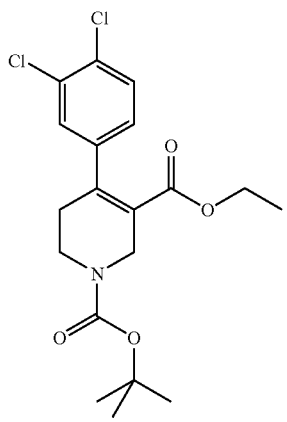

The 1-(1,1-dimethylethyl) 3-ethyl 4-{[(trifluoromethyl)sulfonyl]oxy}-5,6-dihydro-1,3(2H)-pyridinedicarboxylate solution in toluene (coming from preparation described for P71) was cooled to approximately −5° C. Next N,N-diisopropylethylamine (288.10 g, 2.23 mol), water (376.20 g), triphenylphosphine (27.52 g, 0.105 mol), and palladium (II) acetate trimer (7.88 g, 0.0117 mol) were added. The reaction mixture was warmed to 21° C. and stirred for 1 hour. Following the addition of 3,4-dichlorophenylboronic acid (268.80 g, 1.41 mol), the reaction mixture was heated to 70° C. and stirred for 48 minutes (temperature briefly reached 87.4° C. while heating). The reaction was cooled to −6.4° C. followed by the addition of sodium hydroxide (1N, 3286 g) while maintaining the reaction temperature below 5° C. Next, the reaction mixture was warmed to 20° C. and stirred for 1 hour. The layers were separated and carbon DARCO®G-60 (Activated Carbon)(57.57 g) was added to the organic phase. After 2 hours, the reaction mixture was filtered through celite 545. At this point, any remaining aqueous layer was removed and the reaction mixture was cooled to 21° C. Next, sodium bisulfite (20% w/w solution in water, 4330 g) was added while maintaining the reaction temperature below 28° C. The reaction mixture was stirred for 17 hours and 30 minutes followed by layer separation. The organic layer was washed with water (3792 g). After another layer separation, the organic layer containing the title compound was ready to be use in the next stage.

HPLC: Rt=2.94 min (HPLC instrument Agilent 1100 Series analysis performed on a Agilent Zorbax SB C18 (50× 3.0 mm, 1.8 um), mobile phase: water:acetonitrile:TFA (0.05%), gradient from 0 to 95% in 2.5 min, hold for 0.2 min, then re-equilibrate; T=60° C.; flow=1.5 mL/min)

EXAMPLE 1

(1S,6R/1R,6S)-6-(3,4-dichlorophenyl)-1-[(methyloxy)methyl]-3-azabicyclo[4.1.0]heptane hydrochloride (E1)

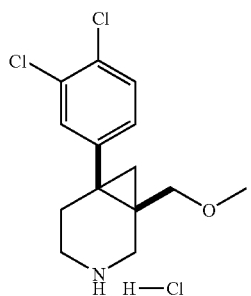

Step A

To a stirred solution of (1S,6R/1R,6S)-1,1-dimethylethyl-6-(3,4-dichlorophenyl)-1-[(methyloxy)methyl]-3-azabicyclo[4.1.0]heptane-3-carboxylate (80 mg, P6) in dry DCM (5 mL) under argon atmosphere, at 0° C., a solution of $CF_3COOH$ (1.5 mL) in dry DCM (5 mL) was added dropwise and the mixture was stirred at 0° C. for 1.5 h. The solvent was evaporated under reduced pressure, the residue kept under vacuum for 2 hours and then purified by preparative HPLC obtaining the trifluoroacetate salt of the title compound (40 mg) [System MDAP FractionLynx—Mass Directed Autopurification System™; Target product: m/z 286 [M+H]⁺ (Column: Luna C18, 250×21 mm, 10 mm; Mobile phase: A: H2O+0.1% TFA; B: $CH_3CN$+0.1% TFA; Gradient: from 20% (B) to 35% (B) in 30 min, −>100% in 3 min, then 100% (B) for 2 min; Flow rate 17 ml/min; UV wavelength range 210-350 nm; Mass range 100-900 amu (ES+); Ionization ES+)]

Step B

To a stirred solution of this material (18 mg) in dry diethyl ether (10 mL) under Argon atmosphere, at 0° C., aqueous NaOH (1M, 10 mL) was added dropwise and the mixture was vigorously stirred for 10 minutes at room temperature. The phases were separated and the watery one was extracted with diethyl ether (2×10 mL), the combined organic phases were dried on anhydrous $Na_2SO_4$ and the solvent removed under reduced pressure obtaining the free base of the title compound (13 mg). To a stirred solution of this compound (13 mg) in dry diethyl ether (1.5 mL) under Argon atmosphere, at 0° C., HCl (1M in diethyl ether, 100 μL) was added dropwise, the mixture was stirred at 0° C. for 10 minutes and for 30 minutes at room temperature. The solvent was removed by decantation and the precipitate was dried under high vacuum for 30 minutes and then for further two hours to give the title compound as a white solid (15 mg).

NMR (¹H, DMSO-d6): δ 8.71 (br. s., 2H) 7.73 (d, 1H) 7.59 (d, 1H) 7.41 (dd, 1H) 3.45 (d, 1H) 3.09-3.16 (m, 2H) 3.04 (s, 3H) 2.92 (d, 1H) 2.73-2.82 (m, 1H) 2.66 (d, 1H) 2.01-2.17 (m, 2H) 1.22-1.29 (m, 2H); MS (m/z): 286 [MH]+

EXAMPLE 2a and 3a (1S,6R)-6-(3,4-dichlorophenyl)-1-[(methyloxy)methyl]-3-azabicyclo[4.1.0]heptane (E2a) and ((1R,6S)-6-(3,4-dichlorophenyl)-1-[(methyloxy)methyl]-3-azabicyclo[4.1.0]heptane (E3a)

18 mg of the free base of (1S,6R/1R,6S)-6-(3,4-dichlorophenyl)-1-[(methyloxy)methyl]-3-azabicyclo[4.1.0]heptane hydrochloride (E1) were submitted to semi-preparative HPLC (chiral column Chiralpak AS-H, 250×21 mm, eluent A: n-hexane; B: isopropanol+0.1% isopropyl amine, gradient isocratic 5% B, flow rate 14 ml/min, detection UV at 230 nm. Retention times given were obtained using an analytical HPLC using a chiral column Chiralpak AS-H, 250×4.6 mm, eluent A: n-hexane; B: isopropanol+0.1% isopropyl amine, gradient isocratic 5% B, flow rate 1 ml/min, detection UV at 210-340 nm.) obtaining:

Example 2a (Enantiomer 1, Rt.=7.99 min) and Example 3a (Enantiomer 2, Rt.=14.92 min).

Determination of the Absolute Configuration of 2a and 3a:

Another batch of E2a and E3a was submitted for Ab Initio VCD (vibrational circular dichroism) analysis to determine the absolute configuration of these optical isomers. Example 2a (Enantiomer 1) corresponded to (1S,6R)-6-(3,4-dichlorophenyl)-1-[(methyloxy)methyl]-3-azabicyclo[4.1.0]heptane

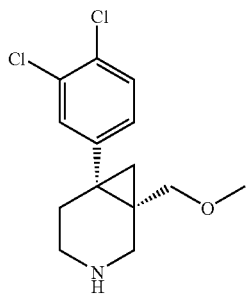

NMR ($^1$H, CDCl$_3$) δ ppm 7.43 (d, 1H), 7.36 (d, 1H), 7.18 (d, 1H), 3.31 (d, 1H), 3.12-3.15 (m, 3H), 3.08 (d, 1H), 2.95 (d, 1H), 2.83 (d, 1H), 2.73-2.80 (m, 1H), 2.63-2.70 (m, 1H), 1.91-2.00 (m, 1H), 1.79-1.87 (m, 1H), 0.99-1.04 (m, 2H)

Example 3a (Enantiomer 2) corresponded to (1R,6S)-6-(3,4-dichlorophenyl)-1-[(methyloxy)methyl]-3-azabicyclo[4.1.0]heptane

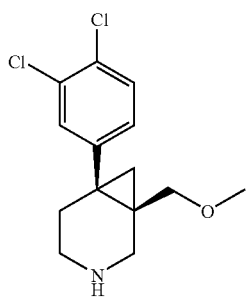

NMR ($^1$H, CDCl$_3$) δ ppm 7.43 (d, 1H), 7.35 (d, 1H), 7.17 (dd, 1H), 3.31 (d, 1H), 3.13 (s, 3H), 3.08 (d, 1H), 2.95 (d, 1H), 2.83 (d, 1H), 2.72-2.80 (m, 1H), 2.62-2.70 (m, 1H), 1.89-2.00 (m, 1H), 1.77-1.87 (m, 1H), 0.94-1.07 (m, 2H)

EXAMPLE 2a (1S,6R)-6-(3,4-dichlorophenyl)-1-[(methyloxy)methyl]-3-azabicyclo[4.1.0]heptane (E2a)

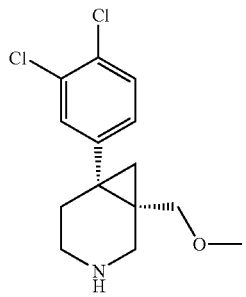

Method B:

1,1-dimethylethyl (1S,6R/1R,6S)-6-(3,4-dichlorophenyl)-1-[(methyloxy)methyl]-3-azabicyclo[4.1.0]hept-4-ene-3-carboxylate (P60, 10 grams, 25.8 mmol) was dissolved in toluene (100 mL). The solution was treated with triethylsilane (3.6 grams, 4.96 mL, 31.1 mmol, 1.2 eq) followed by trifluoroacetic acid (20 grams, 13.46 mL, 181.2 mmol, 7 eq). The reaction was stirred at room temperature for 48 hrs, then quenched with 1N sodium hydroxide (100 mL) and stirred for 10 min. The pH of the mixture was approximately 13. The phases were separated and the toluene phase was washed with 1N sodium hydroxide (100 mL) and water (10 mL) then concentrated in vacuo to give the product as an oil (8.5 grams).

NMR ($^1$H, CDCl$_3$): δ ppm 0.98-1.04 (m, 2H) 1.75-1.87 (m, 2H) 1.89-1.99 (m, 1H) 2.59-2.70 (m, 1H) 2.71-2.80 (m, 1H) 2.82 (d, J=9.80 Hz, 1H) 2.94 (d, J=9.89 Hz, 1H) 3.07 (d, J=12.91 Hz, 1H) 3.12 (d, J=1.01 Hz, 3H) 3.31 (d, J=12.82 Hz, 1H) 7.11-7.21 (m, 1H) 7.35 (dd, J=8.29, 0.96 Hz, 1H) 7.43 (d, J=2.11 Hz, 1H)

Method C:

(2R,3R)-2,3-bis[(phenylcarbonyl)oxy]butanedioic acid -(1S,6R)-6-(3,4-dichlorophenyl)-1-[(methyloxy)methyl]-3-azabicyclo[4.1.0]heptane (1:1) (E34, 37.8 g, 58.7 mmol) were diluted in DCM (500 ml) and treated with aqueous K$_2$CO$_3$ 10% w/w (500 ml). Phases were separated and the aqueous layer was back-extracted with DCM (1×400 mL). The collected organic phases, dried (Na$_2$SO$_4$), were evaporated to give title compound (17.4 g).

NMR ($^1$H, CDCl$_3$): δ ppm 7.45 (s, 1H), 7.36 (d, 1H), 7.19 (d, 1H), 3.32 (d, 1H), 3.14 (s, 3H), 3.09 (d, 1H), 2.96 (d, 1H), 2.84 (d, 1H), 2.73-2.81 (m, 1H), 2.64-2.71 (m, 1H), 1.92-2.00 (m, 1H), 1.79-1.88 (m, 1H), 0.97-1.07 (m, 2H).

Chiral HPLC: (Column: AS-H (25×0.46 cm); Eluent: n-Hexane/(2-propanol+0.1% isopropylamine) 95/5 v/v; Flow: 1 ml/min; DAD: 210-340 nm; CD: 230 nm; Enant1 (Rt=7.828 min)/Enant2 (Rt=14,430 min)=98.88/1.12 area Optical rotation analysis was performed on a further batch of E2a; optical rotation was measured at 589 nm (sodium 'D' line) using a Rudolph Research Analytical AUTOPOL V polarimeter. Experimental conditions: Cell: 0.5 dm (50 mm) thermostated micro-cell held at 25° C.; solvent: CCl$_4$; conc.:

38 mg/450 μl=8.4 gm/1200 ml. Observed Rotation: α=−0.23°; Specific rotation [α]$_D$=−5.47.

EXAMPLE 2b (1S,6R)-6-(3,4-dichlorophenyl)-1-[(methyloxy)methyl]-3-azabicyclo[4.1.0]heptane hydrochloride (E2b)

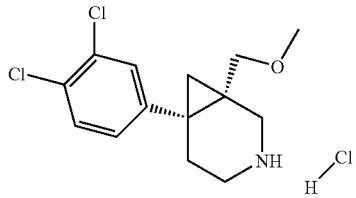

Method A:

To a solution of (1S,6R)-6-(3,4-dichlorophenyl)-1-[(methyloxy)methyl]-3-azabicyclo[4.1.0]heptane (E2a, amount obtained from the chiral semi-preparative HPLC described above) in DCM (0.2 ml) was added 1 equivalent of HCl (1M in Et$_2$O), the solvent evaporated under vacuo and the material thus obtained triturated with Et$_2$O to give 5 mg of the title compound as a white slightly hygroscopic solid.

Method B:

(1S,6R)-6-(3,4-dichlorophenyl)-1-[(methyloxy)methyl]-3-azabicyclo[4.1.0]heptane (E2a, 4.6 g, 16.07 mmol) was dissolved in Et$_2$O (60 ml) and the solution cooled to 0° C. (ice bath). Hydrochloric acid 1M in diethyl ether (17.68 ml, 1.1 eq.) was dropwise added at 0° C. under stirring. A white suspension was formed and the mixture was stirred at 25° C. for 2 hrs. The solid was filtered, washed with diethyl ether (46 ml) and dried under vacuum at 40° C. for 12 hrs to give the title compound (5.0 g) as white solid. 96% yield.

NMR ($^1$H, DMSO-d6, 600 MHz): δ (ppm): 9.05 (bs, 2H), 7.77 (d, 1H), 7.59 (d, 1H), 7.45 (dd, 1H), 3.46 (d, 1H), 3.14 (m, 1H), 3.13 (d, 1H), 3.06 (s, 3H), 2.99 (d, 1H), 2.79 (m, 1H), 2.63 (d, 1H), 2.17 (m, 1H), 2.07 (m, 1H), 1.30 (d, 1H), 1.27 (d, 1H)

EXAMPLE 3b (1R,6S)-6-(3,4-dichlorophenyl)-1-[(methyloxy)methyl]-3-azabicyclo[4.1.0]heptane hydrochloride (E3b)

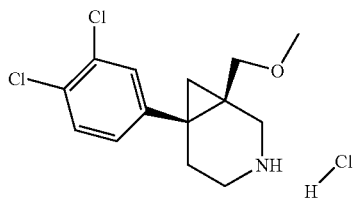

To a solution of ((1R,6S)-6-(3,4-dichlorophenyl)-1-[(methyloxy)methyl]-3-azabicyclo[4.1.0]heptane (E3a, amount obtained from the chiral semi-preparative HPLC described above) in DCM (0.2 ml) was added 1 equivalent of HCl (1M in Et$_2$O), the solvent evaporated under vacuo and the material thus obtained triturated with Et$_2$O to give 5 mg of the title compound as a white slightly hygroscopic solid.

EXAMPLE 4

[(1S,6R/1R,6S)-6-(3,4-dichlorophenyl)-3-azabicyclo[4.1.0]hept-1-yl]methanol (E4)

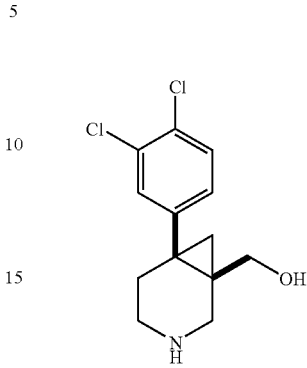

Method A:

2,6-Bis(1,1-dimethylethyl)-4-methylpyridine (35.836 g) was added under Argon atmosphere to a solution of CH$_2$I$_2$ (46.9 g) in dry DCM (260 mL), then ZnEt$_2$ (1M in hexane, 87.5 mL) was added dropwise at 0° C. over 5 mins. After stirring at 0° C. for 30 minutes, the reaction mixture was cooled at −20° C., a solution of 1,1-dimethylethyl 4-(3,4-dichlorophenyl)-5-(hydroxymethyl)-3,6-dihydro-1(2H)-pyridinecarboxylate (2 g, P4) in dry DCM (20 mL) was added dropwise and the reaction mixture was stirred at −20° C. for additional 30 mins and then overnight at room temperature. Aqueous HCl (1M, 300 mL) was added and the reaction mixture was vigorously stirred for 20 minutes, the phases were separated and the watery layer was basified to pH=12 with NaOH 3M.

The watery solution was extracted with diethyl ether (3×150 mL), the organic phase was evaporated and the residue was taken up with saturated NH$_4$Cl (100 mL) and diethyl ether (100 mL) and the mixture was vigorously stirred for 10 mins, then the phases were separated. The watery phase was washed with diethyl ether (3×50 mL), then was basified to pH=12 with NaOH 3M and extracted with diethyl ether (3×150 ml). The combined organic phases were dried on anhydrous Na$_2$SO$_4$ and the solvent was removed under reduced pressure to give 840 mg of impure material.

MS (m/z): 272 [MH]$^+$.

Method B:

To a stirred solution of methyl 6-(3,4-dichlorophenyl)-2-oxo-3-azabicyclo[4.1.0]heptane-1-carboxylate (P16, 0.5 g) in THF (2.5 mL), at 0° C. and under a nitrogen atmosphere, BH$_3$ THF complex (1M/THF, 12.8 mL) was added dropwise, then the reaction mixture was allowed to reach RT and stirred at reflux for 5 h. 1 mL of MeOH and 5 mL of HCl 1.0M in Et2O were added to the reaction mixture and the solution was stirred at room temperature for 2 hours. The mixture was concentrated under reduced pressure and the crude product was purified by FC (eluting with DCM/methanol/aqueous 28% NH4OH 9/1/0.1) to give 82 mg of the title compound as a yellow oil.

Method C:

(1S,6R/1R,6S)-1,1-dimethylethyl-6-(3,4-dichlorophenyl)-1-(hydroxymethyl)-3-azabicyclo[4.1.0]heptane-3-carboxylate (P5, 50 mg, impure compound obtained as described in P5, Method A) was purified by preparative HPLC (Column:Luna C18, 250×21 mm, 10 mm; mobile phase: A: H2O+ 0.1% TFA; B: CH$_3$CN+0.1% TFA; gradient: from 15% (B) to 35% (B) in 30 min, ->100% in 3 min, then 100% (B) for 2 min; flow rate: 17 ml/min; UV wavelength range: 210-350 nm) obtaining its trifluoroacetate salt (23 mg). To a stirred solution of this product (23 mg) in dry diethyl ether (10 mL) under argon atmosphere, at 0° C., NaOH (1M, 10 mL) was added dropwise and the mixture was vigorously stirred for 10 minutes at room temperature then the phases were separated and the watery one was extracted with diethyl ether (2×10 mL). The combined organic phases were dried on anhydrous $Na_2SO_4$ and the solvent was removed at reduced pressure obtaining the free base of the title compound (16 mg).

EXAMPLE 5a and 6a

[(1S,6R or 1R,6S)-6-(3,4-dichlorophenyl)-3-azabicyclo[4.1.0]hept-1-yl]methanol (E5a) and [(1R,6S or 1S,6R)-6-(3,4-dichlorophenyl)-3-azabicyclo[4.1.0]hept-1-yl]methanol (E6a)

[(1S,6R/1R,6S)-6-(3,4-dichlorophenyl)-3-azabicyclo[4.1.0]hept-1-yl]methanol (E4, 82 mg) was submitted to semi-preparative HPLC (chiral column Chiralpak AD-H, 25×4.6 cm, eluent A: n-hexane; B: isopropanol+0.1% isopropylamine 70/30 v/v, flow rate 0.8 ml/min., detection UV at 230 nm.) obtaining:

[(1S,6R or 1R,6S)-6-(3,4-dichlorophenyl)-3-azabicyclo[4.1.0]hept-1-yl]methanol (E5a, Enantiomer 1, Rt.=6.263 min) and [(1R,6S or 1S,6R)-6-(3,4-dichlorophenyl)-3-azabicyclo[4.1.0]hept-1-yl]methanol (E6a, Enantiomer 2, Rt.=15.699 min).

EXAMPLE 5b

[(1S,6R or 1R,6S)-6-(3,4-dichlorophenyl)-3-azabicyclo[4.1.0]hept-1-yl]methanol hydrochloride (E5b)

To a solution of [(1S,6R or 1R,6S)-6-(3,4-dichlorophenyl)-3-azabicyclo[4.1.0]hept-1-yl]methanol (E5a, amount obtained from the preparation described above) in DCM was added 1 equivalent of HCl (1M in $Et_2O$), the solvent evaporated in vacuo and the material thus obtained triturated with $Et_2O$ to give 30 mg of the corresponding hydrochloride salt as a white slightly hygroscopic solid.

EXAMPLE 6b

[(1R,6S or 1S,6R)-6-(3,4-dichlorophenyl)-3-azabicyclo[4.1.0]hept-1-yl]methanol (E6b)

To a solution of [(1R,6S or 1S,6R)-6-(3,4-dichlorophenyl)-3-azabicyclo[4.1.0]hept-1-yl]methanol (E6a, amount obtained from the preparation described above) in DCM was added 1 equivalent of HCl (1M in $Et_2O$), the solvent evaporated in vacuo and the material thus obtained triturated with $Et_2O$ to give 30 mg of the corresponding hydrochloride salt as a white slightly hygroscopic solid.

NMR ($^1$H, DMSO-d6): d ppm 8.78 (d, 2H) 7.76 (d, 1H) 7.58 (dd, 1H) 7.37-7.46 (m, 1H) 4.75 (t, 1H) 3.49-3.60 (m, 1H) 3.06-3.23 (m, 2H) 2.95-3.05 (m, 1H) 2.72-2.88 (m, 2H) 1.99-2.21 (m, 2H) 1.15-1.26 (m, 2H)

EXAMPLE 7

(1S,6R/1R,6S)-6-(3,4-dichlorophenyl)-3-azabicyclo[4.1.0]hept-1-yl]-methanol hydrochloride (E7)

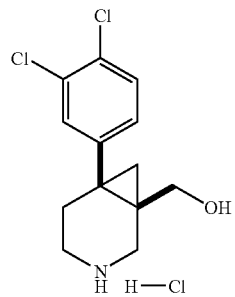

To a stirred solution of [(1S,6R/1R,6S)-6-(3,4-dichlorophenyl)-3-azabicyclo[4.1.0]hept-1-yl]methanol (E4, 16 mg) in dry diethyl ether (1.5 mL) under argon atmosphere, at 0° C., HCl (1M in diethyl ether, 0.12 ml) was added dropwise, the mixture was stirred at 0° C. for 10 minutes and for 30 minutes at room temperature. The solvent was removed by decantation and the precipitate was dried under high vacuum for 30 minutes to give the titled compound as white solid (18 mg).

NMR ($^1$H, DMSO-d6): δ 8.66 (br. s., 2H) 7.73 (d, 1H) 7.57 (d, 1H) 7.40 (dd, 1H) 4.75 (t, 1H) 3.52 (d, 1H) 3.06-3.18 (m, 2H) 2.93-3.03 (m, 1H) 2.70-2.83 (m, 2H) 1.99-2.17 (m, 2H) 1.15-1.24 (m, 2H); MS (m/z): 272 [MH]$^+$

EXAMPLE 8

(1R,6S/1S,6R)-6-(3,4-dichlorophenyl)-3-azabicyclo[4.1.0]heptane (E8)

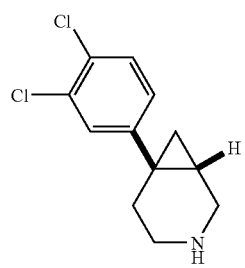

To a solution of (1R,6R/1S,6S)-1-(3,4-dichlorophenyl)-3-azabicyclo[4.1.0]heptan-4-one and (1R,6S/1S,6R)-6-(3,4-dichlorophenyl)-3-azabicyclo[4.1.0]heptan-4-one (640 mg, P11) in dry tetrahydrofurane (16 ml) borane THF (1M in THF, 7.53 ml) was added under $N_2$ and the mixture heated at reflux for 3 h and at room temperature over night and then heated at reflux for 2 h. The mixture was then cooled to 0° C. and methanol (8 mL) followed by hydrochloric acid (1M/ether, 25 mL) were cautiously added monitoring gas evolution and the solution stirred at room temperature over night. Solvents were then removed in vacuo and potassium carbonate (10% solution) was added to the residue. The aqueous layer was extracted with dichloromethane, then the organic phase was washed with a NaCl saturated solution, dried and concentrated under reduced pressure. The title compound was separated by aminic cartridge (eluting with cyclohexane/ethyl acetate from 9/1 to 7/3) to give the title compound in 150 mg yield.

NMR ($^1$H, CDCl$_3$): δ 7.37 (m, 2H), 7.15 (d, 1H), 3.35 (m, 1H), 3.12 (d, 1H), 2.78 (m, 2H), 2.05 (m, 2H), 1.35 (m, 1H), 1.04 (m, 1H), 0.94 (m, 1H); MS (m/z): 242 [MH]$^+$.

EXAMPLE 9a and 10a (1R,6S)-6-(3,4-dichlorophenyl)-3-azabicyclo[4.1.0]heptane (E9a) and (1S,6R)-6-(3,4-dichlorophenyl)-3-azabicyclo[4.1.0]heptane (E10a)

(1R,6S/1S,6R)-6-(3,4-dichlorophenyl)-3-azabicyclo[4.1.0]heptane (E8, 150 mg) was submitted to semi-preparative HPLC (chiral column Chiralpak AD-H, 25×4.6 cm, eluent A: n-hexane; B: isopropanol+0.1% isopropylamine 99/1 v/v, flow rate 1 ml/min., detection UV at 230 nm.) obtaining:

Example 9a (E9a, Enantiomer 1, Rt.=15.22 min) and Example 10a (E10a, Enantiomer 2, Rt.=15.33 min).

Determination of the Absolute Configuration of 9a and 10a:

A new batch of E9a (7 mg) and E10a (9 mg)(prepared following an analogous procedure to that described below for 9B and 10B and then treating the corresponding hydrochloride salts with NaOH to obtain the free bases) was submitted to Ab Initio VCD (vibrational circular dichroism) and comparative VCD analysis to determine the absolute configuration of these optical isomers.

Example 9a (enantiomer 1) corresponded to (1R,6S)-6-(3,4-dichlorophenyl)-3-azabicyclo[4.1.0]heptane

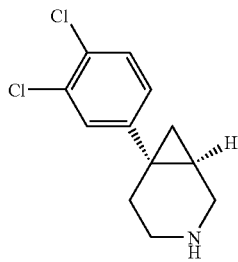

NMR ($^1$H, CDCl$_3$): δ ppm 7.32-7.37 (m, 2H), 7.10 (dd, 1H), 3.34 (dd, 1H), 3.07 (d, 1H), 2.51-2.79 (m, 2H), 1.97-2.08 (m, 1H), 1.85-1.97 (m, 1H), 1.21-1.36 (m, 1H), 0.92-1.01 (m, 1H), 0.81-0.91 (m, 1H)

Example 10a (enantiomer 2) corresponded to (1S,6R)-6-(3,4-dichlorophenyl)-3-azabicyclo[4.1.0]heptane:

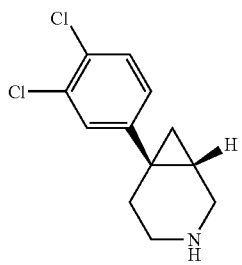

NMR ($^1$H, CDCl$_3$): δ ppm 7.32-7.37 (m, 2H), 7.10 (dd, 1H), 3.34 (dd, 1H), 3.07 (d, 1H), 2.51-2.79 (m, 2H), 1.97-2.08 (m, 1H), 1.85-1.97 (m, 1H), 1.21-1.36 (m, 1H), 0.92-1.01 (m, 1H), 0.81-0.91 (m, 1H)

EXAMPLE 9b (1R,6S)-6-(3,4-dichlorophenyl)-3-azabicyclo[4.1.0]heptane hydrochloride (E9b)

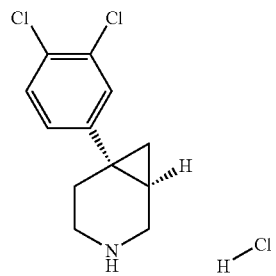

To a solution of (1R,6S)-6-(3,4-dichlorophenyl)-3-azabicyclo[4.1.0]heptane (E9a, 40 mg) in DCM was added 1 equivalent of HCl (1M in Et$_2$O), the solvent evaporated in vacuo and the material thus obtained triturated with Et$_2$O to give 45 mg of the title compound as a white slightly hygroscopic solid.

NMR ($^1$H, MeOH-d$_4$): δ ppm 7.52 (d, 1H) 7.45 (d, 1H) 7.28 (dd, 1.52 Hz, 1H) 3.46-3.65 (m, 7.07 Hz, 1H) 3.10 (d, 1H) 2.88-3.04 (m, 1H) 2.49-2.82 (m, 1H) 1.97-2.28 (m, 2H) 1.37-1.56 (m, 1H) 1.07-1.19 (m, 1H) 0.92-1.06 (m, 1H)

EXAMPLE 10b (1S,6R)-6-(3,4-dichlorophenyl)-3-azabicyclo[4.1.0]heptane hydrochloride (E10b)

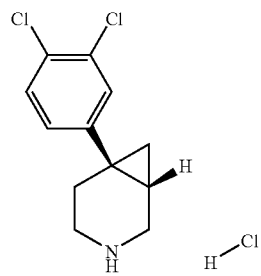

To a solution of (1S,6R)-6-(3,4-dichlorophenyl)-3-azabicyclo[4.1.0]heptane (E10a, 40 mg) in DCM was added 1 equivalent of HCl (1M in Et$_2$O), the solvent evaporated in vacuo and the material thus obtained triturated with Et$_2$O to give 45 mg of the title compound as a white slightly hygroscopic solid.

NMR ($^1$H, MeOH-d$_4$): δ ppm 7.52 (d, 1H) 7.45 (d, 1H) 7.28 (dd, 1.52 Hz, 1H) 3.46-3.65 (m, 7.07 Hz, 1H) 3.10 (d, 1H) 2.88-3.04 (m, 1H) 2.49-2.82 (m, 1H) 1.97-2.28 (m, 2H) 1.37-1.56 (m, 1H) 1.07-1.19 (m, 1H) 0.92-1.06 (m, 1H)

EXAMPLE 11

(1S,4R,6R/1R,4S,6S)-6-(3,4-dichlorophenyl)-4-methyl-1-[(methyloxy)methyl]-3-azabicyclo[4.1.0]heptane (E11)

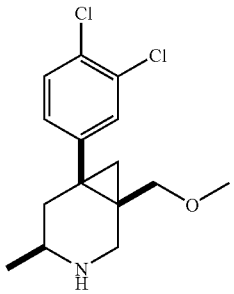

1,1-dimethylethyl (1S,6R/1R,6S)-6-(3,4-dichlorophenyl)-1-(hydroxymethyl)-4-methyl-3-azabicyclo[4.1.0]heptane-3-carboxylate (P68, 70 mg) was dissolved in DMF (30 mL) and cooled to 0 C. °; then sodium hydride 60% dispersed on mineral oil (10.9 mg) was added portionwise. The mixture was stirred at 0° C. for 30 min and then iodomethane (0.017 mL) was added. The mixture was slowly warmed to room temperature and stirred for 1.5 h. Further 7.2 mg of sodium hydride 60% dispersed on mineral oil and 0.017 mL of iodomethane were added and the mixture was stirred for an additional hour. The reaction mixture was then quenched with a saturated solution of NH₄Cl (30 mL) and Et₂O (30 mL) added. The aqueous phase was washed with Et₂O (3×30 mL), the organic phases combined, dried over Na₂SO₄ and concentrated. Purification by chromatography on silica gel eluting with a gradient 10%-30% ethyl acetate/cyclohexane afforded a compound (50 mg) that was dissolved in DCM (1.2 mL), cooled to 0° C. and reacted with trifluoroacetic acid (0.22 mL). The mixture was slowly warmed to room temperature and stirred at this temperature for 2 h. The volatiles were evaporated under vacuum and the residue purified by SCX cartridge eluting first with MeOH and then with 2.0M NH₃ in MeOH. Further purification by preparative HPLC afforded the title compound, 20 mg.

XBridge PREP C18, 100×19 mm, 5 µm
Mobile phase: H₂O+0.1% TFA; B: CH₃CN
Gradient:20(B) for 1 min, 20% to 35% (B) in 12 min, 35% to 100% (B) in 0.5 min, 100% (B) for 1.5 min
Flow rate: 17 mL/min NMR ($^1$H, CDCl₃): δ 7.46 (d, 1H), 7.33 (d, 1H), 7.20 (dd, 1H), 3.54 (d, 1H), 3.06-3.17 (m, 3H), 2.89-3.01 (m, 2H), 2.72 (d, 1H), 2.27-2.53 (m, 1H), 1.91-2.07 (m, 1H), 1.27-1.46 (m, 1H), 1.04 (d, 3H), 0.87-0.98 (m, 2H). MS (m/z): 300 [M+H]⁺.

EXAMPLE 12

(1S,6R)-6-(3,4-dichlorophenyl)-3-methyl-1-[(methyloxy)methyl]-3-azabicyclo[4.1.0]heptane (E12)

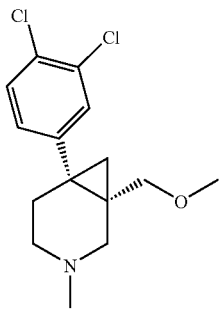

(1S,6R)-6-(3,4-dichlorophenyl)-1-[(methyloxy)methyl]-3-azabicyclo[4.1.0]heptane (E2a, 25 mg) was dissolved in methanol (1 mL); acetic acid (0.015 mL) was added followed by sodium triacetoxyborohydride (27.8 mg) and formaldehyde 37% in water (0.06 mL). The reaction mixture was stirred at room temperature overnight. Volatiles were then evaporated and the residue partitioned between DCM (20 mL) and aqueous sat NaHCO₃ (20 mL) solution, dried and concentrated. Purification by chromatography (NH column) eluting with a gradient 0-100% ethyl acetate-cyclohexane afforded the title compound (16 mg).

NMR ($^1$H, CDCl₃): δ 7.44 (d, 1H), 7.35 (d, 1H), 7.18 (dd, 1H), 3.15 (s, 3H), 2.90 (dd, 2H), 2.78 (d, 1H), 2.70 (d, 1H), 2.23-2.30 (m, 5H), 1.96-2.13 (m, 2H), 1.05 (d, 1H), 1.01 (d, 1H); MS (m/z): 300 [M+H]⁺.

EXAMPLE 13

(1S,6R)-6-(3,4-dichlorophenyl)-3-methyl-1-[(methyloxy)methyl]-3-azabicyclo[4.1.0]heptane hydrochloride (E13)

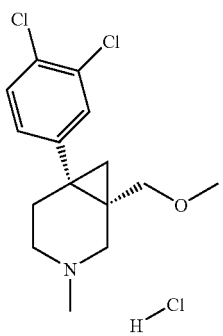

(1S,6R)-6-(3,4-dichlorophenyl)-3-methyl-1-[(methyloxy) methyl]-3-azabicyclo[4.1.0]heptane (E12, 16 mg) was treated with hydrochloric acid 1.0M in diethyl ether (0.064 mL). 0.5 mL of diethyl ether were added and a colourless solid formed. Organic phase was removed after decantation of the solid. Colourless solid obtained as a 5:1 mixture of isomers due protonation on the nitrogen atom (16 mg).

NMR ($^1$H, DMSO-d6): δ. 10.49 (br. s., 1H), 7.84 (d, 1H), 7.57-7.65 (m, 1H), 7.51-7.55 (m, 1H), 3.68-3.66 (m, 1H), 3.22-3.35 (m, 1H), 3.00-3.17 (m, 5H), 2.76-2.93 (m, 2H), 2.68-2.75 (m, 3H), 2.29-2.43 (m, 1H), 2.10-2.21 (m, 1H), 1.32 (d, 1H), 1.27 (d, 1H) (peaks referred to the main species); MS (m/z): 300 [MH]$^+$.

EXAMPLE 14

(1R,6S/1S,6R)-6-[4-chloro-3-(trifluoromethyl)phenyl]-1-[(methyloxy)methyl]-3-azabicyclo[4.1.0]heptane (E14)

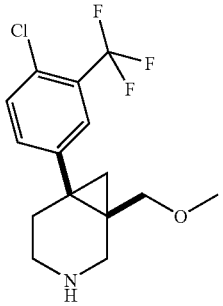

Step A 1,1-dimethylethyl (1R,6S/1S,6R)-6-[4-chloro-3-(trifluoromethyl)phenyl]-1-(hydroxymethyl)-3-azabicyclo[4.1.0]heptane-3-carboxylate (P27, 0.3 g) was dissolved in DMF (5 mL) and cooled to 0° C.; NaH 60% in mineral oil (39 mg) was added and the reaction mixture was stirred at 0° C. for 30 minutes. Iodomethane (92 μl) was then added and mixture slowly warmed to room temperature. Further 2 addition of NaH (20 mg) and MeI (50 μl) each were done and the mixture stirred for an overall time of 1.5 hours. The reaction mixture was then quenched at 0° C. with a saturated solution of NH$_4$Cl (5 mL) and diluted with diethyl ether (20 mL); the organic phase was separated, washed with brine (20 mL), dried and concentrated under vacuum. The crude mixture was then purified by chromatography on silica gel eluting with a gradient 10-50% ethylacetate/cyclohexane to afford 1,1-dimethylethyl (1R,6S)-6-[4-chloro-3-(trifluoromethyl)phenyl]-1-[(methyloxy)methyl]-3-azabicyclo[4.1.0]heptane-3-carboxylate as colourless oil (107 mg).

MS (m/z): 420 [MH]$^+$, 363 [M−56]$^+$.

Step B 1,1-dimethylethyl (1R,6S)-6-[4-chloro-3-(trifluoromethyl)phenyl]-1-[(methyloxy)methyl]-3-azabicyclo[4.1.0]heptane-3-carboxylate coming from step A was dissolved in DCM (4 mL) and TFA (0.2 mL) was added to the solution. The reaction mixture was stirred at room temperature for 1 hour and then volatiles were evaporated in vacuo. The residue was dissolved in DCM (10 mL), washed with a saturated solution of NaHCO$_3$ (10 mL), brine (10 mL), dried and concentrated under vacuum. The residue was purified initially on a SCX cartridge eluting first with MeOH followed by 2.0N NH$_3$ in MeOH and then by chromatography on silica gel eluting with a gradient 3% MeOH/DCM to 8% MeOH/DCM+2% 2.0N NH$_3$ in MeOH to give 55 mg of the title compound.

NMR ($^1$H, CDCl$_3$): δ 7.72 (d, 1H), 7.48-7.53 (m, 1H), 7.42-7.46 (m, 1H), 3.42 (d, 1H), 3.08-3.14 (m, 4H), 3.04 (d, 1H), 2.81-2.90 (m, 1H), 2.66-2.76 (m, 2H), 1.97-2.06 (m, 1H), 1.85-1.93 (m, 2H), 1.11 (d, 1H), 1.04 (d, 1H); MS (m/z): 320 [MH]$^+$.

EXAMPLE 15

(1R,6S/1S,6R)-6-[4-chloro-3-(trifluoromethyl)phenyl]-1-[(methyloxy)methyl]-3-azabicyclo[4.1.0]heptane hydrochloride (E15)

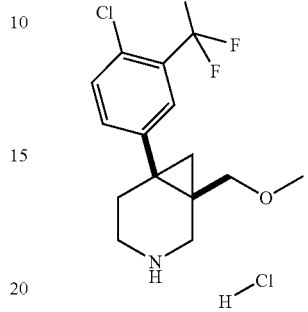

To a solution of (1R,6S/1S,6R)-6-[4-chloro-3-(trifluoromethyl)phenyl]-1-[(methyloxy)methyl]-3-azabicyclo[4.1.0]heptane (E14, 55 mg) in DCM was added 1 equivalent of HCl (1M in Et$_2$O), the solvent evaporated in vacuo and the material thus obtained triturated with Et$_2$O to give 61 mg of the title compound as a white solid.

NMR ($^1$H, DMSO-d6): δ 8.48-8.86 (m, 2H), 7.95 (s, 1H), 7.63-7.77 (m, 2H), 3.51 (d, 1H), 3.13-3.22 (m, 2H), 3.03 (s, 3H), 2.73-2.88 (m, 2H), 2.72-2.88 (m, 2H), 2.05-2.16 (m, 1H), 1.26-1.36 (m, 2H)); MS (m/z): 320 [MH]$^+$.

EXAMPLE 16

(1R,6S/1S,6R)-6-(4-chlorophenyl)-1-[(methyloxy)methyl]-3-azabicyclo[4.1.0]heptane (E16)

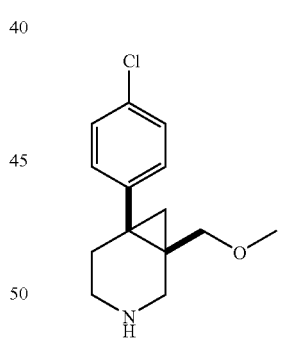

To an ice cooled solution of 1,1-dimethylethyl (1R,6S/1S/6R)-6-(4-chlorophenyl)-1-[(methyloxy)methyl]-3-azabicyclo[4.1.0]heptane-3-carboxylate (P32, impure compound obtained with a similar procedure to that previously described for P32, 280 mg) in dichloromethane (5 mL) under nitrogen, trifluoroacetic acid (1 mL) was added dropwise. The reaction mixture was allowed to room temperature and then stirred for 1 h. The solvent was evaporated under reduced pressure. The crude material was purified through a SCX (5 g) column, then was submitted to preparative HPLC (column: Luna AXIA C18, 100×21 mm, 5 um; Mobile phase: A: H2O+0.1% TFA; B: CH$_3$CN; Gradient: 15% (B)→35% (B) in 15 min (curve 7*), 35% (B)→100% (B) in 2 min, 100% (B) for 0.1 min; Flow rate 17 ml/min; UV range: 210-350 nm; Mass range:

100-900 amu (ES+); Ionization: ES+). The compound obtained was passed through a SCX column to afford the title compound (70 mg).

NMR (¹H, CDCl₃): δ ppm 7.25 (s, 4H) 3.30 (d, 1H) 3.08-3.14 (m, 4H) 2.85-2.91 (m, 2H) 2.63-2.80 (m, 2H) 1.81-1.99 (m, 2H) 0.99-1.05 (m, 2H).

EXAMPLE 17

(1R,6S/1S,6R)-6-(4-chlorophenyl)-1-[(methyloxy)methyl]-3-azabicyclo[4.1.0]heptane hydrochloride (E17)

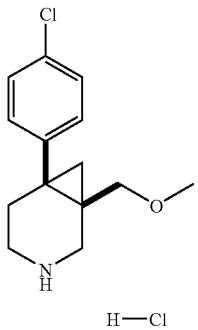

To a solution of (1R,6S/1S,6R)-6-(4-chlorophenyl)-1-[(methyloxy)methyl]-3-azabicyclo[4.1.0]heptane (E16, 70 mg) in anhydrous dichloromethane (2 mL) was added HCl 1.0M in anhydrous diethylether (0.278 mL). The solvent was evaporated under reduced pressure and the resulting solid was triturated with anhydrous diethylether to give the title compound (76 mg).

NMR (¹H, DMSO-d₆): δ ppm 8.33-9.07 (m, 2H) 7.44 (d, 2H) 7.38 (d, 2H) 3.47 (d, 1H) 3.15 (d, 1H) 3.07-3.19 (m, 1H) 3.00-3.07 (m, 3H) 2.94 (d, 1H) 2.74-2.84 (m, 1H) 2.58 (d, 1H) 2.09-2.23 (m, 1H) 1.96-2.09 (m, 1H) 1.27 (d, 1H) 1.21 (d, 1H)

EXAMPLE 18

(1R,6S/1S,6R)-6-(3,4-dichlorophenyl)-1-[(ethyloxy)methyl]-3-azabicyclo[4.1.0]heptane hydrochloride (E18)

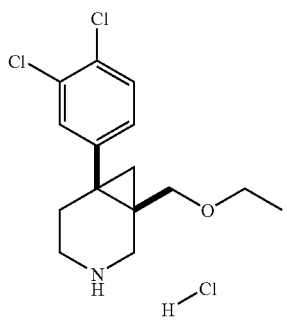

Step A

To a stirred solution of 1,1-dimethylethyl (1R,6S/1S,6R)-6-(3,4-dichlorophenyl)-1-[(ethyloxy)methyl]-3-azabicyclo[4.1.0]heptane-3-carboxylate (P51, 78 mg) in dry DCM (5 mL), under a nitrogen atmosphere, trifluoroacetic acid (1.5 mL) was added and the stirring continued for 2 hrs. After this period of time toluene was added and the solvent evaporated obtaining a crude product that was dissolved in DCM, the organic phase was washed with aqueous concentrated NaHCO3 solution, the organic solvent evaporated. The crude product was purified first by flash-chromatography (eluting with DCM/(Methanol +1% 2N NH₃ in MeOH) from 0 to 20%) and then by LC-MS to give 27 mg of (1R,6S/1S,6R)-6-(3,4-dichlorophenyl)-1-[(ethyloxy)methyl]-3-azabicyclo[4.1.0]heptane, the free base of the title compound.

Step B 10 mg of this compound were dissolved in DCM (1 ml) and 1 equivalent of 1N HCl in Et₂O was added. The solvent was removed in vacuo to give title compound (12 mg).

NMR (¹H, MeOH-d₄): δ 7.58 (d, 1H) 7.38 (d, 1H) 7.25 (dd, 1H) 3.64 (d, 1H) 3.15 (m, 5H) 2.79 (m, 1H) 2.57 (d, 1H) 2.11 (m, 2H) 1.19 (d, 1H) 1.12 (d, 1H) 0.98 (t, 3H);

MS (m/z): 300 [MH]+

EXAMPLE 19a and 20a (1R,6S or 1S,6R)-6-(3,4-dichlorophenyl)-1-[(ethyloxy)methyl]-3-azabicyclo[4.1.0]heptane (E19a) and (1S,6R or 1R,6S)-6-(3,4-dichlorophenyl)-1-[(ethyloxy)methyl]-3-azabicyclo[4.1.0]heptane (E20a)

(1R,6S/1S,6R)-6-(3,4-dichlorophenyl)-1-[(ethyloxy)methyl]-3-azabicyclo[4.1.0]heptane hydrochloride (E18, 28 mg) was then submitted to semi-preparative SFC to give the separated enantiomers, by using a chiral column Chiralpak AD-H (25×4.6 cm), eluent 2-propanol+0.1% isopropylamine 13%, T 35° C., P 100 bar, flow rate 2.0 mL/min, detection DAD 210-340 nm, CD 225 nm. obtaining:

Example 19a (Enantiomer 1, Rt.=14.36 min, 11 mg, colourless oil, MS (m/z): 300 [MH]⁺) and Example 20a (enantiomer 2, Rt.=15.70 min, 7 mg, colourless oil, MS (m/z): 300 [MH]⁺).

EXAMPLE 19b (1R,6S or 1S,6R)-6-(3,4-dichlorophenyl)-1-[(ethyloxy)methyl]-3-azabicyclo[4.1.0]heptane hydrochloride (E19b)

To a solution of (1R,6S or 1S,6R)-6-(3,4-dichlorophenyl)-1-[(ethyloxy)methyl]-3-azabicyclo[4.1.0]heptane (E19a, 11 mg) in DCM (0.2 ml) was added 1 equivalent of HCl (1M in Et₂O), the solvent evaporated under vacuo and the material thus obtained triturated with Et₂O to give 8.9 mg of the title compound as a white slightly hygroscopic solid.

MS (m/z): 300 [MH]⁺

EXAMPLE 20b (1S,6R or 1R,6S)-6-(3,4-dichlorophenyl)-1-[(ethyloxy)methyl]-3-azabicyclo[4.1.0]heptane hydrochloride (E20b)

To a solution of (1S,6R or 1R,6S)-6-(3,4-dichlorophenyl)-1-[(ethyloxy)methyl]-3-azabicyclo[4.1.0]heptane (E20a, 7 mg) in DCM (0.2 ml) was added 1 equivalent of HCl (1M in Et₂O), the solvent evaporated under vacuo and the material thus obtained triturated with Et₂O to give 5.8 mg of the title compound as a white slightly hygroscopic solid.

NMR (¹H, MeOH-d₄): δ 7.70 (d, 1H) 7.49 (d, 1H) 7.36 (dd, 1H) 3.75 (d, 1H) 3.37 (m, 1H) 3.26 (m, 3H) 3.15 (m, 1H) 2.89 (m, 1H) 2.69 (d, 1H) 2.23 (q, 2H) 1.29 (d, 1H) 1.23 (d, 1H) 1.13 (t, 3H); MS (m/z): 300 [MH]⁺

EXAMPLE 21

(1S,6R/1R,6S)-1-[(methyloxy)methyl]-6-{4-[(trifluoromethyl)oxy]phenyl}-3-azabicyclo[4.1.0]heptane (E21)

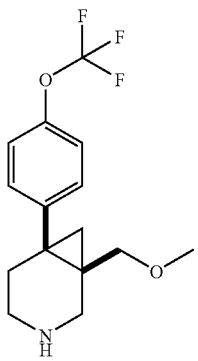

To a stirred solution of (1S,6R/1R,6S)-1,1-dimethylethyl-1-(hydroxymethyl)-6-{4-[(trifluoromethyl)oxy]phenyl}-3-azabicyclo[4.1.0]heptane-3-carboxylate (P36,173 mg) in dry THF (3 mL) under N₂ atmosphere, at 0° C., NaH (60% on mineral oil, 24 mg) was added and the stirring continued for 30 minutes. CH₃I (52 μL) was added dropwise and the reaction was slowly warmed to room temperature and stirred for 3 h. Saturated NH₄Cl aqueous solution was added and then the mixture was concentrated in vacuo. The aqueous phase was extracted with diethyl ether (2 times) and then the combined organic layers were washed with saturated NaCl aqueous solution, dried on anhydrous Na₂SO₄, and evaporated obtaining a crude product. The crude was dissolved in dry DCM (4 mL) and TFA (3.5 mL) was added under N₂ atmosphere at 0° C. The reaction was slowly warmed to room temperature and stirred for 1 h. The mixture was concentrated in vacuo and the residue was purified by a SCX cartridge. The crude thus obtained was purified by HPLC chromatography to give the title compound (35 mg).

Conditions LC: Column Luna AXIA C18, 100×21 mm, 5 μm

Mobile phase A: H2O+0.1% TFA; B: CH₃CN

Gradient: from 20% (B) to 35% (B) in 18 min, from 35% (B) to 80% (B) in 7 min, from 75% (B) to 100% (B) in 1 min, 100% (B) for 3 min.

Flow rate 17 ml/min

UV range 210-350 nm

Mass range 100-900 amu (ES+)

Ionization ES+

R$_t$=3.37 min

MS (m/z): 302[M+H]⁺

EXAMPLE 22

(1S,6R/1R,6S)-1-[(methyloxy)methyl]-6-{4-[(trifluoromethyl)oxy]phenyl}-3-azabicyclo[4.1.0]heptane hydrochloride (E22)

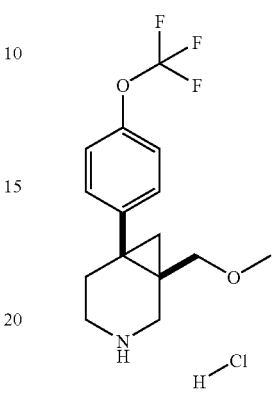

To a stirred solution of (1S,6R/1R,6S)-1-[(methyloxy)methyl]-6-{4-[(trifluoromethyl)oxy]phenyl}-3-azabicyclo[4.1.0]heptane (E21, 35 mg) in dry diethyl ether HCl (1M in diethyl ether, 0.12 ml) was added dropwise. The solvent was removed by decantation and the precipitate was dried under vacuum to give the title compound as white solid (30 mg).

NMR (¹H, MeOH-d₄): δ ppm 7.52 (d, 2H) 7.24 (d, 2H) 3.72 (d, 1H) 3.27 (d, 1H) 3.25-3.21 (m, 1H) 3.16-3.12 (m, 3H) 3.07 (d, 1H) 2.97-2.84 (m, 1H) 2.74 (d, 1H) 2.32-2.12 (m, 2H) 1.31 (d, 1H) 1.22 (d, 1H)

EXAMPLE 23

(1S,6R/1R,6S)-6-[3-chloro-4-(trifluoromethyl)phenyl]-1-[(methyloxy)methyl]-3-azabicyclo[4.1.0]heptane (E23)

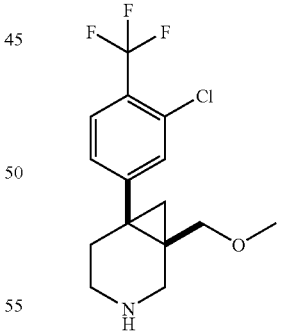

Step A

To a stirred solution of (1S,6R/1R,6S)-phenylmethyl 6-[3-chloro-4-(trifluoromethyl)phenyl]-1-(hydroxymethyl)-3-azabicyclo[4.1.0]heptane-3-carboxylate (430 mg) (P41, impure compound coming from preparation above described) in dry THF (6 mL) under N₂ atmosphere, at 0° C., NaH (60% on mineral oil, 59 mg) was added and the stirring was continued for 30 minutes. CH₃I (113 μL) was added dropwise and the reaction was allowed to reach room temperature and stirred overnight. Saturated NH$_4$Cl aqueous solution was added and then the mixture was concentrated in vacuo. The aqueous phase was extracted with diethyl ether (2 times) and then the combined organic layers were washed with saturated NaCl aqueous solution, dried on anhydrous Na$_2$SO$_4$, and evaporated obtaining a crude product. The crude was purified by flash-chromatography (eluting with cyclohexane/ethyl acetate from 9:1 to 8:2) to give 300 mg of impure phenylmethyl (1R,6S)-6-[3-chloro-4-(trifluoromethyl)phenyl]-1-[(methyloxy)methyl]-3-azabicyclo[4.1.0]heptane-3-carboxylate.

Step B

The impure product thus obtained was dissolved in dry 1,4-dioxane (6 mL) and to the solution a HCl 6N (1 mL) solution was added. The reaction mixture was refluxed for 4 h and then further HCl 6 N (2 mL) was added to the solution. It was stirred at RT overnight and then refluxed for 5 h. The reaction was quenched with aqueous NaOH 3N (pH=12) solution and extracted with Et$_2$O (3 times). The combined organic layers were washed with saturated NaCl aqueous solution, dried and concentrated in vacuo. The residue was purified by a SCX cartridge. The crude thus obtained was purified by HPLC chromatography to give the free base of the title compound (20 mg).

Conditions LC chromatography: Column Gemini C18 AXIA, 50×21 mm, 5 μm Mobile phase A: NH4HCO3 10 mM aq. sol, pH=10; B: CH3CN Gradient: from 30% (B) to 35% (B) in 1 min, from 35% (B) to 75% (B) in 7 min, from 75% (B) to 100% (B) in 1 min, 100% (B) for 1 min.

Flow rate 17 ml/min
UV range 210-350 nm
Mass range 100-900 amu (ES+)
Ionization ES+
Rt=3.38 min
MS (m/z): 320[M+H]+

EXAMPLE 24

(1S,6R/1R,6S)-6-[3-chloro-4-(trifluoromethyl)phenyl]-1-[(methyloxy)methyl]-3-azabicyclo[4.1.0]heptane hydrochloride (E24)

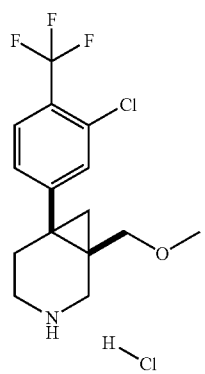

To a stirred solution of the (1S,6R/1R,6S)-6-[3-chloro-4-(trifluoromethyl)phenyl]-1-[(methyloxy)methyl]-3-azabicyclo[4.1.0]heptane (E23, 20 mg) in dry diethyl ether HCl (1M in diethyl ether) was added dropwise. The solvent was removed by decantation and the precipitate was dried under vacuum to give the titled compound as white solid (21 mg).

NMR (free base, $^1$H, CDCl$_3$): δ ppm 7.71 (s, 1H) 7.46 (dd, 2H) 3.40 (d, 1H) 3.12 (s, 3H) 2.99-3.10 (m, 2H) 2.76-2.91 (m, 1H) 2.65-2.76 (m, 2H) 1.91-2.07 (m, 2H) 1.79-1.91 (m, 1H) 1.10 (d, 1H) 1.02 (d, 1H); MS (m/z): 320 [MH]+

EXAMPLE 25

(1R,6S/1S,6R)-1-[(methyloxy)methyl]-6-(2-naphthalenyl)-3-azabicyclo[4.1.0]heptane (E25)

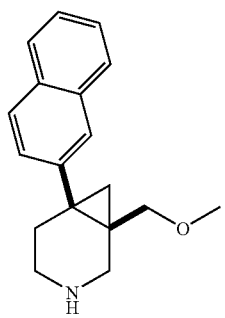

Phenylmethyl (1R,6S/1S,6R)-1-[(methyloxy)methyl]-6-(2-naphthalenyl)-3-azabicyclo[4.1.0]heptane-3-carboxylate (P44, 600 mg) was dissolved in 1,4-dioxane (7 mL) and aqueous 6.0N HCl (7 mL) was added. The reaction mixture was refluxed for 4 hours and then heated to 85° C. for 18 hours. After cooling to room temperature, the aqueous phase was washed with diethyl ether (30 mL), basified with 3.0M NaOH and extracted with DCM (3×50 mL). Organics were combined, dried over Na$_2$SO$_4$ and concentrated. The crude reaction was purified by chromatography on silica gel eluting with 5% MeOH/DCM at first and then with 5% MeOH/DCM+2% 2.0M NH$_3$ in MeOH. The title compound was obtained as colourless oil (145 mg).

NMR ($^1$H, CDCl$_3$): δ 7.77-7.86 (m, 3H), 7.72-7.76 (m, 1H), 7.42-7.52 (m, 3H), 3.37 (d, 1H), 3.18 (d, 1H), 3.10 (s, 3H), 3.02 (d, 1H), 2.80-2.89 (m, 2H), 2.70-2.79 (m, 1H), 1.96-2.08 (m, 2H), 1.25 (d, 1H), 1.11 (d, 1H); MS (m/z): 268 [MH]+.

EXAMPLE 26a and 27a (1R,6S or 1S,6R)-1-[(methyloxy)methyl]-6-(2-naphthalenyl)-3-azabicyclo[4.1.0]heptane (E26a) and
(1S,6R or 1R,6S)-1-[(methyloxy)methyl]-6-(2-naphthalenyl)-3-azabicyclo[4.1.0]heptane (E27a)

(1R,6S/1S,6R)-1-[(methyloxy)methyl]-6-(2-naphthalenyl)-3-azabicyclo[4.1.0]heptane (E25, 140 mg) were submitted to semi-preparative HPLC using a chiral column Chiralcel OJ, 25×4.6 cm, eluent A: n-hexane; B: ethanol 0.1% isopropylamine 85/15, flow rate 0.9 mL/min, detection UV at 228 nm obtaining:

Example 26a (Enantiomer 1, Rt.=5.77 min, 52 mg, colourless oil) and Example 27a (Enantiomer 2, Rt.=7.40 min, 40 mg, colourless oil).

EXAMPLE 28

(1R,6S/1S,6R)-1-[(methyloxy)methyl]-6-(2-naphthalenyl)-3-azabicyclo[4.1.0]heptane hydrochloride (E28)

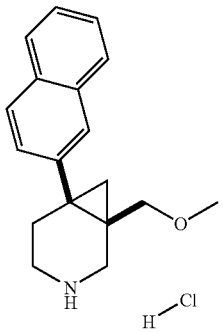

To a solution (1R,6S/1S,6R)-1-[(methyloxy)methyl]-6-(2-naphthalenyl)-3-azabicyclo[4.1.0]heptane (E25, 5 mg) in DCM was added 1 equivalent of HCl (1M in Et$_2$O), the solvent evaporated in vacuo and the material thus obtained triturated with Et$_2$O to give mg of the corresponding hydrochloride salt as a white solid.

MS (m/z): 268 [MH]$^+$.

EXAMPLE 26b (1R,6S or 1S,6R)-1-[(methyloxy)methyl]-6-(2-naphthalenyl)-3-azabicyclo[4.1.0]heptane hydrochloride (E26b)

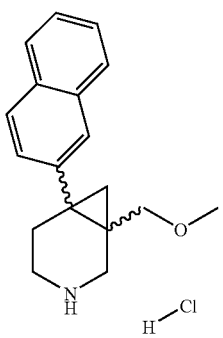

To a solution of (1R,6S or 1S,6R)-1-[(methyloxy)methyl]-6-(2-naphthalenyl)-3-azabicyclo[4.1.0]heptane (E26a, 52 mg) in DCM was added 1 equivalent of HCl (1M in Et$_2$O), the solvent evaporated in vacuo and the material thus obtained triturated with Et$_2$O to give 53 mg of the title compound as a white solid.

NMR ($^1$H, CDCl$_3$): δ 7.24-7.32 (m, 4H), 7.09-7.14 (m, 1H), 6.90-6.98 (m, 2H), 3.32 (d, 1H), 2.76-2.88 (m, 2H), 2.60-2.65 (m, 1H), 2.54-2.58 (m, 3H), 2.40-2.49 (m, 1H), 2.24-2.29 (m, 1H), 1.99-2.10 (m, 1H), 1.76-1.84 (m, 1H), 0.92-0.95 (m, 1H), 0.80-0.84 (m, 1H); MS (m/z): 268 [MH]$^+$.

EXAMPLE 27b (1S,6R or 1R,6S)-1-[(methyloxy)methyl]-6-(2-naphthalenyl)-3-azabicyclo[4.1.0]heptane hydrochloride (E27b)

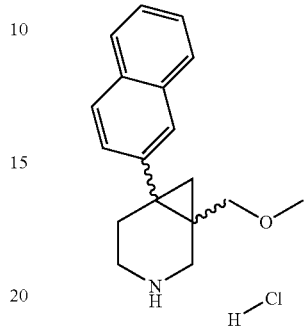

To a solution of (1S,6R or 1R,6S)-1-[(methyloxy)methyl]-6-(2-naphthalenyl)-3-azabicyclo[4.1.0]heptane (E27a, 40 mg) in DCM was added 1 equivalent of HCl (1M in Et$_2$O), the solvent evaporated in vacuo and the material thus obtained triturated with Et$_2$O to give 40 mg of the title compound as a white solid.

NMR ($^1$H, DMSO-d6): δ. 7.83-7.90 (m, 3H), 7.80-7.83 (m, 1H), 7.60 (dd, 1H), 7.44-7.52 (m, 2H), 3.20-3.40 (m, 1H), 3.13 (d, 1H), 2.93-3.05 (m, 5H), 2.74-2.83 (m, 1H), 2.63 (d, 1H), 1.99-2.17 (m, 2H), 1.25-1.32 (m, 2H)); MS (m/z): 268 [MH]$^+$.

EXAMPLE 29

(1S,6R/1R,6S)-6-(3-chloro-4-fluorophenyl)-1-[(methyloxy)methyl]-3-azabicyclo[4.1.0]heptane hydrochloride (E29)

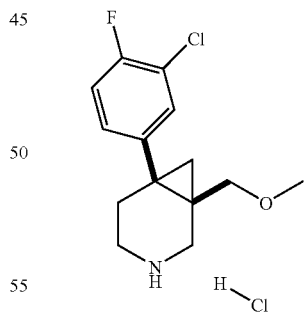

The title compound was prepared according to a similar procedure to that described for Example 18 in 115 mg yield starting from (1S,6R/1R,6S)-1,1-dimethylethyl 6-(3-chloro-4-fluorophenyl)-1-[(methyloxy)methyl]-3-azabicyclo[4.1.0]heptane-3-carboxylate (164 mg, P50).

NMR ($^1$H, DMSO-d$_6$): δ ppm 8.28 (s, 1H) 7.66 (d, 1H) 7.25-7.47 (m, 2H) 3.41 (d, 1H) 3.01-3.14 (m, 5H) 2.92 (d, 1H) 2.75 (d, 1H) 2.68 (d, 1H) 1.98-2.10 (m, 2H) 1.17-1.26 (m, 2H); MS (m/z): 270 [MH]$^+$

EXAMPLE 30

(1R,6S/1S,6R)-6-(3,4-dichlorophenyl)-1-{[(2,2,2-trifluoroethyl)oxy]methyl}-3-azabicyclo[4.1.0]heptane (E30)

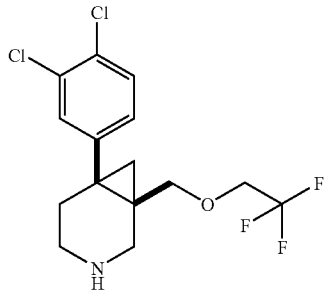

Step a)

To a stirred solution of 2,2,2-trifluoroethanol (12 μl) in DMF (1 mL) sodium hydride (60% in mineral oil, 5.7 mg) was added followed, after 10 min, by a solution of 1-dimethylethyl (1R,6S/1S,6R)-6-(3,4-dichlorophenyl)-1-{[(methylsulfonyl)oxy]methyl}-3-azabicyclo[4.1.0]heptane-3-carboxylate (P69, 60 mg), in DMF (2 mL). After 4 hrs, further 2,2,2-trifluoroethanol (12 μL) in DMF (1 mL) and sodium hydride (60% in mineral oil, 5.7 mg) were added. After 2 days further 2,2,2-trifluoroethanol (12 μL) in DMF (1 mL), and sodium hydride (5.7 mg) were added and the reaction was heated to 60° C. for 5 hrs. DCM and NaHCO3 saturated solution were added and the solvent was removed under reduced pressure to give 1,1-dimethylethyl (1R,6S/1S,6R)-6-(3,4-dichlorophenyl)-1-{[(2,2,2-trifluoroethyl)oxy]methyl}-3-azabicyclo[4.1.0]heptane-3-carboxylate as crude (6 mg).

Step b)

The crude 1,1-dimethylethyl (1R,6S/1S,6R)-6-(3,4-dichlorophenyl)-1-{[(2,2,2-trifluoroethyl)oxy]methyl}-3-azabicyclo[4.1.0]heptane-3-carboxylate (6 mg, E30, Step a) was dissolved in dry DCM (1 mL) and TFA (0.5 mL) was added. The reaction mixture was stirred for 2 hrs and after this period of time the solvent was evaporated to give a crude that was redissolved in DCM. The organic phase was washed with NaHCO3 saturated solution, dried and concentrated. The crude product was purified by flash-chromatography (eluting with DCM/Methanol/NH3/MeOH 2N 49/1/1) to give the title compound (3.9 mg).

NMR ($^1$H, CDCl$_3$): δ 7.5 (s, 1H) 7.45 (d, 1H) 7.35 (m, 1H), 3.9 (d, 2H) 3.7 (d, 1H) 3.6 (m, 2H) 3.25 (d, 1H) 3.15 (m, 2H) 2.3 (m, 1H) 2.2 (m, 1H) 1.25 (m, 2H).

EXAMPLE 31

(1S,6R,7R/1R,6S,7S)-6-(3,4-dichlorophenyl)-7-[(methyloxy)methyl]-3-azabicyclo[4.1.0]heptane (E31)

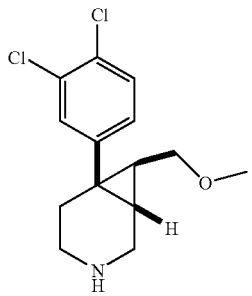

To a stirred solution of 1,1-dimethylethyl (1S,6R/1R,6S)-6-(3,4-dichlorophenyl)-7-[(methyloxy)methyl]-3-azabicyclo[4.1.0]heptane-3-carboxylate and 1,1-dimethylethyl 4-(3,4-dichlorophenyl)-6-[2-(methyloxy)ethyl]-3,6-dihydro-1 (2H)-pyridinecarboxylate (P56, 35 mg) in dry DCM (4 mL) trifluoroacetic acid (0.75 ml) was added. The mixture was stirred at room temperature for 2 h, then the solvent was removed under reduced pressure and the crude purified by flash chromatography (eluting with DCM:MeOH: NH$_3$aq=95:5:0.5) to give 10 mg of a mixture containing the title compound. MS (m/z): 286 [MH]$^+$ (1S,6R,7R/1R,6S,7S)-6-(3,4-dichlorophenyl)-7-[(methyloxy)methyl]-3-azabicyclo[4.1.0]heptane (3.5 mg) was purified and separated from 4-(3,4-dichlorophenyl)-6-[2-(methyloxy)ethyl]-1,2,3,6-tetrahydropyridine by semi-preparative HPLC using a chiral column Chiralpak AS-H, eluent A: n-hexane; B: ethanol, gradient isocratic 30% B, flow rate 0.8 ml/min, detection UV at 225 nm.

NMR ($^1$H, CDCl$_3$): δ 7.37 (d, 1H) 7.33 (d, 1H) 7.13 (dd, 1H) 4.01 (dd, 1H) 3.78 (dd, 1H) 3.44 (s, 3H) 3.28-3.36 (m, 1H) 3.12-3.23 (m, 1H) 2.79-2.89 (m, 1H) 2.52-2.65 (m, 1H) 1.96-2.12 (m, 1H) 1.80-1.96 (m, 1H) 1.28-1.47 (m, 2H); MS (m/z): 286 [MH]$^+$

EXAMPLE 32

(1S,6R/1R,6S)-6-(3,4-dichlorophenyl)-1-[(methyloxy)methyl]-3-azabicyclo[4.1.0]heptane (E32)

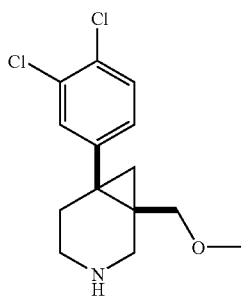

Method A:

The title compound may be obtained according to an analogous procedure to that described above for compound E2a in Method B, starting from 1,1-dimethylethyl (1S,6R/1R,6S)-6-(3,4-dichlorophenyl)-1-[(methyloxy)methyl]-3-azabicyclo[4.1.0]hept-4-ene-3-carboxylate (P59).

Method B:

In a round-bottomed flask, 1,1-dimethylethyl (1S,6R/1R, 6S)-6-(3,4-dichlorophenyl)-1-[(methyloxy)methyl]-3-azabicyclo[4.1.0]heptane-3-carboxylate (P66, 42.33 g, 110 mmol) was dissolved in DCM (450 ml) to give a colourless solution. Trifluoroacetic acid (103 ml, 1343 mmol) was added dropwise keeping the internal temperature below +5° C. with an ice bath. At the end of the addition, the ice bath was removed and the mixture was stirred at room temperature for 2 hrs.

The reaction was quenched by dropwise addition of aqueous potassium carbonate sat. (250 ml) keeping the internal temperature below +10° C. with an ice bath. Then the mixture was diluted with water (200 ml) and DCM (200 ml). The two phases were separated. The aqueous phase was extracted with ethyl acetate (2×150 ml) and the organic (milky solution) was evaporated under vacuum and taken up with ethyl acetate (400 ml). The combined organics were washed with brine (300 ml), dried ($Na_2SO_4$) and evaporated under vacuum to obtain a yellow oil (34 g). It was dissolved in diethyl ether (600 ml) and washed with aqueous potassium carbonate 1M solution (3×200 ml). The organic phase was dried ($Na_2SO_4$) and evaporated under vacuum to afford the title compound (28.9 g) as colourless oil.

NMR ($^1$H, $CDCl_3$): δ ppm 7.45 (s, 1H), 7.36 (d, 1H), 7.19 (d, 1H), 3.32 (d, 1H), 3.14 (s, 3H), 3.09 (d, 1H), 2.96 (d, 1H), 2.84 (d, 1H), 2.73-2.81 (m, 1H), 2.64-2.71 (m, 1H), 1.92-2.00 (m, 1H), 1.79-1.88 (m, 1H), 0.97-1.07 (m, 2H).

HPLC (walk-up): Rt=3.97 min

EXAMPLE 33

(1S,6R)-6-(3,4-dichlorophenyl)-1-[(methyloxy)methyl]-3-azabicyclo[4.1.0]heptane (2R,3R)-2,3-dihydroxybutanedioate (L-tartrate salt) (E33)

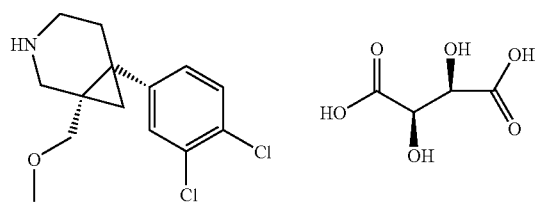

Method a)

3.7 grams of material prepared by a procedure analogous to the method of Step A of Example 38, omitting the azeotropic drying step, was dissolved in isopropyl alcohol (60 ml, 16.7 vols), and to the solution was added L-tartaric acid [(2R,3R)-(+)-Tartaric acid](2.7 grams, 18.1 mmol, 1.4 eq) and the solution was then heated to 80° C. Once at temperature water (12 ml, 3.2 vols) was then added and the solution stirred for 10 min. The resulting solution was then cooled to 0° C. at a rate of 0.2° C./min, and then held at 0° C. for 7 hours. The resulting slurry was then filtered and washed with isopropyl alcohol (10 ml, 2.7 vol) twice. The solid obtained was then dried under high vacuum for 5 hours at 50° C. to give an off white solid of the title compound (3.7 grams, 8.5 mmol, 65% recovery).

NMR ($^1$H, DMSO-d6): δ ppm 1.22 (s, 2H), 2.03 (t, J=5.26 Hz, 2H), 2.67-2.79 (m, 2H), 2.83-2.90 (m, 1H), 3.04 (s, 4H), 3.11 (d, J=13.19 Hz, 1H), 3.43 (d, J=13.55 Hz, 1H), 3.85 (s, 2H), 7.33-7.39 (m, 1H), 7.56-7.60 (m, 1H), 7.68 (d, J=2.01 Hz, 1H).

MS (m/z): 286 [MH]+

Method b)

To 300.1 mg of (1S,6R)-6-(3,4-dichlorophenyl)-1-[(methyloxy)methyl]-3-azabicyclo[4.1.0]heptane (E2a) and 157.3 mg of L-tartaric acid, 0.5 mL of isopropylalcohol (IPA) was added with stirring. A further 0.5 mL was added and the resulting solution heated using an air gun. Heat was removed and a further 2.5 mL IPA added, this resulted in a slurry to which an additional 1 mL of IPA was added to give mobility (giving a total solvent volume of 4.5 mL IPA added). The resulting slurry was temperature cycled between 0 and 40° C. for >24 hours. The sample was then filtered and the solid obtained dried under vacuum at 70° C. for 24 hours.

Figure 3:
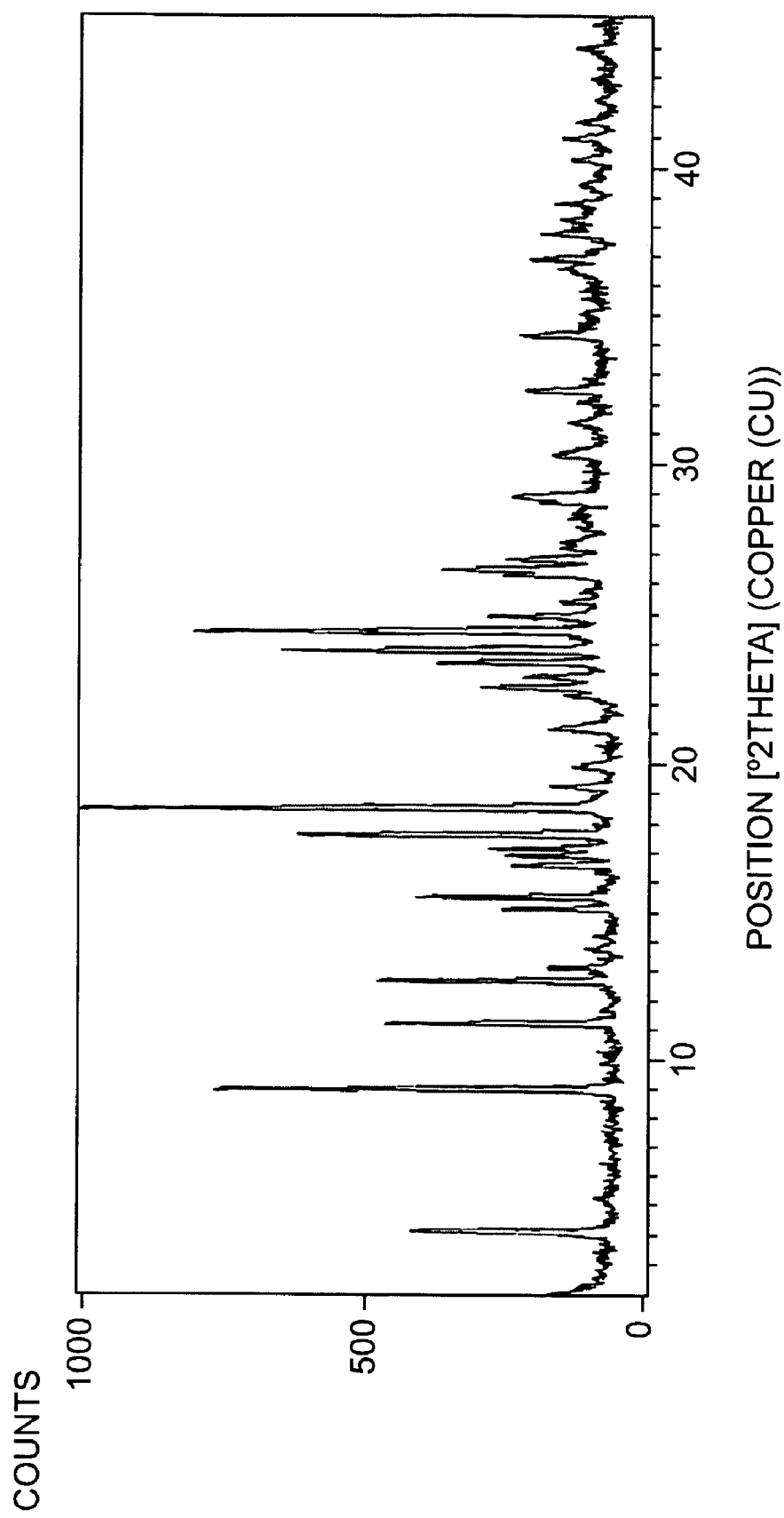
FIG. 3 is a Diffractogram of Form 1 of the title compound E33 of Example 33 [batch produced with method b)].

Diffractogram of Form 1 of the title compound E33 [batch produced with method b)] is shown in FIG. 3.

XRPD Peaks* of Form 1 (with 5% or greater relative intensity) of the title compound Example 33 are illustrated in the Table 3 below (XRPD angles and d spacings are reported):

TABLE 3

| Pos.[°2Th.]] | d-spacing[Å] |
|---|---|
| 4.8 | 18.3 |
| 9.5 | 9.3 |
| 11.7 | 7.6 |
| 13.1 | 6.8 |
| 13.6 | 6.5 |
| 15.5 | 5.7 |
| 15.9 | 5.6 |
| 16.9 | 5.2 |
| 17.2 | 5.2 |
| 17.5 | 5.1 |
| 17.9 | 4.9 |
| 18.8 | 4.7 |
| 23.5 | 3.8 |
| 23.9 | 3.7 |
| 24.5 | 3.6 |
| 24.9 | 3.6 |
| 26.3 | 3.4 |
| 26.5 | 3.4 |
| 26.9 | 3.3 |

[X-Ray Powder Diffraction (XRPD) analysis performed on a PANalytical X'pert Pro powder diffractometer, Model PW3040/60, serial number DY2599 using an X'Celerator detector. Acquisition conditions: radiation: Cu $K_\alpha$, generator tension: 40 kV, generator current: 40 mA, start angle: 2.0 °2θ, end angle: 45.0 °2θ, step size: 0.017 °2θ, time per step: 32.3024 seconds. Sample prepared using zero background (front fill) technique]

Onset of melting point/decomposition [E33, Form 1, batch produced with method b)]: 198° C. (TA instruments Q1000 serial number Q1000-0577. Sample heated at 10° C. $min^{-1}$ in a crimped aluminium pan with a pin-hole lid).

Figure 4:
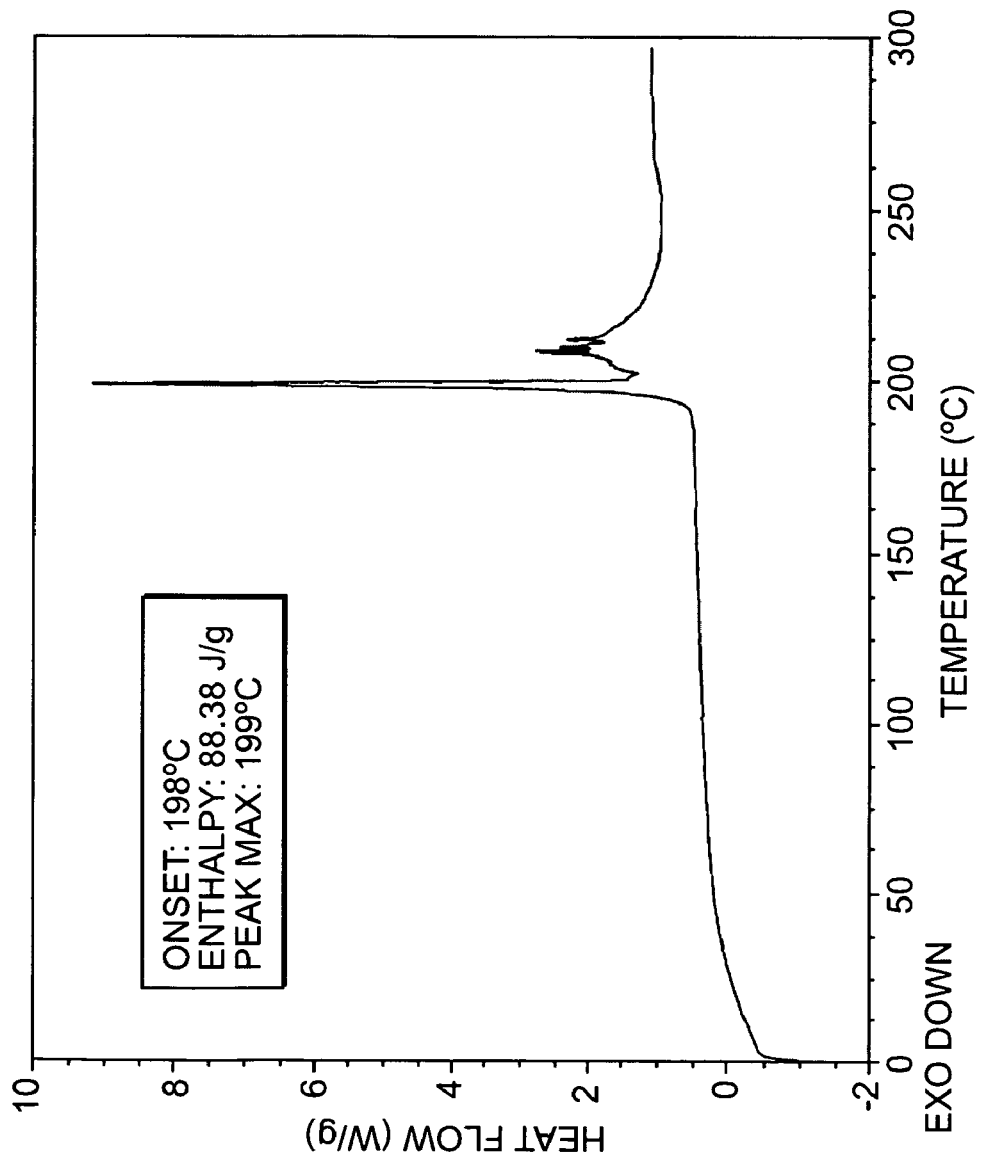
FIG. 4 is a DSC thermogram of Form 1 of the title compound E33 of Example 33 [batch produced with method b)].

DSC thermogram of Form 1 of the title compound Example 33 [batch produced with method b)] is shown in FIG. 4.

Method c)

To 500 mg of material prepared according to Step A of Example 38, dissolved in methanol (5 mL), was charged L-tartaric acid in methanol (1.21 mL, 1 mmol/mL). This was stirred for 15 minutes and a white precipitate formed. This was collected by vacuum filtration and washed with methanol (2 mL) to obtain 246 mg of title compound.

NMR ($^1$H, DMSO-d6): δ ppm 1.24 (s, 2H) 1.99-2.14 (m, 2H) 2.47-2.53 (m, 1H) 2.67 (d, J=9.99 Hz, 1H) 2.72-2.83 (m, 1H) 2.92 (d, J=9.99 Hz, 1H) 3.05 (s, 3H) 3.12 (d, J=13.20 Hz, 1H) 3.47 (d, J=13.38 Hz, 1H) 3.92 (s, 2H) 7.39 (dd, J=8.34, 2.10 Hz, 1H) 7.59 (d, J=8.29 Hz, 1H) 7.70 (d, J=2.05 Hz, 1H)

Figure 5:
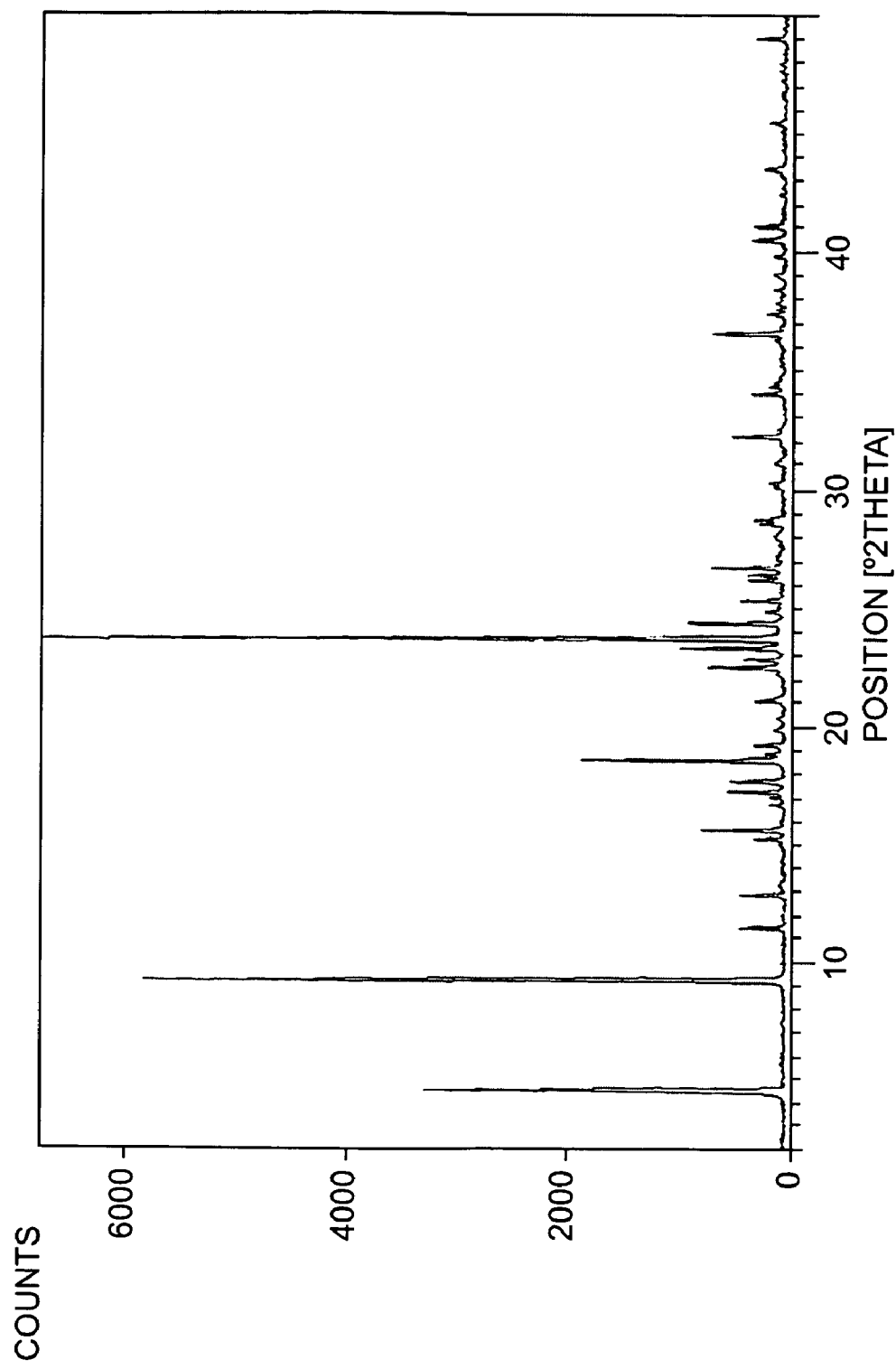
FIG. 5 is a Diffractogram of Form 1 of the title compound E33 of Example 33.

Diffractogram of Form 1 of the title compound E33 is shown in FIG. 5.

XRPD Peaks* of Form 1 of the title compound E33 [batch produced with method c)] are illustrated in the Table 4 below (XRPD angles and d spacings are reported):

TABLE 4

| 2-theta [°] | d-spacing [Å] |
| --- | --- |
| 4.7 | 18.9 |
| 9.4 | 9.4 |
| 11.6 | 7.6 |
| 13.0 | 6.8 |
| 15.7 | 5.6 |
| 17.3 | 5.1 |
| 17.8 | 5.0 |
| 18.7 | 4.8 |
| 22.5 | 3.9 |
| 22.8 | 3.9 |
| 23.3 | 3.8 |
| 23.7 | 3.8 |
| 24.3 | 3.7 |
| 25.3 | 3.5 |
| 26.2 | 3.4 |
| 26.4 | 3.4 |
| 26.7 | 3.3 |
| 32.2 | 2.8 |
| 36.5 | 2.5 |
| 40.4 | 2.2 |

*Values shown here are rounded to one decimal place. The diffraction pattern can shift to slightly higher or lower 2θ values depending on sample displacement.

[X Ray Powder Diffraction (XRPD) analysis was performed on a PANalytical X'Pert-Pro MPD with Johansson Ka1 monochromator, using X'Celerator detector. The acquisition conditions were as follows: Radiation: Cu (Ka1), 1.540598 angstroms (monochromatic); Detector: X'Celerator; Tension: 45 kV; Current: 40 mA; Start angle: 2.0° 2q; End angle: 50.0° 2q; Step size: 0.02°; Time/step: 40.0 sec; Scan speed: 0.05°/sec; Incident beam: 2° fixed anti-scatter slit, and programmable divergence slit; Diffracted beam: 0.02 rad soller slit, and programmable anti-scatter slit; Samples prepared on silicon zero background sample holder)].

In one embodiment, unique and discriminating peaks* of Form 1 of the title compound E33 have been identified and are illustrated in Table 5 below (XRPD angles and d spacings are reported):

TABLE 5

| 2-theta [°] | d-spacing [Å] |
| --- | --- |
| 4.7 | 18.9 |
| 9.4 | 9.4 |
| 15.7 | 5.6 |
| 18.7 | 4.8 |
| 22.5 | 3.9 |
| 23.3 | 3.8 |
| 23.7 | 3.8 |
| 24.3 | 3.7 |
| 26.7 | 3.3 |
| 36.5 | 2.5 |

Onset of melting point/decomposition [E33, Form 1, batch produced with method c)]: 191.17° C. (TA Instruments Model Q1000 DSC; Pan: closed aluminium; Purge gas: N₂, 50 mL/min; Temp range: 30-300° C., 15° C./min).

Figure 6:
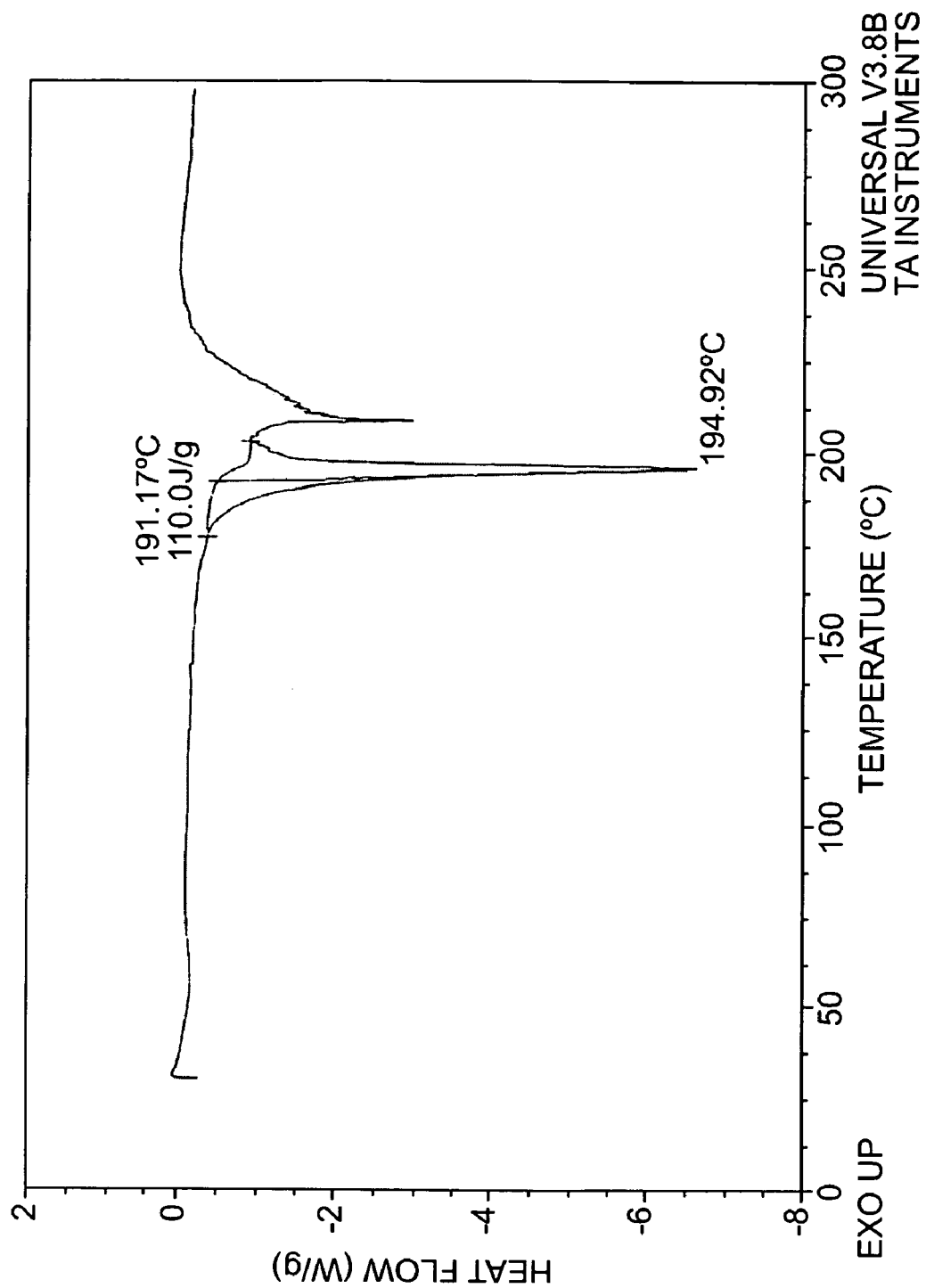
FIG. 6 is a DSC thermogram of Form 1 of the title compound E33 of Example 33 [batch produced with method c)].

DSC thermogram of Form 1 of the title compound E33 [batch produced with method c)] is shown in FIG. 6.

The melt for Form 1 of the title compound E33 is followed by degradation therefore the integration of the peak for different samples can give slightly different Onset, Peak Max and Enthalpy values.

EXAMPLEs 34 and 35

(2R,3R)-2,3-bis[(phenylcarbonyl)oxy]butanedioic acid -(1S,6R)-6-(3,4-dichlorophenyl)-1-[(methyloxy)methyl]-3-azabicyclo[4.1.0]heptane (E34) and (2S, 3S)-2,3-bis[(phenylcarbonyl)oxy]butanedioic acid -(1R,6S)-6-(3,4-dichlorophenyl)-1-[(methyloxy)methyl]-3-azabicyclo[4.1.0]heptane (E35)

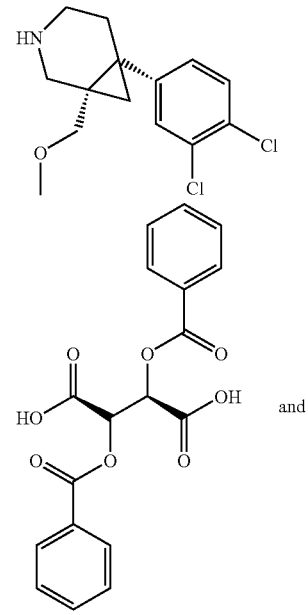

E34

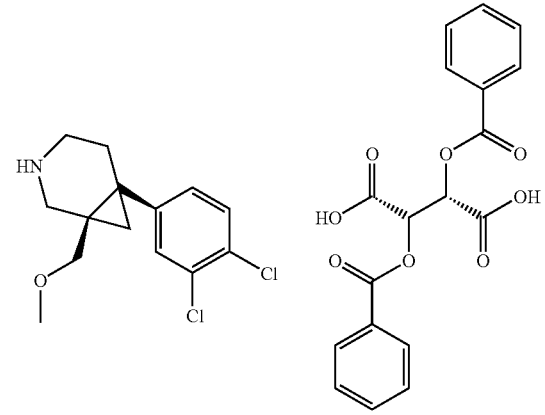

E35

Step a)

To a solution of (1S,6R/1R,6S)-6-(3,4-dichlorophenyl)-1-[(methyloxy)methyl]-3-azabicyclo[4.1.0]heptane (E32, 61.5 g, 215 mmol) in acetone (300 ml), dibenzoyl-L-tartaric acid (115 g, 322 mmol), dissolved in acetone (622 ml), was added dropwise during 1 h. A solid precipitated and the mixture was stirred at room temperature for 2 h. The solid was filtered, washed with acetone (2×100 ml) and dried under vacuum to give compound E34 (35.8 g).

Chiral HPLC (Column: AS-H (25×0.46 cm), 5 micron; Eluent: n-Hexane/(2-propanol+0.1 isopropylamine) 95/5 v/v; Flow: 1 ml/min; wavelength: 225 nm; retention times referred to salt analysis): Enant1 (Rt=12.14 min)/Enant2 (Rt=17.29 min)=86/13 area %

Mother liquors were concentrated under vacuum and the residue was suspended in DCM (700 ml). It was washed with aqueous potassium carbonate sat./water 1:1 (700 ml). The aqueous phase was back-extracted with DCM (2×500 ml). The collected organic phases, dried ($Na_2SO_4$), were evaporated to give residual 6-(3,4-dichlorophenyl)-1-[(methyloxy)methyl]-3-azabicyclo[4.1.0]heptane (45 g).

NMR ($^1$H, $CDCl_3$): δ ppm 7.45 (s, 1H), 7.36 (d, 1H), 7.19 (d, 1H), 3.32 (d, 1H), 3.14 (s, 3H), 3.09 (d, 1H), 2.96 (d, 1H), 2.84 (d, 1H), 2.73-2.81 (m, 1H), 2.64-2.71 (m, 1H), 1.92-2.00 (m, 1H), 1.79-1.88 (m, 1H), 0.97-1.07 (m, 2H).

Chiral HPLC: (Column: AS-H (25×0.46 cm), 5 micron; Eluent: n-Hexane/(2-propanol+0.1 isopropylamine) 95/5 v/v; Flow: 1 ml/min; wavelength: 225 nm; retention times referred to free base): Enant1/Enant2=34/62 area %

Step b)

To residual 6-(3,4-dichlorophenyl)-1-[(methyloxy)methyl]-3-azabicyclo[4.1.0]heptane (45 g, 157 mmol), coming from step a), dissolved in acetone (220 ml), dibenzoyl-D-tartaric acid (85 g, 236 mmol), dissolved in acetone (450 ml), was added dropwise during 45 min. A solid precipitated and the resulting mixture was stirred at room temperature for 2 h. The solid was filtered, washed with acetone (2×100 ml) and dried under vacuum to give compound E35 (43.8 g).

Chiral HPLC: Enant1/Enant2=7.5/90.9 area %

Mother liquors were concentrated under vacuum and the residue was suspended in DCM (700 ml).

It was washed with aqueous potassium carbonate sat./water 1:1 (700 ml). The aqueous phase was back-extracted with DCM (2×500 ml). The collected organic phases, dried ($Na_2SO_4$), were evaporated to give residual 6-(3,4-dichlorophenyl)-1-[(methyloxy)methyl]-3-azabicyclo[4.1.0]heptane (25.6 g).

Chiral HPLC: Enant1/Enant2=54/35 area %

Step c)

To residual 6-(3,4-dichlorophenyl)-1-[(methyloxy)methyl]-3-azabicyclo[4.1.0]heptane (25.6 g, 89 mmol), coming from step b), dissolved in acetone (125 ml), dibenzoyl-L-tartaric acid (48.1 g, 134 mmol), dissolved in acetone (250 ml), was added dropwise during 1 h. A solid precipitated and the resulting mixture was stirred at room temperature for 2 hrs. The solid was filtered, washed with acetone (2×100 ml) and dried under vacuum to afford the compound E34 (15 g).

Chiral HPLC: Enant1/Enant2=92.5/5.5 area %

Mother liquors were concentrated under vacuum and the residue was suspended in DCM (350 ml). It was washed with aqueous potassium carbonate sat./water 1:1 (350 ml). The aqueous phase was back-extracted with DCM (2×300 ml). The collected organic phases, dried (Na2SO4), were evaporated to give residual 6-(3,4-dichlorophenyl)-1-[(methyloxy)methyl]-3-azabicyclo[4.1.0]heptane (18 g).

Chiral HPLC: Enant1/Enant2=37.7/49.7 area %

Step d)

To residual 6-(3,4-dichlorophenyl)-1-[(methyloxy)methyl]-3-azabicyclo[4.1.0]heptane (18 g, 62.89 mmol), coming from step c), dissolved in acetone (90 ml), dibenzoyl-D-tartaric acid (33.8 g, 94.33 mmol), dissolved in acetone (180 ml), was added dropwise during 45 min. A solid precipitated and the resulting mixture was stirred at room temperature for 2 h. The solid was filtered, washed with acetone (2×80 ml) and dried under vacuum to give compound E35 (11 g).

Chiral HPLC: Enant1/Enant2=14.5/84.5 area %

Mother liquors were concentrated under vacuum and the residue was suspended in DCM (500 ml).

It was washed with aqueous potassium carbonate sat./water 1:1 (500 ml). The aqueous phase was back-extracted with DCM (2×300 ml). The collected organic phases, dried (Na2SO4), were evaporated to give residual 6-(3,4-dichlorophenyl)-1-[(methyloxy)methyl]-3-azabicyclo[4.1.0]heptane (12.6 g).

Chiral HPLC: Enant1/Enant2=49.2/31.2 area %

Step e)

To residual 6-(3,4-dichlorophenyl)-1-[(methyloxy)methyl]-3-azabicyclo[4.1.0]heptane (12.6 g, 44 mmol), coming from step d), dissolved in acetone (65 ml), dibenzoyl-L-tartaric acid (23.66 g, 66 mmol), dissolved in acetone (125 ml), was added dropwise during 1 h. A solid precipitated and the resulting mixture was stirred at room temperature for 2 hrs. The solid was filtered, washed with acetone (2×100 ml) and dried under vacuum to afford compound E34 (3.1 g). 10.57% yield.

Chiral HPLC: Enant1/Enant2=94.1/5.0 area %

Step f)

(2R,3R)-2,3-bis[(phenylcarbonyl)oxy]butanedioic acid -(1S,6R)-6-(3,4-dichlorophenyl)-1-[(methyloxy)methyl]-3-azabicyclo[4.1.0]heptane (E34) coming from step a) (35.8 g, 55.54 mmol), step c) (15 g, 23.27 mmol), step e) (3.1 g 4.8 mmol) and a further batch of material (3.1 g, 4.8 mmol) of the same quality were suspended in acetone (570 ml) and heated gently to reflux for 30 min. The mixture was stirred for 2 hrs at room temperature. The solid was filtered to give 47.25 g of white solid. This solid was suspended in acetone (470 ml) and heated to reflux for 30 min. The mixture was stirred for 2 h at room temperature. The solid was filtered to give 41.80 g of white solid. This solid was suspended in acetone (420 ml) and heated to reflux for 30 min. The mixture was stirred for 2 h at room temperature The solid was filtered to give pure compound E34 (38 g) as white solid.

NMR ($^1$H, MeOH-$d_4$): δ ppm 8.14 (d, 4H), 7.57-7.67 (m, 3H), 7.41-7.54 (m, 5H), 7.29-7.38 (m, 1H), 5.93 (s, 2H), 3.61-3.76 (m, 1H), 3.16-3.29 (m, 2H), 3.13 (s, 3H), 2.98-3.07 (m, 1H), 2.79-2.92 (m, 1H), 2.66-2.78 (m, 1H), 2.08-2.29 (m, 2H), 1.12-1.31 (m, 2H)

Chiral HPLC: Enant1/Enant2=99/1 area %

EXAMPLE 36

(1S,6R)-6-(3,4-dichlorophenyl)-1-[(methyloxy)methyl]-3-azabicyclo[4.1.0]heptane butanedioate (Mono-Succinate salt) (E36)

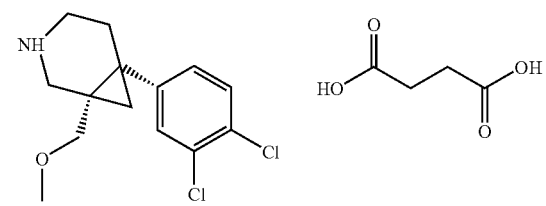

To 300.7 mg of (1S,6R)-6-(3,4-dichlorophenyl)-1-[(methyloxy)methyl]-3-azabicyclo[4.1.0]heptane (E2a) and 123.4 mg of succinic acid, 0.5 mL of isopropylalcohol (IPA) was added with stirring. A further 0.5 mL was added and heat applied using an air gun to aid dissolution. Further solvent additions of 2×0.5 mL, 1 mL, 0.5 mL and 1 mL were added to achieve a mobile slurry (giving a total solvent volume of 4.5 mL IPA added). The resulting slurry was temperature cycled between 0 and 40° C. for three days. The sample was then filtered and the solid title compound obtained dried under vacuum at 70° C. for 24 hours.

NMR ($^1$H, DMSO-d6): 7.67 (d, 1H), 7.59 (d, 1H), 7.36 (dd, 1H), 3.40 (d, 1H), 3.09 (d, 1H), 3.05 (s, 3H), 3.01 (m, 1H), 2.87 (d, 1H), 2.77-2.70 (m, 2H), 2.34 (s, 4H), 2.01 (m, 2H), 1.21 (m, 2H) [NMR analysis performed on a batch obtained with an analogous procedure to that above described]

EXAMPLE 37

(1S,6R)-6-(3,4-dichlorophenyl)-1-[(methyloxy)methyl]-3-azabicyclo[4.1.0]heptane phosphate (monophosphate salt) (E37)

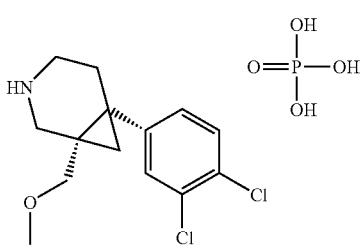

A solution was prepared with 301.5 mg (1S,6R)-6-(3,4-dichlorophenyl)-1-[(methyloxy)methyl]-3-azabicyclo[4.1.0]heptane (E2a, oil) and 0.2 mL aqueous isopropylalcohol 5% w/w water (aq. IPA). To this solution 209.6 microL of phosphoric acid (5M in water) was added with stirring. A further 0.1 mL of solvent was added while stirring yielding a slurry. 0.3 mL and then 0.1 mL of solvent were added to give a mobile slurry. (Total aq. IPA added 0.7 mL). The resulting slurry was temperature cycled between 0 and 40° C. for 24 hours. The sample was then filtered and the solid title compound obtained dried under vacuum at 70° C. for 24 hours.

The analytical data reported below for E37 were generated using alternative batches of the compound.

NMR ($^1$H, DMSO-d6): 7.63 (d, 1H), 7.56 (d, 1H), 7.36 (dd, 1H), 7.27 (d, 1H), 3.03 (s, 3H), 3.01 (d, 1H), 2.90 (d, 1H), 2.85 (m, 1H), 2.69 (d, 1H), 2.64 (m, 1H), 1.95 (m, 2H), 1.17 (m, 2H)

Figure 7:
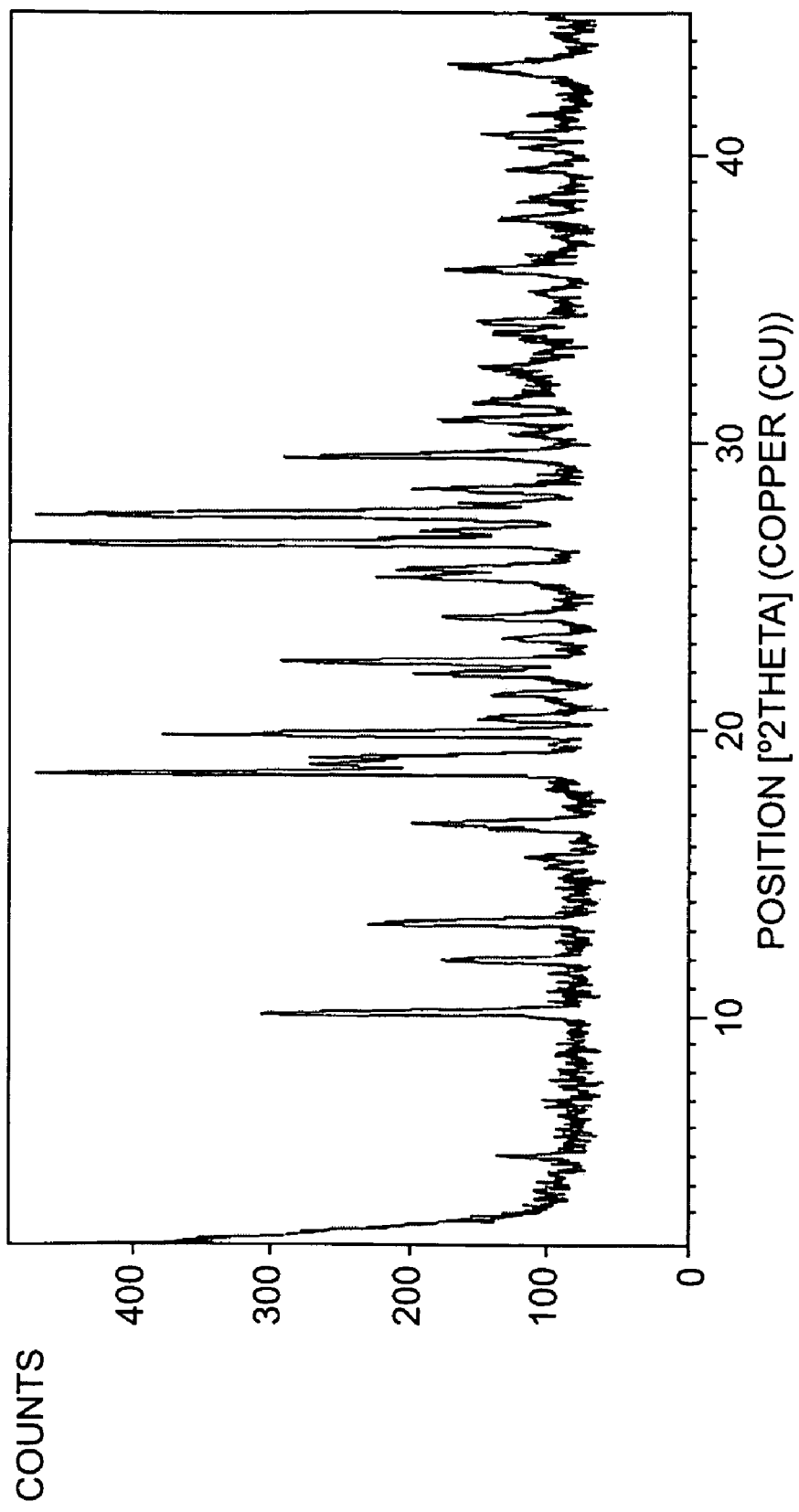
FIG. 7 is a Diffractogram of Form 1 of the title compound E37 of Example 37.

Diffractogram of Form 1 of the title compound E37 is shown in FIG. 7.

XRPD Peaks* of Form 1 (with 5% or greater relative intensity) of the title compound Example 37 are illustrated in the Table 6 below (XRPD angles and d spacings are reported):

| Pos.[°2Th.] | d-spacing[Å] |
|---|---|
| 5.1 | 17.4 |
| 10.2 | 8.7 |
| 12.0 | 7.3 |
| 13.3 | 6.7 |
| 16.8 | 5.3 |

-continued

| Pos.[°2Th.] | d-spacing[Å] |
|---|---|
| 18.5 | 4.8 |
| 18.9 | 4.7 |
| 19.9 | 4.5 |
| 20.4 | 4.4 |
| 21.2 | 4.2 |
| 22.0 | 4.0 |
| 22.5 | 4.0 |
| 23.2 | 3.8 |
| 24.0 | 3.7 |
| 25.3 | 3.5 |
| 25.7 | 3.5 |
| 26.6 | 3.4 |
| 27.5 | 3.2 |
| 28.4 | 3.1 |
| 29.6 | 3.0 |
| 30.8 | 2.9 |

[X-Ray Powder Diffraction analysis performed on a PANalytical X'pert Pro powder diffractometer, Model PW3040/60, serial number DY2599 using an X'Celerator detector. Acquisition conditions: radiation: Cu K$_\alpha$, generator tension: 40 kV, generator current: 40 mA, start angle: 2.0 °2θ, end angle: 45.0 °2θ, step size: 0.017 °2θ, time per step: 32.3024 seconds. Sample prepared using zero background (front fill) technique.].

Figure 8:
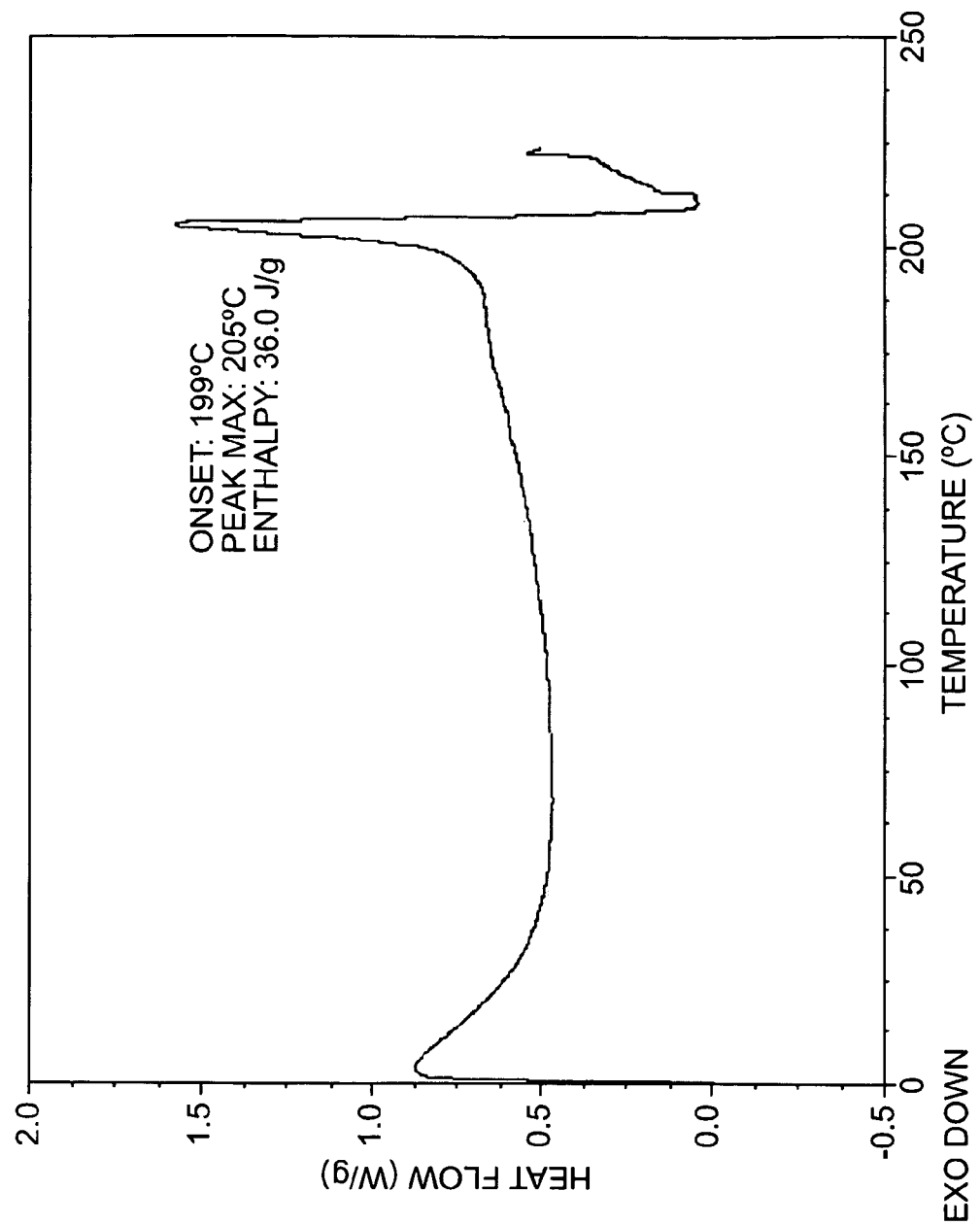
FIG. 8 is a DSC thermogram of Form 1 of the title compound E37 of Example 37.

DSC thermogram of Form 1 of the title compound E37 is shown in FIG. 8.

Onset of melting (E37, Form 1): 199° C. (TA instruments Q1000 serial number Q1000-0577. The sample was heated at 10° C. min$^{-1}$ in a crimped aluminium pan with a pin-hole lid).

The melt for Form 1 of the title compound E37 is followed by degradation therefore the integration of the peak for different samples can give slightly different Onset, Peak Max and Enthalpy values.

EXAMPLE 38

(1S,6R)-6-(3,4-dichlorophenyl)-1-[(methyloxy)methyl]-3-azabicyclo[4.1.0]heptane trifluoroacetate (ratio ion:counterion not determined) (E38)

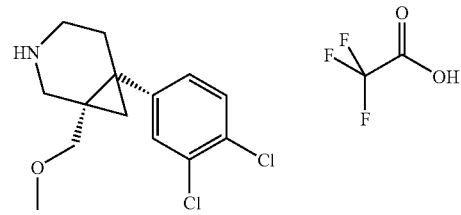

Step A:

1,1-dimethylethyl (1S,6R)-6-(3,4-dichlorophenyl)-1-[(methyloxy)methyl]-3-azabicyclo[4.1.0]hept-4-ene-3-carboxylate (P60, 11 g) was dissolved in toluene (110 ml). The solution was treated with triethylsilane (5.46 ml, 34.17 mmol), followed by trifluoroacetic acid (14.81 ml, 199.3 mmol). The reaction was stirred at room temperature for 24 h, then quenched with sodium hydroxide and stirred for 10 min. The pH of the mixture was approximately 13. The phases were separated and the toluene phase concentrated in vacuo to give a product intermediate as an oil, which was further dried by performance of three azeotropes.

Step B, method A:

3 g of the material produced in step A were dissolved in ethyl acetate and heptane was added until the solution became cloudy. The solution was heated until dissolution and then allowed to cool. Crystals' formation was observed. The solid was then filtered and 1 g of title compound was recovered.

Step B, method B:

6 g of the material produced in Step A were dissolved in 12 mL of ethyl acetate. Heptane (60 mL) was added to this solution and the biphasic mixture was then heated to ~70° C. to obtain a single phase solution. To this solution another portion of heptane (60 mL) was added and the solution heated to reflux (90° C.). The solution was then allowed to cool while stirring to 67° C., at which temperature it was seeded with crystals of the title compound previously obtained as described in Step B, Method A. The solution was then allowed to cool to room temperature overnight.

The resulting precipitate was then filtered by vacuum filtration and washed with heptane (5 mL). Title compound was obtained (1.5 g) as a crystalline solid (25% recovery)

NMR ($^1$H, CDCl$_3$): δ ppm 1.23 (dd, 2H) 2.16-2.25 (m, 1H) 2.31-2.43 (m, 1H) 2.84 (d, J=9.99 Hz, 1H) 2.92-2.97 (m, 1H) 3.15 (s, 3H) 3.18-3.28 (m, 2H) 3.76 (d, J=13.20 Hz, 1H) 7.34-7.39 (m, 1H) 7.40-7.43 (m, 1H) 7.51 (d, J=1.96 Hz, 1H) 9.65 (s, 1H)

Diffractogram of Form 1 of the title compound E38 is reported in FIG. 1.

Peaks* of Form 1 of the title compound Example 38 are illustrated in the Table 1 below (XRPD angles and d spacings are reported):

TABLE 1

| 2-theta [°] | d-spacing [Å] |
|---|---|
| 5.1 | 17.3 |
| 10.0 | 8.8 |
| 10.2 | 8.6 |
| 10.6 | 8.3 |
| 15.4 | 5.7 |
| 18.6 | 4.8 |
| 19.3 | 4.6 |
| 20.6 | 4.3 |
| 21.0 | 4.2 |
| 21.4 | 4.1 |
| 22.2 | 4.0 |
| 23.3 | 3.8 |
| 23.5 | 3.8 |
| 25.5 | 3.5 |
| 25.9 | 3.4 |
| 26.0 | 3.4 |
| 30.4 | 2.9 |
| 31.2 | 2.9 |
| 35.5 | 2.5 |
| 39.5 | 2.3 |

*Values shown here are rounded to one decimal place. The diffraction pattern can shift to slightly higher or lower 2θ values depending on sample displacement.

[X Ray Powder Diffraction (XRPD) analysis was performed on a PANalytical X'Pert-Pro MPD with Johansson Kα1 monochromator, using X'Celerator detector. The acquisition conditions were as follows: Radiation: Cu (Kα1), 1.540598 angstroms (monochromatic); Detector: X'Celerator; Tension: 45 kV; Current: 40 mA; Start angle: 2.0° 2q; End angle: 50.0° 2q; Step size: 0.02°; Time/step: 40.0 sec; Scan speed: 0.05°/sec; Incident beam: 2° fixed anti-scatter slit, and programmable divergence slit; Diffracted beam: 0.02 rad soller slit, and programmable anti-scatter slit; Samples prepared on silicon zero background sample holder)].

In one embodiment, unique and discriminating peaks* of Form 1 of the title compound Example 38 have been identified and are illustrated in Table 2 below (XRPD angles and d spacings are reported):

TABLE 2

| 2-theta [°] | d-spacing [Å] |
|---|---|
| 5.1 | 17.3 |
| 10.2 | 8.6 |
| 10.6 | 8.3 |
| 15.4 | 5.7 |
| 18.6 | 4.8 |
| 19.3 | 4.6 |
| 21.4 | 4.1 |
| 22.2 | 4.0 |

Figure 2:
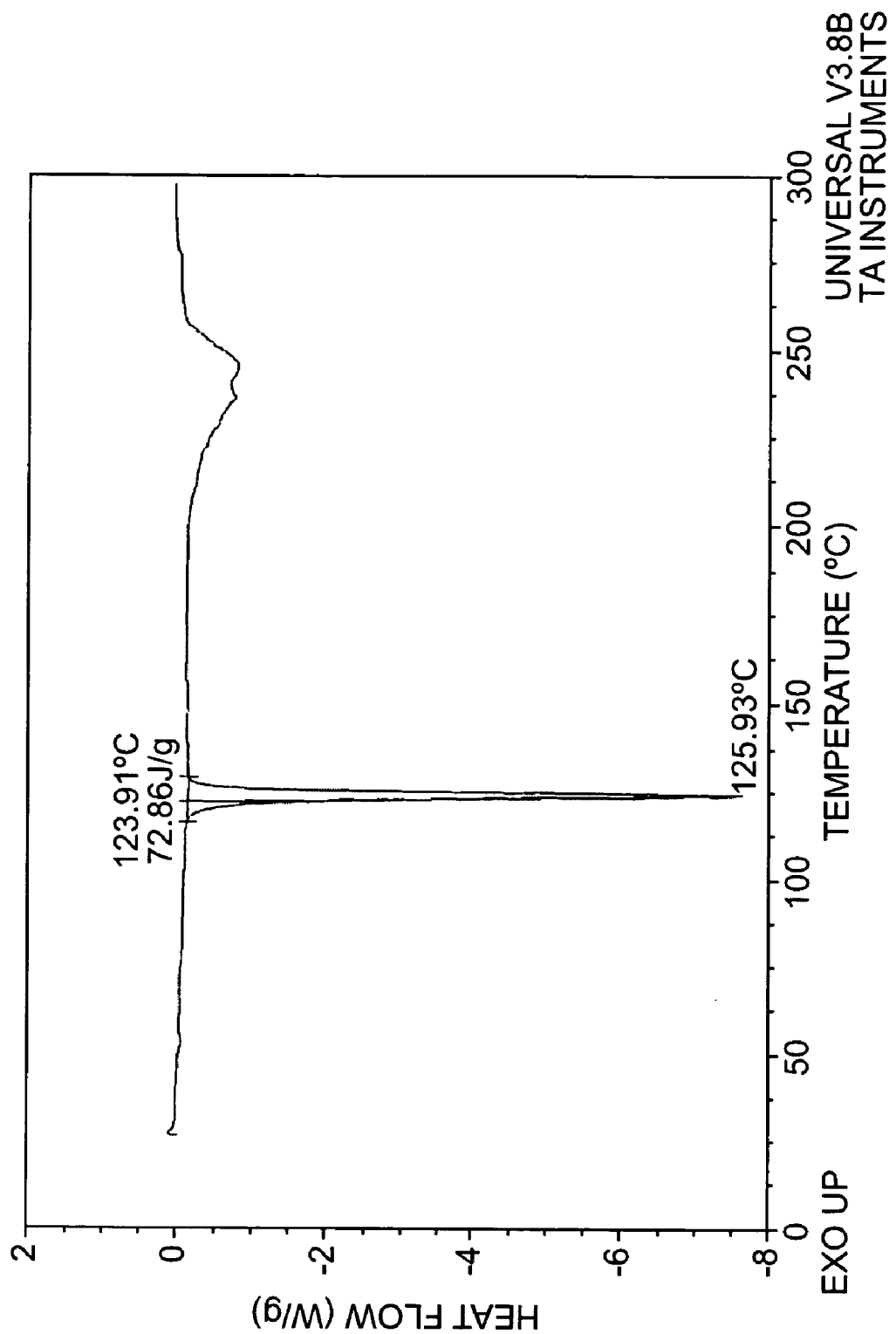
FIG. 2 is a DSC thermogram of Form 1 of the title compound E38 of Example 38.

Onset of melting (E38, Form 1): 123.91° C. (TA Instruments Model Q100 DSC; Pan:closed aluminium; Purge gas: N$_2$, 40 mL/min; Temp range: 30-300° C., 15° C./min). DSC thermogram of Form 1 of the title compound Example 38 is shown in FIG. 2.

It is to be understood that the present invention covers all combinations of particular groups described herein above.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the following claims.

The invention claimed is:

1. (1S,6R)-6-(3,4-dichlorophenyl)-1-[(methyloxy)methyl]-3-azabicyclo[4.1.0]heptane.

2. A pharmaceutical composition comprising the compound as claimed in claim 1, and a pharmaceutically acceptable carrier.

3. A method of treating a condition for which inhibition of serotonin (5-HT), dopamine (DA) and norepinephrine (NE), is beneficial, which comprises administering to a mammal in need thereof an effective amount of the compound as claimed in claim 1.

4. The composition as claimed in claim 2, wherein the composition is in a unit dosage form selected from a tablet, a capsule and an ampoule.

5. The composition as claimed in claim 2 containing 1 to 200 mg of the compound.

6. A method of treating depression which comprises administering to a human in need thereof an effective amount of the compound as claimed in claim 1.

7. The method as claimed in claim 6, wherein the compound is administered in an oral dose of between 1 mg and 500 mg, one to four times per day.

8. The method as claimed in claim 6, wherein the compound is administered in an oral dose of between 1 mg and 200 mg per day.

9. A method of treating an eating disorder which comprises administering to a human in need thereof an effective amount of the compound as claimed in claim 1.

10. The method as claimed in claim 9, wherein the compound is administered in an oral dose of between 1 mg and 500 mg, one to four times per day.

11. The method as claimed in claim 9, wherein the compound is administered in an oral dose of between 1 mg and 200 mg per day.

12. A method of treating obesity which comprises administering to a human in need thereof an effective amount of the compound as claimed in claim 1.

13. The method as claimed in claim 12, wherein the compound is administered in an oral dose of between 1 mg and 500 mg, one to four times per day.

14. The method as claimed in claim 12, wherein the compound is administered in an oral dose of between 1 mg and 200 mg per day.

15. A salt of (1S,6R)-6-(3,4-dichlorophenyl)-1-[(methyloxy)methyl]-3-azabicyclo[4.1.0]heptane.

16. A pharmaceutically acceptable salt of (1S,6R)-6-(3,4-dichlorophenyl)-1-[(methyloxy)methyl]-3-azabicyclo[4.1.0]heptane.

17. A pharmaceutical composition comprising the compound as claimed in claim 16, and a pharmaceutically acceptable carrier.

18. The composition as claimed in claim 17, wherein the composition is in a unit dosage form selected from a tablet, a capsule and an ampoule.

19. The composition as claimed in claim 17 containing 1 to 200 mg of the compound.

20. A method of treating depression which comprises administering to a human in need thereof an effective amount of the compound as claimed in claim 16.

21. The method as claimed in claim 20, wherein the compound is administered in an oral dose of between 1 mg and 500 mg, one to four times per day.

22. The method as claimed in claim 20, wherein the compound is administered in an oral dose of between 1 mg and 200 mg per day.

23. A method of treating an eating disorder which comprises administering to a human in need thereof an effective amount of the compound of claim 16.

24. The method as claimed in claim 23, wherein the compound is administered in an oral dose of between 1 mg and 500 mg, one to four times per day.

25. The method as claimed in claim 23, wherein the compound is administered in an oral dose of between 1 mg and 200 mg per day.

26. A method of treating obesity which comprises administering to a human in need thereof an effective amount of the compound of claim 16.

27. The method as claimed in claim 26, wherein the compound is administered in an oral dose of between 1 mg and 500 mg, one to four times per day.

28. The method as claimed in claim 26, wherein the compound is administered in an oral dose of between 1 mg and 200 mg per day.

29. (1S,6R)-6-(3,4-dichlorophenyl)-1-[(methyloxy)methyl]-3-azabicyclo[4.1.0]heptane phosphate.

30. A pharmaceutical composition comprising the compound as claimed in claim 29, and a pharmaceutically acceptable carrier.

31. The composition as claimed in claim 30, wherein the composition is in a unit dosage form selected from a tablet, a capsule and an ampoule.

32. The composition as claimed in claim 30 containing 1 to 200 mg of the compound.

33. A method of treating depression which comprises administering to a human in need thereof an effective amount of the compound as claimed in claim 29.

34. The method as claimed in claim 33, wherein the compound is administered in an oral dose of between 1 mg and 500 mg, one to four times per day.

35. The method as claimed in claim 33, wherein the compound is administered in an oral dose of between 1 mg and 200 mg per day.

36. A method of treating an eating disorder which comprises administering to a human in need thereof an effective amount of the compound as claimed in claim 29.

37. The method as claimed in claim 36, wherein the compound is administered in an oral dose of between 1 mg and 500 mg, one to four times per day.

38. The method as claimed in claim 36, wherein the compound is administered in an oral dose of between 1 mg and 200 mg per day.

39. A method of treating obesity which comprises administering to a human in need thereof an effective amount of the compound as claimed in claim 29.

40. The method as claimed in claim 39, wherein the compound is administered in an oral dose of between 1 mg and 500 mg, one to four times per day.

41. The method as claimed in claim 39, wherein the compound is administered in an oral dose of between 1 mg and 200 mg per day.

* * * * *